United States Patent
Quinn et al.

(10) Patent No.: US 10,407,671 B2
(45) Date of Patent: Sep. 10, 2019

(54) LYSOSOMAL STORAGE DISEASE ENZYMES

(71) Applicant: Alexion Pharmaceuticals, Inc., New Haven, CT (US)

(72) Inventors: Anthony Quinn, Chestnut Hill, MA (US); Alex J. Harvey, Athens, GA (US)

(73) Assignee: Alexion Pharmaceuticals, Inc., Boston, MA (US)

( * ) Notice: Subject to any disclaimer, the term of this patent is extended or adjusted under 35 U.S.C. 154(b) by 0 days.

(21) Appl. No.: 15/429,247

(22) Filed: Feb. 10, 2017

(65) Prior Publication Data

US 2017/0314000 A1   Nov. 2, 2017

Related U.S. Application Data

(63) Continuation of application No. 15/285,025, filed on Oct. 4, 2016, now abandoned, which is a continuation of application No. 15/177,867, filed on Jun. 9, 2016, now abandoned, which is a continuation of application No. 13/642,790, filed as application No. PCT/US2011/033699 on Apr. 23, 2011, now abandoned.

(60) Provisional application No. 61/343,177, filed on Apr. 23, 2010, provisional application No. 61/396,376, filed on May 26, 2010, provisional application No. 61/403,011, filed on Sep. 9, 2010, provisional application No. 61/456,014, filed on Oct. 29, 2010, provisional application No. 61/432,372, filed on Jan. 13, 2011.

(51) Int. Cl.
| | |
|---|---|
| *C12N 9/20* | (2006.01) |
| *A61K 38/38* | (2006.01) |
| *A61K 31/194* | (2006.01) |
| *A61K 38/46* | (2006.01) |
| *A01K 67/027* | (2006.01) |

(52) U.S. Cl.
CPC ............ *C12N 9/20* (2013.01); *A01K 67/0278* (2013.01); *A61K 31/194* (2013.01); *A61K 38/385* (2013.01); *A61K 38/465* (2013.01); *C12Y 301/01013* (2013.01); *A01K 2217/052* (2013.01); *A01K 2227/30* (2013.01); *A01K 2267/01* (2013.01); *C12N 2740/10041* (2013.01)

(58) Field of Classification Search
CPC .. A61K 38/385; A61K 31/194; A61K 38/465; C12N 2740/10041; C12N 9/20; A01K 2267/01; A01K 2217/052; A01K 67/0278; A01K 2227/30; A01L 2217/052; C12Y 301/01013
See application file for complete search history.

(56) References Cited

U.S. PATENT DOCUMENTS

| | | | |
|---|---|---|---|
| 5,767,115 A | 6/1998 | Rosenblum et al. | |
| 5,929,304 A | 7/1999 | Radin | |
| 6,534,300 B1 | 3/2003 | Canfield | |
| 6,670,165 B2 | 12/2003 | Canfield | |
| 6,800,472 B2 | 10/2004 | Canfield et al. | |
| 6,849,257 B2 | 2/2005 | Grabowski et al. | |
| 7,033,780 B1 | 4/2006 | McCarthy et al. | |
| 8,124,732 B2 | 2/2012 | Harvey | |
| 8,178,609 B2 | 5/2012 | Grynkiewicz et al. | |
| 8,183,003 B2 | 5/2012 | Crawford et al. | |
| 8,232,073 B2 | 7/2012 | Crawford et al. | |
| 8,663,631 B2 | 3/2014 | Quinn | |
| 8,945,542 B2 | 2/2015 | Heartlein | |
| 2002/0193303 A1 | 12/2002 | Kapeller-Libermann | |
| 2003/0059420 A1 | 3/2003 | Grabowski et al. | |
| 2003/0064467 A1 | 4/2003 | Baker et al. | |
| 2004/0038365 A1 | 2/2004 | Xiao | |
| 2004/0175798 A1 | 9/2004 | Wan et al. | |
| 2004/0223960 A1 | 11/2004 | Grabowski et al. | |
| 2005/0112691 A1 | 5/2005 | Callewaert et al. | |
| 2005/0181474 A1 | 8/2005 | Giordano et al. | |
| 2007/0009500 A1 | 1/2007 | Blazar et al. | |
| 2007/0264249 A1 | 11/2007 | Grabowski et al. | |
| 2007/0270364 A1 | 11/2007 | Janknecht | |
| 2007/0270367 A1 | 11/2007 | Testa et al. | |
| 2008/0025958 A1 | 1/2008 | Daneman et al. | |
| 2008/0025959 A1 | 1/2008 | Daneman | |
| 2008/0206223 A1 | 8/2008 | Van Brae et al. | |

(Continued)

FOREIGN PATENT DOCUMENTS

| | | |
|---|---|---|
| EP | 1267914 | 4/2009 |
| RU | 2008134120 | 2/2010 |

(Continued)

OTHER PUBLICATIONS

Zhu et al., Production of human monoclonal antibody in eggs of chimeric chickens. Nat. Biotechnol., 2005, vol. 23(9): 1159-1169. (Year: 2005).*

(Continued)

*Primary Examiner* — Ganapathirama Raghu

(74) *Attorney, Agent, or Firm* — McDermott Will & Emery LLP

(57) ABSTRACT

The present invention provides compositions of recombinant human lysosomal acid lipase having particular glycosylation patterns for internalization into target cells, a vector containing the nucleic acid encoding human lysosomal acid lipase, a host cell transformed with the vector, pharmaceutical compositions comprising the recombinant human lysosomal acid lipase and method of treating conditions associated with lysosomal acid lipase deficiency.

20 Claims, 38 Drawing Sheets

Specification includes a Sequence Listing.

(56) References Cited

U.S. PATENT DOCUMENTS

| | | |
|---|---|---|
| 2008/0249287 A1 | 10/2008 | Rossomando et al. |
| 2008/0255050 A1 | 10/2008 | ZhongMao |
| 2008/0292618 A1 | 11/2008 | Weisbart |
| 2009/0178147 A1 | 7/2009 | Harvey |
| 2009/0297496 A1 | 12/2009 | Grabowski |
| 2010/0160253 A1 | 6/2010 | Coombe et al. |
| 2010/0184947 A1 | 7/2010 | Kuik-Romeijn et al. |
| 2010/0196393 A1 | 8/2010 | Banks et al. |
| 2010/0233084 A1 | 9/2010 | Narasimhaswamy et al. |
| 2010/0062982 A1 | 11/2010 | Harvey |
| 2010/0291050 A1 | 11/2010 | Sturk et al. |
| 2011/0091442 A1 | 4/2011 | Boyd et al. |
| 2011/0213328 A1 | 9/2011 | Keimel et al. |
| 2011/0230416 A1 | 9/2011 | Khrestchatisky et al. |
| 2012/0064055 A1 | 3/2012 | Quinn |
| 2012/0093795 A1 | 4/2012 | Garcia et al. |
| 2012/0190642 A1 | 7/2012 | Grynkiewicz et al. |
| 2012/0232133 A1 | 9/2012 | Balazes et al. |
| 2012/0288447 A1 | 11/2012 | Lee et al. |
| 2013/0209436 A1 | 8/2013 | Quinn et al. |
| 2015/0030582 A1* | 1/2015 | Harvey ............... A61K 38/465 424/94.6 |

FOREIGN PATENT DOCUMENTS

| | | |
|---|---|---|
| WO | 1992/16212 | 10/1992 |
| WO | 1995/008532 | 3/1995 |
| WO | 1996/04001 | 2/1996 |
| WO | 1997/05771 | 2/1997 |
| WO | 1998/11206 | 3/1998 |
| WO | 2000/09153 | 2/2000 |
| WO | 2000/77239 | 12/2000 |
| WO | 2001/56596 | 8/2001 |
| WO | 2001/97829 | 12/2001 |
| WO | 2007/030375 | 3/2007 |
| WO | 2007/084737 | 7/2007 |
| WO | 12007/137303 | 11/2007 |
| WO | 2010/033854 A2 | 3/2010 |
| WO | 2011/133960 | 10/2011 |
| WO | 2012/050695 | 4/2012 |
| WO | 2012/112677 | 8/2012 |
| WO | 2012/112681 | 8/2012 |
| WO | 2012/159052 | 11/2012 |
| WO | 2012/162807 | 12/2012 |
| WO | 2012/177639 | 12/2012 |
| WO | 2012/177778 | 12/2012 |
| WO | 2013/020064 | 2/2013 |

OTHER PUBLICATIONS

McCoy et al., "Treatment of Cholesteryl Ester Storage Disease with Combined Cholestyramine and Lovastatin," Ann NY Acad. Sci., pp. 453-454 (1991).
Marsh et al., "Apolipoprotein B Metabolism in Humans: Studies with Stable Isotope-Labeled Amino Acid Precursors," Atherosclerosis, 162:227-244 (2002).
Marshall et al., "Wolman's Disease: A Rare Lipidosis with Adrenal Calcification," Arch. Dis. Childhood, 44:331-341 (1969).
Shome et al., "The Middle-East Connection of Wolman Disease," Saudi. Med. J., 23(5): 597-601 (2002).
Maslen et al., "Occurrence of a mutation associated with Wolman disease in a family with cholesteryl ester storage disease," J. Inher. Metab. Dis., 18:620-623 (1995).
Mayatepek et al., "Fatal genetic defect causing Wolman Disease," J. Inher. Metab. Dis., 22:93-94 (1999).
Meikle et al., "Prevalence of Lysosomal Storage Disorders," JAMA, 281(3):249-254 (1999).
Melling et al., "Localised massive tumourous xanthomatosis of the small intestine," Int. J. Colorectal Dis., 22:1401-1404(2007).
Michels et al., "Pulmonary vascular obstruction associated with cholesteryi ester storage disease," The Journal of Pediatrics, 94:621-622 (1979).

Michels et al., "Cholesteryl Lignocerate Hydrolysis in Adrenoleukodystrophy," Pediat. Res. 14:21-23 (1980).
Mistry et al., "Therapeutic delivery of proteins to macrophages: implications for treatment of Gaucher's disease," The Lancet, 348:1555-1556 (1996).
McPhee et al., "Effects of AAV-2 mediated aspartoacylase gene transfer in the tremor rat model of Canavan disease," Molecular Brain Research, 135:112-121 (2005).
Mon et al., "Identification of the Mannan-Binding Protein from Rat Livers as a Hepatocyte Protein Distinct from the Mannan Receptor on Sinusoidal Cells," Archives of Biochemistry and Biophysics, 222(2):542-552 (1983).
Muntoni et al., "Prevalence of Cholesteryl Ester Storage Disease," Arterioscler. Thomb. Vasc. Biol., 27:1866-1868 (2007).
Muntoni et al., "Homozygosity for a splice junction mutation in exon 8 of the gene encoding lysosomal acid lipase in a Spanish kindred with cholesterol ester disease (CESD)," Hum Genet, 95:491-494 (1995).
Muntoni et al., "A missense mutation (Thr-6Pro) in the lysosomal acid lipase (LAL) gene is present with a high frequency in three different ethnic populations: impact on serum lipoprotein concentrations," Hum Genet, 97:265-267 (1996).
Nakagawa et al., "Cloning of rat lysosomal acid lipase cDNA and identification of the mutation in the rat model of Wolman's disease," J. Lipra Res 36:2212-2213 (1995).
Nègre-Salvayre et al., "UV-treated lipoproteins J. Lipid Res. as a model system for the study of the biological effects of lipid peroxides on cultured cells. 4. Calcium is involved in the cytotoxicity of UV-treated LDL on lymphoid cell lines," Biochimica et Biophysics Acta, 1123:1207-215 (1992).
Nobili et al., "Treatment of nonalcoholic fatty liver disease in adults and children: a closer look at the arsenal," J Gastroenterol, (2011). DOI 10.1007/s00535-011-0467.
Noorman et al., "The mannose receptor, localization and role in the clearance of tissue-type plasminogen activator," Fibrinolysis & Proteolysis, 12(4):241-250 (1998).
Odievre, "Clinical presentation of Metabolic Liver Disease," J. Inher. Metab. Dis., 14:526-530 (1991).
Özmen et al., "Wolman's disease: ultrasonographic and computed tomographic findings," Pediatr Radiol, 22:541-542 (1992).
Ameis et al., "Lysosomal acid lipase: A pivotal enzyme in the pathogenesis of cholesteryl ester storage disease and Wolman disease," Z Gastroenterol (Suppl. 3) 34:66-67 (1996).
Beaudet et al., "Acid lipase in cultured fibroblasts: cholesterol ester storage disease," J. Lab. Clin. Med., 84:54-55 (1974).
Brown et al., "Use of Nile Red Stain in the Detection of Cholesteryl Ester Accumulation in Acid Lipase-Deficient Fibroblasts," Arch Pathol Lab Med, 112:295-296 (1988).
Carter et al., "Cholesterol Ester Storage Disease," Pediat. Radiol, 2:135-136 (1974).
Coelho et al., "Cholesterylester Storage Disease Report of a case," Arq Gastroenterol, 24(3/4):184-187, (1987).
Dincsoy et al., "Cholesterol Ester Storage Disease and Mesenteric Lipodystrophy," Am. J. Pathol., 81:263-264 (1984).
Drevon et al., "The Effects of Cholesterol/Fat Feeding on Lipid Levels and Morphological Structures in Liver, Kidney and Spleen in Guinea Pigs," Acta path. microbial. scand. Sect. A, 85:1-18 (1977).
Edelstein, et al., "Cholesteryl Ester Storage Disease: A Patient with Massive Splenomegaly and Splenic Abscess," The American Journal of Gastroenterology, 83:687-688. (1988).
Elleder et al., "Subclinical course of cholesterol ester storage disease (CESD) diagnosed in adulthood," Virchows Archiv A Pathological Anatomy and Histopathology, 416:3457-365 (1990).
Elleder et al., "Subclinical course of cholesteryl ester storage disease in an adult with hypercholesterolemia, accelerated atherosclerosis, and liver cancer," Journal of Hepatology, 32:528-534 (2000).
Ferry et al., "Liver Transplantation for Cholesteryl Ester Storage Disease," Journal of Pediatric Gastroenterology and Nutrition, 12:376-378 (1991).
Fulcher, et al., "Pediatric Case of the Day", RadioGraphics, 18(2):533-534 (1988).

(56) References Cited

OTHER PUBLICATIONS

Haller et al., "Gallbladder Dysfunction in Cholesterol Ester Storage Disease," JPGN, 50(5):556-557 (2010).
Hill et al., "CT Findings in Acid Lipase Deficiency: Wolman Disease and Cholesteryl Ester Storage Disease," Journal of Computer Assisted Tomography, 7(5):815-818 (1983).
Iverson et al., "Asymptomatic cholesteryl ester storage disease in an adult controlled with simvastatin," Ann Clin Biochem, 34:433-436 (1997).
Jeschke et al., "Cholesteryl Ester Storage Disease, Clinical and Morphological Aspects," Cholesterylester-Speicherkrankheit, 120(8):601-604 (1982).
Justus et al., "Lebermorphologie and Klinik eins Falls von Cholesterinester-Speicherkrankheit," Dtsch. Z. Verdau-Stoffwechs. krankh. 48:198-207 (1988).
Kale et al., "End-Stage Renal Disease in a Patient with Cholesteryl Ester Storage Disease following Successful Liver Transplantation and Cyclosporine Immunosuppression," Journal of Pediatric Gastroenterology and Nutrition, 20:95-97 (1995).
Künnert et al., "Zur Diagnostik and Morphologie der Leber bei Cholesterolester-Speicher-krankheit," Zbl. Allg. Pathol. a. pathol. Anat. 123:71-84 (1979).
Künnert et al., "Cholesteryl ester storage disease and sea-blue histiocytes," Zentralbl. Allg. Pathol. Pathol. Anat. 133:517-525 (1987).
Kuntz et al., "Cholesterinester-Speicherkrankheit der Leber," Leber Magen Darm 11, Nr. 6:258-263 (1981).
Leone et al., "Use of simvastatin plus cholestyramine in the treatment of lysosomal acid lipase deficiency," The Journal of Pediatrics, 119(6):1008-1009 (1991).
Leone et al., "Treatment and liver transplantation for cholesterol ester storage disease," The Journal of Pediatrics, 127 (3):509-510 (1995).
Liu et al., "Phenotypic Correction of Feline Lipoprotein Lipase Deficiency by Adenoviral Gene Transfer," Human Gene Therapy, 11:21-32 (2000).
Pfeifer et al., "Cholesteryl Ester Storage Disease: Report on Four Cases," Virchows Arch. B. Cel Path. 33:17-34 (1980).
Pisciotta et al., "Cholesteryl Ester Storage Disease (CESD) due to novel mutations in the LIPA gene," Molecular Genetics and Metabolism, 79:143-148 (2009).
Rassoul et al., "Long-term administration of the HMG-CoA reductase inhibitor lovastatin in two patients with cholesteryl ester storage disease," International Journal of Clinic Pharmacology and Therapeutics, vol. 39, No. 5:199-204 (2001).
Salvayre et al., "Maladie de Wolman et polycorie cholestérolique de l'adulte (cholesteryl ester storage disease): Nuoveaux moyens d'etude et de diagnostic," Ann. Biol. Clin. 44:611-617 (1986).
Vuillemenot et al., "Intrathecal tripeptidyl-peptidase 1 reduces lysosomal storage in a canine model of late infantile neuronal ceroid lipofuscinosis," Molecular Genetics and Metabolism, 104:325-337 (2011).
Walters et al., "Cholesterol esterase activities in commercial pancreatic enzyme preparations and implications for use in pancreatic insufficient cystic fibrosis," Journal of Clinical Pharmacy and Therapeutics, 26:425-431 (2001).
Wang et al., "SREBP-1, a Membrane-bound Transcription Factor Released by Sterol-Regulated Proteolysis," Cell, 77:53-62 (1994).
Warner et al., "Separation and Characterization of the Acid Lipase and Neutral Esterases from Human Liver," Am. J. Hum Genet, 32:869-879 (1980).
Warner et al., "Purification of the Lysosomal Acid Lipase from Human Liver and Its Role in Lysosomal Lipid Hydorlysis," The Journal of Biological Chemistry, 246(6):2952-2957 (1981).
Wolman, "Proposed Treatment for Infants With Wolman Disease," Pediatrics, 83:1074-1075 (1989).
Wolman, "Primary Familial Xanthomatosis with Involvement and Calcification of the Adrenals: Report of Two or More Cases in Siblings of a Previously Described Infant," Pediatrics, 28:742-757 (1961).

Xu et al., "Turnover and Distribution of Intravenously Administered Mannose-Terminated Human Acid [beta]-Glucosidase in Murine and Human Tissues," Pediatric Research, 39(2):313-322 (1996).
Yagyu et al., "Overexpressed lipoprotein lipase protects against atherosclerosis in apolipoprotein E knockout mice," Journal of Lipid research, 40:1677:1678 (1999).
Yan et al., "Macrophage-Specific Expression of Human Lysosomal Acid Lipase Corrects Inflammation and Pathogenic Phenotypes in lal-/-Mice," The American Journal of Pathology, 169(3):916-917 (2006).
Yokoyama et al., "Long-term treatment of a homozygous cholesteryl ester storage disease with combined cholestryamine and lovastatin," J. Inher. Metab. Dis. 15:219-292 (1992).
Zhang et al., "Biotherapeutic target or sink: analysis of the macrophage mannose receptor tissue distribution in murine models of lysosomal storage diseases," J. Inherit Metab Disl 34:795-809 (2011).
Young et al., "Deficiency of Acid Esterase Activity in Wolman's Disease," Archives of Disease in Childhood, 45:664-665 (1970).
Zuliani et al., "Characterization of a New Form of Inherited Hypercholesterolemia: Familial Recessive Hypercholesterolemia," Arterioscler Throm Vasc Biol, 19:802-809 (1999).
Wolman, "Involvement of Nervous Tissue in Primary Familial Xanthosmatosis with Adrenal Calcification," Path Europe, 3:259-265 (1968).
Hollak et al., "Alglucerase: Practical Guidance on Appropriate Dosage and Administration in Patients with Gaucher Disease," Biodrugs, 9(1):11-13.
Sheriff et al., Characterization of Lysosomal Acid Lipase by Site-Directed Mutagenesis and Heterologous Expression., J. Biol. Chem., 270:27766-27772 (1995).
Synageva Biopharma Corp., and Synageva Biopharma Limited, plaintiffs v. Children's Hospital Research Foundation, Children's Hospital Foundation, Cincinnati, Ohio and Children's Hospital Medical Center, defendants, Tribunal de Grande Instance of Paris, Mar. 26, 2013, "Pleadings No. 1".
Synageva Biopharma Corp., and Synageva Biopharma Limited, plaintiffs v. Children's Hospital Research Foundation, Children's Hospital Foundation, Cincinnati, Ohio and Children's Hospital Medical Center, defendants, Summons Before the High Court of Paris, 2012.
Synageva Biopharma Limited, claimant v. Children's Hospital Research Foundation, defendant, in the High Court of Justice, Chancery division, Patents Court, Claim No. HC 12 C00211, "Statement of Opposition" (2013).
Synageva Biopharma Limited, claimant v. Children's Hospital Research Foundation, defendant, in the High Court of Justice, Chancery division, Patents Court, Claim No. HC 12 C00211, "Grounds of Invalidity" (2012).
Synageva Biopharma Limited, claimant v. Children's Hospital Research Foundation, defendant, in the High Court of Justice, Chancery division, Patents Court, Claim No. HC 12 C00211, "Amended Grounds of Invalidity" (2013).
Schiffmann, "Infusion of α-Galactosidase A Reduces Tissue Globotriaosylceramide Storage in Patients with Fabry Disease," PNAS, 97(1):365-370 (2000).
Ahn et al., "Identification of the Genes Differently Expressed in Human Dendritic Cell Subsets by cDNA Subtraction and Microarray Analysis," Blood, 100:1742-1754 (2002).
Nègre et al., "Acid Lipases and Acid Cholesterol Esterases: Wolman'Disease and Cholesteryl Ester Storage Disease," Path Biol., 36(2): 167-181 (1988).
Elleder et al., "Lysosomal Acid Lipase Deficiency. Overview of Czech Patients," Cas Lek Cesk, 131(23),719-724 (1999).
Martinez et al., "7 Years Experience with Hepatic Transplantation in Children," 6(1):7-10 (1993).
Tanaka et el., Acid Lipase Deficiency: Wolman Disease and Cholesteryl Ester Storage Disease, Nippon Rinsho, 53(12):3004-3008 (1995).
Scriver et al., "The Metabolic and Molecular Bases of Inherited Disease," 7th Ed. V II, McGraw-Hill, New York, pp. 2563-2587, 1995.
Mao et al., "Sortase-Mediated Protein Ligation: A New Method of Protein Engineering," J. Am. Chem Soc. 126, 2670-2671, 2004.

(56) References Cited

OTHER PUBLICATIONS

Salvayre et al., "Lipases et Cholesterol Esterases Acides: Maladie De Wolman et Cholesteryl Ester Storage Disease (Polycorie Cholesterolique de L'Adulte)" Path Biol, 36, 167-181, 1988.

Furbish et al., "Uptake and Distribution of Placental Glucocerebrosidase in Rat Hepatic Cells and Effects of Sequential Deglycosylation," Biochimica et Biophysica Acta, 673 425-434, 1981.

Dalgic "Cholestryl Ester Storage Disease in a Young Child Presenting as isolated Hepatomegaly Treated with Simvastatin," The Turkish Journal of Pediatrics, 48:148-151 (2006).

Tadiboylina "Treatment of Dyslipidemia with Lovastatin and Ezetimibe in an Adolescent with Cholesterol Ester Storage Disease," Lipids in Health and Disease, 4(26): 1-6 (2005).

Bailey "An Overview of Enzyme Replacement Therapy for Lysosomal Storage Diseases" The Online Journal of Issues in Nursing, 13(1):1-4 (2008).

Kim "Successful Management of Difficult Infusion-Associated Reactions in a Young Patient with Mucopolysaccharidosis Type VI Receiving Recombinant Human Arylsulfatase B (Galsulfase [Naglazyme])" Pediatrics, 121(3):714-717 (2008).

Albrecht Dehmel, Opposition Submission 1, pp. 1-56, Jan. 28, 2010 European Patent Register.

Albrecht Dehmel, Opposition Submission 2, pp. 1-17, Apr. 4, 2011, European Patent Register.

Albrecht Dehmel, Opposition Submission 3, pp. 1-8, Aug. 22, 2011, European Patent Register.

Synageva Biopharma Corp., v. Children's Hospital Research Foundation, "Grounds of Invalidity of European Patent 1267914," pp. 1-11, Jan. 16, 2012, UK High Court of Justice, Chancery Division, Patents Court.

Akcoren et al., Cholesteryl Ester Storage Disease: Case Report During Childhood, Pediatric and Developmental Pathology, 2:574-576 (1999).

Anderson et al., "Lysosomal Acid Lipase Mutations that Determine Phenotype in Wolman and Cholesterol Ester Storage Disease," Mol. Genet. Metab., 68:333-345 (1999).

Anderson et al., "Mutations at the Lysosomal Acid Cholesteryl Ester Hydrolase Gene Locus in Wolman Disease," PNAS, 91:2718-2722 (1994).

Arterburn et al., "Orthotopic Liver Transplantation for Cholesteryl Ester Storage Disease," J. Clin. Gastroenterology, 13:482-485 (1991).

Aslanidis et al., "Genetic and Biochemical Evidence that CESD and Wolman Disease are Distinguished by Residual Lysosomal Acid Lipase Activity," Genomics, 33:85-93 (1996).

Besley et al., "Cholesterol Ester Storage Disease in an Adult Presenting with Sea-Blue Hiocytosis," Clin., Genet., 26:195-203 (1984).

Boldrini et al., "Wolman Disease and Cholesteryl Ester Storage Disease Diagnosed by Histological and Ultrastructural Examination of Intestinal and Liver Biopsy," Path. Res. Practice, 200:231-240 (2004).

Brown et al., "Restoration of a Regulatory Response to Low Density Lipoprotein in Acid Lipase Deficient Human Fibroblast," J. of Biol. Chem, 251:3277-3286 (1976).

Gunning et al., "Isolation and Characterization of Full-Length cDNA Clones for Human a-, 13-, and y-Actin mRNAs: Skeletal but Not Cyoplasmic Actins Have an Amino-Terminal Cysteine that is Subsequently Removed," Molecular and Cellular Biology, 3(5):787-795 (1983).

Guzzetta et al., "Elective Subtotal Splenectomy," Ann. Surg., 211 (1): 34-42 (1990).

Hafner et al., "The Human Primary Hepatocyte Transcriptome Reveals Novel Insights into Atorvastatin and Rosuvastatin Action," Pharmacogenetics and Genomics, 21(11):741-750 (2011).

Hakala et al., "Lysosomal Enzymes are Released from cultured Human macrophages, Hydrolyze LDL in Vitro, and are Present Extracellularly in Human Atherosclerotic Lesions," Arteriosclerosis, Thrombosis, and Vascular Biology, 23:1430-1436, (2003).

Hoeg et al., "Characterization of Neutral and Acid Ester Hydrolase in Wolman's Disease," Biochimica et Biophysics Acta, 711:59-65 (1982).

Hoeg et al., "Cholesteryl Ester Storage Disease and Wolman Disease: Phenotypic Variants of Lysosomal Acid Cholesteryl Ester Hydrolase Deficiency," Am. J. Hum. Genet, 36:1190-1203 (1984).

Holbrook et al., "Tolerization as a Tool for Generating Novel Monoclonal Antibodies," Immunology and Cell Biology, 80:319-322 (2002).

Hollak et al., "Alglucerase Practical Guidance on Appropriate Dosage and Administration in Patients with Gaucher Disease," Biodrugs, 9(1):11-23 (1998).

Hooper et al., "A Novel Missense LIPA Gene Mutation, N98S, in a Patient with Cholesteryl Ester Storage Disease," Clinics Chimica Acta, 398:152-154 (2008).

Hopkins et al., "Human Genetics and Coronary Heart Perspective," Annu. Rev. Nutr., 9:303-45 (1989).

Hua et al., "SREBP-2, A Second Basic-Helix-Leucine Zipper Protein that Stimulates Transcription by Binding to a Sterol Regulatory Element" Proc. Natl. Acad. Sci., 90:11603-11607 (1993).

Heinz et al., "Identification and in Situ Localization of the Insulin-Like Growth Factor-II/Mannose-6-Phosphate (IGF-II/M6P) Receptor in the Rat Gastrointestinal Tract: Comparison with the IGF-1 Receptor," U.S. National Institutes of Health, 129(4):1769-1778 (1991).

Imanaka et al., "Characterization of Lysosomal Acid Lipase Purified from Rabbit Liver," J. Biochem. 96:1089-1101 (1984).

Ishibashi et al., "Hypercholesterolemia in Low Density Lipoprotein Receptor Knockout Mice and its Reversal by Adenovirus-Mediated Gene Delivery," J. Clin. Invest, 92:883-893 (1993).

Hatanaka et al., "Human IgA-Binding Peptides Selected from Random Peptide Libraries: Affinity Maturation and Application in IgA Purification," J. Bio. Chem. in Press, M112 389742, pp. 1-12 (2012).

Jirtle et al., "Modulation of Insulin-Like Growth Factor-II/Mannose 6-Phosphate Receptors and Transforming Growth Factor-⊕1 during Liver Regeneration," The Journal of Biological Chemistry, 266(33):22444-22450 (1991).

Jolly et al., "Lysosomal Storage Diseases of Animals: an Essay in Comparative Pathology," Vet Pathol., 34:527-548 (1997).

Kahana et al., "Primary Familial Xanthomatosis with Adrenal Involvement (Wolman's Disease); Report of a further Case with Nervous System Involvement and pathogenetic Considerations," Pediatrics, 42(1):71-76 (1968).

Kawashiri et al., "Gene Therapy for Lipid Disorders,"Curr. Control Trials Cardiovascular Med., 1:120-127 (2000).

Kelly et al., "Characterization of Plasma Lipids and Lipoproteins in Cholesteryl Ester Storage Disease," Biochemical Medicine, 33:29-37 (1985).

Kikuchi et al., "Evaluation of Jejunal Function in VVolman's Disease," Journal of Pediatric Gastroenterology and Nutrition, 12(1): 6569 (1991).

Klima et al., "A Splice Junction Mutation Causes Deletion of a 72-Base Exon from the mRNA for Lysosomal Acid Lipase in a Patient with Cholesteryl Ester Storage Disease," J. Clin. Invest., 92:2713-2718 (1993).

Koch et al., "Assignment of LIPA, Associated with Human Acid Lipase Deficiency, to Human Chromosome 10 and Comparative Assignment to Mouse Chromosome 19," Somatic Cell Genetics, 7(3):345-358 (1981).

Kodlitsch et al., "Splice-Site Mutations in Atherosclerosis Candidate Genes Relating Individual Information to Phenotype," Circulation, 100:693-699 (1999).

Kolodny et al., "Current Concepts in Genetics; Lysosomal Storage Disease," The New England Journal of Medicine, 294(22):1217-1220 (1976).

Kostner et al., "Plasma Lipids and Lipoproteins of a Patient with Cholesteryl Ester Storage Disease," J. Inher. Metab. Dis. 8:9-12 (1985).

Kowel et al., "Low Density Lipoprotein Receptor-Related Protein Mediated Uptake of Cholesteryl Esters Derived from apoprotein E-Enriched Lipoproteins," Proc. Natl. Acad. Sci., 86:5810-5814 (1989).

(56) References Cited

OTHER PUBLICATIONS

Krivit et al., "Wolman Disease Successfully Treated by Bone Marrow Transplantation," Bone Marrow Transplantation, 26:567-570 (2000).
Kuriwaki et al., Morphological Characteristics of Lipid Accumulation in Liver-Constituting Cells of Acid Lipase Deficiency Rats (Wolman's Disease Model Rats), Pathology International, 49:291-297 (1999).
Laird et al., "Simplified Mammalian DNA Isolation Procedure," Nucleic Acids Research, 19(15):4293 (1991).
Lake et al., "Wolman's Disease Deficiency of E600-Resistant Acid Esterase Activity with Storage of Lipids in Lysosomes," The Journal of Pediatrics, 76(2):262-266 (1970).
Lake et al., "Histochemical Detection of the Enzyme Deficiency in Blood Films in Wolman's Disease," J. Clin. Path., 24:617-620 (1971).
Lashford et al., "Lysosomal Storage Disorders," Gene Therapy Technologies, Applications and Regulations, John Wiley & Sons, 1999.
Lee et al., "Mannose Receptor-Mediated Regulation of Serum Glycoprotein Homeostasis," Science, 295:1898-1901 (2002).
Lee et al., "Intragenic Deletion as a Novel Type of Mutation in Wolman Disease," Molecular Genetics and Metabolism, 104:703-705 (2011).
Leonova et al., "Proteolytic Processing Patterns of prosapasin in Insect and Mammalian Cells," The Journal of Biological Chemistry, 271(29):17312-17320 (1996).
Leslie et al., "A Mouse Model of Galactose-1-Phosphate Uridyl Transferase Deficiency," Biochemical and Molecular Medicine, 59:7-12 (1996).
Levy et al., "Cholesteryl Ester Storage Disease: Complex Molecular Effects of Chronic Lovastatin Therapy," Journal of Lipid Research, 33:1005-1015 (1992).
Lew et al., "A Mannose Receptor Mediates Mannosyl-Rich glycoprotein-Induced Mitogenesis in Bovine Airway Smooth Muscle Cells," J. Clin. Invest., 94:1855-1863 (1994).
Li et al., "Gsh-1, An Orphan Hox Gene, is Required for Normal pituitary Development," The EMBO Journal, 15(4):714-724 (1996).
Lohse et al., "Human Lysosomal Acid Lipase/Cholesteryl Ester Hydrolase and Human Gastric Lipase: Identification of the Catalytically Active Serine, Aspartic Acid, and Histidine Residues," Journal of Lipid Research, 38:892-903 (1997).
Lohse et al., "Human Lysosomal Acid Lipase/Cholesteryl Ester Hydrolase and Human Gastric Lipase:Site-Directed Mutagenesis of Cys227 and Cys236 Results in Substrate-Dependent Reduction of Enzymatic Activity," Journal of Lipid Research,38:1896-1905 (1997).
Lohse et al., "The Acid Lipase Gene Family: Three Enzymes, One Highly Conserved Gene Structure," Journal of Lipid Research, 38:881-891 (1997).
Lohse et al., "Molecular Defects Underlying Wolman Disease Appear to be More Heterogeneous than those Resulting in Cholesteryl Ester Storage Disease," Journal of Lipid Research, 40:221-228 (1999).
Lohse et al., "Compound Heterozygosity for a Wolman Mutation is Frequent Among Patients with Cholesteryl Ester Storage Disease," Journal of Lipid Research, 41:23-31 (2000).
Longhi et al., "Cholesteryl Ester Storage Disease: Risk Factors for Atherosclerosis in a 15-Year-Old Boy," J. Inner. Metab. Dis., 11(2):143-145 (1988).
Lough et al., "Wolman's Disease: An Electron Microscope, Histochemical, and Biochemical Study," Arch. Path, 89:103-110 (1970).
Lowden et al., "Wolman's Disease: A Microscopic and Biochemical Study Showing Accumulation of Ceroid and Esterified Cholesterol," C.M.A. Journal, 102:402-405 (1970).
Lübke et al., "Proteomics of the Lysosome," Biochim Biophys Acta, 1793(4):625-635 (2009).
Cagle et al., "Clinicopathologic Conference: Pulmonary Hypertension in an 18 Year Old Girl With Cholesteryl Ester Storage Disease (CESD)," Am. J. of Med. Genetics, 24:711-722 (1986).

Chatrath et al., "Cholesterol Ester Storage Disease (CESD) Diagnosed in an Asymptomatic Adult," Dig. Dis. Sci., 54:168-173 (2008).
Coates et al., "Genetic Variation of Human Mononuclear Leukocyte Lysosomal Acid Lipase Activity," Atherosclerosis, 62:11-20 (1986).
Desnick et al., "Advances in the Treatment of Inherited Metabolic Diseases," Chapter 5, pp. 281-369 (1981).
Du et al., "Lysosomal Acid Lipase Deficiency: Correction of Lipid Storage by Adenovirus-Mediated Gene Transfer in Mice," Hum. Gen Thur., 13:1361-1372 (2002).
Du et al., "MRI of Fat Distribution in a Mouse Model of Lysosomal Acid Lipase Deficiency," AJR 184:658-662 (2005).
Du et al., "Targeted Disruption of the Mouse Lysosomal Acid Lipase Gene: Long-Term Survival with Massive Cholesteryl Ester and Triglyceride Storage," Hum. Mol. Genet., 7:1347-1354 (1998).
Du et al., "Tissue and Cellular Specific Expression of Murine Lysosomal Acid Lipase mRNA and Protein," Journal of Lipid Research, 37:937-949 (1996).
Du et el., "Enzyme Therapy for Lysosomal Acid Lipase Deficiency in the Mouse Model," Am. J. Hum. Genetics. 67: (4 Supp 2): 427 (2000).
Grabowski et al., "Enzyme Supplementation for Treatment of Artherosclerosis Using Lysosomal Acid Lipase," Therapy for Genetic Disorders, The American Journal of Human Genetics, 67(4) (Suppl. 2)(Abstract No. 136) (2000).
Ikeda et al., "Production of Recombinant Human Lysosomal Acid Lipase in Schizosaccharomyces Pombe: Development of a Fed-Batch Fermentation and Purification Process," J. of Bioscience and Bioengineering, 98:366-373 (2004).
Krivit et al., "Woman's Disease: A Review of Treatment with Bone Marrow Transplantation and Consideration for the Future," Bone Marrow Transplantation, 10(Suppl 1):97-101 (1992).
Kuriyama et al., "Lysosomal Acid Lipase Deficiency in Rats: Lipid Analyses and Lipase Activites in Liver and Spleen," J. of Lipid Research, 31:1605-1612 (1992).
Kyriakides et al., "Lipid Accumulations and Acid Lipase Deficiency in Fibroblasts from a Family with Woman's Disease and Their Apparent Correction in Vitro," J. of Lab. Clin. Med., 80:810-816 (1972).
Lian et al., "Lysosomal Acid Lipase Deficiency Causes Respiratory Inflammation and Destruction in the Lung," Am. J. Physio. Lung Cell Mol. Physiol., 286:L801-L807 (2004).
Meyers et al., "The Use of Parenteral Hyperalimentation and Elemental Formula Feeding in the Treatment of Wolman Disease," Nutrition Research, 5:423-429 (1985).
Pagani et al. "New Lysosomal Acid Lipase Gene Mutants Explain the Phynotype of Wolman Disease and Cholestery Ester Storage Disease," J. of Lipid Research, 39:1382-1388 (1998).
Pariyarath et al., "L273S Missense Substitution I Human Lysosomal Acid Lipase Creates a New N-Glycosylation Site," FEBS Letter, 379:79-82 (1996).
Pastores et al., "Enzyme Therapy for the Lysosomal Storage Disorders: Principles, Patents, Practice and Prospects," Expert Opin. Therapeutic Patients. 13(8):1157-1172 (2003).
Pozanansky et al., "Enzyme Replacement Therapy in Fibroblast from a Patient with Cholesteryl Ester Storage Disease," FASEB J., 3:152-156 (1989).
Radar et al., "Expression of Adenoviral Vector Containing the cDNA for Human Lysosomal Acid Lipase in HELA and Wolman Cells," FASEB J. 10(3):Abstract No. 1341 (Annual Meeting of Professional Research Scientists) (1996).
Radar et al., "Gene Therapy for Dyslipidemia: Clinical Prospects," Curr. Atherosc. Rep. 1:58-69 (1999).
Rothe et al., "Altered Manonuclear Phagocyte Differentiation Associated with Genetic Defects of the Lysosomal Acid Lipase," Atherosclerosis, 130:215-221 (1997).
Sande et al., "Human Lysosomal Acid Lipase/Cholesteryl Ester Hydrolase, Purification and Properties of the Form Secreted by Fibroblasts in Microcarrier Culture," J. of Biological Chem., 260:15186-15193 (1985).
Sando et al., "Recognition and Receptor-Mediated Endocytosis of the Lysosomal Acid Lipase Secreted by Cultured Human Fibroblasts," J. of Lipid Research 23:114-123 (1982).

(56) References Cited

OTHER PUBLICATIONS

Stein et al., "Successful Treatment of Wolman Disease by Unrelated Umbilical Ccrd Blood Transplantation," Europ. J. Pediatrics, 166(7):663-666 (2007).
Wolman et al., "Wolman Disease and It's Treatment," Clin. Pediatr., 34(4):207-212 (1995).
Yoshida et al., "Genetic Lipid Storage Disease with Lysososmal Acid Lipase Deficiency in Rats," Lab. Animal Sci., 40:486-489 (1990).
Zschenker et al., "Characterization of Lysosomal Acid Lipase Mutations in the Signal Peptide and Mature Polypeptide Regions Causing Wolman Disease," Journal of Lipid Research, 42:1033-1040 (2001).
Zschenker et al., "Lysosomal Acid Lipase as a Preproprotein," J. Biochem., 136:65-72 (2004).
International Search Report for PCT/US2011/051096, dated Feb. 2, 2012.
Office Action dated Jan. 18, 2013 from Corresponding U.S. Appl. No. 13/229,558.
Pariyarathuparambil, R.: 'Human Lysosomal Acid Lipase: Functional Characterization by Molecular Genetic Analysis and Site-Directed Mutagenesis Studies.' SISSA Digital Library PhD Thesis, [Online] 1995, Retrieved from the Internet: [retrieved on Aug. 5, 2012].
Tietge et al., "Phenotypic Correction of Lipid Storage and Growth Arrest in Wolman disease Fibroblasts by Gene Transfer of Lysosomal Acid Lipase," Human Gene Therapy, 12(3):279-289 (2001).
Supplementary European Search Report dated Aug. 6, 2014 from Corresponding European Application No. 12746845.
International Preliminary Report of Patentability dated Apr. 30, 2013 from Corresponding International Application No. PCT/US2011/033699.
Carpenter et al., "Peripheral administration of low pH solutions causes activation and sensitisation of convergent dorsal horn neurones in the anaesthetised rat," Neurosci. Lett., 298:179-182 (2001).
Zhu et al., "Production of human monoclonal antibody in eggs of chimeric chickens," Nature Biotechnology, vol. 23, No. 9, 1159-1169 (2005).
Lysosomes; http://www.ncbi.nlm.nih.gov/books/NBK9953/, 3 pages downloaded on May 13, 2015.
Sanyal et al., "Endpoints and Clinical Trial Design for Nonalcoholic Steatohepatitis," Hepatology, 54(1):344-345 (2011).
Thavarungkul et al., "Cholesterol Ester Storage Disease: A Reported Case," J. Med. Assoc. Thai; 78(3):164-168 (1995).
Tylki-Szymańska et al, "Clinical, biochemical and histological analysis of seven patients with cholesteryl ester storage disease," Acta Paediatrica Japonica, 39:643-646 (1997).
Pagani et. al, "Cysteine residues in human lysosomal acid lipase are involved in selective cholesteryl esterase activity," Biochem J. 326:265-269 (1997).
Pagani et al., "A histidine to tyrosine replacement in lysosomal acid lipase causes cholesteryl ester storage disease," Human Molecular Genetics, 3(9): 1605-1609 (1994).
Pagani et al., "Expression of lysosomal acid lipase mutants detected in three patients with cholesteryl ester storage disease," Human Molecular Genetics, 5(10):1611-1617 (1996).
Patrick et al., "Deficiency of an Acid Lipase in Wolman's Disease," Nature, 222:1067-1068 (1969).
Pentchev et al., "Incorporation of Exogenous Enzymes into Lysosomes: A Theoretical and Practical Means for Correcting Lysosomal Blockage," American Chemical Society, 150-151 (1978).
Poorthuis et al., "The frequency of lysosomal storage disease in The Netherlands," Hum genet, 105:151-156 (1999).
Poupětová et al., "LSDS with Neurologic Involvement: The birth prevalence of lysosomal storage disorders in the Czech Republic: comparison with data in different populations," J. Inherit Metab Dis, 33:387-396 (2010).
Raivio et al., "Genetic Diseases of Metabolism," Annu. Rev. Biochem 41:543-576 (1972).

Redonnet-Vernhet et al., "Cholesteryl Ester Storage Disease: Relationship between Molecular Defects and in Situ Activity of Lysosomal Acid Lipase," Biochemical and Molecular Medicine, 62:42-49 (1997).
Ries et al., "Different Missense Mutations in Histidine-108 of Lysosomal Acid Lipase Cause Cholesteryl Ester Storage Diseases in Unrelated Compound Heterozygous and Hemizygous Individuals," Human Mutation, 12:44-51 (1998).
Ries et al., "Transcriptional regulation of lysosomal acid lipase in differentiating monocytes is mediated by transcription factors Sp1 and AP-2," Journal of Lipid Research, 39:2125-2126 (1998).
Ries et al., "A new mutation in the gene for lysosomal acid lipase leads to Wolman disease in an African kindred," Journal of Lipid Research, 37:1761-1762 (1996).
Riva et al., "Hepatocarcinoma in a child with cholesterol ester storage disease," Digestive and Liver Disease, 40:784 (2008).
Rosenbaum et al., "Thiadiazole Carbamates: Potent Inhibitors of Lysosomal Acid Lipase and Potential Neimann-Pick Type C Disease Therapeutics," J Med Chem., 53(14):5281-5289 (2010).
Rosenthal, "Nonalcoholic Fatty Liver Disease in Pediatric Patients—A Problem that is 'Enormous' and 'Growing,'" JPEN J Parenter Enteral Nutr 36:7S (2012).
Rothe, et al., "Altered mononuclear phagocyte differentiation associated with genetic defects of the lysosomal acid lipase," Atherosclerosis, 130:215-221 (1997).
Roussel et al., "Crystal Structure of Human Gastric Lipase and Model of Lysosomal Acid Lipase, Two Lipolytic Enzymes of Medical Interest," The Journal of Biological Chemistry, 274(24)16995-17002 (1999).
Röyttä et al., "Wolman disease: morphological, clinical and genetic studies on the first Scandinavian cases," Clin Genet, 42:1-7 (1992).
Russell et al., "Recombinant proteins for genetic disease," Clin Gent 55:389-394 (1999).
Salvetti et al., "Gene therapy of lysosomal storage disorders," British Medical Bulletin, 51(1):106-122 (1995).
Sande et al., "Intercellular Transport of lysosomal acid lipase mediates lipoprotein cholesteryl ester metabolism in a human vascular endothelial cell-fibroblast coculture system," Cell Regulation, 1:661-674 (1990).
Schaub et al., "Wolman's Disease: Clinical, Biochemical and Ultrastructural in an Unusual Case Without Striking Adrenal Calcification" Eur. J. Ped., 135:45-53 (1980).
Schiff et al., "Hepatic Cholesterol Ester Storage Disease, a Familial Disorder," American Journal of Medicine, 44:538-546 (1968).
Yu et al., "Boosting Brain Uptake of a Therapeutic Antibody by Reducing Its Affinity for a Transcytosis Target," Sci Transl Med, 3:84ra44 (2011).
Phillipps et al., "Secretion of insulin-like growth factor-II into bile of rats of different ages," Biol Neonate, 78(2):106-12 (2000).
Seedorf et al., "A Novel Variant of Lysosomal Acid Lipase (Lue336→Pro) Associated With Acid Lipase Deficiency and Cholesterol Ester Storage Disease," Arteriosclerosis, Thrombosis, and Vascular Biology, 15:773-778 (1995).
Shimada et al., "Suppression of diet-induced atherosclerosis in low density lipoprotein receptor knockout mice overexpressing lipoprotein lipase," Proc. Natl. Acad. Sci, USA, 93:7242-7246 (1996).
Skinner et al., "Cholesterol Curves to Identify Norms by Age and Sex in Healthy Weight Children," Clin Pediatr, 51:233 (2012).
Sloan et al., "Enzyme Deficiency in Cholesteryl Ester Storage Disease," the Journal of Clinical Investigation, 51:1923-1924 (1972).
Sly et al., "Enzyme therapy in mannose receptor-null mucopolysaccharidosis VII mice defines roles for the mannose 6-phosphate and mannose receptors," PNAS, 103(41):15172-15177 (2006).
Spiegel-Adolf et al., "Hematologic Studies in Niemann-Pick and Wolman's Disease," Confin. Neurol, 28:399-406 (1966).
Stahl et al., "Evidence for receptor-mediated binding of glycoproteins, glycoconjugates, and lysosomal gylcosidases by alveolar macrophages," Cell Biology, 75(3):1399-1403 (1978).
Sternby et al., "Carboxyl Ester Lipase (Bile Salt-Stimulated Lipase), Colipase, Lipase, and Phospholipase A2 Levels in Pancreatic Enzyme Supplements," Scand J Gastroenterol 32:261-267 (1997).
Surve et al., "Wolman Disease: Diagnosis by Leucocyte Acid Lipase Estimation," Indian Journal of Pediatrics, 72:353-354 (2005).

(56) References Cited

OTHER PUBLICATIONS

Suzuki et al., "Are animal models useful for understanding the pathophysiology of lysosomal storage disease?" Acta Paediatr Suppl, 443:54-62 (2003).
Takahashi et al., "Distribution of murine mannose receptor expression from early embryogenesis through to adulthood," Cell Tissue Res 292:311-323 (1998).
Takasaki et al., "Structure of the N-Asparagine-linked Oligosaccharide Units of Human Placental ⊕-Glucocerebrosidase," The Journal of Biological Chemistry, 259(16):10112-10117 (1984).
Tarantino et al., "Lovastatin therapy for cholesterol ester storage disease in two sisters," The Journal of Ped., 118(1):131-135 (1991).
Thompson et al., "Role of cholesterol in regulating apolipoprotein B secretion by the liver," Journal of Lipid Research, 37:439-440 (1996).
Todoroki et al., "Accumulated lipids, aberrant fatty acid composition and defective cholesterol ester hydrolase activity cholesterol ester storage disease," Ann Clin Biochem, 37:187-193 (2000).
Tolar et al., "Long-term metabolic, endocrine, and neuropsychological outcome of hematopoietic cell transplantation for Wolman disease," Bone Marrow Transplantation, 43:21-27 (2009).
Uniyal et al., "Wolman's Disease," Indian Pediatrics, 32:232-233 (1995).
Van Berkel, "The role of non-parenchymal cells in liver metabolism," TIBS 202-205, Sep. 1979.
Van Erum et al., "Cholesteryl Ester Storage Disease with Secondary Lecithin Cholesterol Acyl Transferase Deficiency," J. Inher. Metab. Dis 11 Suppl. 2:146-148 (1988).
Varki et al., "Studies of synthesis, structure and function of the phosphorylated oligosaccharides of lysosomal enzymes," J. Biosci, 5(1):101-104 (1983).
Vom Dahl et al., "Lysosomal storage disease as differential diagnosis of hepatosplenomegaly," Best Practice & Research Clinical Gastroenterology, 24:619-628 (2010).
Von Figura et al., "Lysosomal Enzymes and Their Receptors," Ann. Rev. Biochem, 55:167-193 (1986).
Pastores, G.M. "Therapeutic approaches for lysosomal storage diseases". Ther Adv Endocrinol Metab (2010), 1(4), 177-188.
Wang, C.S. et al, "Impact of increasing alanine aminotransferase levels within normal range on incident diabetes". Journal of Formosan Medical Association (2012) 111, 201-208.
Quinn, A. et al, "SBC-102, a recombinant enzyme replacement therapy, corrects key abnormalities due to lysosomal acidlipase deficiency", Abstract Submission, American Society of Human Genetics Meeting, Nov. 6, 2010.
Quinn, A. et al, "SBC-102, a recombinant enzyme replacement therapy, corrects key abnormalities due to lysosomal acidlipase deficiency", Poster Presentation, American Society of Human Genetics Meeting, Nov. 6, 2010.
Presentation by Synageva BioPharma Corp., Jefferies Healthcare Conference, "Dedicated to Rare Diseases", Jun. 4, 2012.
Furo Ventures B.V., Opposition Papers submitted in European Patent Application No. EP 11758644.6, pp. 1-162, Nov. 25, 2015.
Summary of NCT01371825 Clinical Trial, Jul. 19, 2011.
Summary of NCT01307098 Clinical Trial, Mar. 1, 2011.
"Synageva BioPharma Presents Data at the American Society of Human Genetics on SBC-102 for Lysosomal Acid Lipase Deficiency", BusinessWire News, Nov. 4, 2010.
Leavitt, M. et al., "Recombinant Lysosomal Acid Lipase Normalizes Liver Weight, Transaminases and Histopathologoial Abnormalities in an in Vivo Model of Cholesteryl Ester Storage Disease", Journal of Hepatology, 2011, vol. 54, p. S358.
Leavitt, M. et al., "Recombinant Lysosomal Acid Lipase Normalizes Liver Weight, Transaminases and Histopathologcial Abnormalities in an in Vivo Model of Cholesteryl Ester Storage Disease", Poster Presentation, the International Liver Congress, Berlin, Germany, Mar. 30, 2011.
Ameis, Detlev, et al., "Purification, characterization and molecular cloning of human hepatic lysosomal acid lipase," Eur. J. Biochem., vol. 219, 905-914, 1994.

Anderson, Richard A., et al., "Cloning and Expression of cDNA encoding Human Lysosmal Acid Lipase/Cholesteryl Ester Hydrolase," The Journal of Biological Chemistry, vol. 266 No. 33, 22479-22484, 1991.
Anderson, Richard A., et al., "In Situ Localization of the Genetic Locus Encoding the Lysosomal Acid Lipase/Cholesteryl Esterase (LIPA) Deficient in Wolman Disease to Chromosome 10q23.2-823.3," Genomics 15, 245-247, 1993.
Du Hong, et al., "Wolman disease/cholesteryl ester storage disease: efficacy of plant-produced human lysosomal acid lipase in mice," Journal of Lipid Research, vol. 49, 1646-1657, 2008.
Du, Hong, et al., "Enzyme therapy for lysosomal acid lipase deficiency in the mouse," Human Molecular Genetics, vol. 10, No. 16, 1639-1648, 2001.
Du, Hong, et al., "Molecular and Enzymatic Analyses of Lysosomal Acid Lipase in Cholesteryl Ester Storage Disease," Molecular Genetics and Metabolism, vol. 64, 126-134, 1998.
Du, Hong, et al., "The role of Mannosylated Enzyme and the Mannose Receptor in Enzyme Replacement Therapy," Am. J. Hum. Genet., vol. 77, 1061-1074, 2005.
Office Action issued in U.S. Appl. No. 13/229,568 dated Jan. 18, 2013.
Zschenker et al., "Systematic Mutagenesis of Potential Glycosylation Sites of Lysosmal Acid Lipase," J. Biochem., 137:387-394 (2005).
GenBank Accession No. AAA59519: Lysosomal Acid Lipase/Cholesteryl Esterase [*Homo sapiens*] 7. (1995).
Skropeta, "The Effect of Individual N-Glycans on Enzyme Activity," Bioorg. Med. Chem., 17:2645-2653 (2009).
Anderson et al., "Cloning and Expression of cDNA Encoding Human Lysosomal Acid Lipase/Cholesteryl Ester Hydrolase," J. Biol. Chem., 266:22479-22484 (1991).
Smith et al., "Peptide Sequences Mediating Tropism to Intact Blood-Brain Barrier: An in Vivo Biodistribution Study Using Phage Display," Peptides, 38:172-180 (2012).
Jeyakumar et al., "Storage Solutions: Treating Lysosomal Disorders of the Brain," Nature Reviews Neuroscience, 6:713-725 (2005).
Begley et al., "Lysosomal Storage Diseases and the Blood-Brain Barrier," Current Pharmaceutical Design, 14:1566-1580 (2008).
Bertrand et al., "Transport Characteristics of a Novel Peptide Platform for CNS Therapeutics," J Cell. Molecular Medicine, 14(12):2827-2839 (2010).
Ameis et al., "A 5' Splice-Region Mutation and a Dinucleotide Deletion in the Lysosomal Acid Lipase Gene in Two Patients with Cholesteryl Ester Storage Disease,"Journal of Lipid Research, 36:241-250 (1995).
Abramov et al., "Generalized Xanthomatosis with Calcified Adrenals," Journal of Diseases of Children, pp. 282-286 (1956).
K-T Von Trotha et al., "Influence of Lysosomal Acid Lipase Polymorphisms on Chromosome 10 on the Risk of Alzheimer's Disease and Cholesterol Metabolism," 402:(3):262-266 (2006).
Du et al., "Enzyme Therapy for Lysosomal Acid Lipase Deficiency in the Mouse Model," FASEB J. vol. 10(2):427, Abstract 2409 (1996).
Achord, et al., "Human α-Glucuronidase: In Vivo Clearance and in Vitro Uptake by a Glycoprotein Recognition System on Reticuloendothelial Cells," Cell, 15:269-278 (1978).
Al Essa et al., "Wolman Disease: A Review," Curr Paed Res, 3(1):1-12 (1999).
Aslanidis et al., "Genomic Organization of the Human Lysosomal Acid Lipase Gene (LIPA)," Genomics, 20:329-331 (1994).
Assmann et al., "Acid Lipase Deficiency: Wolman Disease and Cholesteryl Ester Storage Disease," Part 16: Lysosomal Disorders, pp. 1-49 (2001).
Asumendi et al., "Hepatic Sinusoidal Endothelium Heterogeneity with Respect to Mannose Receptor Activity is Interleukin-1 Dependent," 23(6):1521-1529 (1996).
Avert et al., "Cholesteryl Ester Hydrolysis in J774 Macrophages Occurs in the Cytoplasm and Lysosomes," Journal of Lipid Research, 40:405-414 (1999).
Baenziger et al., "Structural Determinants of Concanavalin a Specificity for Oligosaccharides," 254(7):2400-2407(1979).

(56) References Cited

OTHER PUBLICATIONS

Barton et al., "Therapeutic Response to Intravenous Infusions of Glucocerebrosidase in a Patient with Gaucher Disease," 87:1913-1916 (1990).
Barton et al., "Replacement Therapy for Inherited Enzyme Deficiency—Macrophage Targeted Glucocerebrosidase for Gaucher's Disease," The New England Journal of Medicine, pp. 1464-1470(1991).
Beaudet et al., "Cholesterol Ester Storage Disease: Clinical, Biochemical, and Pathological Studies," The Journal of Pediatrics, 90(6):910-914 (1977).
Cox, "Effect of Lysosomal Cholesterol Accumulation on Lysosomal and Vacuolar-Atpase Activity," Submitted to the Faculty of the Graduate School of Vanderbilt University, pp. 1-108 (2007).
Beutler et al., "Enzyme Replacement Therapy for Gaucher Disease," Blood, 78(5):1183-1189 (1991).
Biggs et al., "A Manual Colorimetric Assay of Triglycerides in Serum," Clinical Chemistry, 21(3):437-441 (1975).
Bijsterbosch et al., "Quantitative Analysis of the Targeting of Mannose-Terminal Glucocerebrosidase Predominant Uptake by Liver Endothelial Cells," Eur. J. Biochem, 237:344-349 (1996).
Bindu et al., "Cholesterol Ester Storage Disease with Unusual Neurological Manifestations in Two Siblings: A Report from South India," Journal of Child Neurology, 22(12):1401-1404 (2007).
Brady et al., "Modifying Exogenous Glucocerebrosidase for Effective Replacement Therapy in Gaucher Disease," J. Inher. Metab. Dis., 17:510-519 (1994).
Brecher et al., "Effect of Atherosclerosis on Lysosomal Cholesterol Esterase Activity in Rabbit Aorta," Journal of Lipid Research, 18:154-160 (1977).
Briggs et al., "Nuclear Protein that Binds Sterol Regulatory Element of Low Density Lipoprotein Receptor Promoter," 268(19):14490-14496 (1993).
Brown et al., "Multivalent Feedback Regulation of HMG CoA Reductase, a Control Mechanism Coordinating Isoprenoid Synthesis and Cell Growth," Journal of Lipid Research, 21:505-517 (1980).
Brown et al., "A Receptor-Mediated Pathway for Cholesterol Homeostasis," Science, 232(4746):34-47 (1986).
Brumshtein et al., "Characterization of Gene-Activated Human Acid-⊕-Glucosidase: Crystal Structure, Glycan Composition, and Internalization into Macrophages," 20(1):24-32 (2010).
Brumshtein et al., "Structural Comparison of Differently Glycosylated Forms of acid-⊕-Glucosidase, the defective Enzyme in Gaucher Disease," Acta Crystallographica Section D, 62:1458-1465 (2006).
Burke et al., Deficient Activity of Hepatic Acid Lipase in Cholesterol Ester Storage Disease, Science, 176 (4032):309-310(1972).
Burton et al., "Purification and Properties of Human Placental Acid Lipase," Biochimica et Biophysics Acta, 618:449-460(1980).
Burton et al., "Lysosomal Acid Lipase in Cultivated Fibroblasts:Characterization of Enzyme Activity in Normal and Enzymatically Deficient Cell Lines," Clinics Chimica Acta, 101:25-32 (1980).
Burton et al., "Acid Lipase Cross-Reacting Material in Wolman Disease and Cholesterol Ester Storage Disease," Am J Hum Genet, 33:203-208 (1981).
Byrd et al., "Wolman's Disease: Ultrastructural Evidence of Lipid Accumulation in Central and Peripheral Nervous Systems," Acta Neuropathol, 45:37-42 (1979).
Cagle et al., "Clinicopathologic Conference: Pulmonary Hypertension in an 18-Year-Old girl with Cholesteryl Ester Storage Disease (CESD)," American Journal of Medical Genetrics, 24:711-722(1986).
Chatterjee et al., "Evaluation of Urinary Cells in Acid Cholesteryl Ester Hydrolase Deficiency," Clinical Genetics, 29:360-368 (1986).
Chobanian et al., "Effects of Hypertension and of Antihypertensive Therapy on Atherosclerosis," Suppl. I. Hypertension, 8(4):15-21 (1986).
Chowdhury et al., "A Fourteen Years Old Boy with Cholesterol Ester Storage Disease," J Medicine, 10:146-148 (2009).

Christomanou et al., "Prenatal Monitoring for Wolman's Disease in a Pregnancy at Risk," Clinical Case Reports, 57:440-441 (1981).
Coates et al., "Prenatal Diagnosis of Wolman Disease," American Journal of Medical Genetics, 2:397-407(1978).
Colin et al., "Modification of Pancreatic Lipase Properties by Directed Molecular Evolution," Protein Engineering, Design and Selection, pp. 1-9, (2010) downloaded from peds.oxfordjournals.org.
File History dated Sep. 23, 2010 from European Patent Application No. 01908927.7.
Cortner et al., "Genetic Variation of Lysosomal Acid Lipase," Pediatric Research, 10:927-932 (1976).
Crocker et al., "Wolmans Disease: Three New Patients with a Recently Described Lipidosis," Pediatrics, 35:627-640 (1965).
Cummings et al., Increased Hepatic Secretion of Very-Low-Density Lipoprotein Apolipoprotein B-100 in Cholesteryl Ester Storage Disease, 41(1):111-114 (1995).
D'Agostino et al., "Cholesterol Ester Storage Disease: Clinical, Biochemical, and pathological Studies of Four New Cases," Journal of Pediatric Gastroenterology and Nutrition, 7:446-450 (1988).
Dahl et al., "Hepatosplenomegalic Lipidosis: What Unless Gaucher? Adult Cholesteryl Ester Storage Disease (CESD) with Anemia, Mesenteric Lipodystrophy, Increased Plasma Chitotriosidase Activity and a Homozygous Lysosomal Acid Lipase—1 Exon 8 /Splice Junction Mutation," Journal of Hepatology 31:741-746 (1999).
Daly et al., "Neonatal Gene Transfer Leads to Widespread Correction of Pathology in a Murine Model of Lysosomal Storage Disease," Proc. Natl. Acad, 96:2296-2300 (1999).
Davis, et al., Role of Acid Lipase in Cholesteryl Ester Accumulation During Atherogenesis; Correlation of Enzyme Activity with Acid Lipase-Containing Macrophages in Rabbit and Human Lesions, Atherosclerosis, 55:205-215 (1985).
De Duve "The Participation of Lysosomes in the Transformation of Smooth Muscle Cells to Foamy Cells in the Aorta of Cholesterol-Fed Rabbits," Acta Cardiologica Suppl., pp. 9-25 (1975).
De Grey et al., "Medical Bioremediation: Prospects for the Application of Microbial Catabolic Diversity to aging and Several Major Age-Related Diseases," Ageing Research Reviews, 4:315-338 (2005).
Decarlis et al., "Combined Hyperlipidaemia as a Presenting Sign of Cholesteryl Ester Storage Disease," JIMD Short Report, Online, 3 pages (2009).
Desai et al., "Cholesteryl Ester Storage Disease: Pathologic Changes in an Affected Fetus," American Journal of Medical Genetics, 26:689-698 (1987).
Desnick et al., "Toward Enzyme Therapy for Lysosomal Storage Diseases," Physiological Reviews, 56(1):56-98 (1976).
Di Bisceglie, Cholesteryl Ester Storage Disease: Hepatopathology and Effects of Therapy with Lovastatin, Hepatology, 11(5):764-772 (1990).
Doebber et al., "Enhanced Macrophage Uptake of Synthetically Glycosylated Human Placental ⊕-Glucocerebrosidase," The Journal of Biological Chemistry, 257(5):2193-2199 (1982).
Drebber et al., "Severe Chronic Diarrhea and Weight Loss in Cholesteryl Ester Storage Disease: A Case Report," World Journal Gastroenterol, 11(15):2364-2366 (2005).
Du et al., "Human Transcription Factor USF Stimulates Transcription through the Initiator Elements of the HIV-1 and the Ad-ML Promoters," The EMBO Journal, 12(2):501-511 (1993).
Du et al., "Lysosomal Acid Lipase-Deficient Mice: Depletion of White and Brown Fat, Severe Hepatosplenomegaly, and Shortened Life Span," Journal of Lipid Research, 42(4):489-500 (2001).
Du et al., "Reduction of Atherosclerotic Plaques by Lysosomal Acid Lipase Supplementation," Arterioscler Thromb. Vasc. Biol., 24:147-154 (2004).
Du et al., "Lysosomal Acid Lipase and Atherosclerosis," Curr. Opin. Lipidol., 15:539-544 (2004).
Du et al., "Mouse Lysosomal Acid Lipase: Characterization of the Gene and Analysis of Promoter Activity," Gene, 208:285-295(1998).
Dustin et al., "A Mannose 6-Phosphate-Containing N-Linked Glycopeptide Derived from Lysosomal Acid Lipase is Bound to MHC Classll in B Lymphoblastoid Cell Lines," J. Imrnunol., 156:1841-1847 (1996).

(56) References Cited

OTHER PUBLICATIONS

Elleder et al., "Testis—A Novel Storage Site in Human Cholesteryl Ester Storage Disease Autopsy Report of an Adult Case with a Long-Standing Subclinical Course Complicated by Accelerated Atherosclerosis and Liver Carcinoma," Virchows Arch, 436:82-87 (2000).

Written Opinion dated Nov. 5, 2001 from PCT Application No. PCT/US01/03481.

Essa et al., "Wolman Disease: A Review," Curr. Paed. Res., 3:(1):1-12 (1999).

Ezekowitz et al., "Molecular Characterization of the Human Macrophage Mannose Receptor: Demonstration of Multiple Carbohydrate Recognition-Like Domains and Phagocytosis of Yeasts in Cos-1 Cells," J. Exp. Med., 172:1785-1794 (1990).

Ezekowitz et al., "The Structure and Function of Vertebrate Mannose Lectin-Like Proteins," J. Cell. Sci. Suppl., 9:121-133 (1988).

Fadden et al., "Molecular Characterization of the Rat Kupffer Cell Glycoprotein Receptor," Glycobiology, 13(7):529-537 (2003).

Fiete et al., "The macrophage/endothelial cell mannose receptor cDNA encodes a protein that binds oligosaccharides terminating with S04-4-GalNAc,31,4GlcNAcf3 or Man at independent sites," Proc. Natl. Acad. Sci., 94:11256-11261 (1997).

Fitoussi et al., "New Pathogenetic Hypothesis for Wolman Disease: Possible Role of Oxidized Low-Density Lipoproteins in Adrenal Necrosis and Calcification," Biochem, J., 301:267-273 (1994).

Fitzky et al., "7-Dehydrocholesterol-Dependent Proteolysis of HMG-CoA Reductase Suppresses Sterol Biosynthesis in a Mouse Model of Smith-Lemli-Opitz/RSH Syndrome," The Journal of Clinical Investigation, 108(6):905-915 (2001).

Foger et al., "Unusual Presentation of Cholesterol Ester Storage Disease (CESD): Report on New Family," Atherosclerosis, 109:132 Abstract 155 (1994).

Folch et al., "A Simple Method for the Isolation and Purification of Total Lipide from Animal Tissues," J. Bio. Chem, 226:497-509 (1957).

Friedman et al., "A Comparison of the Pharmacological Properties of Carbohydrate Remodeled Recombinant and Placental-Derived b-Glucocerebrosidase: Implications for Clinical Efficacy in Treatement of Gaucher Disease," Blood, 93(9):2807-2816 (1999).

Fujiyama et al., "A New Mutation (LIPA Tyr22X) of Lysosomal Acid Lipase Gene in a Japanese Patient with Wolman Disease," Human Mutation, 8:377-380 (1996).

Gasche et al., "A Novel Variant of Lysosomal Acid Lipase in Cholesteryl Ester Storage Disease Associated with Mild Phenotype and Improvement on Lovastatin," Journal of Hepatology, 27:744-750 (1997).

Gerlai et al., "Gene-Targeting Studies of Mammalian Behavior: Is it the Mutation or the Background Genotype," Trends Neurosci, 19:177-181 (1996).

Gidiri et al., Letter to the Editor, European Journal of Obstetrics and Gynecology and Reproductive Biology, 142:81-87 (2009).

Ginsberg et al., Suppression of Apolipoprotein B Production during Treatment of Cholesteryl Ester Storage Disease with Lovastatin, J. Clin. Invest., 80:1692-1697 (1987).

Glueck et al., "Safety and Efficacy of Treatment of Pediatric Cholesteryl Ester Storage Disease with Lovastatin," Pediatric Research, 32:559-565 (1992).

Goldstein et al., "Role of Lysosomal Acid Lipase in the Metabolism of Plasma Low Density Lipoprotein," The Journal of Biological Chemistry, 250(21):8487-8795, (1975).

Grabowski et al., "Enzyme Therapy for Lysosomal Storage Disease: Principles, Practice and Prospects," Annu. Rev. Genomics Hum. Genet., 4:403-436 (2003).

Groener et al., "Difference in Substrate Specificity Between Human and Mouse Lysosomal Acid Lipase: Low Affinity for cholesteryl Ester in Mouse Lysosomal Acid Lipase," Biochimica et Biophysica Acta, 1487:155-162 (2000).

Opposition against European Patent 1267914, dated Jan. 28, 2010.

Guazzi et at., "Wolman's Disease. Distribution and Significance of the Central Nervous System lesions," Path. Europ., 3:266-277 (1968).

Suzuki, N. et. al., "Site-specific N-glycosylation of chicken serum IgG", Glycobiology, vol. 14, No. 3, pp. 275-292, 2004.

* cited by examiner

```
         1                                                          60
rhLAL    MKMRFLGLVVCLVLWTLHSEGSGGKLTAVDPETNMNVSEIISYWGFPSEEYLVETEDGYI
Natural  MKMRFLGLVVCLVLWTLHSEGSGGKLTAVDPETNMNVSEIISYWGFPSEEYLVETEDGYI 61                                                         120
rhLAL    LCLNRIPHGRKNHSDKGPKPVVFLQHGLLADSSNWVTNLANSSLGFILADAGFDVWMGNS
Natural  LCLNRIPHGRKNHSDKGPKPVVFLQHGLLADSSNWVTNLANSSLGFILADAGFDVWMGNS 121                                                        180
rhLAL    RGNTWSRKHKTLSVSQDEFWAFSYDEMAKYDLPASINFILNKTGQEQVYYVGHSQGTTIG
Natural  RGNTWSRKHKTLSVSQDEFWAFSYDEMAKYDLPASINFILNKTGQEQVYYVGHSQGTTIG 181                                                        240
rhLAL    FIAFSQIPELAKRIKMFFALGPVASVAFCTSPMAKLGRLPDHLIKDLFGDKEFLPQSAFL
Natural  FIAFSQIPELAKRIKMFFALGPVASVAFCTSPMAKLGRLPDHLIKDLFGDKEFLPQSAFL 241                                                        300
rhLAL    KWLGTHVCTHVILKELCGNLCFLLCGFNERNLNMSRVDVYTTHSPAGTSVQNMLHWSQAV
Natural  KWLGTHVCTHVILKELCGNLCFLLCGFNERNLNMSRVDVYTTHSPAGTSVQNMLHWSQAV 301                                                        360
rhLAL    KFQKFQAFDWGSSAKNYFHYNQSYPPTYNVKDMLVPTAVWSGGHDWLADVYDVNILLTQI
Natural  KFQKFQAFDWGSSAKNYFHYNQSYPPTYNVKDMLVPTAVWSGGHDWLADVYDVNILLTQI 361                              399
rhLAL    TNLVFHESIPEWEHLDFIWGLDAPWRLYNKIINLMRKYQ  (SEQ ID NO:1)
Natural  TNLVFHESIPEWEHLDFIWGLDAPWRLYNKIINLMRKYQ  (SEQ ID NO:20)
```

FIG. 1

```
   1  ATGAAAATGC GGTTCTTGGG GTTGGTGGTC TGTTTGGTTC TCTGGACCCT
  51  GCATTCCGAG GGGTCCGGAG GGAAACTGAC AGCTGTGGAT CCTGAAACAA
 101  ACATGAATGT CAGTGAAATT ATCTCTTACT GGGGATTCCC TAGTGAGGAA
 151  TACCTAGTTG AGACAGAAGA TGGATATATT CTGTGCCTTA ACCGAATTCC
 201  TCATGGGAGG AAGAACCATT CTGACAAAGG TCCCAAACCA GTTGTCTTCC
 251  TGCAACATGG CTTGCTGGCA GATTCTAGTA ACTGGGTCAC AAACCTTGCC
 301  AACAGCAGCC TGGGCTTCAT TCTTGCTGAT GCTGGTTTTG ACGTGTGGAT
 351  GGGCAACAGC AGAGGAAATA CCTGGTCTCG GAAACATAAG ACACTCTCAG
 401  TTTCTCAGGA TGAATTCTGG GCTTTCAGTT ATGATGAGAT GGCAAAATAT
 451  GACCTACCAG CTTCCATTAA CTTCATTCTG AATAAGACTG GCCAAGAACA
 501  AGTGTATTAT GTGGGTCATT CTCAAGGCAC CACTATAGGT TTTATAGCAT
 551  TTTCACAGAT CCCTGAGCTG GCTAAAAGGA TTAAAATGTT TTTTGCCCTG
 601  GGTCCTGTGG CTTCCGTCGC CTTCTGTACT AGCCCTATGG CCAAACTGGG
 651  ACGACTGCCA GATCATCTCA TTAAGGACCT CTTTGGAGAC AAAGAATTTC
 701  TTCCCCAGAG TGCGTTTTTG AAGTGGCTGG GTACCCACGT TTGCACTCAT
 751  GTCATACTGA AGGAGCTCTG TGCAAATCTC TGTTTTCTTC TGTGTGGATT
 801  TAATGAGAGA AATTTAAATA TGTCTAGAGT GGATGTGTAT ACAACACATT
 851  CTCCTGCTGG AACTTCTGTG CAAAACATGT TACACTGGAG CCAGGCTGTT
 901  AAATTCCAAA AGTTTCAAGC CTTTGACTGG GGAAGCAGTG CCAAGAATTA
 951  TTTTCATTAC AACCAGAGTT ATCCTCCCAC ATACAATGTG AAGGACATGC
1001  TTGTGCCGAC TGCAGTCTGG AGCGGGGGTC ACGACTGGCT TGCAGATGTC
1051  TACGACGTCA ATATCTTACT GACTCAGATC ACCAACTTGG TGTTCCATGA
1101  GAGCATTCCG AATGGGAGC ATCTTGACTT CATTTGGGGC CTGGATGCCC
      (SEQ ID NO:5)
```

FIG. 2

Sequence of pALVIN-OVR1-I-SBC102-dSA (10882 bp)

| Feature | Location (bp) |
|---|---|
| SIN LTR | 521-693 (complement strand) |
| DHSIII enhancer | 1069-2720 |
| OV promoter | 2720-3851 |
| Intron | 3899-5487 |
| hLAL CDS | 5505-6704 |
| OV 3'UTR | 6719-7392 |
| partial gag CDS | 7404-7657 (complement strand) |
| LTR | 7955-8300 (complement strand) |
| Ampicillin resistance gene | 9764-10621 (complement strand) |

```
   1 CTTTCCCCGT CAAGCTCTAA ATCGGGGCT  CCCTTTAGGG TTCCGATTTA GTGCTTTACG
  61 GCACCTCGAC CCCAAAAAAC TTGATTAGGG TGATGGTTCA CGTAGTGGGC CATCGCCCTG
 121 ATAGACGGTT TTTCGCCCTT TGACGTTGGA GTCCACGTTC TTTAATAGTG GACTCTTGTT
 181 CCAAACTGGA ACAACACTCA ACCCTATCTC GGTCTATTCT TTTGATTTAT AAGGGATTTT
 241 GCCGATTTCG GCCTATTGGT TAAAAAATGA GCTGATTTAA CAAAAATTTA ACGCGAATTT
 301 TAACAAAATA TTAACGCTTA CAATTTCCAT TCGCCATTCA GGCTGCGCAA CTGTTGGGAA
 361 GGGCGATCGG TGCGGGCCTC TTCGCTATTA CGCCAGCTGG CGAAAGGGGG ATGTGCTGCA
 421 AGGCGATTAA GTTGGGTAAC GCCAGGGTTT TCCCAGTCAC GACGTTGTAA AACGACGGCC
 481 AGTGAGCGCG TATTCCCTAA CGATCACGTC GGGGTCACCA AATGAAGCCT TCTGCTTCAT
 541 GCATGTGCTC GTAGTCGTCA GGGAATCAAC GGTCCGGCCA TCAACCCAGG TGCACACCAA
 601 TGTGGTGAAT GGTCAAATGG CGTTTATTGT ATCGAGCTAG GCACTTAAAT ACAATATCTC
 661 TGCAATGCGG AATTCAGTGG TTCGTCCAAT CCGTCCCCCT CCCTATGCAA AAGCGAAACT
 721 ACTATATCCT GAGGGGACTC CTAACCGCGT ACAACCGAAG CCCCGCTTTT CGCCTAAACA
 781 TGCTATTGTC CCCTCAGTCA AGCCTTGCCC GTTACAACCC GATTCGCAAG CCTTGCCCTC
 841 CCCACATTAT CCGTAGCATT ATTTCCTAGC AGTCATCAGA GCTACAGAAG ATACTCTATG
 901 CTGTAGCCAA GTCTACAAGT TTACTATTCA GCGACCTCCT ATATTCCGCG TGCCAGCCGA
 961 TCAATTACCA ATCCAACCAG CTATCACACG GAATACAAGA ACTCGCCTAC GCTCTTCTTT
1021 CGGGCTGCTT ATAAGCCTCC TGTAATTTTT TTATATTCCT CGCTCGAGTC TCTTCAGAAT
1081 GGCACAGCAC CGCTGCAGAA AAATGCCAGG TGGACTATGA ACTCACATCC AAAGGAGCTT
1141 GACCTGATAC CTGATTTTCT TCAAACAGGG GAAACAACAC AATCCCACAA AACAGCTCAG
1201 AGAGAAACCA TCACTGATGG CTACAGCACC AAGGTATGCA ATGGCAATCC ATTCGACATT
1261 CATCTGTGAC CTGAGCAAAA TGATTTATCT CTCCATGAAT GGTTGCTTCT TTCCCTCATG
1321 AAAAGGCAAT TTCCACACTC ACAATATGCA ACAAAGACAA ACAGAGAACA ATTAATGTGC
1381 TCCTTCCTAA TGTTAAAATT GTAGTGGCAA AGAGGAGAAC AAAATCTCAA GTTCTGAGTA
1441 GGTTTTAGTG ATTGGATAAG AGGCTTTGAC CTGTGAGCTC ACCTGGACTT CATATCCTTT
1501 TGGATAAAAA GTGCTTTTAT AACTTTCAGG TCTCCGAGTC TTTATTCATG AGACTGTTGG
1561 TTTAGGGACA GACCCACAAT GAAATGCCTG GCATAGGAAA GGGCAGCAGA GCCTTAGCTG
1621 ACCTTTTCTT GGGACAAGCA TTGTCAAACA ATGTGTGACA AAACTATTTG TACTGCTTTG
1681 CACAGCTGTG CTGGGCAGGG CAATCCATTG CCACCTATCC CAGGTAACCT TCCAACTGCA
1741 AGAAGATTGT TGCTTACTCT CTCTAGACCC CCAAGTCAAA CCAACTATGC AGGTATGCTG
1801 ACAACACTAT GATGACAGCC TGTTCTGATC AAGATCTCAT TTGTTCATGG ACAATTTTTG
1861 TTGCTTGCAG CTGGTCTTCC ATTGGGAAAG AGTGTAGTAT ATCCTTCTCA TCTGACAGAA
1921 AAGCAGAAAT TCTCATGCTC CACACTTAAT CTACATTGTT TTAAACCACC GGCTACTTCT
1981 TGGAGAGGAA AAATGGCTTT TATAAGACTC ACAAAACAAA GCTCTGCAAG TCAAATGCAT
2041 ACAAAACTGT TCTGTAGGTC TGGAATCAGG ACACTATGTG GAAGTCAAAT AGAGCAGCTT
2101 TAAAAAGCCT TTGGGATCAT TCTCATCTTA TATTTGCAGC ACGATACTAT GACAGTGATA
2161 ACTGACATAA CTGCATCAAT TTCCTTGATA TTTTATTTGT CTTAAAGTAC AAGACATAGA
2221 GATGGACGTA AAGATGGACA TATGACTCAG GTCTGGACAG GTCCGTGGTC CATGTATGAT
2281 AAAAGAGATG AAGGGAAGGA GAATTGAGAC TGTCTAAGAA GGGCTTCAGG GACGTTCTGA
2341 AGGCAGATTT GACTGAATCA GATGTACTGT CCAAGTCTCA TATGTAGCAA TGGAAGGCTG
2401 ATATTGGAGA AATATAAAGA AATGGCTGTG AACTCAAAGT GACCCTGAAC AGAAAAGGGA
2461 TATGGAGTTA AAATAATGTC ACAGAACTGA GGTTTATATG ATATACCATG GGCTGCAGAG
2521 GGTCAGAGTG CTCCACCATG GGCCTCTCTT GGGCTGCAGG GAACTTCTGT TCTACACCTG
2581 GAACACCTCC TGCCCTCCTC CGCACTGACC TCAGTGTCAT CAGGGCTGTT TCTCTCACAT
2641 TTTCTCACTC ACCTCTCCCA ACTACCATTG TACAGCAGTT GTTCTTACAT ATTGCTCCTC
2701 CTGAGGTACA TCTAGCATCG TTAAGTCCTC AGACTTGGCA AGGAGAATGT AGATTTCCAC
2761 AGTATATATG TTTTCACAAA AGGAAGGAGA GAAACAAAAG AAAATGGCAC TGACTAAACT
```

FIG. 4A

```
2821  TCAGCTAGTG GTATAGGAAA GTAATTCTGC TTAACAGAGA TTGCAGTGAT CTCTATGTAT
2881  GTCCTGAAGA ATTATGTTGT ACTTTTTTCC CCCATTTTTA AATCAAACAG TGCTTTACAG
2941  AGGTCAGAAT GGTTTCTTTA CTGTTTGTCA ATTCTATTAT TTCAATACAG AACAATAGCT
3001  TCTATAACTG AAATATATTT GCTATTGTAT ATTATGATTG TCCCTCGAAC CATGAACACT
3061  CCTCCAGCTG AATTTCACAA TTCCTCTGTC ATCTGCCAGG CCATTAAGTT ATTCATGGAA
3121  GATCTTTGAG GAACACTGCA AGTTCATATC ATAAACACAT TTGAAATTGA GTATTGTTTT
3181  GCATTGTATG GAGCTATGTT TTGCTGTATC CTCAGAATAA AAGTTTGTTA TAAAGCATTC
3241  ACACCCATAA AAAGATAGAT TTAAATATTC CAACTATAGG AAAGAAAGTG TGTCTGCTCT
3301  TCACTCTAGT CTCAGTTGGC TCCTTCACAT GCACGCTTCT TTATTTCTCC TATTTTGTCA
3361  AGAAATAAT AGGTCAAGTC TTGTTCTCAT TTATGTCCTG TCTAGCGTGG CTCAGATGCA
3421  CATTGTACAT ACAAGAAGGA TCAAATGAAA CAGACTTCTG GTCTGTTACT ACAACCATAG
3481  TAATAAGCAC ACTAACTAAT AATTGCTAAT TATGTTTTCC ATCTCCAAGG TTCCCACATT
3541  TTTCTGTTTT CTTAAAGATC CCATTATCTG GTTGTAACTG AAGCTCAATG GAACATGAGC
3601  AATATTTCCC AGTCTTCTCT CCCATCCAAC AGTCCTGATG GATTAGCAGA ACAGGCAGAA
3661  AACACATTGT TACCCAGAAT TAAAAACTAA TATTTGCTCT CCATTCAATC CAAAATGGAC
3721  CTATTGAAAC TAAAATCTAA CCCAATCCCA TTAAATGATT TCTATGGTGT CAAAGGTCAA
3781  ACTTCTGAAG GGAACCTGTG GGTGGGTCAC AATTCAGACT ATATATTCCC CAGGGCTCAG
3841  CCAGTGTCTG TACATACAGC TAGAAAGCTG TATTGCCTTT AGCAGTCAAG CTCGAAAGGT
3901  AAGCAACTCT CTGGAATTAC CTTCTCTCTA TATTAGCTCT TACTTGCACC TAAACTTTAA
3961  AAAATTAACA ATTATTGTGC TATGTGTTGT ATCTTTAAGG GTGAAGTACC TGCGTGATAC
4021  CCCCTATAAA AACTTCTCAC CTGTGTATGC ATTCTGCACT ATTTTATTAT GTGTAAAAGC
4081  TTTGTGTTTG TTTTCAGGAG GCTTATTCTT TGTGCTTAAA ATATGTTTTT AATTTCAGAA
4141  CATCTTATCC TGTCGTTCAC TATCTGATAT GCTTTGCAGT TTGCTTGATT AACTTCTAGC
4201  CCTACAGAGT GCACAGAGAG CAAAATCATG GTGTTCAGTG AATTCTGGGG AGTTATTTTA
4261  ATGTGAAAAT TCTCTAGAAG TTTAATTCCT GCAAAGTGCA GCTGCTGATC ACTACACAAG
4321  ATAAAAATGT GGGGGGTGCA TAAACGTATA TTCTTACAAT AATAGATACA TGTGAACTTA
4381  TATACAGAAA AGAAAATGAG AAAAATGTGT GTGTGTATAC TCACACACGT GGTCAGTAAA
4441  AACTTTTGAG GGGTTTAATA CAGAAAATCC AATCCTGAGG CCCCAGCACT CAGTACGCAT
4501  ATAAAGGGCT GGGCTCTGAA GGACTTCTGA CTTTCACAGA TTATATAAAT CTCAGGAAAG
4561  CAACTAGATT CATGCTGGCT CCAAAAGCTG TGCTTTATAT AAGCACACTG GCTATACAAT
4621  AGTTGTACAG TTCAGCTCTT TATAATAGAA ACAGACAGAA CAAGTATAAA TCTTCTATTG
4681  GTCTATGTCA TGAACAAGAA TTCATTCAGT GGCTCTGTTT TATAGTAAAC ATTGCTATTT
4741  TATCATGTCT GCATTTCTCT TCTGTCTGAA TGTCACCACT AAAATTTAAC TCCACAGAAA
4801  GTTTATACTA CAGTACACAT GCATATCTTT GAGCAAAGCA AACCATACCT GAAAGTGCAA
4861  TAGAGCAGAA TATGAATTAC ATGCGTGTCT TTCTCCTAGA CTACATGACC CCATATAAAT
4921  TACATTCCTT ATCTATTCTG CCATCACCAA AACAAAGGTA AAAATACTTT TGAAGATCTA
4981  CTCATAGCAA GTAGTGTGCA ACAAACAGAT ATTTCTCTAC ATTTATTTTT AGGGAATAAA
5041  AATAAGAAAT AAAATAGTCA GCAAGCCTCT GCTTTCTCAT ATATCTGTCC AAACCTAAAG
5101  TTTACTGAAA TTTGCTCTTT GAATTTCCAG TTTTGCAAGC CTATCAGATT GTGTTTTAAT
5161  CAGAGGTACT GAAAAGTATC AATGAATTCT AGCTTTCACT GAACAAAAAT ATGTAGAGGC
5221  AACTGGCTTC TGGGACAGTT TGCTACCCAA AAGACAACTG AATGCAAATA CATAAATAGA
5281  TTTATGAATA TGGTTTTGAA CATGCACATG AGAGGTGGAT ATAGCAACAG ACACATTACC
5341  ACAGAATTAC TTTAAAACTA CTTGTTAACA TTTAATTGCC TAAAAACTGC TCGTAATTTA
5401  CTGTTGTAGC CTACCATAGA GTACCCTGCA TGGTACTATG TACAGCATTC CATCCTTACA
5461  TTTTCACTGT TCTGCTGTTT GCTCTAGACA ACTCAGAGTT CACCATGAAA ATGCGGTTCT
5521  TGGGGTTGGT GGTCTGTTTG GTTCTCTGGA CCCTGCATTC CGAGGGGTCC GGAGGGAAAC
5581  TGACAGCTGT GGATCCAGAA ACAAACATGA ATGTCAGTGA AATTATCTCT TACTGGGGAT
5641  TCCCTAGTGA GGAATACCTA GTTGAGACAG AAGATGGATA TATTCTGTGC CTTAACCGAA
5701  TTCCTCATGG GAGGAAGAAC CATTCTGACA AAGGTCCCAA ACCAGTTGTC TTCCTGCAAC
5761  ATGGCTTGCT GGCAGATTCT AGTAACTGGG TCACAAACCT TGCCAACAGC AGCCTGGGCT
5821  TCATTCTTGC TGATGCTGGT TTTGACGTGT GGATGGGCAA CAGCAGAGGA ATACCTGGT
5881  CTCGGAAACA TAAGACACTC TCAGTTTCTC AGGATGAATT CTGGGCTTTC AGTTATGATG
5941  AGATGGCAAA ATATGACCTA CCAGCTTCCA TTAACTTCAT TCTGAATAAG ACTGGCCAAG
6001  AACAAGTGTA TTATGTGGGT CATTCTCAAG GCACCACTAT AGGTTTTATA GCATTTTCAC
6061  AGATCCCTGA GCTGGCTAAA AGGATTAAAA TGTTTTTTGC CCTGGGTCCT GTGGCTTCCG
6121  TCGCCTTCTG TACTAGCCCT ATGGCCAAAC TGGGACGACT GCCAGATCAT CTCATTAAGG
6181  ACCTCTTTGG AGACAAAGAA TTTCTTCCCC AGAGTGCGTT TTTGAAGTGG CTGGGTACCC
6241  ACGTTTGCAC TCATGTCATA CTGAAGGAGC TCTGTGGAAA TCTCTGTTTT CTTCTGTGTG
6301  GATTTAATGA GAGAAATTTA AATATGTCTA GAGTGGATGT GTATACAACA CATTCTCCTG
6361  CTGGAACTTC TGTGCAAAAC ATGTTACACT GGAGCCAGGC TGTTAAATTC CAAAAGTTTC
6421  AAGCCTTTGA CTGGGGAAGC AGTGCCAAGA ATTATTTTCA TTACAACCAG AGTTATCCTC
```

FIG. 4B

```
6481   CCACATACAA TGTGAAGGAC ATGCTTGTGC CGACTGCAGT CTGGAGCGGG GGTCACGACT
6541   GGCTTGCAGA TGTCTACGAC GTCAATATCT TACTGACTCA GATCACCAAC TTGGTGTTCC
6601   ATGAGAGCAT TCCGGAATGG GAGCATCTTG ACTTCATTTG GGGCCTGGAT GCCCCTTGGA
6661   GGCTTTATAA TAAGATTATT AATCTAATGA GGAAATATCA GTGATTCGAA GCGGCCGCAA
6721   GAAGAAAGCT GAAAAACTCT GTCCCTTCCA ACAAGACCCA GAGCACTGTA GTATCAGGGG
6781   TAAAATGAAA AGTATGTTAT CTGCTGCATC CAGACTTCAT AAAAGCTGGA GCTTAATCTA
6841   GAAAAAAAAT CAGAAAGAAA TTACACTGTG AGAACAGGTG CAATTCACTT TTCCTTTACA
6901   CAGAGTAATA CTGGTAACTC ATGGATGAAG GCTTAAGGGA ATGAAATTGG ACTCACAGTA
6961   CTGAGTCATC ACACTGAAAA ATGCAACCTG ATACATCAGC AGAAGGTTTA TGGGGGAAAA
7021   ATGCAGCCTT CCAATTAAGC CAGATATCTG TATGACCAAG CTGCTCCAGA ATTAGTCACT
7081   CAAAATCTCT CAGATTAAAT TATCAACTGT CACCAACCAT TCCTATGCTG ACAAGGCAAT
7141   TGCTTGTTCT CTGTGTTCCT GATACTACAA GGCTCTTCCT GACTTCCTAA AGATGCATTA
7201   TAAAAATCTT ATAATTCACA TTTCTCCCTA AACTTTGACT CAATCATGGT ATGTTGGCAA
7261   ATATGGTATA TTACTATTCA AATTGTTTTC CTTGTACCCA TATGTAATGG GTCTTGTGAA
7321   TGTGCTCTTT TGTTCCTTTA ATCATAATAA AAACATGTTT AAGCAAACAC TTTTCACTTG
7381   TAGTATTTGA AGGTACCGGA TCTCGAGCCG CCTTCAATGC CCCCAAAACC AATCCCCAGG
7441   TTTTTAACTC TCCCGATTTT CCAAGTACCA TAGCCCGCTG AGAGAGCGCC GCGGTAATGG
7501   GATCCCAGGA CCCCGGGGAA TATAAGTCTG AGGGGACGT AAGCAACCCT TCCTTTTGTA
7561   ACAGGGACAA CATAGCCCCT ATTTCCTTCT TAGAAGGAGA GGTTTTCCCG CAATAGGTCT
7621   TACACGCGGA CGAAATCACC TTTATGACGG CTTCCATGCT TGATCCACCG GGCGACCGGA
7681   ATCACGCAGA GCAACCGGAA TCACGCCTGG GGTGGACCGC TCAGTCGTCG GGCTTCCTTC
7741   CCGTCTTCCA ACGACTCTCT GAGTTCTCGG TAGGGTATGT TGGCCCCCTG CAGTAGGGCT
7801   CCCTCCGACG CCACTCAGCT TCTGCCCTCC TAAGCGCAG CCCCCTCTAC TAGGGTCATC
7861   GTCCGCTCCC CGAATAAGCG AGACGGATGA GGACAGGATC GCCACGCCGC CTGTGGCCGA
7921   CCACTATTCC CTAACGATCA CGTCGGGGTC ACCAAATGAA GCCTTCTGCT TCATGCATGT
7981   GCTCGTAGTC GTCAGGGAAT CAACGGTCCG GCCATCAACC CAGGTGCACA CCAATGTGGT
8041   GAATGGTCAA ATGGCGTTTA TTGTATCGAG CTAGGCACTT AAATACAATA TCTCTGCAAT
8101   GCGGAATTCA GTGGTTCGTC CAATCCGTGT TAGACCCGTC TGTTGCCTTC CTAACAAGGC
8161   ACGATCTAC CACGATCATA CCACCTTACT CCCACCAATC GGCATGCACG GTGCTTTTTC
8221   TCTCCTTATA AGGCATGTTG CTAACTCATC GTTACATAAG CATGTTGCAA GACTACAAGA
8281   GTATTGCATA AGACTACATT TCCCCCTCCC TATGCAAAAG CGAAACTACT ATATCCTGAG
8341   GGGACTCCTA ACCGCGTACA ACCGAAGCCC CGCTTTTCGC CTAAACATGC TATTGTCCCC
8401   TCAGTCAAGC CTTGCCCGTT ACAACCCGAT TCGCAAGCCT TGCCCTCCCC ACATTATCCG
8461   TAGCATTATT TCCTAGCAGT CATCAGAGCT ACAGAAGATA CTCTATGCTG TAGCCAAGTC
8521   TACAAGTTTA CTATTCAGCG ACCTCCTATA TTCCGCGTGC CAGCCGATCA ATTACCAATG
8581   CGCGCTTGGC GTAATCATGG TCATAGCTGT TTCCTGTGTG AAATTGTTAT CCGCTCACAA
8641   TTCCACACAA CATACGAGCC GGAAGCATAA AGTGTAAAGC CTGGGGTGCC TAATGAGTGA
8701   GCTAACTCAC ATTAATTGCG TTGCGCTCAC TGCCCGCTTT CCAGTCGGGA AACCTGTCGT
8761   GCCAGCTGCA TTAATGAATC GGCCAACGCG CGGGGAGAGG CGGTTTGCGT ATTGGGCGT
8821   CTTCCGCTTC CTCGCTCACT GACTCGCTGC GCTCGGTCGT TCGGCTGCGG CGAGCGGTAT
8881   CAGCTCACTC AAAGGCGGTA ATACGGTTAT CCACAGAATC AGGGGATAAC GCAGGAAAGA
8941   ACATGTGAGC AAAAGGCCAG CAAAAGGCCA GGAACCGTAA AAAGGCCGCG TTGCTGGCGT
9001   TTTTCCATAG GCTCCGCCCC CCTGACGAGC ATCACAAAAA TCGACGCTCA AGTCAGAGGT
9061   GGCGAAACCC GACAGGACTA TAAAGATACC AGGCGTTTCC CCCTGGAAGC TCCCTCGTGC
9121   GCTCTCCTGT TCCGACCCTG CCGCTTACCG GATACCTGTC CGCCTTTCTC CCTTCGGGAA
9181   GCGTGGCGCT TTCTCATAGC TCACGCTGTA GGTATCTCAG TTCGGTGTAG GTCGTTCGCT
9241   CCAAGCTGGG CTGTGTGCAC GAACCCCCCG TTCAGCCCGA CCGCTGCGCC TTATCCGGTA
9301   ACTATCGTCT TGAGTCCAAC CCGGTAAGAC ACGACTTATC GCCACTGGCA GCAGCCACTG
9361   GTAACAGGAT TAGCAGAGCG AGGTATGTAG GCGGTGCTAC AGAGTTCTTG AAGTGGTGGC
9421   CTAACTACGG CTACACTAGA AGGACAGTAT TTGGTATCTG CGCTCTGCTG AAGCCAGTTA
9481   CCTTCGGAAA AAGAGTTGGT AGCTCTTGAT CCGGCAAACA AACCACCGCT GGTAGCGGTG
9541   GTTTTTTTGT TTGCAAGCAG CAGATTACGC GCAGAAAAAA AGGATCTCAA GAAGATCCTT
9601   TGATCTTTTC TACGGGTCT GACGCTCAGT GGAACGAAAA CTCACGTTAA GGGATTTTGG
9661   TCATGAGATT ATCAAAAGG ATCTTCACCT AGATCCTTTT AAATTAAAAA TGAAGTTTTA
9721   AATCAATCTA AAGTATATAT GAGTAAACTT GGTCTGACAG TTACCAATGC TTAATCAGTG
9781   AGGCACCTAT CTCAGCGATC TGTCTATTTC GTTCATCCAT AGTTGCCTGA CTCCCCGTCG
9841   TGTAGATAAC TACGATACGG GAGGGCTTAC CATCTGGCCC CAGTGCTGCA ATGATACCGC
9901   GAGACCCACG CTCACCGGCT CCAGATTTAT CAGCAATAAA CCAGCCAGCC GGAAGGGCCG
9961   AGCGCAGAAG TGGTCCTGCA ACTTTATCCG CCTCCATCCA GTCTATTAAT TGTTGCCGGG
10021  AAGCTAGAGT AAGTAGTTCG CCAGTTAATA GTTTGCGCAA CGTTGTTGCC ATTGCTACAG
10081  GCATCGTGGT GTCACGCTCG TCGTTTGGTA TGGCTTCATT CAGCTCCGGT TCCCAACGAT
```

FIG. 4C

```
10141   CAAGGCGAGT TACATGATCC CCCATGTTGT GCAAAAAAGC GGTTAGCTCC TTCGGTCCTC
10201   CGATCGTTGT CAGAAGTAAG TTGGCCGCAG TGTTATCACT CATGGTTATG GCAGCACTGC
10261   ATAATTCTCT TACTGTCATG CCATCCGTAA GATGCTTTTC TGTGACTGGT GAGTACTCAA
10321   CCAAGTCATT CTGAGAATAG TGTATGCGGC GACCGAGTTG CTCTTGCCCG GCGTCAATAC
10381   GGGATAATAC CGCGCCACAT AGCAGAACTT TAAAAGTGCT CATCATTGGA AAACGTTCTT
10441   CGGGGCGAAA ACTCTCAAGG ATCTTACCGC TGTTGAGATC CAGTTCGATG TAACCCACTC
10501   GTGCACCCAA CTGATCTTCA GCATCTTTTA CTTTCACCAG CGTTTCTGGG TGAGCAAAAA
10561   CAGGAAGGCA AAATGCCGCA AAAAAGGGAA TAAGGGCGAC ACGGAAATGT TGAATACTCA
10621   TACTCTTCCT TTTTCAATAT TATTGAAGCA TTTATCAGGG TTATTGTCTC ATGAGCGGAT
10681   ACATATTTGA ATGTATTTAG AAAAATAAAC AAATAGGGGT TCCGCGCACA TTTCCCCGAA
10741   AAGTGCCACC TGACGCGCCC TGTAGCGGCG CATTAAGCGC GGCGGGTGTG GTGGTTACGC
10801   GCAGCGTGAC CGCTACACTT GCCAGCGCCC TAGCGCCCGC TCCTTTCGCT TTCTTCCCTT
10861   CCTTTCTCGC CACGTTCGCC GG
        (SEQ ID NO: 6)
```

FIG. 4D

DNA sequence of the proviral region (7780 bp)

| Feature | Location (bp) |
|---|---|
| SIN LTR | 1-173 (complement strand) |
| DHSIII enhancer | 549-2200 |
| OV promoter | 2200-3331 |
| Intron | 3379-4967 |
| hLAL CDS | 4985-6184 |
| OV 3'UTR | 6199-6872 |
| partial gag CDS | 6884-7137 (complement strand) |
| LTR | 7435-7780 (complement strand) |

```
   1  AATGAAGCCT TCTGCTTCAT GCATGTGCTC GTAGTCGTCA GGGAATCAAC GGTCCGGCCA
  61  TCAACCCAGG TGCACACCAA TGTGGTGAAT GGTCAAATGG CGTTTATTGT ATCGAGCTAG
 121  GCACTTAAAT ACAATATCTC TGCAATGCGG AATTCAGTGG TTCGTCCAAT CCGTCCCCCT
 181  CCCTATGCAA AAGCGAAACT ACTATATCCT GAGGGGACTC CTAACCGCGT ACAACCGAAG
 241  CCCCGCTTTT CGCCTAAACA TGCTATTGTC CCCTCAGTCA AGCCTTGCCC GTTACAACCC
 301  GATTCGCAAG CCTTGCCCTC CCCACATTAT CCGTAGCATT ATTTCCTAGC AGTCATCAGA
 361  GCTACAGAAG ATACTCTATG CTGTAGCCAA GTCTACAAGT TTACTATTCA GCGACCTCCT
 421  ATATTCCGCG TGCCAGCCGA TCAATTACCA ATCCAACCAG CTATCACACG GAATACAAGA
 481  ACTCGCCTAC GCTCTTCTTT CGGGCTGCTT ATAAGCCTCC TGTAATTTTT TTATATTCCT
 541  CGCTCGAGTC TCTTCAGAAT GGCACAGCAC CGCTGCAGAA AAATGCCAGG TGGACTATGA
 601  ACTCACATCC AAAGGAGCTT GACCTGATAC CTGATTTTCT TCAAACAGGG GAAACAACAC
 661  AATCCCACAA AACAGCTCAG AGAGAAACCA TCACTGATGG CTACAGCACC AAGGTATGCA
 721  ATGGCAATCC ATTCGACATT CATCTGTGAC CTGAGCAAAA TGATTTATCT CTCCATGAAT
 781  GGTTGCTTCT TTCCCTCATG AAAAGGCAAT TTCCACACTC ACAATATGCA ACAAAGACAA
 841  ACAGAGAACA ATTAATGTGC TCCTTCCTAA TGTTAAAATT GTAGTGGCAA AGAGGAGAAC
 901  AAAATCTCAA GTTCTGAGTA GGTTTTAGTG ATTGGATAAG AGGCTTTGAC CTGTGAGCTC
 961  ACCTGGACTT CATATCCTTT TGGATAAAAA GTGCTTTTAT AACTTTCAGG TCTCCGAGTC
1021  TTTATTCATG AGACTGTTGG TTTAGGGACA GACCCACAAT GAAATGCCTG GCATAGGAAA
1081  GGGCAGCAGA GCCTTAGCTG ACCTTTTCTT GGGACAAGCA TTGTCAAACA ATGTGTGACA
1141  AAACTATTTG TACTGCTTTG CACAGCTGTG CTGGGCAGGG CAATCCATTG CCACCTATCC
1201  CAGGTAACCT TCCAACTGCA AGAAGATTGT TGCTTACTCT CTCTAGACCC CCAAGTCAAA
1261  CCAACTATGC AGGTATGCTG ACAACACTAT GATGACAGCC TGTTCTGATC AAGATCTCAT
1321  TTGTTCATGG ACAATTTTTG TTGCTTGCAG CTGGTCTTCC ATTGGGAAAG AGTGTAGTAT
1381  ATCCTTCTCA TCTGACAGAA AAGCAGAAAT TCTCATGCTC CACACTTAAT CTACATTGTT
1441  TTAAACCACC GGCTACTTCT TGGAGAGGAA AAATGGCTTT TATAAGACTC ACAAAACAAA
1501  GCTCTGCAAG TCAAATGCAT ACAAAACTGT TCTGTAGGTC TGGAATCAGG ACACTATGTG
1561  GAAGTCAAAT AGAGCAGCTT TAAAAAGCCT TTGGGATCAT TCTCATCTTA TATTTGCAGC
1621  ACGATACTAT GACAGTGATA ACTGACATAA CTGCATCAAT TTCCTTGATA TTTTATTTGT
1681  CTTAAAGTAC AAGACATAGA GATGGACGTA AAGATGGACA TATGACTCAG GTCTGGACAG
1741  GTCCGTGGTC CATGTATGAT AAAAGAGATG AAGGGAAGGA GAATTGAGAC TGTCTAAGAA
1801  GGGCTTCAGG GACGTTCTGA AGGCAGATTT GACTGAATCA GATGTACTGT CCAAGTCTCA
1861  TATGTAGCAA TGGAAGGCTG ATATTGGAGA AATATAAAGA AATGGCTGTG AACTCAAAGT
1921  GACCCTGAAC AGAAAAGGGA TATGAGTTA AATAATGTC ACAGAACTGA GGTTTATATG
1981  ATATACCATG GGCTGCAGAG GGTCAGAGTG CTCCACCATG GGCCTCTCTT GGGCTGCAGG
2041  GAACTTCTGT TCTACACCTG GAACACCTCC TGCCCTCCTC CGCACTGACC TCAGTGTCAT
2101  CAGGGCTGTT TCTCTCACAT TTTCTCACTC ACCTCTCCCA ACTACCATTG TACAGCAGTT
2161  GTTCTTACAT ATTGCTCCTC CTGAGGTACA TCTAGCATCG TTAAGTCCTC AGACTTGGCA
2221  AGGAGAATGT AGATTTCCAC AGTATATATG TTTTCACAAA AGGAAGGAGA GAAACAAAAG
2281  AAAATGGCAC TGACTAAACT TCAGCTAGTG GTATAGGAAA GTAATTCTGC TTAACAGAGA
2341  TTGCAGTGAT CTCTATGTAT GTCCTGAAGA ATTATGTTGT ACTTTTTTCC CCCATTTTTA
2401  AATCAAACAG TGCTTTACAG AGGTCAGAAT GGTTTCTTTA CTGTTTGTCA ATTCTATTAT
2461  TTCAATACAG AACAATAGCT TCTATAACTG AAATATATTT GCTATTGTAT ATTATGATTG
2521  TCCCTCGAAC CATGAACACT CCTCCAGCTG AATTTCACAA TTCCTCTGTC ATCTGCCAGG
2581  CCATTAAGTT ATTCATGGAA GATCTTTGAG GAACACTGCA AGTTCATATC ATAAACACAT
2641  TTGAAATTGA GTATTGTTTT GCATTGTATG GAGCTATGTT TTGCTGTATC CTCAGAATAA
2701  AAGTTTGTTA TAAAGCATTC ACACCCATAA AAAGATAGAT TTAAATATTC CAACTATAGG
2761  AAAGAAAGTG TGTCTGCTCT TCACTCTAGT CTCAGTTGGC TCCTTCACAT GCACGCTTCT
2821  TTATTTCTCC TATTTTGTCA AGAAAATAAT AGGTCAAGTC TTGTTCTCAT TTATGTCCTG
```

FIG. 5A

```
2881  TCTAGCGTGG  CTCAGATGCA  CATTGTACAT  ACAAGAAGGA  TCAAATGAAA  CAGACTTCTG
2941  GTCTGTTACT  ACAACCATAG  TAATAAGCAC  ACTAACTAAT  AATTGCTAAT  TATGTTTTCC
3001  ATCTCCAAGG  TTCCCACATT  TTTCTGTTTT  CTTAAAGATC  CCATTATCTG  GTTGTAACTG
3061  AAGCTCAATG  GAACATGAGC  AATATTTCCC  AGTCTTCTCT  CCCATCCAAC  AGTCCTGATG
3121  GATTAGCAGA  ACAGGCAGAA  AACACATTGT  TACCCAGAAT  TAAAAACTAA  TATTTGCTCT
3181  CCATTCAATC  CAAAATGGAC  CTATTGAAAC  TAAAATCTAA  CCCAATCCCA  TTAAATGATT
3241  TCTATGGTGT  CAAAGGTCAA  ACTTCTGAAG  GGAACCTGTG  GGTGGGTCAC  AATTCAGACT
3301  ATATATTCCC  CAGGGCTCAG  CCAGTGTCTG  TACATACAGC  TAGAAAGCTG  TATTGCCTTT
3361  AGCAGTCAAG  CTCGAAAGGT  AAGCAACTCT  CTGGAATTAC  CTTCTCTCTA  TATTAGCTCT
3421  TACTTGCACC  TAAACTTTAA  AAAATTAACA  ATTATTGTGC  TATGTGTTGT  ATCTTTAAGG
3481  GTGAAGTACC  TGCGTGATAC  CCCCTATAAA  AACTTCTCAC  CTGTGTATGC  ATTCTGCACT
3541  ATTTTATTAT  GTGTAAAAGC  TTTGTGTTTG  TTTTCAGGAG  GCTTATTCTT  TGTGCTTAAA
3601  ATATGTTTTT  AATTTCAGAA  CATCTTATCC  TGTCGTTCAC  TATCTGATAT  GCTTTGCAGT
3661  TTGCTTGATT  AACTTCTAGC  CCTACAGAGT  GCACAGAGAG  CAAAATCATG  GTGTTCAGTG
3721  AATTCTGGGG  AGTTATTTTA  ATGTGAAAAT  TCTCTAGAAG  TTTAATTCCT  GCAAAGTGCA
3781  GCTGCTGATC  ACTACACAAG  ATAAAAATGT  GGGGGGTGCA  TAAACGTATA  TTCTTACAAT
3841  AATAGATACA  TGTGAACTTA  TATACAGAAA  AGAAAATGAG  AAAAATGTGT  GTGTGTATAC
3901  TCACACACGT  GGTCAGTAAA  AACTTTGAG  GGGTTAATA  CAGAAAATCC  AATCCTGAGG
3961  CCCCAGCACT  CAGTACGCAT  ATAAAGGGCT  GGGCTCTGAA  GGACTTCTGA  CTTTCACAGA
4021  TTATATAAAT  CTCAGGAAAG  CAACTAGATT  CATGCTGGCT  CCAAAAGCTG  TGCTTTATAT
4081  AAGCACACTG  GCTATACAAT  AGTTGTACAG  TTCAGCTCTT  TATAATAGAA  ACAGACAGAA
4141  CAAGTATAAA  TCTTCTATTG  GTCTATGTCA  TGAACAAGAA  TTCATTCAGT  GGCTCTGTTT
4201  TATAGTAAAC  ATTGCTATTT  TATCATGTCT  GCATTTCTCT  TCTGTCTGAA  TGTCACCACT
4261  AAAATTTAAC  TCCACAGAAA  GTTTATACTA  CAGTACACAT  GCATATCTTT  GAGCAAAGCA
4321  AACCATACCT  GAAAGTGCAA  TAGAGCAGAA  TATGAATTAC  ATGCGTGTCT  TTCTCCTAGA
4381  CTACATGACC  CCATATAAAT  TACATTCCTT  ATCTATTCTG  CCATCACCAA  AACAAAGGTA
4441  AAAATACTTT  TGAAGATCTA  CTCATAGCAA  GTAGTGTGCA  ACAAACAGAT  ATTTCTCTAC
4501  ATTTATTTTT  AGGGAATAAA  AATAAGAAAT  AAAATAGTCA  GCAAGCCTCT  GCTTTCTCAT
4561  ATATCTGTCC  AAACCTAAAG  TTTACTGAAA  TTTGCTCTTT  GAATTTCCAG  TTTTGCAAGC
4621  CTATCAGATT  GTGTTTTAAT  CAGAGGTACT  GAAAAGTATC  AATGAATTCT  AGCTTTCACT
4681  GAACAAAAAT  ATGTAGAGGC  AACTGGCTTC  TGGGACAGTT  TGCTACCCAA  AAGACAACTG
4741  AATGCAAATA  CATAAATAGA  TTTATGAATA  TGGTTTTGAA  CATGCACATG  AGAGGTGGAT
4801  ATAGCAACAG  ACACATTACC  ACAGAATTAC  TTTAAAACTA  CTTGTTAACA  TTTAATTGCC
4861  TAAAAACTGC  TCGTAATTTA  CTGTTGTAGC  CTACCATAGA  GTACCCTGCA  TGGTACTATG
4921  TACAGCATTC  CATCCTTACA  TTTTCACTGT  TCTGCTGTTT  GCTCTAGACA  ACTCAGAGTT
4981  CACCATGAAA  ATGCGGTTCT  TGGGGTTGGT  GGTCTGTTTG  GTTCTCTGGA  CCCTGCATTC
5041  CGAGGGGTCC  GGAGGGAAAC  TGACAGCTGT  GGATCCAGAA  ACAAACATGA  ATGTCAGTGA
5101  AATTATCTCT  TACTGGGGAT  TCCCTAGTGA  GGAATACCTA  GTTGAGACAG  AAGATGGATA
5161  TATTCTGTGC  CTTAACCGAA  TTCCTCATGG  GAGGAAGAAC  CATTCTGACA  AAGGTCCCAA
5221  ACCAGTTGTC  TTCCTGCAAC  ATGGCTTGCT  GGCAGATTCA  AGTAACTGGG  TCACAAACCT
5281  TGCCAACAGC  AGCCTGGGCT  TCATTCTTGC  TGATGCTGGT  TTTGACGTGT  GGATGGGCAA
5341  CAGCAGAGGA  ATACCTGGT  CTCGGAAACA  TAAGACACTC  TCAGTTTCTC  AGGATGAATT
5401  CTGGGCTTTC  AGTTATGATG  AGATGGCAAA  ATATGACCTA  CCAGCTTCCA  TTAACTTCAT
5461  TCTGAATAAG  ACTGGCCAAG  AACAAGTGTA  TTATGTGGGT  CATTCTCAAG  GCACCACTAT
5521  AGGTTTTATA  GCATTTTCAC  AGATCCCTGA  GCTGGCTAAA  AGGATTAAAA  TGTTTTTTGC
5581  CCTGGGTCCT  GTGGCTTCCG  TCGCCTTCTG  TACTAGCCCT  ATGGCCAAAC  TGGGACGACT
5641  GCCAGATCAT  CTCATTAAGG  ACCTCTTTGG  AGACAAAGAA  TTTCTTCCCC  AGAGTGCGTT
5701  TTTGAAGTGG  CTGGGTACCC  ACGTTTGCAC  TCATGTCATA  CTGAAGGAGC  TCTGTGGAAA
5761  TCTCTGTTTT  CTTCTGTGTG  GATTTAATGA  GAGAAATTTA  AATATGTCTA  GAGTGGATGT
5821  GTATACAACA  CATTCTCCTG  CTGGAACTTC  TGTGCAAAAC  ATGTTACACT  GGAGCCAGGC
5881  TGTTAAATTC  CAAAAGTTTC  AAGCCTTTGA  CTGGGGAAGC  AGTGCCAAGA  ATTATTTTCA
5941  TTACAACCAG  AGTTATCCTC  CCACATACAA  TGTGAAGGAC  ATGCTTGTGC  CGACTGCAGT
6001  CTGGAGCGGG  GGTCACGACT  GGCTTGCAGA  TGTCTACGAC  GTCAATATCT  TACTGACTCA
6061  GATCACCAAC  TTGGTGTTCC  ATGAGAGCAT  TCCGGAATGG  GAGCATCTTG  ACTTCATTTG
6121  GGGCCTGGAT  GCCCCTTGGA  GGCTTTATAA  TAAGATTATT  AATCTAATGA  GGAAATATCA
6181  GTGATTCGAA  GCGGCGCGCAA  GAAGAAAGCT  GAAAAACTCT  GTCCCTTCCA  ACAAGACCCA
6241  GAGCACTGTA  GTATCAGGGG  TAAAATGAAA  AGTATGTTAT  CTGCTGCATC  CAGACTTCAT
6301  AAAAGCTGGA  GCTTAATCTA  GAAAAAAAAT  CAGAAAGAAA  TTACACTGTG  AGAACAGGTG
6361  CAATTCACTT  TTCCTTTACA  CAGAGTAATA  CTGGTAACTC  ATGGATGAAG  GCTTAAGGGA
6421  ATGAAATTGG  ACTCACAGTA  CTGAGTCATC  ACACTGAAAA  ATGCAACCTG  ATACATCAGC
6481  AGAAGGTTTA  TGGGGAAAAA  ATGCAGCCTT  CCAATTAAGC  CAGATATCTG  TATGACCAAG
```

FIG. 5B

```
6541  CTGCTCCAGA  ATTAGTCACT  CAAAATCTCT  CAGATTAAAT  TATCAACTGT  CACCAACCAT
6601  TCCTATGCTG  ACAAGGCAAT  TGCTTGTTCT  CTGTGTTCCT  GATACTACAA  GGCTCTTCCT
6661  GACTTCCTAA  AGATGCATTA  TAAAAATCTT  ATAATTCACA  TTTCTCCCTA  AACTTTGACT
6721  CAATCATGGT  ATGTTGGCAA  ATATGGTATA  TTACTATTCA  AATTGTTTTC  CTTGTACCCA
6781  TATGTAATGG  GTCTTGTGAA  TGTGCTCTTT  TGTTCCTTTA  ATCATAATAA  AAACATGTTT
6841  AAGCAAACAC  TTTTCACTTG  TAGTATTTGA  AGGTACCGGA  TCTCGAGCCG  CCTTCAATGC
6901  CCCCAAAACC  AATCCCCAGG  TTTTTAACTC  TCCCGATTTT  CCAAGTACCA  TAGCCCGCTG
6961  AGAGAGCGCC  GCGGTAATGG  GATCCCAGGA  CCCCGGGGAA  TATAAGTCTG  AGGGGGACGT
7021  AAGCAACCCT  TCCTTTTGTA  ACAGGGACAA  CATAGCCCCT  ATTTCCTTCT  TAGAAGGAGA
7081  GGTTTTCCCG  CAATAGGTCT  TACACGCGGA  CGAAATCACC  TTTATGACGG  CTTCCATGCT
7141  TGATCCACCG  GGCGACCGGA  ATCACGCAGA  GCAACCGGAA  TCACGCCTGG  GGTGGACCGC
7201  TCAGTCGTCG  GGCTTCCTTC  CCGTCTTCCA  ACGACTCTCT  GAGTTCTCGG  TAGGGTATGT
7261  TGGCCCCCTG  CAGTAGGGCT  CCCTCCGACG  CCACTCAGCT  TCTGCCCTCC  TAAGCCGCAG
7321  CCCCCTCTAC  TAGGGTCATC  GTCCGCTCCC  CGAATAAGCG  AGACGGATGA  GGACAGGATC
7381  GCCACGCCGC  CTGTGGCCGA  CCACTATTCC  CTAACGATCA  CGTCGGGGTC  ACCAAATGAA
7441  GCCTTCTGCT  TCATGCATGT  GCTCGTAGTC  GTCAGGGAAT  CAACGGTCCG  GCCATCAACC
7501  CAGGTGCACA  CCAATGTGGT  GAATGGTCAA  ATGGCGTTTA  TTGTATCGAG  CTAGGCACTT
7561  AAATACAATA  TCTCTGCAAT  GCGGAATTCA  GTGGTTCGTC  AATCCGTGT   TAGACCCGTC
7621  TGTTGCCTTC  CTAACAAGGC  ACGATCATAC  CACGATCATA  CCACCTTACT  CCCACCAATC
7681  GGCATGCACG  GTGCTTTTC   TCTCCTTATA  AGGCATGTTG  CTAACTCATC  GTTACATAAG
7741  CATGTTGCAA  GACTACAAGA  GTATTGCATA  AGACTACATT
```

(SEQ ID NO:7)

FIG. 5C

DNA Sequence of pALVIN-OV-1.1-I (10762 bp)

| Feature | Location (bp) |
|---|---|
| Stuffer | 1-2734 |
| OV 3'UTR | 2750-3423 |
| partial gag CDS | 3435-3688 (complement strand) |
| LTR | 3986-4331 (complement strand) |
| Ampicillin resistance gene | 5795-6652 (complement strand) |
| SIN LTR | 7434-7606 (complement strand) |
| OV promoter | 7975-9106 |
| Intron | 9154-10742 |
| ATG of ovalbumin or POI | 10760-10762 |

```
   1 nnnnnnnnnn nnnnnnnnnn nnnnnnnnnn nnnnnnnnnn nnnnnnnnnn nnnnnnnnnn
  61 nnnnnnnnnn nnnnnnnnnn nnnnnnnnnn nnnnnnnnnn nnnnnnnnnn nnnnnnnnnn
 121 nnnnnnnnnn nnnnnnnnnn nnnnnnnnnn nnnnnnnnnn nnnnnnnnnn nnnnnnnnnn
 181 nnnnnnnnnn nnnnnnnnnn nnnnnnnnnn nnnnnnnnnn nnnnnnnnnn nnnnnnnnnn
 241 nnnnnnnnnn nnnnnnnnnn nnnnnnnnnn nnnnnnnnnn nnnnnnnnnn nnnnnnnnnn
 301 nnnnnnnnnn nnnnnnnnnn nnnnnnnnnn nnnnnnnnnn nnnnnnnnnn nnnnnnnnnn
 361 nnnnnnnnnn nnnnnnnnnn nnnnnnnnnn nnnnnnnnnn nnnnnnnnnn nnnnnnnnnn
 421 nnnnnnnnnn nnnnnnnnnn nnnnnnnnnn nnnnnnnnnn nnnnnnnnnn nnnnnnnnnn
 481 nnnnnnnnnn nnnnnnnnnn nnnnnnnnnn nnnnnnnnnn nnnnnnnnnn nnnnnnnnnn
 541 nnnnnnnnnn nnnnnnnnnn nnnnnnnnnn nnnnnnnnnn nnnnnnnnnn nnnnnnnnnn
 601 nnnnnnnnnn nnnnnnnnnn nnnnnnnnnn nnnnnnnnnn nnnnnnnnnn nnnnnnnnnn
 661 nnnnnnnnnn nnnnnnnnnn nnnnnnnnnn nnnnnnnnnn nnnnnnnnnn nnnnnnnnnn
 721 nnnnnnnnnn nnnnnnnnnn nnnnnnnnnn nnnnnnnnnn nnnnnnnnnn nnnnnnnnnn
 781 nnnnnnnnnn nnnnnnnnnn nnnnnnnnnn nnnnnnnnnn nnnnnnnnnn nnnnnnnnnn
 841 nnnnnnnnnn nnnnnnnnnn nnnnnnnnnn nnnnnnnnnn nnnnnnnnnn nnnnnnnnnn
 901 nnnnnnnnnn nnnnnnnnnn nnnnnnnnnn nnnnnnnnnn nnnnnnnnnn nnnnnnnnnn
 961 nnnnnnnnnn nnnnnnnnnn nnnnnnnnnn nnnnnnnnnn nnnnnnnnnn nnnnnnnnnn
1021 nnnnnnnnnn nnnnnnnnnn nnnnnnnnnn nnnnnnnnnn nnnnnnnnnn nnnnnnnnnn
1081 nnnnnnnnnn nnnnnnnnnn nnnnnnnnnn nnnnnnnnnn nnnnnnnnnn nnnnnnnnnn
1141 nnnnnnnnnn nnnnnnnnnn nnnnnnnnnn nnnnnnnnnn nnnnnnnnnn nnnnnnnnnn
1201 nnnnnnnnnn nnnnnnnnnn nnnnnnnnnn nnnnnnnnnn nnnnnnnnnn nnnnnnnnnn
1261 nnnnnnnnnn nnnnnnnnnn nnnnnnnnnn nnnnnnnnnn nnnnnnnnnn nnnnnnnnnn
1321 nnnnnnnnnn nnnnnnnnnn nnnnnnnnnn nnnnnnnnnn nnnnnnnnnn nnnnnnnnnn
1381 nnnnnnnnnn nnnnnnnnnn nnnnnnnnnn nnnnnnnnnn nnnnnnnnnn nnnnnnnnnn
1441 nnnnnnnnnn nnnnnnnnnn nnnnnnnnnn nnnnnnnnnn nnnnnnnnnn nnnnnnnnnn
1501 nnnnnnnnnn nnnnnnnnnn nnnnnnnnnn nnnnnnnnnn nnnnnnnnnn nnnnnnnnnn
1561 nnnnnnnnnn nnnnnnnnnn nnnnnnnnnn nnnnnnnnnn nnnnnnnnnn nnnnnnnnnn
1621 nnnnnnnnnn nnnnnnnnnn nnnnnnnnnn nnnnnnnnnn nnnnnnnnnn nnnnnnnnnn
1681 nnnnnnnnnn nnnnnnnnnn nnnnnnnnnn nnnnnnnnnn nnnnnnnnnn nnnnnnnnnn
1741 nnnnnnnnnn nnnnnnnnnn nnnnnnnnnn nnnnnnnnnn nnnnnnnnnn nnnnnnnnnn
1801 nnnnnnnnnn nnnnnnnnnn nnnnnnnnnn nnnnnnnnnn nnnnnnnnnn nnnnnnnnnn
1861 nnnnnnnnnn nnnnnnnnnn nnnnnnnnnn nnnnnnnnnn nnnnnnnnnn nnnnnnnnnn
1921 nnnnnnnnnn nnnnnnnnnn nnnnnnnnnn nnnnnnnnnn nnnnnnnnnn nnnnnnnnnn
1981 nnnnnnnnnn nnnnnnnnnn nnnnnnnnnn nnnnnnnnnn nnnnnnnnnn nnnnnnnnnn
2041 nnnnnnnnnn nnnnnnnnnn nnnnnnnnnn nnnnnnnnnn nnnnnnnnnn nnnnnnnnnn
2101 nnnnnnnnnn nnnnnnnnnn nnnnnnnnnn nnnnnnnnnn nnnnnnnnnn nnnnnnnnnn
2161 nnnnnnnnnn nnnnnnnnnn nnnnnnnnnn nnnnnnnnnn nnnnnnnnnn nnnnnnnnnn
2221 nnnnnnnnnn nnnnnnnnnn nnnnnnnnnn nnnnnnnnnn nnnnnnnnnn nnnnnnnnnn
2281 nnnnnnnnnn nnnnnnnnnn nnnnnnnnnn nnnnnnnnnn nnnnnnnnnn nnnnnnnnnn
2341 nnnnnnnnnn nnnnnnnnnn nnnnnnnnnn nnnnnnnnnn nnnnnnnnnn nnnnnnnnnn
2401 nnnnnnnnnn nnnnnnnnnn nnnnnnnnnn nnnnnnnnnn nnnnnnnnnn nnnnnnnnnn
2461 nnnnnnnnnn nnnnnnnnnn nnnnnnnnnn nnnnnnnnnn nnnnnnnnnn nnnnnnnnnn
2521 nnnnnnnnnn nnnnnnnnnn nnnnnnnnnn nnnnnnnnnn nnnnnnnnnn nnnnnnnnnn
2581 nnnnnnnnnn nnnnnnnnnn nnnnnnnnnn nnnnnnnnnn nnnnnnnnnn nnnnnnnnnn
2641 nnnnnnnnnn nnnnnnnnnn nnnnnnnnnn nnnnnnnnnn nnnnnnnnnn nnnnnnnnnn
2701 nnnnnnnnnn nnnnnnnnnn nnnnnnnnnn nnnnnTTCGA AGCGGCCGCA AGAAGAAAGC
2761 TGAAAAACTC TGTCCCTTCC AACAAGACCC AGAGCACTGT AGTATCAGGG GTAAATGAA
```

FIG. 6A

```
2821  AAGTATGTTA  TCTGCTGCAT  CCAGACTTCA  TAAAAGCTGG  AGCTTAATCT  AGAAAAAAAA
2881  TCAGAAAGAA  ATTACACTGT  GAGAACAGGT  GCAATTCACT  TTTCCTTTAC  ACAGAGTAAT
2941  ACTGGTAACT  CATGGATGAA  GGCTTAAGGG  AATGAAATTG  GACTCACAGT  ACTGAGTCAT
3001  CACACTGAAA  AATGCAACCT  GATACATCAG  CAGAAGGTTT  ATGGGGAAA   AATGCAGCCT
3061  TCCAATTAAG  CCAGATATCT  GTATGACCAA  GCTGCTCCAG  AATTAGTCAC  TCAAAATCTC
3121  TCAGATTAAA  TTATCAACTG  TCACCAACCA  TTCCTATGCT  GACAAGGCAA  TTGCTTGTTC
3181  TCTGTGTTCC  TGATACTACA  AGGCTCTTCC  TGACTTCCTA  AAGATGCATT  ATAAAAATCT
3241  TATAATTCAC  ATTTCTCCCT  AAACTTTGAC  TCAATCATGG  TATGTTGGCA  AATATGGTAT
3301  ATTACTATTC  AAATTGTTTT  CCTTGTACCC  ATATGTAATG  GGTCTTGTGA  ATGTGCTCTT
3361  TTGTTCCTTT  AATCATAATA  AAAACATGTT  TAAGCAAACA  CTTTTCACTT  GTAGTATTTG
3421  AAGGTACCGG  ATCTCGAGCC  GCCTTCAATG  CCCCCAAAAC  CAATCCCCAG  GTTTTTAACT
3481  CTCCCGATTT  TCCAAGTACC  ATAGCCCGCT  GAGAGAGCGC  CGCGGTAATG  GGATCCCAGG
3541  ACCCCGGGGA  ATATAAGTCT  GAGGGGACG   TAAGCAACCC  TTCCTTTTGT  AACAGGGACA
3601  ACATAGCCCC  TATTTCCTTC  TTAGAAGGAG  AGGTTTTCCC  GCAATAGGTC  TTACACGCGG
3661  ACGAAATCAC  CTTTATGACG  GCTTCCATGC  TTGATCCACC  GGGCGACCGG  AATCACGCAG
3721  AGCAACCGGA  ATCACGCCTG  GGGTGGACCG  CTCAGTCGTC  GGGCTTCCTT  CCCGTCTTCC
3781  AACGACTCTC  TGAGTTCTCG  GTAGGGTATG  TTGGCCCCCT  GCAGTAGGGC  TCCCTCCGAC
3841  GCCACTCAGC  TTCTGCCCTC  CTAAGCCGCA  GCCCCTCTA   CTAGGGTCAT  CGTCCGCTCC
3901  CCGAATAAGC  GAGACGGATG  AGGACAGGAT  CGCCACGCCG  CCTGTGGCCG  ACCACTATTC
3961  CCTAACGATC  ACGTCGGGGT  CACCAAATGA  AGCCTCTGC   TTCATGCATG  TGCTCGTAGT
4021  CGTCAGGGAA  TCAACGGTCC  GGCCATCAAC  CCAGGTGCAC  ACCAATGTGG  TGAATGGTCA
4081  AATGGCGTTT  ATTGTATCGA  GCTAGGCACT  TAAATACAAT  ATCTCTGCAA  TGCGGAATTC
4141  AGTGGTTCGT  CCAATCCGTG  TTAGACCCGT  CTGTTGCCTT  CCTAACAAGG  CACGATCATA
4201  CCACGATCAT  ACCACCTTAC  TCCCACCAAT  CGGCATGCAC  GGTGCTTTTT  CTCTCCTTAT
4261  AAGGCATGTT  GCTAACTCAT  CGTTACATAA  GCATGTTGCA  AGACTACAAG  AGTATTGCAT
4321  AAGACTACAT  TTCCCCCTCC  CTATGCAAAA  GCGAAACTAC  TATATCCTGA  GGGGACTCCT
4381  AACCGCGTAC  AACCGAAGCC  CCGCTTTTCG  CCTAAACATG  CTATTGTCCC  CTCAGTCAAG
4441  CCTTGCCCGT  TACAACCCGA  TTCGCAAGCC  TTGCCCTCCC  CACATTATCC  GTAGCATTAT
4501  TTCCTAGCAG  TCATCAGAGC  TACAGAAGAT  ACTCTATGCT  GTAGCCAAGT  CTACAAGTTT
4561  ACTATTCAGC  GACCTCCTAT  ATTCCGCGTG  CCAGCCGATC  AATTACCAAT  GCGCGCTTGG
4621  CGTAATCATG  GTCATAGCTG  TTTCCTGTGT  GAAATTGTTA  TCCGCTCACA  ATTCCACACA
4681  ACATACGAGC  CGGAAGCATA  AAGTGTAAAG  CCTGGGGTGC  CTAATGAGTG  AGCTAACTCA
4741  CATTAATTGC  GTTGCGCTCA  CTGCCCGCTT  TCCAGTCGGG  AAACCTGTCG  TGCCAGCTGC
4801  ATTAATGAAT  CGGCCAACGC  GCGGGGAGAG  GCGGTTTGCG  TATTGGGCGC  TCTTCCGCTT
4861  CCTCGCTCAC  TGACTCGCTG  CGCTCGGTCG  TTCGGCTGCG  GCGAGCGGTA  TCAGCTCACT
4921  CAAAGCGGT   AATACGGTTA  TCCACAGAAT  CAGGGGATAA  CGCAGGAAAG  AACATGTGAG
4981  CAAAAGGCCA  GCAAAAGGCC  AGGAACCGTA  AAAAGGCCGC  GTTGCTGGCG  TTTTTCCATA
5041  GGCTCCGCCC  CCCTGACGAG  CATCACAAAA  ATCGACGCTC  AAGTCAGAGG  TGGCGAAACC
5101  CGACAGGACT  ATAAAGATAC  CAGGCGTTTC  CCCCTGGAAG  CTCCCTCGTG  CGCTCTCCTG
5161  TTCCGACCCT  GCCGCTTACC  GGATACCTGT  CCGCCTTTCT  CCCTTCGGGA  AGCGTGGCGC
5221  TTTCTCATAG  CTCACGCTGT  AGGTATCTCA  GTTCGGTGTA  GGTCGTTCGC  TCCAAGCTGG
5281  GCTGTGTGCA  CGAACCCCCC  GTTCAGCCCG  ACCGCTGCGC  CTTATCCGGT  AACTATCGTC
5341  TTGAGTCCAA  CCCGGTAAGA  CACGACTTAT  CGCCACTGGC  AGCAGCCACT  GGTAACAGGA
5401  TTAGCAGAGC  GAGGTATGTA  GGCGGTGCTA  CAGAGTTCTT  GAAGTGGTGG  CCTAACTACG
5461  GCTACACTAG  AAGGACAGTA  TTTGGTATCT  GCGCTCTGCT  GAAGCCAGTT  ACCTTCGGAA
5521  AAAGAGTTGG  TAGCTCTTGA  TCCGGCAAAC  AAACCACCGC  TGGTAGCGGT  GGTTTTTTTG
5581  TTTGCAAGCA  GCAGATTACG  CGCAGAAAAA  AAGGATCTCA  AGAAGATCCT  TTGATCTTTT
5641  CTACGGGGTC  TGACGCTCAG  TGGAACGAAA  ACTCACGTTA  AGGGATTTTG  GTCATGAGAT
5701  TATCAAAAAG  GATCTTCACC  TAGATCCTTT  TAAATTAAAA  ATGAAGTTTT  AAATCAATCT
5761  AAAGTATATA  TGAGTAAACT  TGGTCTGACA  GTTACCAATG  CTTAATCAGT  GAGGCACCTA
5821  TCTCAGCGAT  CTGTCTATTT  CGTTCATCCA  TAGTTGCCTG  ACTCCCCGTC  GTGTAGATAA
5881  CTACGATACG  GGAGGGCTTA  CCATCTGGCC  CCAGTGCTGC  AATGATACCG  CGAGACCCAC
5941  GCTCACCGGC  TCCAGATTTA  TCAGCAATAA  ACCAGCCAGC  CGGAAGGGCC  GAGCGCAGAA
6001  GTGGTCCTGC  AACTTTATCC  GCCTCCATCC  AGTCTATTAA  TTGTTGCCGG  GAAGCTAGAG
6061  TAAGTAGTTC  GCCAGTTAAT  AGTTTGCGCA  ACGTTGTTGC  CATTGCTACA  GGCATCGTGG
6121  TGTCACGCTC  GTCGTTTGGT  ATGGCTTCAT  TCAGCTCCGG  TTCCCAACGA  TCAAGGCGAG
6181  TTACATGATC  CCCCATGTTG  TGCAAAAAAG  CGGTTAGCTC  CTTCGGTCCT  CCGATCGTTG
6241  TCAGAAGTAA  GTTGGCCGCA  GTGTTATCAC  TCATGGTTAT  GGCAGCACTG  CATAATTCTC
6301  TTACTGTCAT  GCCATCCGTA  AGATGCTTTT  CTGTGACTGG  TGAGTACTCA  ACCAAGTCAT
6361  TCTGAGAATA  GTGTATGCGG  CGACCGAGTT  GCTCTTGCCC  GGCGTCAATA  CGGGATAATA
6421  CCGCGCCACA  TAGCAGAACT  TTAAAAGTGC  TCATCATTGG  AAAACGTTCT  TCGGGGCGAA
```

FIG. 6B

```
 6481  AACTCTCAAG  GATCTTACCG  CTGTTGAGAT  CCAGTTCGAT  GTAACCCACT  CGTGCACCCA
 6541  ACTGATCTTC  AGCATCTTTT  ACTTTCACCA  GCGTTTCTGG  GTGAGCAAAA  ACAGGAAGGC
 6601  AAAATGCCGC  AAAAAAGGGA  ATAAGGGCGA  CACGGAAATG  TTGAATACTC  ATACTCTTCC
 6661  TTTTTCAATA  TTATTGAAGC  ATTTATCAGG  GTTATTGTCT  CATGAGCGGA  TACATATTTG
 6721  AATGTATTTA  GAAAAATAAA  CAAATAGGGG  TTCCGCGCAC  ATTTCCCCGA  AAAGTGCCAC
 6781  CTGACGCGCC  CTGTAGCGGC  GCATTAAGCG  CGGCGGGTGT  GGTGGTTACG  CGCAGCGTGA
 6841  CCGCTACACT  TGCCAGCGCC  CTAGCGCCCG  CTCCTTTCGC  TTTCTTCCCT  TCCTTTCTCG
 6901  CCACGTTCGC  CGGCTTTCCC  CGTCAAGCTC  TAAATCGGGG  GCTCCCTTTA  GGGTTCCGAT
 6961  TTAGTGCTTT  ACGGCACCTC  GACCCCAAAA  AACTTGATTA  GGGTGATGGT  TCACGTAGTG
 7021  GGCCATCGCC  CTGATAGACG  GTTTTTCGCC  CTTTGACGTT  GGAGTCCACG  TTCTTTAATA
 7081  GTGGACTCTT  GTTCCAAACT  GGAACAACAC  TCAACCCTAT  CTCGGTCTAT  TCTTTTGATT
 7141  TATAAGGGAT  TTTGCCGATT  TCGGCCTATT  GGTTAAAAAA  TGAGCTGATT  TAACAAAAAT
 7201  TTAACGCGAA  TTTTAACAAA  ATATTAACGC  TTACAATTTC  CATTCGCCAT  TCAGGCTGCG
 7261  CAACTGTTGG  GAAGGGCGAT  CGGTGCGGGC  CTCTTCGCTA  TTACGCCAGC  TGGCGAAAGG
 7321  GGGATGTGCT  GCAAGGCGAT  TAAGTTGGGT  AACGCCAGGG  TTTTCCCAGT  CACGACGTTG
 7381  TAAAACGACG  GCCAGTGAGC  GCGTATTCCC  TAACGATCAC  GTCGGGGTCA  CCAAATGAAG
 7441  CCTTCTGCTT  CATGCATGTG  CTCGTAGTCG  TCAGGGAATC  AACGGTCCGG  CCATCAACCC
 7501  AGGTGCACAC  CAATGTGGTG  AATGGTCAAA  TGGCGTTTAT  TGTATCGAGC  TAGGCACTTA
 7561  AATACAATAT  CTCTGCAATG  CGGAATTCAG  TGGTTCGTCC  AATCCGTCCC  CCTCCCTATG
 7621  CAAAAGCGAA  ACTACTATAT  CCTGAGGGGA  CTCCTAACCG  CGTACAACCG  AAGCCCCGCT
 7681  TTTCGCCTAA  ACATGCTATT  GTCCCCTCAG  TCAAGCCTTG  CCCGTTACAA  CCCGATTCGC
 7741  AAGCCTTGCC  CTCCCCACAT  TATCCGTAGC  ATTATTTCCT  AGCAGTCATC  AGAGCTACAG
 7801  AAGATACTCT  ATGCTGTAGC  CAAGTCTACA  AGTTTACTAT  TCAGCGACCT  CCTATATTCC
 7861  GCGTGCCAGC  CGATCAATTA  CCAATCCAAC  CAGCTATCAC  ACGGAATACA  AGAACTCGCC
 7921  TACGCTCTTC  TTTCGGGCTG  CTTATAAGCC  TCCTGTAATT  TTTTTATATT  CCTCGTTAAG
 7981  TCCTCAGACT  TGGCAAGGAG  AATGTAGATT  TCCACAGTAT  ATATGTTTTC  ACAAAAGGAA
 8041  GGAGAGAAAC  AAAAGAAAAT  GGCACTGACT  AAACTTCAGC  TAGTGGTATA  GGAAAGTAAT
 8101  TCTGCTTAAC  AGAGATTGCA  GTGATCTCTA  TGTATGTCCT  GAAGAATTAT  GTTGTACTTT
 8161  TTTCCCCCAT  TTTTAAATCA  AACAGTGCTT  TACAGAGGTC  AGAATGGTTT  CTTTACTGTT
 8221  TGTCAATTCT  ATTATTTCAA  TACAGAACAA  TAGCTTCTAT  AACTGAAATA  TATTTGCTAT
 8281  TGTATATTAT  GATTGTCCCT  CGAACCATGA  ACACTCCTCC  AGCTGAATTT  CACAATTCCT
 8341  CTGTCATCTG  CCAGGCCATT  AAGTTATTCA  TGGAAGATCT  TTGAGGAACA  CTGCAAGTTC
 8401  ATATCATAAA  CACATTTGAA  ATTGAGTATT  GTTTTGCATT  GTATGGAGCT  ATGTTTTGCT
 8461  GTATCCTCAG  AATAAAGTT   TGTTATAAAG  CATTCACACC  CATAAAAAGA  TAGATTTAAA
 8521  TATTCCAACT  ATAGGAAAGA  AAGTGTGTCT  GCTCTTCACT  CTAGTCTCAG  TTGGCTCCTT
 8581  CACATGCACG  CTTCTTTATT  TCTCCTATTT  TGTCAAGAAA  ATAATAGGTC  AAGTCTTGTT
 8641  CTCATTTATG  TCCTGTCTAG  CGTGGCTCAG  ATGCACATTG  TACATACAAG  AAGGATCAAA
 8701  TGAAACAGAC  TTCTGGTCTG  TTACTACAC   CATAGTAATA  AGCACACTAA  CTAATAATTG
 8761  CTAATTATGT  TTTCCATCTC  CAAGGTTCCC  ACATTTTTCT  GTTTTCTTAA  AGATCCCATT
 8821  ATCTGGTTGT  AACTGAAGCT  CAATGGAACA  TGAGCAATAT  TTCCCAGTCT  TCTCTCCCAT
 8881  CCAACAGTCC  TGATGGATTA  GCAGAACAGG  CAGAAAACAC  ATTGTTACCC  AGAATTAAAA
 8941  ACTAATATTT  GCTCTCCATT  CAATCCAAAA  TGGACCTATT  GAAACTAAAA  TCTAACCCAA
 9001  TCCCATTAAA  TGATTTCTAT  GGTGTCAAAG  GTCAAACTTC  TGAAGGGAAC  CTGTGGGTGG
 9061  GTCACAATTC  AGACTATATA  TTCCCCAGGG  CTCAGCCAGT  GTCTGTACAT  ACAGCTAGAA
 9121  AGCTGTATTG  CCTTTAGCAG  TCAAGCTCGA  AAGGTAAGCA  ACTCTCTGGA  ATTACCTTCT
 9181  CTCTATATTA  GCTCTTACTT  GCACCTAAAC  TTTAAAAAAT  TAACAATTAT  TGTGCTATGT
 9241  GTTGTATCTT  TAAGGGTGAA  GTACCTGCGT  GATACCCCCT  ATAAAAACTT  CTCACCTGTG
 9301  TATGCATTCT  GCACTATTTT  ATTATGTGTA  AAAGCTTTGT  GTTTGTTTTC  AGGAGGCTTA
 9361  TTCTTTGTGC  TTAAAATATG  TTTTTAATTT  CAGAACATCT  TATCCTGTCG  TTCACTATCT
 9421  GATATGCTTT  GCAGTTTGCT  TGATTAACTT  CTAGCCCTAC  AGAGTGCACA  GAGAGCAAAA
 9481  TCATGGTGTT  CAGTGAATTC  TGGGGAGTTA  TTTTAATGTG  AAAATTCTCT  AGAAGTTTAA
 9541  TTCCTGCAAA  GTGCAGCTGC  TGATCACTAC  ACAAGATAAA  AATGTGGGG   GTGCATAAAC
 9601  GTATATTCTT  ACAATAATGA  ATACATGTGA  ACTTATATAC  AGAAAAGAAA  ATGAGAAAAA
 9661  TGTGTGTGTG  TATACTCACA  CACGTGGTCA  GTAAAAACTT  TGAGGGGTT   TAATACAGAA
 9721  AATCCAATCC  TGAGGCCCCA  GCACTCAGTA  CGCATATAAA  GGGCTGGGCT  CTGAAGGACT
 9781  TCTGACTTTC  ACAGATTATA  TAAATCTCAG  GAAAGCAACT  AGATTCATGC  TGGCTCCAAA
 9841  AGCTGTGCTT  TATATAAGCA  CACTGGCTAT  ACAATAGTTG  TACAGTTCAG  CTCTTTATAA
 9901  TAGAAACAGA  CAGAACAAGT  ATAAATCTTC  TATTGGTCTA  TGTCATGAAC  AAGAATTCAT
 9961  TCAGTGGCTC  TGTTTTATAG  TAAACATTGC  TATTTTATCA  TGTCTGCATT  TCTCTTCTGT
10021  CTGAATGTCA  CCACTAAAAT  TTAACTCCAC  AGAAAGTTTA  TACTACAGTA  CACATGCATA
10081  TCTTTGAGCA  AAGCAAACCA  TACCTGAAAG  TGCAATAGAG  CAGAATATGA  ATTACATGCG
```

FIG. 6C

```
10141   TGTCTTTCTC  CTAGACTACA  TGACCCCATA  TAAATTACAT  TCCTTATCTA  TTCTGCCATC
10201   ACCAAAACAA  AGGTAAAAAT  ACTTTTGAAG  ATCTACTCAT  AGCAAGTAGT  GTGCAACAAA
10261   CAGATATTTC  TCTACATTTA  TTTTTAGGGA  ATAAAAATAA  GAAATAAAAT  AGTCAGCAAG
10321   CCTCTGCTTT  CTCATATATC  TGTCCAAACC  TAAAGTTTAC  TGAAATTTGC  TCTTTGAATT
10381   TCCAGTTTTG  CAAGCCTATC  AGATTGTGTT  TTAATCAGAG  GTACTGAAAA  GTATCAATGA
10441   ATTCTAGCTT  TCACTGAACA  AAAATATGTA  GAGGCAACTG  GCTTCTGGGA  CAGTTTGCTA
10501   CCCAAAAGAC  AACTGAATGC  AAATACATAA  ATAGATTTAT  GAATATGGTT  TTGAACATGC
10561   ACATGAGAGG  TGGATATAGC  AACAGACACA  TTACCACAGA  ATTACTTTAA  AACTACTTGT
10621   TAACATTTAA  TTGCCTAAAA  ACTGCTCGTA  ATTTACTGTT  GTAGCCTACC  ATAGAGTACC
10681   CTGCATGGTA  CTATGTACAG  CATTCCATCC  TTACATTTTC  ACTGTTCTGC  TGTTTGCTCT
10741   AGACAACTCA  GAGTTCACCA  TG
```

(SEQ ID NO:8)

FIG. 6D

DNA sequence of SBC102 adaptor (242 bp)

| Feature | Location (bp) |
|---|---|
| From OV gene | 1-149 |
| Partial hLAL CDS | 150-242 |

```
  1  CCIGGTTGT TAACATTTAA TTGCCTAAAA ACTGCTGGTA ATTTACTGTT GTAGCCTACT
 61  ATAGAGTACC CTGCATGGTA CTATGTACAG CATTCCATCC TTACATTTTC ACTGTTCTGC
121  TGTTTGCTCT AGACAACTCA GAGTTCACCA TGAAAATGCG GTTCTTGGGG TTGGTGGTCT
181  GTTTGGTTCT CTGGACCCTG CATTCCGAGG GGTCCGGAGG GAAACTGACA GCTGTGGATC
241  CT
```

(SEQ ID NO:9)

FIG. 7

DNA sequence of Syn SBC102 (1575 bp)

| Feature | Location (bp) |
|---|---|
| Partial OV promoter | 1-355 |
| hLAL CDS | 356-1575 |

```
   1  CCATTATCTG  GTTGTAACTG  AAGCTCAATG  GAACATGAGC  AATATTTCCC  AGTCTTCTCT
  61  CCCATCCAAC  AGTCCTGATG  GATTAGCAGA  ACAGGCAGAA  AACACATTGT  TACCCAGAAT
 121  TAAAAACTAA  TATTTGCTCT  CCATTCAATC  CAAAATGGAC  CTATTGAAAC  TAAAATCTAA
 181  CCCAATCCCA  TTAAATGATT  TCTATGGTGT  CAAAGGTCAA  ACTTCTGAAG  GGAACCTGTG
 241  GGTGGGTCAC  AATTCAGACT  ATATATTCCC  CAGGGCTCAG  CCAGTGTCTG  TACATACAGC
 301  TAGAAAGCTG  TATTGCCTTT  AGCAGTCAAG  CTCGAAAGAC  AACTCAGAGT  TCACCATGAA
 361  AATGCGGTTC  TTGGGGTTGG  TGGTCTGTTT  GGTTCTCTGG  ACCCTGCATT  CCGAGGGGTC
 421  CGGAGGGAAA  CTGACAGCTC  TGGATCCTGA  AACAAACATG  AATGTCAGTG  AAATTATCTC
 481  TTACTGGGGA  TTCCCTAGTG  AGGAATACCT  AGTTGAGACA  GAAGATGAT   ATATTCGTG
 541  CCTTAACCGA  ATTCTCATG   GGAGGAAGAA  CCATTCTGAC  AAAGGTCCCA  AACCAGTTGT
 601  CTTCCTGCAA  CATGGCTTGC  TGCAGATTC   TAGTAACTGG  GTCACAAACC  TTGCCAACAG
 661  CAGCCTGGGC  TTCATTCTTG  CTGATGCTGG  TTTTGACGTG  TGGATGGGCA  ACAGCAGAGG
 721  AAATACCTGG  TCTCGGAAAC  ATAGACACT   CTCAGTTTCT  CAGGATGAAT  TCTGGGCTTT
 781  CAGTTATGAT  GAGATGGCAA  AATATGACCT  ACCAGCTTCC  ATTAACTTCA  TTCTGAATAA
 841  GACTGGCCAA  GAACAAGTGT  ATTATGTGGG  TCATTCTCAA  GGCACCACTA  TAGGTTTTAT
 901  AGCATTTTCA  CAGATCCCTG  AGCTGGCTAA  AAGGATTAAA  ATGTTTTTG   CCCTGGGTCC
 961  TGTGGCTTCC  GTCGCCTTCT  GTACTAGCCC  TATGGCCAAA  CTGGGACGAC  TGCCAGATCA
1021  TCTCATTAAG  GACCTCTTTG  GAGACAAAGA  ATTCTTCCC   CAGAGTGCGT  TTTTGAAGTG
1081  GCTGGGTACC  CACGTTGCA   TTCATGTCAT  ACTGAAGGAG  CTCTGTGGAA  ATCTCTGTTT
1141  TCTTCTGTGT  GGATTTAATG  AGAGAAATTT  AAATATGTCT  AGAGTGGATG  TGTATACAAC
1201  ACATTCTCCT  GCTGGAACTT  CTGTGCAAAA  CATGTTACAC  TGGAGCCAGG  CTGTTAAATT
1261  CCAAAAGTTT  CAAGCCTTTG  ACTGGGGAAG  CAGTGCCAAG  AATTATTTTC  ATTACAACCA
1321  GAGTTATCCT  CCCACATACA  ATGTGAAGGA  CATGCTTGTG  CCGACTGCAG  TCTGGAGCGG
1381  GGGTCACGAC  TGGCTGCAG   ATGTCTACGA  CGTCAATATC  TTACTGACTC  AGATCACCAA
1441  CTTGGTGTTC  CATGAGAGCA  TTCCGGAATG  GGAGCATCTT  GACTTCATTT  GGGGCCTGGA
1501  TGCCCCTTGG  AGGCTTTATA  ATAAGATTAT  TAATCTAATG  AGGAAATATC  AGTGATTCGA
1561  AGCGGCCGCC  CCGGG
```

(SEQ ID NO:10)

FIG. 8

DNA sequence of OVR1 promoter (2789 bp)

| Feature | Location (bp) |
|---|---|
| From DHSIII region of OV gene | 7-1658 |
| OV promoter | 1658-2789 |

```
   1  CTCGAGTCTC TTCAGAATGG CACAGCACCG CTGCAGAAAA ATGCCAGGTG GACTATGAAC
  61  TCATCCAA   AGGAGCTTGA CCTGATACCT GATTTCTTC  AAACAGGGGA AACAACACAA
 121  TCCCACAAAA CAGCTCAGAG AGAAACCATC ACTGATGGCT ACAGCACCAA GGTATGCAAT
 181  GGCAATCCAT TCGACATTCA TCTGTGACCT GAGCAAAATG ATTTATCTCT CCATGAATGG
 241  TTGCTTCTTT CCCTCATGAA AAGGCAATTT CCACACTCAC AATATGCAAT AAAGACAAAC
 301  AGAGAACAAT TAATGTGCTC CTTCCTAATG TTAAAATTGT AGTGGCAAAG AGGAGAACAA
 361  AATCTCAAGT TCTGAGTAGG TTTTAGTGAT TGGATAAGAG GCTTTGACCT GTGAGCTCAC
 421  CTGGACTTCA TATCCTTTTG GATAAAAAGT GCTTTTATAA CTTTCAGGTC TCCGAGTCTT
 481  TATTCATGAG ACTGTTGGTT TAGGGACAGA CCCACAATGA AATGCCTGGC ATAGGAAAGG
 541  GCAGCAGAGC CTTAGCTGAC CTTTTCTTGG GACAAGCATT GTCAAACAAT GTGTCACAAA
 601  ACTATTTGTA CTGCTTTGCA CAGCTGTGCT GGGCAGGGCA ATCCATTGCC ACCTATCCCA
 661  GGTAACCTTC CAACTGCAAG AAGATTGTTG CTTACTCTCT CTAGACCCCC AAGTCAAACC
 721  AACTATGCAG GTATGCTGAC AACACTATGA TGACAGCCTG TTCTGATCAA GATCTCATTT
 781  GTTCATGGAC AATTTTTGTT GCTTGCAGCT GGTCTTCCAT TGGAAAGAG  TGTAGTATAT
 841  CCTTCTCATC TGACAGAAAA GCAGAAATTC TCATGCTCCA CACTTAATCT ACATTGTTTT
 901  AAACCACCGG CTACTTCTTG GAGAGGAAAA ATGGCTTTTA TAAGACTCAC AAAACAAAGC
 961  TCTGCAAGTC AAATGCATAC AAAACTGTTC TGTAGGTCTG GAATCAGGAC ACTATGTGGA
1021  AGTCAAATAG AGCAGCTTTA AAAAGCCTTT GGGATCATTC TCATCTTATA TTTGCAGCAC
1081  GATACTATGA CAGTGATAAC TGACATAACT GCATCAATTT CCTTGATATT TTATTTGTCT
1141  TAAAGTACAA GACATAGAGA TGGACGTAAA GATGGACATA TGACTCAGGT CTGGACAGGT
1201  CCGTGGTCCA TGTATGATAA AAGAGATGAA GGGAAGGAGA ATTGAGACTG TCTAAGAAGG
1261  GCTTCAGGGA CGTTCTGAAG GCAGATTTGA CTGAATCAGA TGTACTGTCC AAGTCTCATA
1321  TGTAGCAATG GAAGGCTGAT ATTGGAGAAA TATAAAGAAA TGGCTGTGAA CTCAAAGTGA
1381  CCCTGAACAG AAAAGGGATA TGGAGTTAAA ATAATGTCAC AGAACTGAGG TTTATATGAT
1441  ATACCATGGG CTGCAGAGGG TCAGAGTCCT CCACCATGGG CCTCTCTTGG GCTGCAGGGA
1501  ACTTCTGTTC TACACCTGGA ACACCTCCTG CCCTCCTCCG CACTGACCTC AGTGTCATCA
1561  GGGCTGTTTC TCTCACATTT TCTCACTCAC CTCTCCCAAC TACCATTGTA CAGCAGTTGT
1621  TCTTACATAT TGCTCCTCCT GAGGTACATC TAGCATCGTT AAGTCCTCAG ACTTGGCAAG
1681  GAGAATGTAG ATTTCCACAG TATATATGTT TTCACAAAAG GAGGAGAGA  AACAAAGAA
1741  AATGGCACTG ACTAAACTTC AGCTAGTGGT ATAGGAAAGT AATTCTGCTT AACAGAGATT
1801  GCAGTGATCT CTATGTATGT CCTGAAGAAT TATGTTGTAC TTTTTTCCCC CATTTTTAAA
1861  TCAAACAGTG CTTTACAGAG GTCAGAATGG TTTCTTTACT GTTTGTCAAT TCTATTATTT
1921  CAATACAGAA CAATAGCTTC TATAACTGAA ATATATTTGC TATTGTATAT TATGATTGTC
1981  CCTCGAACCA TGAACACTCC TCCAGCTGAA TTTCACAATT CCTCTGTCAT CTGCCAGGCC
2041  ATTAAGTTAT TCATGGAAGA TCTTTGAGGA ACACTGCAAG TTCATATCAT AAACACATTT
2101  GAAATTGAGT ATTGTTTTGC ATTGTATGGA GCTATGTTTT GCTGTATCCT CAGAATAAAA
2161  GTTTGTTATA AAGCATTCAC ACCCATAAAA AGATAGATTT AAATATTCCA ACTATAGGAA
2221  AGAAAGTGTG TCTGCTCTTC ACTCTAGTCT CAGTTGGCTC CTTCACATGC ACGCTTCTTT
2281  ATTTCTCCTA TTTTGTCAAG AAAATAATAG GTCAAGTCTT GTTCTCATTT ATGTCCTGTC
2341  TAGCGTGGCT CAGATGCACA TTGTACATAC AAGAAGGATC AAATGAAACA GACTTCTGGT
2401  CTGTTACTAC AAGCATAGTA ATAAGCACAC TAACTAATAA TTGCTAATTA TCTTTTCCAT
2461  CTCCAAGGTT CCCACATTTT TCTGTTTCT  TAAAGATCCC ATTATCTGGT TGTAACTGAA
2521  GCTCAATGGA ACATGAGCAA TATTTCCCAG TCTTCTCTCC CATCCAACAG TCCTGATGGA
2581  TTAGCAGAAC AGGCAGAAAA CACATTGTTA CCCAGAATTA AAAACTAATA TTTGCTCTCC
2641  ATTCAATCCA AAATGGACCT ATTGAAACTA AAATCTAACC CAATCCCATT AAATGATTTC
2701  TATGTGTCA  AAGGTCAAAC TTCTGAAGGG AACCTGTGGG TGGGTCACAA TTCAGACTAT
2761  ATATTCCCCA GGGCTCAGCC AGTGTCTGT
      (SEQ ID NO: 11)
```

FIG. 9

Square = N-Acetyl Glucosamine

Filled Square = Mannose-6-Phosphate

Circle = Mannose

Filled Circle = Galactose

Filled Triangle = Fucose

LYSOSOMAL STORAGE DISEASE ENZYMES

RELATED APPLICATIONS

This application is a continuation of U.S. patent application Ser. No. 15/285,025, filed on Oct. 4, 2016, abandoned, which is a continuation of U.S. patent application Ser. No. 15/177,867, filed on Jun. 9, 2016, abandoned, which is a continuation of U.S. patent application Ser. No. 13/642,790, filed on Apr. 30, 2013, abandoned, the U.S. national stage of PCT/US2011/033699, filed Apr. 23, 2011, which claims the benefit of U.S. Provisional Application No. 61/343,177, filed on Apr. 23, 2010, U.S. Provisional Application No, 61/396, 376, filed on May 26, 2010, U.S. Provisional Application No. 61/403,011, filed on Sep. 9, 2010, U.S. Provisional Application No. 61/456,014, filed on Oct. 29, 2010, U.S. Provisional Application No. 61/432,372, filed on Jan. 13, 2011. The entire teachings of the above applications are incorporated herein by reference.

REFERENCE TO SEQUENCE LISTING SUBMITTED ELECTRONICALLY

This application contains a Sequence Listing which has been submitted electronically in ASCII format and which is incorporated by reference in its entirety. Said ASCII file is named 73710763_1.txt, is 68 KB in size and was created on Feb. 1, 2017.

BACKGROUND OF THE INVENTION

Lysosomal Acid Lipase (LAL) deficiency is a very rare lysosomal storage disease (LSD) characterized by a failure to breakdown cholesteryl esters (CE) and triglycerides (TAG) in lysosomes due to a deficiency of the enzyme. LAL deficiency resembles other lysosomal storage disorders with the accumulation of substrate in a number of tissues and cell types. In LAL deficiency substrate accumulation is most marked in cells of the reticuloendothelial system including Kupffer cells in the liver, histiocytes in the spleen and in the lamina propria of the small intestine. Reticuloendothelial cells express the macrophage mannose/N-acetylglucosamine receptor (also known as macrophage mannose receptor or MMR, CD206), which mediates binding, cell uptake and lysosomal internalization of proteins with GlcNAc or mannose terminated N-glycans, and provides a pathway for the potential correction of the enzyme deficiency in these key cell types.

LAL deficiency is a multi-system disease that most commonly manifests with gastrointestinal, liver and cardiovascular complications and is associated with significant morbidity and mortality. The clinical effects of LAL deficiency are due to a massive accumulation of lipid material in the lysosomes in a number of tissues and a profound disturbance in cholesterol and lipid homeostatic mechanisms, including substantial increases in hepatic cholesterol synthesis. LAL deficiency presents of at least two phenotypes, Wolman Disease (WD) and Cholesteryl Ester Storage Disease (CESD).

Wolman Disease is the most aggressive presentation of LAL deficiency. This phenotype is characterized by gastrointestinal and hepatic manifestations including growth failure, malabsorption, steatorrhea, profound weight loss and hepatomegaly. Wolman Disease is rapidly progressive and fatal usually within the first year of life. Case report review indicates survival beyond 12 months of age is highly unusual for patients who present with growth failure due to LAL deficiency in the first year of life. In this most aggressive form, growth failure is the predominant clinical feature and is a key contributor to the early mortality. Hepatic involvement as evidenced by liver enlargement and elevation of transaminases is also common in infants. Physical findings include abdominal distention with hepatomegaly and splenomegaly, and radiographic examination often reveals calcification of the adrenal glands. Laboratory evaluations typically reveal elevated levels of serum transaminases and absent or markedly reduced LAL enzyme activity. Elevated blood levels of cholesterol and triglycerides are also seen in patients.

Current treatment options for Wolman Disease are extremely limited. Antibiotics are administered to infants with pyrexia and/or evidence of infection. Steroid replacement therapy for adrenal insufficiency and specialized nutritional support may be prescribed and while there is no evidence that these interventions prevents death, it is also unclear at present if they have an impact on short term survival. In a series of four patients with LAL deficiency treated with bone marrow transplantation, all four patients died due to complications of the procedure within months of transplantation.

Patients with LAL deficiency can also present later in life with predominant liver and cardiovascular involvement and this is often called Cholesteryl Ester Storage Disease (CESD). In CESD, the liver is severely affected with marked hepatomegaly, hepatocyte necrosis, elevation of transaminases, cirrhosis and fibrosis. Due to the increased levels of CE and TG, hyperlipidemia and accelerated atherosclerosis are also seen in LAL deficiency. Particularly, an accumulation of fatty deposits on the artery walls is described early in life. The deposits narrow the arterial lumen and can lead to vessel occlusion increasing the risk of significant cardiovascular events including myocardial infarction and strokes. The presentation of CESD is highly variable with some patients going undiagnosed until complications manifest in late adulthood, while others can have liver dysfunction presenting in early childhood. CESD is associated with shortened lifespan and significant ill health; the life expectancy of those with CESD depends on the severity of the associated complications.

Current treatment options for the CESD phenotype are focused on controlling lipid accumulation through diet that excludes foods rich in cholesterol and triglycerides and suppression of cholesterol synthesis and apolipoprotein B production through administration of cholesterol lowering drugs. Although some clinical improvement may be seen, the underlying disease manifestations persist and disease progression still occurs.

In most cases, therapy for LAL deficiencies requires life-long treatment. In addition, due to the high cost of protein therapeutics, it is desirable to administer a minimum effective amount of therapeutic to treat LAL deficiency. However, to date, there is no effective therapy for treating LAL deficiency, particularly the patients suffering from Wolman Disease and CESD. Therefore, there is a strong need for an effective therapy with a minimized frequency of administration in order to improve the quality of life for patients. There is also a need for a high expressing and robust protein production platform which can produce LAL proteins that are stable and efficiently targeted to the lysosomal compartment in the affected tissue cells in patients.

SUMMARY OF THE INVENTION

Disclosed herein are compositions of LAL which are particularly suited for use in therapy, for example, for treatment of conditions associated with LAL deficiency. The LAL molecules described herein contain particular glycan structures which afford efficient and rapid uptake into lysosomes of cells when administered into a subject, for example, a human subject.

In one aspect, the compositions disclosed herein comprise human LAL wherein a substantial percentage of the human LAL contain at least one mannose-6-phosphate glycan moiety, which can serve as a ligand for internalization by the mannose-6-phosphate receptor on the surface of cells found, for example, on hepatocytes. In one embodiment, 30% or more, for example, at least 30%, at least 40%, at least 50%, at least 60%, at least 70%, at least 80%, at least 90%, at least 95%, at least 97%, or at least 99%, of the LAL contained in the composition contains at least one mannose-6-phosphate moiety. The mannose-6-phosphate moiety can be found, for example, on an N-glycan structure located at one or more residues selected from the group consisting of $Asn^{15}$, $Asn^{51}$, $Asn^{80}$, $Asn^{140}$, $Asn^{252}$ and $Asn^{300}$ of SEQ ID NO:2.

In another aspect, the compositions disclosed herein comprise human LAL wherein a substantial percentage of the human LAL does not contain a sialic acid moiety in any of its N-glycan structures, which can sometimes interfere with internalization of the enzyme into cells. In one embodiment, 15% or less, for example, 10% or less, 5% or less, 2% or less, 1% or less, or essentially none, of the LAL contained in the composition contains a sialic acid moiety in any of its N-glycan structures.

In another aspect, the compositions disclosed herein comprise human LAL wherein a substantial percentage of the human LAL does not contain a fucose moiety in any of its N-glycan structures. In one embodiment, 50% or less, for example, 50% or less, 40% or less, 30% or less, 20% or less, 10% or less, 5% or less, 2% or less, 1% or less, or essentially none, of the LAL contained in the composition contains a fucose moiety in any of its N-glycan structures.

In yet another aspect, vectors, host cells, expression systems and associated methods suitable for producing the LAL-containing compositions are described.

Typically, the LAL of the invention discussed and disclosed herein is human LAL. In one embodiment, the composition comprising LAL includes the mature LAL having the amino acid sequence of:

(SEQ ID NO: 2)
SGGKLTAVDPETNMMNVSEIISYWGFPSEEYLVETEDGYILCLNRIPHGRK

NHSDKGPKPVVFLQHGLLADSSNWVTNLANSSLGFILADAGFDVWMGNSR

GNTWSRKHKTLSVSQDEFWAFSYDEMAKYDLPASINFILNKTGQEQVYYV

GHSQGTTIGFIAFSQIPELAKRIKMFFALGPVASVAFCTSPMAKLGRLPD

HLIKDLFGDKEFLPQSAFLKWLGTHVCTHVILKELCGNLCFLLCGFNERN

LNMSRVDVYTTHSPAGTSVQNMLHWSQAVKFQKFQAFDWGSSAKNYFHYN

QSYPPTYNVKDMLVPTAVWSGGHDWLADVYDVNILLTQITNLVFHESIPE

WEHLDFIWGLDAPWRLYNKIINLMRKYQ.

In another embodiment, the mature LAL has the amino acid sequence of:

(SEQ ID NO: 3)
GKLTAVDPETNMMNVSEIISYWGFPSEEYLVETEDGYILCLNRIPHGRKNH

SDKGPKPVVFLQHGLLADSSNWVTNLANSSLGFILADAGFDVWMGNSRGN

TWSRKHKTLSVSQDEFWAFSYDEMAKYDLPASINFILNKTGQEQVYYVGH

SQGTTIGFIAFSQIPELAKRIKMFFALGPVASVAFCTSPMAKLGRLPOHL

IKDLFGDKEFLPQSAFLKWLGTHVCTHVILKELCGNLCFLLCGFNERNLN

MSRVDVYTTHSPAGTSVQNMLHWSQAVKFQKFQAFDWGSSAKNYFHYNQS

YPPTYNVKDMLVPTAVWSGGHDWLADVYDVNILLTQITNLVFHESIPEWE

HLDFIWGLDAPWRLYNKIINLMRKYQ.

In another embodiment, the mature LAL has the amino acid sequence of:

(SEQ ID NO: 4)
TAVDPETNMMNVSEIISYWGFPSEEYLVETEDGYILCLNRIPHGRKNHSDK

GPKPVVFLQHGLLADSSNWVTNLANSSLGFILADAGFDVWMGNSRGNTWS

RKHKTLSVSQDEFWAFSYDEMAKYDLPASINFILNKTGQEQVYYVGHSQG

TTIGFIAFSQIPELAKRIKMFFALGPVASVAFCTSPMAKLGRLPDHLIKD

LFGDKEFLPQSAFLKWLGTHVCTHVILKELCGNLCFLLCGFNERNLNMSR

VDVYTTHSPAGTSVQNMLHWSQAVKFQKFQAFDWGSSAKNYFHYNQSYPP

TYNVKDMLVPTAVWSGGHDWLADVYDVNILLTQITNLVFHESIPEWEHLD

FIWGLDAPWRLYNKIINLMRKYQ.

In another embodiment, the mature LAL has the amino acid sequence of:

(SEQ ID NO: 19)
AVDPETNMMNVSEIISYWGFPSEEYLVETEDGYILCLNRIPHGRKNHSDKG

PKPVVFLQHGLLADSSNWVTNLANSSLGFILADAGFDVWMGNSRGNTWSR

KHKTLSVSQDEFWAFSYDEMAKYDLPASINFILNKTGQEQVYYVGHSQGT

TIGFIAFSQIPELAKRIKMFFALGPVASVAFCTSPMAKLGRLPOHLIKDL

FGDKEFLPQSAFLKWLGTHVCTHVILKELCGNLCFLLCGFNERNLNMSRV

DVYTTHSPAGTSVQNMLHWSQAVKFQKFQAFDWGSSAKNYFHYNQSYPPT

YNVKDMLVPTAVWSGGHDWLADVYDVNILLTQITNLVFHESIPEWEHLDF

IWGLDAPWRLYNKIINLMRKYQ.

In another embodiment, the mature LAL is a mixture of at least two polypeptides selected from the group consisting of: SEQ ID NO:2, SEQ ID NO:3, SEQ ID NO:4, and SEQ ID NO:19.

The invention also provides for compositions which contain isolated mixtures of an individual type of useful protein molecule, such as those proteins disclosed herein, where one or more of the protein molecules contained in the mixture has a specific oligosaccharide structure attached, in particular an oligosaccharide structure disclosed herein. For example, the invention provides for isolated mixtures of LAL molecules, for example, human LAL molecules which contain an LAL molecule glycosylated with one or more of the following structures A-n to O-n:

A-n
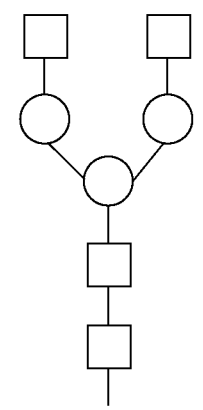
B-n
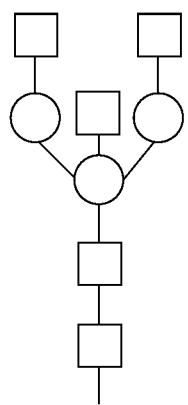
C-n
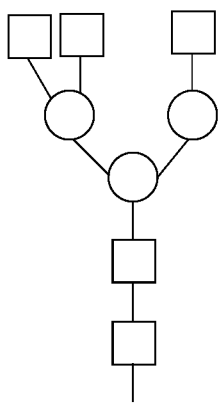
D-n
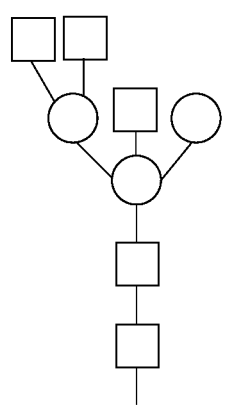
E-n
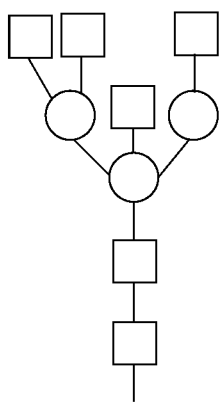
F-n
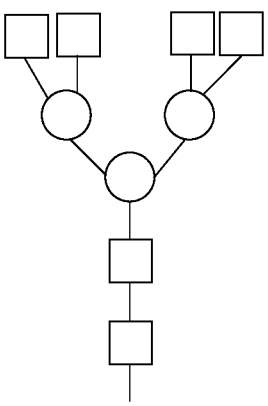
G-n
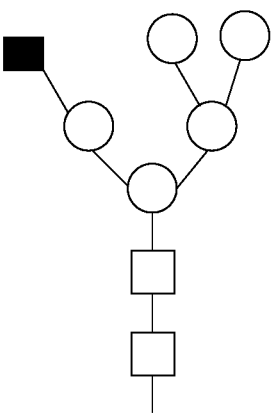

7
-continued
H-n
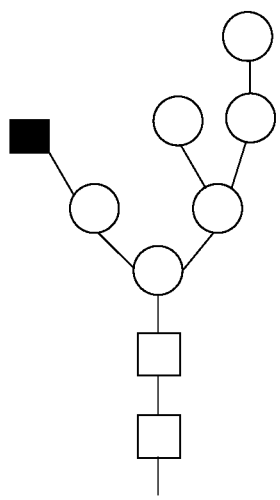
I-n
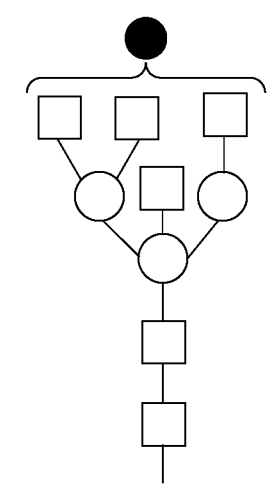
J-n
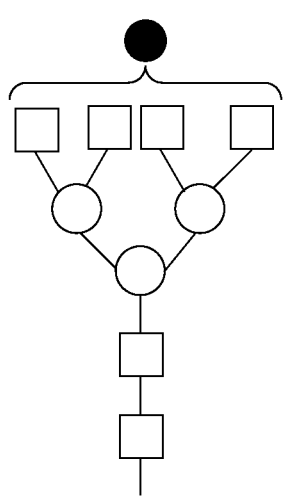
8
-continued
K-n
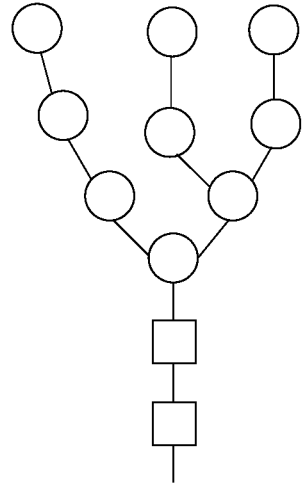
L-n
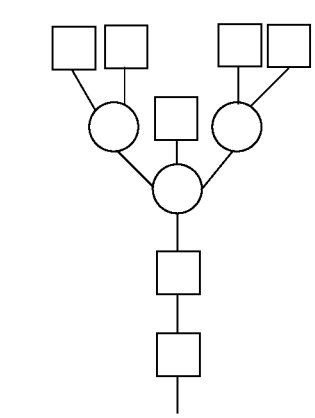
M-n
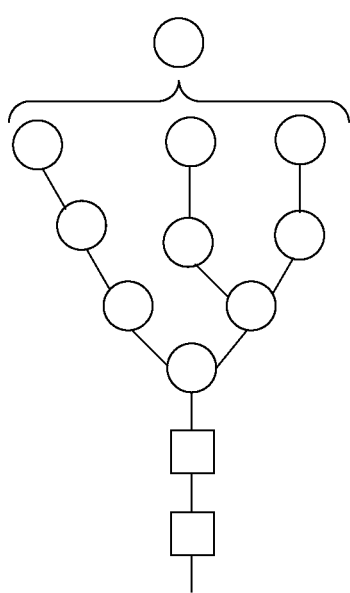

-continued

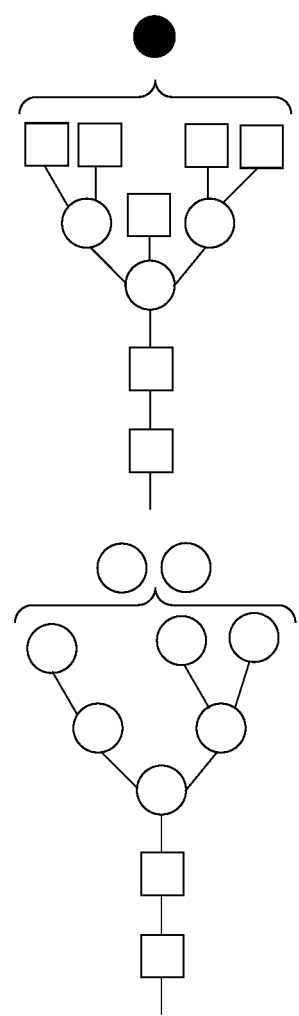

Square = N-Acetyl Glucosamine
Filled Square = Mannose-6-Phosphate
Circle = Mannose
Filled Circle = Galactose
Filled Triangle = Fucose According to one aspect of the present invention, a composition comprises any isolated individual or combination of the polypeptides described above. In one embodiment, the composition can be a pharmaceutical composition, for example, a formulation that further comprises pharmaceutically acceptable carriers, such that the composition is, for example, suitable for administration into a subject (e.g., a human, particularly a patient suffering from or diagnosed with a condition). The composition can be administered any number of ways, including by intravenous administration. In another embodiment, the composition can further comprise a second agent. Such an agent can be a medicament, or an agent which can influence or modify a biological process when administered into a subject. For example, the second agent can be an immunomodulatory agent. Such immunomodulatory agents can include any agent which, when administered together (i.e., administered at the same time as, or shortly before or after) with any of the LAL compositions described herein, may have the effect of reducing the immunogenicity of the LAL composition in the subject (e.g., Rituximab, or any other B-cell depleting antibody).

In a final aspect, methods and compositions for the treatment of symptoms associated with LAL deficiency are disclosed.

Additional objects and aspects of the present invention will become more apparent upon review of the detailed description set forth below when taken in conjunction with the accompanying figures and sequences.

BRIEF DESCRIPTION OF THE DRAWINGS

FIG. 1 depicts the amino acid sequences of human LAL. The amino acid sequence of the recombinant hLAL shows 100% homologous to that of natural human LAL. The mature form of hLAL is underlined.

FIG. 2 depicts the nucleotide sequence of recombinant hLAL, the rhLAL transgene of pALVIN-OVR1-I-hLAL-dSA.

FIG. 3A depicts a diagram of human LAL retrovirus expression vector used in the production of transducing particles is diagrammed (the DNA sequence of the plasmid is located in Appendix A). FIG. 3B depicts pALVIN-OVR1-I-hLAL-dSA proviral region that has been integrated into the genome. SIN LTR, self-inactivating long terminal repeat; OV DHSIII enhancer, DNase hypersensitive site III of the ovalbumin gene; OV Intron; ovalbumin 5' untranslated region and intron 1; hLAL, human LAL cDNA; OV 3' UTR, ovalbumin gene 3' untranslated region; partial gag, partial, gag gene; LTR, long terminal repeat.

FIGS. 4A-4D depicts a nucleotide sequence of pALVIN-OVR1-I-hLAL-dSA.

FIGS. 5A-5C depicts a nucleotide sequence of pALVIN-OVR1-I-hLAL-dSA proviral region that has been integrated into the genome.

FIGS. 6A-6D depicts a nucleotide sequence of pALVIN-OV-1.1-I vector.

FIG. 7 depicts a nucleotide sequence of rhLAL adaptor.

FIG. 8 depicts a nucleotide sequence of rhLAL including the partial ovalbumin promoter.

FIG. 9 depicts a nucleotide sequence of OVR1 promoter.

FIG. 12A illustrates schematic of the integrated transgene and flanking genomic regions is shown with the known position of the transgene BlpI site and predicted position of the flanking genomic BlpI sites. The position of the OV promoter probe and the hLAL coding sequence probe (hLAL probe) are indicated by the black bars. The positions of the 4.3 kb and 10.6 kb bands detected in the Southern analysis are shown as well as the predicted sizes of the genomic and transgene portions of the 4.3 kb and 10.6 kb bands. FIG. 12B illustrates a Southern blot of genomic DNA digested with BlpI and probed with the OV probe. WT CTRL is genomic DNA isolated from a non-transgenic chicken. The ID numbers of the G1 transgenics are indicated above the lanes. The position and size (kb) of the molecular weight markers are shown to the left of the blot. The position and size of the detected transgene fragment (4.3 kb) and endogenous ovalbumin gene (4.1 kb) are shown to the right of the blot. FIG. 12C depicts a Southern blot was probed with the hLAL probe. The position and size of the detected transgene fragment (10.6 kb) is shown to the right of the blot. FIG. 12D depicts a section of the image shown in FIG. 12B at a larger scale to demonstrate the presence of the 4.1 and 4.3 kb bands.

DETAILED DESCRIPTION OF THE INVENTION

Definitions

Figure 3A:
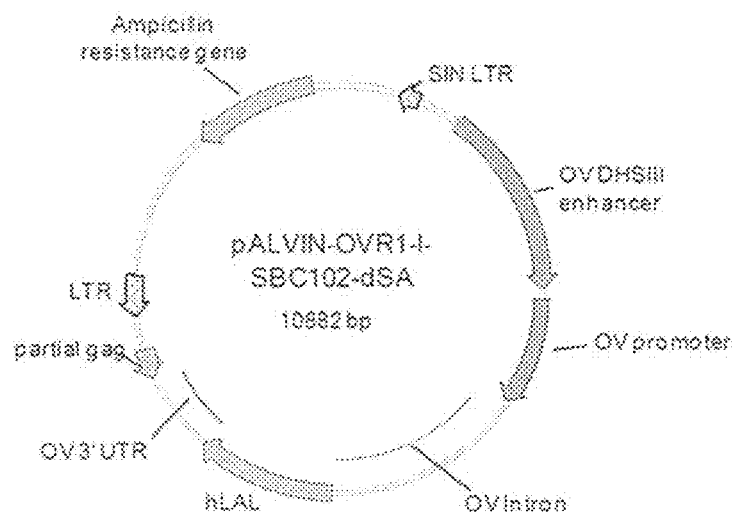
FIGS. 3A and 3B depict diagrams of pALVIN-OVR1-I-hLAL-dSA and its proviral region.

Certain definitions are set forth herein to illustrate and define the meaning and scope of the various terms used to describe the invention herein.

As used herein, the term "acceptable" with respect to a formulation, composition or ingredient, as used herein, means having no persistent detrimental effect on the general health of the subject being treated.

As used herein, the term "administration" or "administering" refers to providing a recombinant human lysosomal acid lipase of the invention to a subject in need of treatment.

A "nucleic acid or polynucleotide sequence" includes, but is not limited to, eukaryotic mRNA, cDNA, genomic DNA, and synthetic DNA and RNA sequences, comprising the natural nucleoside bases adenine, guanine, cytosine, thymidine, and uracil. The term also encompasses sequences having one or more modified bases.

The term "avian" as used herein refers to any species, subspecies or race of organism of the taxonomic class ava, such as, but not limited to chicken, turkey, duck, goose, quail, pheasants, parrots, finches, hawks, crows and ratites including ostrich, emu and cassowary. The term includes the various known strains of *Gallus gallus*, or chickens, (for example, White Leghorn, Brown Leghorn, Barred-Rock, Sussex, New Hampshire, Rhode Island, Australorp, Minorca, Amrox, California Gray), as well as strains of turkeys, pheasants, quails, duck, ostriches and other poultry commonly bred in commercial quantities. It also includes an individual avian organism in all stages of development, including embryonic and fetal stages.

"Therapeutic proteins" or "pharmaceutical proteins" include an amino acid sequence which in whole or in part makes up a drug.

A "coding sequence" or "open reading frame" refers to a polynucleotide or nucleic acid sequence which can be transcribed and translated (in the case of DNA) or translated (in the case of mRNA) into a polypeptide in vitro or in vivo when placed under the control of appropriate regulatory sequences. The boundaries of the coding sequence are determined by a translation start codon at the 5' (amino) terminus and a translation stop codon at the 3' (carboxy) terminus. A transcription termination sequence is usually located 3' to the coding sequence. A coding sequence may be flanked on the 5' and/or 3' ends by untranslated regions.

"Exon" refers to that part of a gene which, when transcribed into a nuclear transcript, is "expressed" in the cytoplasmic mRNA after removal of the introns or intervening sequences by nuclear splicing.

Nucleic acid "control sequences" or "regulatory sequences" refer to promoter sequences, translational start and stop codons, ribosome binding sites, polyadenylation signals, transcription termination sequences, upstream regulatory domains, enhancers, and the like, as necessary and sufficient for the transcription and translation of a given coding sequence in a defined host cell. Examples of control sequences suitable for eukaryotic cells are promoters, polyadenylation signals, and enhancers. All of these control sequences need not be present in a recombinant vector so long as those necessary and sufficient for the transcription and translation of the desired gene are present.

"Operably or operatively linked" refers to the configuration of the coding and control sequences so as to perform the desired function. Thus, control sequences operably linked to a coding sequence are capable of effecting the expression of the coding sequence. A coding sequence is operably linked to or under the control of transcriptional regulatory regions in a cell when DNA polymerase binds the promoter sequence and transcribes the coding sequence into mRNA that can be translated into the encoded protein. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

The terms "heterologous" and "exogenous" as they relate to nucleic acid sequences such as coding sequences and control sequences, denote sequences that are not normally associated with a region of a recombinant construct or with a particular chromosomal locus, and/or are not normally associated with a particular cell. Thus, an "exogenous" region of a nucleic acid construct is an identifiable segment of nucleic acid within or attached to another nucleic acid molecule that is not found in association with the other molecule in nature. For example, an exogenous region of a construct could include a coding sequence flanked by sequences not found in association with the coding sequence in nature. Another example of an exogenous coding sequence is a construct where the coding sequence itself is not found in nature (e.g., synthetic sequences having codons different from the native gene). Similarly, a host cell transformed with a construct or nucleic acid which is not normally present in the host cell would be considered exogenous for purposes of this invention.

As used herein the terms "N-glycan," "oligosaccharide," "oligosaccharide structure," "glycosylation pattern," "glycosylation profile" and "glycosylation structure" have essentially the same meaning and each refer to one or more structures which are formed from sugar residues and are attached to glycosylated proteins.

"Exogenous protein" as used herein refers to a protein not naturally present in a particular tissue or cell, a protein that is the expression product of an exogenous expression construct or transgene, or a protein not naturally present in a given quantity in a particular tissue or cell. A protein that is exogenous to an egg is a protein that is not normally found in the egg. For example, a protein exogenous to an egg may be a protein that is present in the egg as a result of the expression of a coding sequence present in a transgene of the animal laying the egg.

"Endogenous gene" refers to a naturally occurring gene or fragment thereof normally associated with a particular cell.

"LAL" means "human lysosomal acid lipase," "SBC-102" or "human lysosomal acid lipase molecule" and these terms are used interchangeably throughout the specification.

The expression products described herein may consist of proteinaceous material having a defined chemical structure. However, the precise structure depends on a number of factors, particularly chemical modifications common to proteins. For example, since all proteins contain ionizable amino and carboxyl groups, the protein may be obtained in acidic or basic salt form, or in neutral form. The primary amino acid sequence may be derivatized using sugar molecules (glycosylation) or by other chemical derivatizations involving covalent or ionic attachment with, for example, lipids, phosphate, acetyl groups and the like, often occurring through association with saccharides. These modifications may occur in vitro or in vivo, the latter being performed by a host cell through post-translational processing systems. Such modifications may increase or decrease the biological activity of the molecule, and such chemically modified molecules are also intended to come within the scope of the invention.

Alternative methods of cloning, amplification, expression, and purification will be apparent to the skilled artisan. Representative methods are disclosed in Sambrook, Fritsch, and Maniatis, Molecular Cloning, a Laboratory Manual, 2nd Ed., Cold Spring Harbor Laboratory (1989).

"Vector" means a polynucleotide comprised of single strand, double strand, circular, or supercoiled DNA or RNA. A typical vector may be comprised of the following elements operatively linked at appropriate distances for allowing functional gene expression: replication origin, promoter, enhancer, 5' mRNA leader sequence, ribosomal binding site, nucleic acid cassette, termination and polyadenylation sites, and selectable marker sequences. One or more of these elements may be omitted in specific applications. The nucleic acid cassette can include a restriction site for insertion of the nucleic acid sequence to be expressed. In a functional vector the nucleic acid cassette contains the nucleic acid sequence to be expressed including translation initiation and termination sites. An intron optionally may be included in the construct, for example, 5' to the coding sequence. A vector is constructed so that the particular coding sequence is located in the vector with the appropriate regulatory sequences, the positioning and orientation of the coding sequence with respect to the control sequences being such that the coding sequence is transcribed under the "control" of the control or regulatory sequences. Modification of the sequences encoding the particular protein of interest may be desirable to achieve this end. For example, in some cases it may be necessary to modify the sequence so that it may be attached to the control sequences with the appropriate orientation; or to maintain the reading frame.

The control sequences and other regulatory sequences may be ligated to the coding sequence prior to insertion into a vector. Alternatively, the coding sequence can be cloned directly into an expression vector which already contains the control sequences and an appropriate restriction site which is in reading frame with and under regulatory control of the control sequences.

A "promoter" is a site on the DNA to which RNA polymerase binds to initiate transcription of a gene. In some embodiments the promoter can be modified by the addition or deletion of sequences, or replaced with alternative sequences, including natural and synthetic sequences as well as sequences which may be a combination of synthetic and natural sequences. Many eukaryotic promoters contain two types of recognition sequences: the TATA box and the upstream promoter elements. The former, located upstream of the transcription initiation site, is involved in directing RNA polymerase to initiate transcription at the correct site, while the latter appears to determine the rate of transcription and is upstream of the TATA box Enhancer elements can also stimulate transcription from linked promoters, but many function exclusively in a particular cell type. Many enhancer/promoter elements derived from viruses, e.g., the SV40 promoter, the cytomegalovirus (CMV) promoter, the rous-sarcoma virus (RSV) promoter, and the murine leukemia virus (MLV) promoter are all active in a wide array of cell types, and are termed "ubiquitous." Alternatively, non-constitutive promoters such as the mouse mammary tumor virus (MMTV) promoter may also be used in the present invention. The nucleic acid sequence inserted in the cloning site may have any open reading frame encoding a polypeptide of interest, with the proviso that where the coding sequence encodes a polypeptide of interest, it should lack cryptic splice sites which can block production of appropriate mRNA molecules and/or produce aberrantly spliced or abnormal mRNA molecules.

As used herein, the term "pharmaceutical composition" refers to a mixture of a compound described herein with other chemical components, such as carriers, stabilizers, diluents, dispersing agents, suspending agents, thickening agents, and/or excipients.

The term "poultry derived" or "avian derived" refers to a composition or substance produced by or obtained from poultry. "Poultry" refers to avians that can be kept as livestock, including but not limited to, chickens, duck, turkey, quail and ratites. For example, "poultry derived" may refer to chicken derived, turkey derived and/or quail derived.

A "retroviral particle," "transducing particle," or "transduction particle" refers to a replication-defective or replication-competent virus capable of transducing non-viral DNA or RNA into a cell. In one particularly useful embodiment, retroviral particles used to produce transgenic avians in accordance with the invention are made as disclosed in U.S. Pat. No. 7,524,626, issued Apr. 28, 2009, the disclosure of which is incorporated in its entirety herein by reference.

The terms "transformation," "transduction" and "transfection" all denote the introduction of a polynucleotide into an avian blastodermal cell. "Magnum" is that part of the oviduct between the infundibulum and the isthmus containing tubular gland cells that synthesize and secrete the egg white proteins of the egg.

The term "transgene" refers to heterologous nucleotide sequence inserted into an avian genome in accordance with the invention. "Transgene" can specifically refer to an exogenous coding sequence, an exogenous coding sequence linked to an exogenous promoter or other regulatory sequence, all nucleotide sequence between two retoroviral LTRs and/or retroviral LTRs and nucleotide sequence between the LTRs wherein the LTRs are of a retrovirus used to introduce the transgene.

The term "optimized" is used in the context of "optimized coding sequence", wherein the most frequently used codons for each particular amino acid found in the egg white proteins ovalbumin, lysozyme, ovomucoid, and ovotransferrin are used in the design of the optimized human interferon-α 2b (IFN-α 2b) polynucleotide sequence that is inserted into vectors of the present invention. More specifically, the DNA sequence for optimized human IFN-α 2b is based on the hen oviduct optimized codon usage and is created using the BACKTRANSLATE program of the Wisconsin Package, Version 9.1 (Genetics Computer Group Inc., Madison, Wis.) with a codon usage table compiled from the chicken (*Gallus gallus*) ovalbumin, lysozyme, ovomucoid, and ovotransferrin proteins. For example, the percent usage for the four codons of the amino acid alanine in the four egg white proteins is 34% for GCU, 31% for GCC, 26% for GCA, and 8% for GCG. Therefore, GCU is used as the codon for the majority of alanines in an optimized coding sequence. The vectors containing the gene for the optimized human protein are used to produce transgenic avians that express transgenic poultry derived protein in their tissues and eggs.

As used herein, the term "subject" encompasses mammals and non-mammals. Examples of mammals include, but are not limited to, humans, chimpanzees, apes monkeys, cattle, horses, sheep, goats, swine; rabbits, dogs, cats, rats, mice, guinea pigs, and the like.

As used herein, the term "therapeutically effective amount" refers to any amount of a compound which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

The term "treat," "treating" or "treatment" refers to methods of alleviating, abating or ameliorating a disease or condition symptoms, preventing additional symptoms, ameliorating or preventing the underlying causes of symptoms, inhibiting the disease or condition, arresting the development of the disease or condition, relieving the disease or condition, causing regression of the disease or condition, relieving a condition caused by the disease or condition, or stopping the symptoms of the disease or condition either prophylactically and/or therapeutically.

LAL Compositions

The invention is generally drawn to compositions comprising enzymes useful for therapy, for example, in the treatment of lysosomal storage diseases. In one aspect, the invention is drawn to lysosomal storage disease enzymes such as LAL with a glycosylation pattern that renders the molecule amenable for internalization by certain cell types. Also included in the invention are recombinant human proteins including LAL in isolated or purified form. The isolation of the lysosomal storage disease enzymes (such as LAL) can be accomplished by methodologies readily apparent to a practitioner skilled in the art of protein purification.

In one embodiment, the invention is directed to lysosomal storage disease enzymes including, but not limited to LAL, having an N-linked glycosylation pattern described herein.

In one aspect, the compositions disclosed herein comprise human LAL wherein a substantial percentage of the human LAL contain a mannose-6-phosphate glycan moiety, which can serve as a ligand for internalization by the mannose-6- phosphate receptor on the surface of cells found, for example, on hepatocytes. In one embodiment, 30% or more, for example, at least 30%, at least 40%, at least 50%, at least 60%, at least 70%, at least 80%, at least 90%, at least 95%, at least 97%, or at least 99%, of the LAL contained in the composition contains at least one mannose-6-phosphate moiety. The mannose-6-phosphate moiety can be found, for example, on an N-glycan structure located at one or more residues selected from the group consisting of $Asn^{15}$, $Asn^{51}$, $Asn^{80}$, $Asn^{140}$, $Asn^{252}$ and $Asn^{300}$ of SEQ ID NO:2. Glycan structures containing mannose-6-phosphate moieties include, for example, G-n and H-n shown in FIG. 16.

The recombinant human LAL according to the present invention contains multiple N-linked carbohydrate chains (e.g., about 5 or 6 carbohydrate chains). N-linked glycosylation structures at each of the five or six sites can be selected from one of A-n, B-n, C-n, D-n, E-n, F-n, G-n, H-n, I-n, J-n, K-n, L-n, M-n, N-n and O-n as shown in FIG. 16

Figure 16:
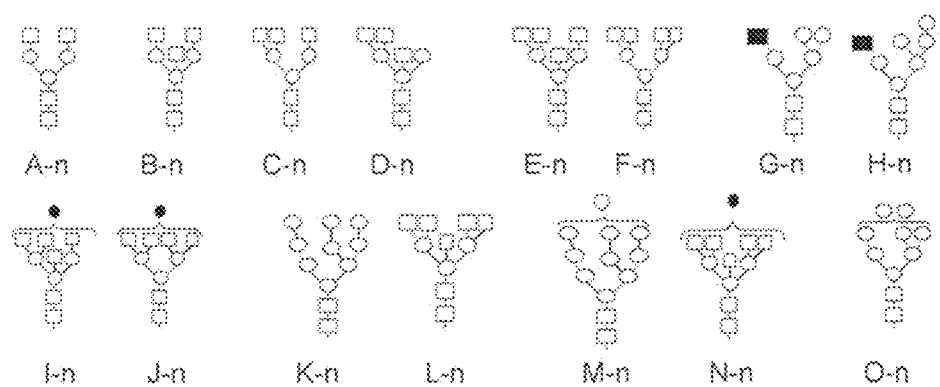
FIG. 16 depicts N-glycans found as an N-linked Glycosylation structure in LAL produced in accordance with the invention. Square, N-Acetyl glucosamine; Filled square, mannose-6-phosphate; circle, mannose; filled circle; galactose; and filled triangle, fucose.

Also described herein are a mixture of LAL molecules (e.g., more than one LAL molecule can be present in a mixture such as the LAL molecules set forth in SEQ ID NOs: 2, 3, 4 and 19) wherein some or all of the LAL molecules have one or more glycosylation structures selected from Structure A-n, Structure B-n, Structure C-n, Structure D-n, Structure E-n, Structure F-n, Structure G-n, Structure H-n, Structure I-n, Structure J-n, Structure K-n, Structure L-n, Structure M-n, Structure N-n and Structure O-n (FIG. 16). In one embodiment, the mixture of lysosomal acid lipase molecules is purified or isolated, for example, isolated from an egg or purified or isolated from egg white produced in a transgenic avian.

The invention also includes an individual LAL molecule comprising a Structure A-n. The invention also includes an individual LAL molecule comprising a Structure B-n. The invention also includes an individual LAL molecule comprising a Structure C-n. The invention also includes an individual LAL molecule comprising a Structure D-n. The invention also includes an individual LAL molecule comprising a Structure E-n. The invention also includes an individual LAL molecule comprising a Structure F-n. The invention also includes an individual LAL molecule comprising a Structure G-n. The invention also includes an individual LAL molecule comprising a Structure H-n. The invention also includes an individual LAL molecule comprising a Structure I-n. The invention also includes an individual LAL molecule comprising a Structure J-n. The invention also includes an individual LAL molecule comprising a Structure K-n. The invention also includes an individual LAL molecule comprising a Structure L-n. The invention also includes an individual lysosomal acid lipase molecule comprising a Structure M-n. The invention also includes an individual LAL molecule comprising a Structure N-n. The invention also includes an individual LAL molecule comprising a Structure O-n.

N-linked oligosaccharides attached to human LAL according to the present invention have a paucity of terminal sialic acid and galactose residues. That is, only minor amounts of the N-linked oligosaccharide structures are terminally sialylated and few galactose residues are present as well. Further, terminal N-Acetyl Glucosamine (GlcNAc) is present extensively on the N-linked oligosaccharide structures of the LAL described herein. As such, LAL produced in accordance with the invention can be targeted to cells such as monocyte macrophages and Kupffer cells.

One aspect of the invention provides compositions of LAL having essentially no sialic acid. In another aspect, the compositions disclosed herein comprise recombinant human LAL wherein a substantial percentage of the human LAL does not contain a sialic acid moiety in any of its N-glycan structures, which can interfere with internalization of the enzyme into cells. In one embodiment, 15% or less, for example, 10% or less, 5% or less, 2% or less, 1% or less, or essentially none, of the LAL contained in the composition contains a sialic acid moiety in any of its N-glycan structures.

In another embodiment, about 95% or more of the N-linked oligosaccharides present on the individual LAL molecule of the invention do not contain sialic acid. In another embodiment, about 90% or more of the N-linked oligosaccharides present on the individual LAL molecule of the invention do not contain sialic acid. In another embodiment, about 80% or more of the N-linked oligosaccharides present on the individual LAL molecule of the invention do not contain sialic acid. In another embodiment, more than about 70% or more of the N-linked oligosaccharides present on the individual LAL molecule of the invention do not contain sialic acid.

In still another embodiment, essentially none of the N-linked oligosaccharides structure types present on the LAL molecules of the invention contain sialic acid. In another embodiment, about 90% or more of the N-linked oligosaccharides structure types found to be associated with the LAL molecules of the invention do not contain sialic acid. For example, if there are 20 oligosaccharide structure types, then 18 or more of the structure types do not contain sialic acid. In another embodiment, about 80% or more of the N-linked oligosaccharides structure types found to be associated with the LAL molecules of the invention do not contain sialic acid. In another embodiment, about 70% or more of the N-linked oligosaccharides structure types found to be associated with the LAL molecules of the invention do not contain sialic acid. In another embodiment, about 60% or more of the N-linked oligosaccharides structure types found to be associated with the LAL molecules of the invention do not contain sialic acid. In another embodiment, about 50% or more of the N-linked oligosaccharides structure types found to be associated with the LAL molecules of the invention do not contain sialic acid.

According to one aspect of the invention, LAL as described herein contain high levels of terminal N-Acetyl Glucosamine In one aspect, about 95% or more of the N-linked oligosaccharides present on the individual LAL molecule of the invention contain a terminal N-Acetyl Glucosamine In another embodiment, about 90% or more of the N-linked oligosaccharides present on the individual LAL molecule of the invention contain a terminal N-Acetyl Glucosamine In another embodiment, about 80% or more of the N-linked oligosaccharides present on the individual LAL molecule of the invention contain a terminal N-Acetyl Glucosamine. In another embodiment, about 70% or more of the N-linked oligosaccharides present on the individual LAL molecule of the invention contain a terminal N-Acetyl Glucosamine In another embodiment, about 60% or more of the N-linked oligosaccharides present on the individual LAL molecule of the invention contain a terminal N-Acetyl Glucosamine In another embodiment, about 50% or more of the N-linked oligosaccharides present on the individual LAL molecule of the invention contain a terminal N-Acetyl Glucosamine.

In one embodiment, all of the N-linked oligosaccharides structure types present on the LAL molecules of the invention contain a terminal N-Acetyl Glucosamine. In another embodiment, about 90% or more of the N-linked oligosaccharides structure types present on the LAL molecules of the invention contain a terminal N-Acetyl Glucosamine For example, if there are 20 oligosaccharide structure types, then 18 or more of the structure types do not contain a terminal N-Acetyl Glucosamine In another embodiment, about 80% or more of the N-linked oligosaccharides structure types present on the LAL molecules of the invention contain a terminal N-Acetyl Glucosamine. In another embodiment, about 70% or more of the N-linked oligosaccharides structure types present on the LAL molecules of the invention contain a terminal N-Acetyl Glucosamine. In another embodiment, about 60% or more of the N-linked oligosaccharides structure types present on the LAL molecules of the invention contain a terminal N-Acetyl Glucosamine In another embodiment, about 50% or more of the N-linked oligosaccharides structure types present on the LAL molecules of the invention contain a terminal N-Acetyl Glucosamine.

In another aspect of the invention, the compositions disclosed herein comprise human LAL wherein a substantial percentage of the human LAL does not contain a fucose moiety in any of its N-glycan structure. In one embodiment, 50% or less, for example, 50% or less, 40% or less, 30% or less, 20% or less, 10% or less, 5% or less, 2% or less, 1% or less, or essentially none, of the LAL contained in the composition contains a fucose moiety in any of its N-glycan structure.

In one embodiment, fucose is essentially not present on the N-linked oligosaccharide structures of the LAL produced in accordance of the invention. In another embodiment, about 95% or more of the N-linked oligosaccharides present on the individual LAL molecule of the invention do not contain fucose. In another embodiment, about 90% or more of the N-linked oligosaccharides present on the individual LAL molecule of the invention do not contain fucose. In another embodiment, about 85% or more of the N-linked oligosaccharides present on the individual LAL molecule of the invention do not contain fucose. In another embodiment, about 80% or more of the N-linked oligosaccharides present on the individual LAL molecule of the invention do not contain fucose. In another embodiment, about 70% or more of the N-linked oligosaccharides present on the individual LAL molecule of the invention do not contain fucose. In another embodiment, about 60% or more of the N-linked oligosaccharides present on the individual LAL molecule of the invention do not contain fucose. In another embodiment, about 50% or more of the N-linked oligosaccharides present on the LAL of the invention do not contain fucose.

In one embodiment, essentially none of the N-linked oligosaccharides structure types present on the LAL molecules of the invention contain fucose. In another embodiment, about 95% or more of the N-linked oligosaccharides structure types present on the LAL molecules of the invention do not contain fucose. For example, if there are 20 oligosaccharide structure types, then 19 or more of the structure types do not contain fucose. In another embodiment, about 90% or more of the N-linked oligosaccharides structure types present on the LAL molecules of the invention do not contain fucose. In another embodiment, about 85% or more of the N-linked oligosaccharides structure types present on the LAL molecules of the invention do not contain fucose. In another embodiment, about 80% or more of the N-linked oligosaccharides structure types present on the LAL molecules of the invention do not contain fucose. In another embodiment, about 70% or more of the N-linked oligosaccharides structure types present on the LAL molecules of the invention do not contain fucose.

As discussed above, certain monosaccharides are abundantly present in LAL molecules produced in accordance with the present invention. The total monosaccharide species analyzed includes fucose, N-acetyl galactosamine, N-acetyl glucosamine, galactose, glucose, mannose, mannose-6-phosphate, N-acetyl neuraminic acid and N-glycolyl neuraminic acid. Fucose can be present between about 0% and about 1% of the total monosaccharide composition. N-acetyl galactosamine can be present between about 0% and about 1% of the total monosaccharide composition. N-acetyl glucosamine can be present between about 35% and about 50% of the total monosaccharide composition. Galactose can be present between about 1-10% of the total monosaccharide composition. Glucose is present at 0% of the total monosaccharide composition. Mannose is present between about 32% and about 50% of the total monosaccharide composition. Mannose-6-phosphate is present between about 1% and about 11% of the total monosaccharide composition.

In one embodiment, LAL produced in accordance with the present invention do not contain any xylose. In addition, because there is essentially no N-acetylgalactosamine (Gal-Nac) in LAL produced in accordance with the invention, one aspect of the invention includes a composition of LAL having no O-linked glycosylation.

LAL has 6 potential sites in its amino acid sequence for N-linked glycosylation, for example, $Asn^{36}$, $Asn^{72}$, $Asn^{101}$, $Asn^{161}$, $Asn^{273}$, and $Asn^{321}$ as in SEQ ID NO:1. Five of these, $Asn^{36}$, $Asn^{101}$ $Asn^{161}$, $Asn^{273}$ and $Asn^{321}$ are glycosylated while $Asn^{72}$ can be unglycosylated or substantially unglycosylated (substantially unglycosylated means in a mixture of LAL molecules, fewer $Asn^{72}$ are glycosylated than any of $Asn^{36}$, $Asn^{101}$, $Asn^{161}$, $Asn^{273}$ and $Asn^{321}$) (see FIG. 17). Accordingly, one aspect of the invention is a composition of LAL which is unglycosylated and/or substantially unglycosylated at $Asn^{72}$. LAL having a glycosylated $Asn^{72}$ is within the scope of the invention. The positions of Asn described herein are based on the LAL amino acid sequence set forth in SEQ ID NO:1. It will be apparent to those skilled in the art that the numbering of Asn (i.e., the position of asparagine) can vary depending on individual LAL molecule and be readily determined in other LAL molecules such as those whose amino acid sequences are set forth in SEQ ID NOs:2, 3, 4 and 19.

Figure 17:
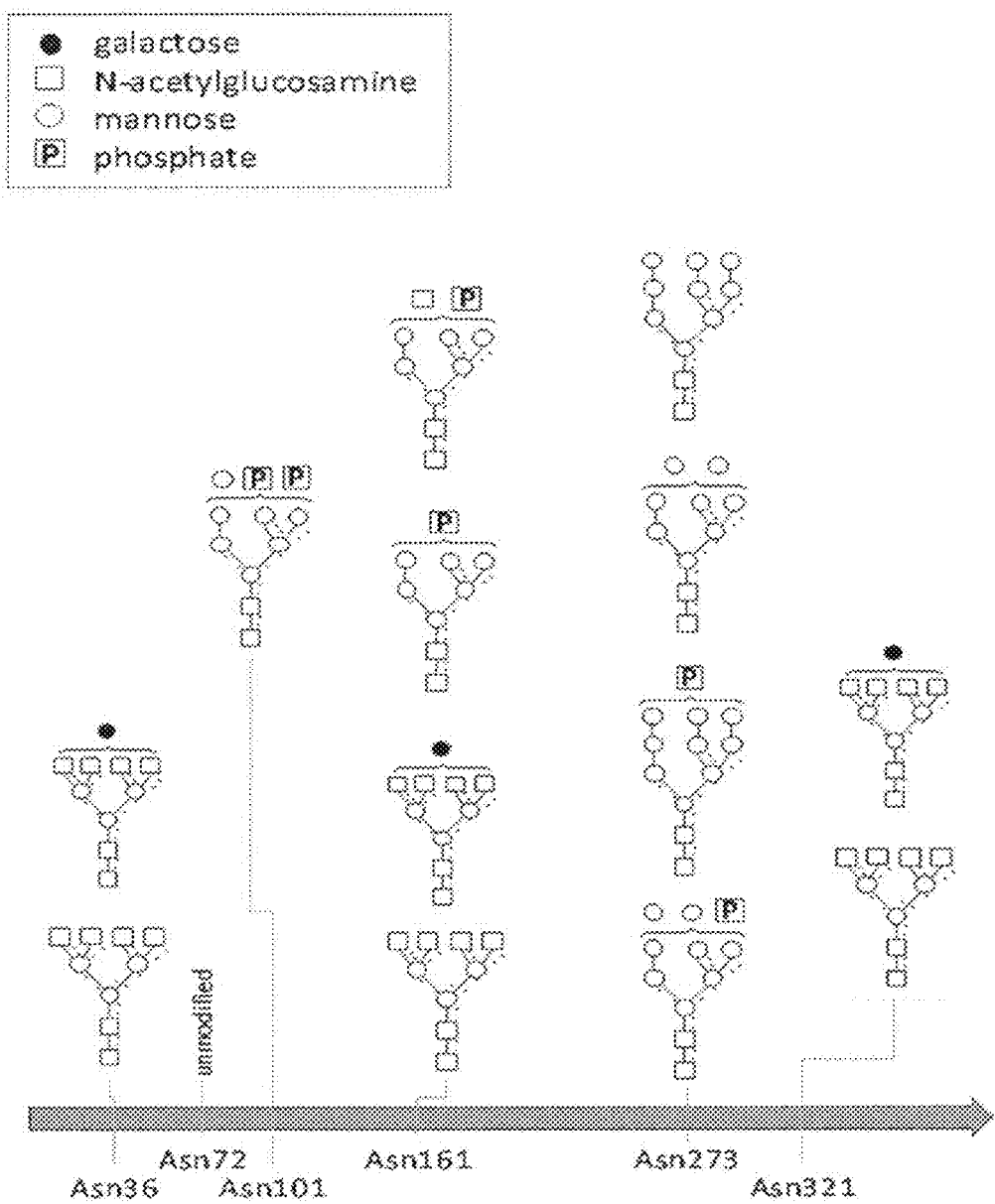
FIG. 17 depicts the relative position of predicted N-glycan sites indicated on the LAL polypeptide (arrow) set forth in SEQ ID NO:1. N-glycans that are structurally representative of those detected at each site are shown. Square, N-Acetyl glucosamine; Filled square, mannose-6-phosphate; circle, mannose; filled circle; galactose; and filled triangle, fucose.

The LAL molecules produced in accordance with the present invention contain N-glycan structures comprising a mixture of bi-, tri- and tetraantennary structures with N-acetylglucosamine, mannose and mannose-6-phosphate (M6P) as the major sugars (FIGS. 16 and 17). According to one aspect of the invention, M6P-modified N-glycans reside at least at $Asn^{101}$, $Asn^{161}$ and $Asn^{273}$. Thus, one embodiment of the present invention includes a composition of LAL having M6P-modified N-glycans residing at any one of $Asn^{101}$, $Asn^{161}$ or $Asn^{273}$. In yet another embodiment, the present invention includes a composition of LAL having M6P-modified N-glycans residing at $Asn^{273}$. In another embodiment, the present invention includes a composition of LAL having monophosphorylated N-glycans (M6P) residing at any one of $Asn^{101}$, $Asn^{161}$ or $Asn^{273}$. In yet another embodiment, the present invention includes a composition of LAL having monophosphorylated N-glycans residing at $Asn^{161}$ and $Asn^{273}$. In yet another embodiment, the present invention includes a composition of LAL having monophosphorylated N-glycans residing at $Asn^{101}$ and $Asn^{273}$. In one specific embodiment, a LAL produced in accordance with the present invention can contain bisphosphorylated mannose (bis-M6P) at $Asn^{101}$.

The LAL molecules produced in accordance with the present invention contain reduced levels of galactose (e.g., "Gal"). One aspect of the present invention includes a composition of LAL having terminal galactose at any one of $Asn^{36}$, $Asn^{161}$ or $Asn^{321}$. In yet another embodiment, the present invention includes a composition of LAL having terminal galactose at $Asn^{36}$ and $Asn^{161}$. In yet another embodiment, the present invention includes a composition of LAL having terminal galactose at $Asn^{161}$ and $Asn^{321}$. In yet another embodiment, the present invention includes a composition of LAL having terminal galactose at $Asn^{36}$ and $Asn^{321}$. In yet another embodiment, the present invention includes a composition of LAL having terminal galactose at $Asn^{36}$, $Asn^{161}$ and $Asn^{321}$. In yet another embodiment, the present invention includes a composition of LAL having no terminal galactose.

Various types of N-glycans were found in LAL at different N-linked glycosylation sites. The N-glycan structures include a mixture of bi-, tri- and tetraantennary structures with N-acetylglucosamine, mannose and mannose-6-phosphate (M6P) as the major sugars. Specifically, in one embodiment of the present invention, LAL contains an N-glycan structure selected from GlcNAc4Man3GlcNAc2 or Gal1 GlcNAc4Man3GlcNAc2 at the first N-linked glycosylation site (e.g., $Asn^{36}$ as in SEQ ID NO:1). In another embodiment, LAL contains no glycosylation or is substantially unglycosylated at the second N-linked glycosylation site (e.g., $Asn^{72}$ as in SEQ ID NO:1). In yet another embodiment, LAL contains Phos2Man7GlcNAc2 at its third N-linked glycosylation site (e.g., $Asn^{101}$ as in SEQ ID NO:1). In yet another embodiment, LAL contains a N-glycan structure selected from Phos1Man6GlcNAc2, GlcNAc1Phos1Man6GlcNAc2, Man3GlcNAc2, GlcNAc2Man3GlcNAc2, GlcNAc3Man3GlcNAc2, GlcNAc4Man3GlcNAc2, or Gal1GlcNAc4Man3GlcNAc2 at its fourth N-linked glycosylation site (e.g., $Asn^{161}$ as in SEQ ID NO:1). In yet another embodiment, LAL contains a N-glycan structure selected from Man7GlcNAc2, Man8GlcNAc2, Man9GlcNAc2, Phos1Man8GlcNAc2, or Phos1Man9GlcNAc2 at its fifth N-linked glycosylation site (e.g., $Asn^{273}$ as in SEQ ID NO:1). In yet another embodiment, LAL contains a N-glycan structure selected from GlcNAc2Man3GlcNAc2, GlcNAc3Man3GlcNAc2, GlcNAc4Man3GlcNAc2, Gal1GlcNAc4Man3GlcNAc2, GlcNAc5Man3GlcNAc2, Gal1GlcNAc5Man3GlcNAc2, GlcNAc6Man3GlcNAc2, or Gal1GlcNAc6Man3GlcNAc2 at its sixth N-linked glycosylation site (e.g., $Asn^{321}$ as in SEQ ID NO:1).

According to certain aspects of the invention, compositions of LAL include LAL glycosylated at $Asn^{36}$, $Asn^{72}$, $Asn^{101}$ $Asn^{161}$, $Asn^{273}$ and $Asn^{321}$ of SEQ ID NO:1 (or corresponding Asparagine residues within SEQ ID NOs: 2, 3, 4, and 19) with one N-glycan at the designated Asn position as shown below:
  a) at $Asn^{36}$, GlcNAc4Man3GlcNAc2, or
     Gal1GlcNAc4Man3GlcNAc2;
  b) at $Asn^{72}$, no glycosylation;
  c) at $Asn^{101}$, Phos2Man7GlcNAc2;
  d) at $Asn^{161}$, Phos1Man6GlcNAc2,
     GlcNAc1Phos1Man6GlcNAc2;
     Man3GlcNAc2;
     GlcNAc2Man3GlcNAc2;
     GlcNAc3Man3GlcNAc2;
     GlcNAc4Man3GlcNAc2, or
     Gal1GlcNAc4Man3GlcNAc2;
  e) at $Asn^{273}$, Man7GlcNAc2,
     Man8GlcNAc2,
     Man9GlcNAc2,
     Phos1Man8GlcNAc2, or
     Phos1Man9GlcNAc2; and
  f) at $Asn^{321}$, GlcNAc2Man3GlcNAc2,
     GlcNAc3Man3GlcNAc2,
     GlcNAc4Man3GlcNAc2,
     Gal1GlcNAc4Man3GlcNAc2,
     GlcNAc5Man3GlcNAc2,
     Gal1GlcNAc5Man3GlcNAc2,
     GlcNAc6Man3GlcNAc2, or
     Gal1GlcNAc6Man3GlcNAc2,
where Man=mannose,
  GlcNAc=N-Acetyl Glucosamine,
  Phos=phosphate, and
  Gal=galactose.

In one embodiment, Gal1GlcNAc4Man3GlcNAc2 can be found as a glycan component at any one of $Asn^{36}$, $Asn^{161}$ or $Asn^{321}$ in LAL produced in accordance with the invention. In one specific embodiment, Gal1GlcNAc4Man3GlcNAc2 can be found as a glycan component of $Asn^{36}$, $Asn^{161}$ and $Asn^{321}$.

In the LAL of the present invention, $Asn^{101}$ and $Asn^{273}$ display the high-mannose-type having about 6 to about 10 mannose molecules (MAN6-MAN10 as described herein) as a major component. Accordingly, one aspect of the present invention includes a composition of LAL having a high mannose structure at $Asn^{101}$ or $Asn^{273}$. In another embodiment, a composition of LAL of the invention can comprise a N-glycan structure having at least 6 mannose at $Asn^{101}$ or $Asn^{273}$. In another embodiment, a composition of LAL contains a N-glycan having 7, 8 or 9 mannose at $Asn^{101}$ or $Asn^{273}$. In yet another embodiment, the present invention includes a composition of LAL having 7, 8 or 9 mannose at $Asn^{101}$ and $Asn^{273}$. In yet another embodiment, the present invention includes a composition of LAL having 7, 8 or 9 mannose at $Asn^{101}$ and/or $Asn^{273}$ and at least one of the mannose is phosphorylated.

It is to be understood that the glycosylation sites and the numbers associated with Asn described above is based on the amino acid sequence of LAL set forth in SEQ ID NO:1 and that the glycosylation profiles described above in context of SEQ ID NO:1 also apply to LAL molecules set forth in SEQ ID NOs: 2, 3, 4 and 19 though the numbering of corresponding Asn may vary depending on LAL molecule. For example, $Asn^{36}$ in SEQ ID NO:1 corresponds to $Asn^{15}$ in SEQ ID NO:2, $Asn^{13}$ in SEQ ID NO:3, $Asn^{10}$ in SEQ ID NO:4 and $Asn^{9}$ in SEQ ID NO:19. $Asn^{72}$ in SEQ ID NO:1 corresponds to $Asn^{51}$ in SEQ ID NO:2, $Asn^{49}$ in SEQ ID NO:3, $Asn^{46}$ in SEQ ID NO:4 and $Asn^{45}$ in SEQ ID NO:19. $Asn^{101}$ in SEQ ID NO:1 corresponds to $Asn^{80}$ in SEQ ID NO:2, $Asn^{78}$ in SEQ ID NO:3, $Asn^{75}$ in SEQ ID NO:4 and $Asn^{74}$ in SEQ ID NO:19. $Asn^{161}$ in SEQ ID NO:1 corresponds to $Asn^{140}$ in SEQ ID NO:2, $Asn^{138}$ in SEQ ID NO:3, $Asn^{135}$ in SEQ ID NO:4 and $Asn^{134}$ in SEQ ID NO:19. $Asn^{273}$ of SEQ ID NO:1 corresponds to $Asn^{252}$ in SEQ ID NO:2, $Asn^{250}$ in SEQ ID NO:3, $Asn^{247}$ in SEQ ID NO:4 and $Asn^{246}$ in SEQ ID NO:19. $Asn^{321}$ of SEQ ID NO:1 corresponds to $Asn^{300}$ in SEQ ID NO:2, $Asn^{298}$ in SEQ ID NO:3, $Asn^{295}$ in SEQ ID NO:4 and $Asn^{294}$ in SEQ ID NO:19.

For example, in one embodiment, the LAL is N-linked glycosylated at least at one position selected from the group consisting of $Asn^{15}$, $Asn^{51}$, $Asn^{80}$, $Asn^{140}$, $Asn^{252}$ and $Asn^{300}$ of SEQ ID NO:2. In another embodiment, the LAL is N-linked glycosylated at $Asn^{15}$, $Asn^{80}$, $Asn^{140}$, $Asn^{252}$ and $Asn^{300}$ of SEQ ID NO:2. In yet another embodiment, N-glycan structures of LAL of SEQ ID NO:2 have no xylose while less than 15%, 10%, 5%, or 1% of N-glycan structures contain sialic acid; less than 50%, 40%, 30%, 20%, 10%, 5% or 1% of N-glycan structures contain fucose; and at least 30%, 50%, 60%, 70%, 80%, 90% and 95% of N-glycan structures contain phosphorylated mannose (M6P). S In one embodiment, the LAL is N-linked glycosylated at least at one position selected from the group consisting of $Asn^{13}$, $Asn^{49}$, $Asn^{78}$, $Asn^{138}$, $Asn^{250}$ and $Asn^{298}$ of SEQ ID NO:3. In another embodiment, the LAL is N-linked glycosylated at $Asn^{13}$, $Asn^{78}$, $Asn^{138}$, $Asn^{250}$ and $Asn^{298}$ of SEQ ID NO:3. In yet another embodiment, N-glycan structures of LAL of SEQ ID NO:3 have no xylose while less than 15%, 10%, 5%, or 1% of N-glycan structures contain sialic acid; less than 50%, 40%, 30%, 20%, 10%, 5% or 1% of N-glycan structures contain fucose; and at least 30%, 50%, 60%, 70%, 80%, 90% and 95% of N-glycan structures contain phosphorylated mannose (M6P).

In one embodiment, the LAL is N-linked glycosylated at least at one position selected from the group consisting of $Asn^{10}$, $Asn^{46}$, $Asn^{75}$, $Asn^{135}$, $Asn^{247}$ and $Asn^{295}$ of SEQ ID NO:4. In another embodiment, the LAL is N-linked glycosylated at $Asn^{10}$, $Asn^{75}$, $Asn^{135}$, $Asn^{247}$ and $Asn^{295}$ of SEQ ID NO:4. In yet another embodiment, N-glycan structures of LAL of SEQ ID NO:4 have no xylose while less than 15%, 10%, 5%, or 1% of N-glycan structures contain sialic acid; less than 50%, 40%, 30%, 20%, 10%, 5% or 1% of N-glycan structures contain fucose; and at least 30%, 50%, 60%, 70%, 80%, 90% and 95% of N-glycan structures contain phosphorylated mannose (M6P).

In one embodiment, the LAL is N-linked glycosylated at least at one position selected from the group consisting of $Asn^9$, $Asn^{45}$, $Asn^{74}$, $Asn^{134}$, $Asn^{246}$ and $Asn^{294}$ of SEQ ID NO:19. In another embodiment, the LAL is N-linked glycosylated at $Asn^9$, $Asn^{74}$, $Asn^{134}$, $Asn^{246}$ and $Asn^{294}$ of SEQ ID NO:19. In yet another embodiment, N-glycan structures of LAL of SEQ ID NO:4 have no xylose while less than 15%, 10%, 5%, or 1% of N-glycan structures contain sialic acid; less than 50%, 40%, 30%, 20%, 10%, 5% or 1% of N-glycan structures contain fucose; and at least 30%, 50%, 60%, 70%, 80%, 90% and 95% of N-glycan structures contain phosphorylated mannose (M6P).

The composition according to the present invention can be produced a number of ways, including by use of transgenic avians, transgenic fish, transgenic mammals, for example, transgenic goats or in transgenic plants, such as tobacco and duck weed (Lemna minor) and certain types of cell culture.

The present invention also contemplates compositions comprising PEGylated LAL. LAL enzyme as described herein can be PEGylated as disclosed, for example, in U.S. Patent publication No. 20070092486, published Apr. 26, 2007, the disclosure of which is incorporated it its entirety herein by reference.

In one embodiment, the derived glycosylation pattern is obtained through expression specialized expression systems, for example, from avian oviduct cells, for example, tubular gland cells. For example, glycosylation patterns disclosed herein have been demonstrated to be present on lysosomal storage disease enzymes produced in oviduct cells of an avian such as a chicken in accordance with the present invention.

Proteins produced in accordance with the invention can be purified from egg white by any useful procedure such as those apparent to a practitioner of ordinary skill in the art of protein purification. For example, the human LAL (hLAL) produced in transgenic avians in accordance with the invention can be purified from egg white by methods apparent to practitioners of ordinary skill in the art of protein purification. An example of a purification protocol for LAL present in egg white is described in the Examples.

The invention includes the eggs and egg white and the avians (e.g., chicken turkey and quail) that lay the eggs and produce the egg white containing lysosomal acid lipase molecules of the invention comprising one or more of the glycosylation structures disclosed herein.

Expression of LAL in Avians

Disclosed herein are vectors and methods for the stable introduction of exogenous nucleic acid sequences into the genome of avians to express desired proteins such as those which benefit (e.g., attain an increased efficacy) from the addition of mannose-6-phospahate such as lysosomal enzymes including, without limitation, lysosomal acid lipase (LAL) and other proteins such as those specifically disclosed herein. In particular, transgenic avians are produced which express exogenous sequences in their oviducts and which deposit exogenous proteins, such as pharmaceutical proteins, into their eggs. Avian eggs that contain such exogenous proteins are also described herein. Also disclosed herein are novel forms of LAL which are efficiently expressed in the oviduct of transgenic avians and deposited into avian eggs.

One aspect of the invention relates to compositions containing LAL, i.e., LAL molecules produced in accordance with the invention. In a particularly useful embodiment, the LAL is purified or isolated. For example, the LAL has been removed from the contents of a hard shell egg laid by a transgenic avian. In one particularly useful embodiment, the LAL is human LAL. In one embodiment, the LAL of the invention has a glycosylation pattern resulting from the LAL being produced in an oviduct cell of an avian. For example, the compositions can contain a mixture of LAL molecules produced in avians, for example, chickens, in accordance with the invention and isolated from egg white. In one useful embodiment, the LAL containing compositions are pharmaceutical formulations.

In one aspect, the invention is drawn to compositions containing isolated LAL molecules, for example, human LAL molecules, wherein the LAL is produced in an avian which contains a transgene encoding the LAL. In one embodiment, the LAL is produced in an oviduct cell (e.g., a tubular gland cell) of a transgenic avian (e.g., transgenic chicken) and the LAL is isolated from egg white of the transgenic avian. In one embodiment, the LAL is glycosylated in the oviduct cell (e.g., tubular gland cell) of the bird, for example, a chicken.

In another aspect, methods for producing exogenous proteins such as lysosomal storage disease enzymes, for example, LAL, in specific tissues of avians, are provided. Such exogenous proteins may be expressed in the oviduct, blood and/or other cells and tissues of the avian. In one embodiment, transgenes are introduced into embryonic blastodermal cells, for example, near stage X, to produce a transgenic avian, such that the protein of interest is expressed in the tubular gland cells of the magnum of the oviduct, secreted into the lumen, and deposited into the egg white of a hard shell egg. A transgenic avian so produced can carry the transgene in its germ line providing transmission of the exogenous transgene to the avian's offspring stably in a Mendelian fashion.

The present invention encompasses methods of producing exogenous protein such as LAL in an avian oviduct. The methods may include a first step of providing a vector that contains a coding sequence and a promoter operably linked to the coding sequence, so that the promoter can effect expression of the nucleic acid in the avian oviduct. Transgenic cells and/or tissues can be produced, wherein the vector is introduced into avian embryonic blastodermal cells, either freshly isolated, in culture, or in an embryo, so that the vector sequence is inserted into the avian genome. A mature transgenic avian which expresses the exogenous protein such as LAL in its oviduct can be derived from the transgenic cells and/or tissue.

In one aspect of the invention, production of a transgenic avian is accomplished by transduction of embryonic blastodermal cells with replication-defective or replication-competent retroviral particles carrying the transgene between the 5' and 3' LTRs of the retroviral rector. For instance, an avian leukosis virus (ALV) retroviral vector or a murine leukemia virus (MLV) retroviral vector may be used which comprises a modified pNLB plasmid containing an exogenous gene that is inserted downstream of a segment of a promoter region. An RNA copy of the modified retroviral vector, packaged into viral particles, can be used to infect embryonic blastoderms which develop into transgenic avians.

Another aspect of the invention provides a vector which includes a coding sequence and a promoter in operational and positional relationship such that the coding sequence is expressed in an avian oviduct. Such vectors include, but are not limited to, an avian leukosis virus (ALV) retroviral vector, a murine leukemia virus (MLV) retroviral vector, and a lentivirus vector. In addition, the vector may be a nucleic acid sequence which includes an LTR of an avian leukosis virus (ALV) retroviral vector, a murine leukemia virus (MLV) retroviral vector, or a lentivirus vector. The promoter is sufficient for effecting expression of the coding sequence in the avian oviduct. The coding sequence codes for an exogenous protein which is deposited into the egg white of a hard shell egg. As such, the coding sequence codes for exogenous proteins such as transgenic poultry derived proteins such as transgenic poultry derived lysosomal acid lipase (TPD LAL).

In one embodiment, vectors used in the methods of the invention contain a promoter which is particularly suited for expression of exogenous proteins in avians and their eggs. As such, expression of the exogenous coding sequence may occur in the oviduct and blood of the transgenic avian and in the egg white of its avian egg. The promoters include, but are not limited to, a cytomegalovirus (CMV) promoter, a rous-sarcoma virus (RSV) promoter, a β-actin promoter (e.g., a chicken β-actin promoter), a murine leukemia virus (MLV) promoter, a mouse mammary tumor virus (MMTV) promoter, an ovalbumin promoter, a lysozyme promoter, a conalbumin promoter, an ovomucoid promoter, an ovomucin promoter, and an ovotransferrin promoter. Optionally, the promoter may be a segment of at least one promoter region, such as a segment of the ovalbumin, lysozyme, conalbumin, ovomucoid, ovomucin, and ovotransferrin promoter region. In one embodiment, the promoter is a combination or a fusion of one or more promoters or a fusion of a portion of one or more promoters such as ovalbumin, lysozyme, conalbumin, ovomucoid, ovomucin, and ovotransferrin promoters.

In one embodiment, the vector includes a signal peptide coding sequence which is operably linked to the coding sequence, so that upon translation in a cell, the signal peptide directs secretion of the exogenous protein expressed by the vector, such as human LAL, into the egg white of a hard shell egg.

One aspect of the invention provides for coding sequences for exogenous proteins produced as disclosed herein wherein the coding sequence is codon optimized for expression in an avian, for example, in a chicken. Codon optimization may be determined from the codon usage of at least one, and preferably more than one, protein expressed in an avian cell (e.g., a chicken cell). For example, the codon usage may be determined from the nucleic acid sequences encoding the proteins ovalbumin, lysozyme, ovomucin and ovotransferrin of chicken. For example, the DNA coding sequence for the exogenous protein may be codon optimized using the BACKTRANSLATE® program of the Wisconsin Package, version 9.1 (Genetics Computer Group, Inc., Madison, Wis.) with a codon usage table compiled from the chicken (*Gallus gallus*) ovalbumin, lysozyme, ovomucoid, and ovotransferrin proteins.

One important aspect of the present invention relates to avian hard shell eggs (e.g., chicken hard shell eggs) which contain an exogenous peptide or protein including, but not limited to, a human LAL. The exogenous peptide or protein such as human LAL may be encoded by a transgene of a transgenic avian. Often, the exogenous peptide or protein (e.g., LAL) is glycosylated. The protein may be present in any useful amount. In one embodiment, the protein is present in an amount in a range of between about 0.01 µg per hard-shell egg and about 1 gram per hard-shell egg. In another embodiment, the protein is present in an amount in a range of between about 1 µg per hard-shell egg and about 1 gram per hard-shell egg. For example, the protein may be present in an amount in a range of between about 10 µg per hard-shell egg and about 1 gram per hard-shell egg (e.g., a range of between about 10 µg per hard-shell egg and about 400 milligrams per hard-shell egg).

In one embodiment, the exogenous protein of the invention is present in the egg white of the egg. In one embodiment, the protein is present in an amount in a range of between about 1 ng per milliliter of egg white and about 0.2 gram per milliliter of egg white. For example, the protein may be present in an amount in a range of between about 0.1 µg per milliliter of egg white and about 0.2 gram per milliliter of egg white (e.g., the protein may be present in an amount in a range of between about 1 µg per milliliter of egg white and about 100 milligrams per milliliter of egg white. In one embodiment, the protein is present in an amount in a range of between about 1 µg per milliliter of egg white and about 50 milligrams per milliliter of egg white. For example, the protein may be present in an amount in a range of about 1 µg per milliliter of egg white and about 10 milligrams per milliliter of egg white (e.g., the protein may be present in an amount in a range of between about 1 µg per milliliter of egg white and about 1 milligrams per milliliter of egg white). In one embodiment, the protein is present in an amount of more than 0.1 µg per milliliter of egg white. In one embodiment, the protein is present in an amount of more than 0.5 µg per milliliter of egg white. In one embodiment, the protein is present in an amount of more than 1 µg per milliliter of egg white. In one embodiment, the protein is present in an amount of more than 1.5 µg per milliliter of egg white.

The avians of the invention which produce exogenous proteins disclosed herein (e.g., LAL) which are developed from the blastodermal cells into which the vector has been introduced are the G0 generation and can be referred to as "founders." Founder birds are typically chimeric for each inserted transgene. That is, only some of the cells of the G0 transgenic bird contain the transgene(s). The G0 generation typically is also hemizygous for the transgene(s). The G0 generation may be bred to non-transgenic animals to give rise to G1 transgenic offspring which are also hemizygous for the transgene and contain the transgene(s) in essentially all of the bird's cells. The G1 hemizygous offspring may be bred to non-transgenic animals giving rise to G2 hemizygous offspring or may be bred together to give rise to G2 offspring homozygous for the transgene. Substantially all of the cells of birds which are positive for the transgene that are derived from G1 offspring contain the transgene(s). In one embodiment, hemizygotic G2 offspring from the same line can be bred to produce G3 offspring homozygous for the transgene. In one embodiment, hemizygous G0 or G1 animals, for example, are bred together to give rise to homozygous G1 offspring containing two copies of the transgene(s) in each cell of the animal. These are merely examples of certain useful breeding methods and the present invention contemplates the employment of any useful breeding method such as those known to individuals of ordinary skill in the art.

In one embodiment, the invention provides for the LAL to be isolated. That is, the LAL contained in the composition may be an isolated LAL. For example, the LAL may be isolated from egg white. The isolated LAL may be LAL molecules having a variety of glycosylation structures among the LAL molecules.

By the methods of the present invention, transgenes can be introduced into avian embryonic blastodermal cells to produce a transgenic chicken, transgenic turkey, transgenic quail and other avian species, that carry the transgene in the genetic material of its germ-line tissue in order to produce proteins of the invention. The blastodermal cells are typically stage VII-XII cells, or the equivalent thereof, and in one embodiment are near stage X.

Some vectors useful in carrying out the methods of the present invention are described herein. In one embodiment, the coding sequence and the promoter of the vector are both positioned between 5' and 3' LTRs before introduction into blastodermal cells. In one embodiment, the vector is retroviral and the coding sequence and the promoter are both positioned between the 5' and 3' LTRs of the retroviral vector. In one useful embodiment, the LTRs or retroviral vector is derived from the avian leukosis virus (ALV), murine leukemia virus (MLV), or lentivirus.

In one embodiment, vectors are used for transfecting blastodermal cells and generating stable integration into the avian genome contain a coding sequence and a promoter in operational and positional relationship to express the coding sequence in the tubular gland cell of the magnum of the avian oviduct, wherein the exogenous protein such as an lysosomal enzyme (e.g., LAL) is deposited in the egg white of a hard shell egg.

The promoter may optionally be a segment of the ovalbumin promoter region which is sufficiently large to direct expression of the coding sequence in the tubular gland cells. Truncating the ovalbumin promoter and/or condensing the critical regulatory elements of the ovalbumin promoter so that it retains sequences required for expression in the tubular gland cells of the magnum of the oviduct, while being small enough that it can be readily incorporated into vectors is included within the scope of the invention. In one embodiment, a segment of the ovalbumin promoter region may be used. This segment comprises the 5'-flanking region of the ovalbumin gene.

The promoter may also be a promoter that is largely, but not entirely, specific to the magnum, such as the lysozyme promoter. The promoter may also be a mouse mammary tumor virus (MMTV) promoter. Alternatively, the promoter may be a constitutive promoter (e.g., a cytomegalovirus (CMV) promoter, a rous-sarcoma virus (RSV) promoter, a murine leukemia virus (MLV) promoter, etc.). In one embodiment, the promoter is a cytomegalovirus (CMV) promoter, a MDOT promoter, a rous-sarcoma virus (RSV) promoter, a murine leukemia virus (MLV) promoter, a mouse mammary tumor virus (MMTV) promoter, an ovalbumin promoter, a lysozyme promoter, a conalbumin promoter, an ovomucoid promoter, an ovomucin promoter and/or an ovotransferrin promoter. Optionally, the promoter may be at least one segment of a promoter region, such as a segment of the ovalbumin, lysozyme, conalbumin, ovomucoid, ovomucin, and ovotransferrin promoter region.

In one method of transfecting blastodermal cells, a packaged retroviral-based vector is used to deliver the vector into embryonic blastodermal cells so that the vector is integrated into the avian genome.

Useful retrovirus for randomly introducing a transgene into the avian genome is the replication-deficient avian leucosis virus (ALV), the replication-deficient murine leukemia virus (MLV), or the lentivirus. In one embodiment, a pNLB vector is modified by inserting a region of the ovalbumin promoter and one or more exogenous genes between the 5' and 3' long terminal repeats (LTRs) of the retrovirus genome. The invention contemplates that any coding sequence placed downstream of a promoter that is active in tubular gland cells can be expressed in the tubular gland cells. For example, the ovalbumin promoter can be expressed in the tubular gland cells of the oviduct magnum because the ovalbumin promoter drives the expression of the ovalbumin protein and is active in the oviduct tubular gland cells.

Any of the vectors described herein can also optionally include a coding sequence encoding a signal peptide that directs secretion of the protein expressed by the vector's coding sequence from the tubular gland cells of the oviduct. This aspect effectively broadens the spectrum of exogenous proteins that may be deposited in avian eggs using the methods described herein. Where an exogenous protein would not otherwise be secreted, the vector containing the coding sequence is modified to comprise a DNA sequence comprising about 60 bp encoding a signal peptide from the lysozyme gene. The DNA sequence encoding the signal peptide is inserted in the vector such that it is located at the N-terminus of the protein encoded by the DNA.

Another aspect of the invention involves the use of internal ribosome entry site (IRES) elements in any of the vectors of the present invention to allow the translation of two or more proteins from a dicistronic or polycistronic mRNA. The IRES units are fused to 5' ends of one or more additional coding sequences which are then inserted into the vectors at the end of the original coding sequence, so that the coding sequences are separated from one another by an IRES.

In one embodiment when using an IRES, post-translational modification of the product is facilitated because one coding sequence can encode an enzyme capable of modifying the other coding sequence product. For example, the first coding sequence may encode collagen which would be hydroxylated and made active by the enzyme encoded by the second coding sequence wherein an IRES is employed as is understood in the art.

In another aspect, the coding sequences of vectors used in any of the methods of the present invention are provided with a 3' untranslated region (3' UTR) to confer stability to the RNA produced. When a 3' UTR is added to a retroviral vector, the orientation of the promoter, gene X and the 3' UTR must be reversed in the construct, so that the addition of the 3' UTR does not interfere with transcription of the full-length genomic RNA. In one embodiment, the 3' UTR may be that of the ovalbumin or lysozyme genes, or any 3' UTR that is functional in a magnum cell, i.e., the SV40 late region.

In one embodiment, a constitutive promoter is used to express the coding sequence of a transgene in the avian. In this case, expression is not limited to the magnum; expression also occurs in other tissues within the avian (e.g., blood). The use of such a transgene, which includes a constitutive promoter and a coding sequence, is particularly suitable for effecting or driving the expression of a protein in the oviduct and the subsequent secretion of the protein into the egg.

Transducing particles (i.e., transduction particles) are produced for the vector and titered to determine the appropriate concentration that can be used to inject embryos. Avian eggs are windowed according to the Speksnijder procedure (U.S. Pat. No. 5,897,998, the disclosure of which is incorporated in its entirety herein by reference), and eggs are injected with transducing particles. Eggs hatch about 21 days after injection and male birds are selected for breeding. In order to screen for G0 roosters which contain the transgene in their sperm, DNA is extracted from rooster sperm samples. The G0 roosters with the highest levels of the transgene in their sperm samples are bred to nontransgenic hens by artificial insemination. Blood DNA samples are screened for the presence of the transgene. The serum of transgenic roosters is tested for the presence of exogenous protein. If the exogenous protein is confirmed, the sperm of the transgenic roosters is used for artificial insemination of nontransgenic hens. A certain percent of the offspring then contains the transgene (e.g., more than 50%). When exogenous protein is present in eggs produced in accordance with the present invention the protein may be isolated. The protein may also be tested for biological activity.

The methods of the invention which provide for the production of exogenous protein in the avian oviduct and the production of eggs which contain exogenous protein involve an additional step subsequent to providing a suitable vector and introducing the vector into embryonic blastodermal cells so that the vector is integrated into the avian genome. The subsequent step involves deriving a mature transgenic avian from the transgenic blastodermal cells produced in the previous steps. Mature transgenic avians can be obtained from the cells of a blastodermal embryo which has been transfected or transduced with the vector directly within the embryo. The resulting embryo is allowed to develop and the chick allowed to mature.

The transgenic avian produced from blastodermal cells is known as a founder. Some founders will carry the transgene in tubular gland cells in the magnum of their oviducts. These avians will express the exogenous protein encoded by the transgene in their oviducts. The exogenous protein may also be expressed in other tissues (e.g., blood) in addition to the oviduct. If the exogenous protein contains the appropriate signal sequence(s), it will be secreted into the lumen of the oviduct and into the egg white of the egg.

Some founders are germ-line founders. A germ-line founder is a founder that carries the transgene in genetic material of its germ-line tissue, and may also carry the transgene in oviduct magnum tubular gland cells that express the exogenous protein. Therefore, in accordance with the invention, the transgenic avian may have tubular gland cells expressing the exogenous protein, and the offspring of the transgenic avian may also have oviduct magnum tubular gland cells that express the exogenous protein. Alternatively, the offspring express a phenotype determined by expression of the exogenous gene in specific tissue(s) of the avian. In one embodiment, the transgenic avian is a chicken or a turkey.

Pharmaceutical Compositions & Therapeutic Methods

While it is possible that, for use in therapy, therapeutic proteins produced as described herein may be administered in raw form, it is preferable to administer the therapeutic proteins as part of a pharmaceutical formulation. Therefore, further provided are pharmaceutical formulations comprising poultry derived glycosylated therapeutic proteins such as LAL or a pharmaceutically acceptable derivative thereof together with one or more pharmaceutically acceptable carriers thereof and, optionally, other therapeutic and/or prophylactic ingredients and methods of administering such pharmaceutical formulations. The carrier(s) must be "acceptable" in the sense of being compatible with the other ingredients of the formulation and not deleterious to the recipient thereof. Methods of treating a patient (e.g., quantity of pharmaceutical protein administered, frequency of administration and duration of treatment period) using pharmaceutical compositions of the invention can be determined using standard methodologies known to physicians of skill in the art.

Compositions comprising carriers, including composite molecules, are formulated by well-known conventional methods (see, for example, Remington's Pharmaceutical Sciences, 14th Ed., Mack Publishing Co., Easton, Pa.), the entire teachings of which are incorporated herein by reference. The carrier may comprise a diluent. In one embodiment, the pharmaceutical carrier can be a liquid and the recombinant human LAL can be in the form of a solution. The pharmaceutical carrier can be wax, fat, or alcohol. In one embodiment, the wax- or fat-based carrier does not contain ester. In another embodiment, the pharmaceutically acceptable carrier may be a solid in the form of a powder, a lyophilized powder, or a tablet. In one embodiment, the carrier may comprise a liposome or a microcapsule.

The pharmaceutical formulations include those suitable for administration by injection including intramuscular, subcutaneous and intravenous administration. Pharmaceutical formulations include those suitable for oral, rectal, nasal, topical (including buccal and sub-lingual), vaginal or parenteral. The pharmaceutical formulations also include those for administration by inhalation or insufflation. The formulations may, where appropriate, be conveniently presented in discrete dosage units and may be prepared by any of the methods well known in the art of pharmacy. The methods of producing the pharmaceutical formulations typically include the step of bringing the therapeutic protein into association with liquid carriers or finely divided solid carriers or both and then, if necessary, shaping the product into the desired formulation.

Pharmaceutical formulations suitable for oral administration may conveniently be presented as discrete units such as capsules, cachets or tablets each containing a predetermined amount of the active ingredient; as a powder or granules; as a solution; as a suspension; or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils) or preservatives.

LAL may also be formulated for parenteral administration (e.g., by injection, for example, bolus injection or continuous infusion) and may be presented in unit dose form in ampoules, pre-filled syringes, small volume infusion or in multi-dose containers with an added preservative. The therapeutic proteins can be injected by, for example, subcutaneous injections, intramuscular injections, and intravenous infusions or injections.

The LAL may take such forms as suspensions, solutions, or emulsions in oily or aqueous vehicles, and may contain formulatory agents such as suspending, stabilizing and/or dispersing agents. It is also contemplated that the therapeutic protein may be in powder form, obtained by aseptic isolation of sterile solid or by lyophilization from solution, for constitution with a suitable vehicle, e.g., sterile, pyrogen-free water, before use.

For intravenous infusions or injection, the LAL produced in accordance of the invention can be formulated as an aqueous supension or solution. Excipients suitable for the formulation for intravenous infusion or injection can include one of the following: trisodium citrate dehydrate, citric acid and human serum albumin The pharmaceutical formulation can also include other suitable excipients well known in the art used for other products for lysosomal storage disorders. The pH of LAL produced in accordance with the invention is maintained between about 5.6 and about 6.2. Preferably, the pH of the LAL formulation is maintained at 5.9±0.2.

For topical administration to the epidermis, the therapeutic proteins of the invention produced according to the invention may be formulated as ointments, creams or lotions, or as a transdermal patch. Ointments and creams may, for example, be formulated with an aqueous or oily base with the addition of suitable thickening and/or gelling agents. Lotions can be formulated with an aqueous or oily base and can also contain one or more emulsifying agents, stabilizing agents, dispersing agents, suspending agents, thickening agents or coloring agents.

Formulations suitable for topical administration in the mouth include lozenges comprising active ingredient in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Pharmaceutical formulations suitable for rectal administration wherein the carrier is a solid are most preferably represented as unit dose suppositories. Suitable carriers include cocoa butter and other materials commonly used in the art, and the suppositories may be conveniently formed by a mixture of the active compound with the softened or melted carrier(s) followed by chilling and shaping in molds.

Formulations suitable for vaginal administration may be presented as pessaries, tampons, creams, gels, pastes, foams or sprays containing in addition to the active ingredient, such carriers as are known in the art to be appropriate.

For intra-nasal administration the therapeutic proteins of the invention may be used as a liquid spray or dispersible powder or in the form of drops. Drops may be formulated with an aqueous or non-aqueous base also comprising one or more dispersing agents, solubilizing agents or suspending agents. Liquid sprays are conveniently delivered from pressurized packs.

For administration by inhalation, therapeutic proteins according to the invention may be conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

For administration by inhalation or insufflation, the therapeutic proteins according to the invention may take the form of a dry powder composition, for example, a powder mix of the compound and a suitable powder base such as lactose or starch. The powder composition may be presented in unit dosage form in, for example, capsules or cartridges or, e.g., gelatin or blister packs from which the powder may be administered with the aid of an inhalator or insufflator.

When desired, the above described formulations adapted to give sustained release of the active ingredient, may be employed.

The pharmaceutical compositions described herein may also contain other active ingredients such as antimicrobial agents, or preservatives.

In addition, it is contemplated that the therapeutic proteins disclosed herein may be used in combination with other therapeutic agents. For example, the invention provides methods for pretreatment with a pharmaceutically effective dose of an antihistamine to minimize or prevent potential infusion-related anaphylactic reactions. For example, the antihistamine may be any pharmaceutically acceptable antihistamine (e.g. diphenhydramine) as disclosed herein and as known in the art. In one embodiment, the antihistamine is administered in a dose between about 1 mg and about 10 mg per kilogram of body weight. For example, the antihistamine may be administered in a dose of about 5 mg per kilogram. In one embodiment, the antihistamine is administered between about 10 minutes and about 90 minutes, for example, about 30 minutes to about 60 minutes, prior to administration of lysosomal acid lipase using an ambulatory system connected to the vascular access port. In one embodiment, the dose of diphenhydramine effectively counteracts potential anaphylactic infusion reactions.

Immunosuppressants such as antihistamines, corticosteroids, sirolimus, voclosporin, ciclosporin, methotrexate, IL-2 receptor directed antibodies, T-cell receptor directed antibodies, TNF-α directed antibodies or fusion proteins (infliximab, etanercept or adalimumab), CTLA4-Ig (e.g., abatacept), anti-OX-40 antibodies can also be administered before, during or after LAL administration if an anaphylactic reaction or adverse immune response is experienced by the patient.

The invention also contemplates therapy involving administration of LAL-containing compositions in combination with one or more cholesterol lowering agents (e.g., HMG-CoA reductase inhibitors). Non-limiting examples of such agents include: atorvastatin (Lipitor® and Torvast®), fluvastatin (Lescol®), lovastatin (Mevacor®, Altocor®, Altoprev®), pitavastatin (Livalo®, Pitava®), pravastatin (Pravachol®, Selektine®, Lipostat®), rosuvastatin (Crestor®) and simvastatin (Zocor®, Lipex®).

Compositions or proteins described herein can be used to treat a variety of conditions. For example, there are conditions for which treatment therapies are known to practitioners of skill in the art. The present invention contemplates that the therapeutic proteins (e.g., LAL) produced in an avian system containing a poultry derived glycosylation pattern can be employed to treat such conditions. That is, the treatment of conditions known to be treatable by conventionally produced therapeutic proteins by using therapeutic proteins produced as described herein is also contemplated. For example, LAL produced as described herein can be used to treat conditions resulting from or associated with LAL deficiency or insufficiency (collectively, "LAL deficiency"), such as Wolman disease and cholesteryl ester storage disease (CESD). As described herein, LAL deficiency also contemplates conditions in which expression of LAL is reduced due to a condition (e.g., a genetic mutation), physiological or environmental factors which leads to a reduction or deficiency of LAL produced in the body. LAL produced as described herein can also be used to treat other conditions such as atherosclerosis, fatty liver disease, non-alcoholic fatty liver disease, nonalcoholic steatohepatitis (NASH) and cirrhosis. LAL produced as described herein can also be used to treat other conditions such as those disclosed in U.S. Pat. No. 6,849,257, issued Feb. 1, 2005, the disclosure of which is incorporated in its entirety herein by reference, U.S. publication No. 2009/0297496, published Dec. 3, 2009; US publication No. 2004/0223960, published Nov. 11, 2004; US publication No. 2007/0264249, published Nov. 15, 2009, the disclosures of which (i.e., the disclosures of each of these four patent publications) are incorporated in their entirety herein by reference.

It is also contemplated that LAL produced as disclosed herein can be used to treat certain specific conditions including pancreatitis, for example, chronic pancreatitis and/or acute pancreatitis as well as alcohol induced pancreatic injury such as alcohol induced pancreatitis.

LAL produced by any useful method, such as the ones disclosed herein, is contemplated for use to treat diseases due to alcohol induced cell injury including, but not limited to, those alcohol induced cell injuries that result in accumulation of lipid esters in body tissue such as, but not limited to, liver, spleen, gut and cardiovascular tissue. The invention also contemplates the treating of malabsorption by administering LAL.

One aspect of the invention is drawn to methods of treating a patient comprising administering to a patient a therapeutically effective amount of a composition comprising recombinant human LAL as described herein. The patient can be suffering or diagnosed with any number of conditions, including those associated with LAL deficiency. In one embodiment, the therapeutically effective amount is an amount that increases the red blood cell count in a patient by a desired amount. It is contemplated that LAL produced in accordance with the invention can be used to treat chronic kidney disease, for example, where tissues fail to sustain production of lysosomal acid lipase.

It is also contemplated that LAL produced by any useful method may be useful for the treatment of patients with Tangier disease and familial hypoalphalipoproteinemia. Tangier disease/familial hypoalphalipoproteinemia is associated with the accumulation of cholesterol esters in macrophages accompanied by hepatosplenomegaly and/or lymphadenopathy along with low levels of high-density lipoproteins (HDL) which can be treated by the administration of LAL. For example, without wishing to limit the invention to any particular theory or mechanism of operation, it is believed that impaired LAL activity decreases ABCA1 expression and conversely an increased LAL activity obtained by the administration of LAL to a patient with Tangier disease/familial hypoalphalipoproteinemia will increase ABCA1 expression to overcome the effects of an ABCA1 gene with a reduced functional activity as a result of polymorphism.

For the treatment of a condition, generally, the dosage administered can vary depending upon known factors such as age, health and weight of the recipient, type of concurrent treatment, frequency of treatment, and the like. Usually, a dosage of active ingredient can be between about 0.0001 and about 10 milligrams per kilogram of body weight. Precise dosage, frequency of administration and time span of treatment can be determined by a physician skilled in the art of administration of the respective therapeutic protein.

In addition, it has been discovered that dosages of 1 mg/kg and less can be effective in treating LAL deficiencies. The present invention provides methods of treating conditions comprising administering to a mammal (e.g. a patient, preferably a human patient) a therapeutically effective dose of lysosomal acid lipase between one time every 5 days and one time every 25 days, for example, between one time every 7 days and one time every 14 days. In one embodiment, the dose of lysosomal acid lipase administered is between about 0.1 mg and about 50 mg per kilogram of body weight, for example, the dose may be between about 1 mg and 5 mg per kilogram.

In one particularly useful embodiment, the invention provides methods of treating a condition by administering a dose of lysosomal acid lipase of between about 0.1 mg and 1.0 mg per kilogram of body weight in accordance with any therapeutically effective dosage regime such as those described herein.

The invention provides methods for treating any complication of LAL deficiency which may benefit from administering a therapeutically effective dose of LAL. In one embodiment, malabsorption and growth failure may be treated in accordance with the methods described herein. In another embodiment, complications seen in LAL deficiency patients including but not restricted to hepatomegaly and liver dysfunction may be treated using the methods provided herein.

The invention provides for treatment with recombinant LAL (e.g. recombinant human LAL) that can be produced by any useful protein expression system, for example, transgenic mammals and avians as is understood in the art. Other protein expression systems may include, but are not limited to, cell culture, bacteria, and plant systems.

The invention encompasses the administration of recombinant LAL as a part of a pharmaceutically acceptable composition by any route which may achieve the intended therapeutic effect, as determined by a physician skilled in the art. In one embodiment, the LAL may be administered by intravenous infusion over a period of about five hours. For example, the infusion may be facilitated by an ambulatory infusion pump connected to a vascular access port (e.g. a Port-a-Cath).

The invention also includes monitoring clinical and pathological presentation of the conditions, for example, Wolman Disease and CESD, in the mammal (e.g. the human patient). In one embodiment, the assessments consist of but are not limited to: lipid analysis, chest x-ray, liver function tests, stool chart, plasma mevalonic acid, immunogenicity, plasma lysosomal acid lipase, chitotriosidase, PARC, portal hypertension, anthropometry, volume and characterization of the liver, spleen, and gastrointestinal tract using, for example, imaging technology. For example, the aforementioned imaging technology may consist of ultrasound, magnetic resonance imaging, and nuclear magnetic resonance spectroscopy.

EXAMPLES

The present invention is further exemplified by the following examples. The examples are for illustrative purpose only and are not intended, nor should they be construed as limiting the invention in any manner.

Example 1

Construction of Vector (pALVIN-OVR1-I-hLAL-dSA) Carrying Recombinant Human Lysosomal Acid Lipase (rhLAL) Coding Sequence The nucleotide sequence of the hLAL gene in the pALVIN-OVR1-I-hLAL-dSA vector encodes a protein that is identical to the amino acid sequence of the protein produced by the human lysosomal acid lipase gene (GenBank Accession, NP_000226) (FIG. 1). Transcription of this sequence and subsequent translation of the resultant mRNA produces a 399 amino acid precursor protein, which is processed to a mature 378 amino acid protein identical to human LAL (GenBank Accession, NP_000226) (FIG. 1) as set forth in SEQ ID NO:1. Expression of the hLAL gene (see FIG. 2 for the cDNA sequence) in this Example is controlled by non-coding elements derived from the ovalbumin gene including enhancer, promoter, intronic, and 5' and 3' untranslated sequences. The ovalbumin gene produces ovalbumin, the major protein constituent of egg white. Activity of the chicken ovalbumin promoter is very specific to the cells within the chicken oviduct that produce egg white; expression in other tissues is minimal.

The plasmid vector pALVIN-OVR1-I-hLAL-dSA (FIG. 3A; the nucleotide sequence of which is shown in FIG. 4) was used to produce a replication-deficient retrovirus (RDR) that stably integrated the hLAL transgene into the genome of the founder (XLL109). This plasmid vector includes retroviral nucleotide sequences required for viral RNA packaging, reverse transcription and integration, but does not contain the intact sequences for the viral gag, pol and env genes. The methods used to generate the retroviral vector and their use in subsequent transgenesis procedures are described herein.

Figure 3B:
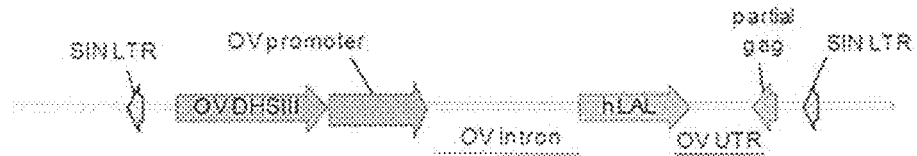

The retroviral portion of pALVIN-OVR1-I-hLAL-dSA is based on the ALV vector, pNLB. pNLB was modified such that the LTRs would be self-inactivating (SIN) (FIG. 3B). To accomplish this, 273 bp of the 3' LTR was deleted, which includes the enhancer and CAAT box of the U3 region. Because the inactivated U3 region at the 3' end of the retroviral sequence serves as a template for a new U3 region present at the 5' end of an integrated provirus, 5' LTR is normally also inactivated. The deletion of LTR sequences in the SIN construct decreases promoter interference on the internal promoter from the LTR, and minimizes the possibility for recombination of sequences to form a replication competent retrovirus. The new vector is termed pALVIN for ALV inactivation vector.

Downstream of the 5' LTR are the partial gag and env coding sequences, which were carried over from the pNLB vector. In pALVIN-OVR1-I-hLAL-dSA, a small portion (12%) of the gag protein precursor sequence remains (55% of the p19 mature peptide sequence) and a small portion (1.7%) of the env precursor sequence of RAV2 remains (GenBank Accession, AF033808). These truncated gag and env regions are unable to produce functional proteins needed to create replication competent retrovirus (Cosset, 1991).

Transcriptional and translational control elements of the chicken ovalbumin gene were inserted into pALVIN to create pALVIN-OV-1.1-I (sequence of which is shown in FIGS. 6A-6D; SEQ ID NO: 8). The first section of pALVIN-OV-1.1-I is composed of a contiguous section of the chicken ovalbumin gene which includes the 1.1 kb proximal promoter region, the first exon, first intron and part of the $2^{nd}$ exon. The next section is a stuffer insert fragment that takes the place of the ovalbumin protein coding sequences. The stuffer is followed by the 3' untranslated region (UTR) of the chicken ovalbumin gene, which includes sequences that facilitate proper processing of the mRNA, including polyadenylation. In general, the stuffer fragment is replaced by DNA fragments encoding the desired protein, in this case hLAL. The result is a vector that has specific elements that promote regulated transcriptional expression and translation of an mRNA in the oviduct of transgenic chickens, that closely mimics regulation of the endogenous ovalbumin mRNA, and that allows high expression of the protein of interest in egg white.

The pALVIN-OV-1.1-I vector includes the first intron of the ovalbumin gene. Because the intron is susceptible to splicing during the production and packaging of the retroviral RNA genome, we inserted the expression cassette in the opposite orientation relative to the LTRs. In this way the intron is not recognizable in the retroviral RNA and is packaged without splicing. For convenience all maps in this document are drawn with the LTRs in the opposite orientation and the expression cassette in the forward or clockwise orientation.

pALVIN-OV-1.1-I is the base vector into which the coding sequence (CDS) of hLAL was inserted. Two DNA fragments, hLAL adaptor and Syn hLAL, which make up the hLAL CDS and sequences required for compatibility with pALVIN-OV-1.1-I, were synthesized at Integrated DNA Technologies, Coralville, Iowa, (see FIGS. 7 and 8; SEQ ID NOs: 9 and 10). A 229 bp HpaI/BamHI fragment of hLAL adaptor and a 1113 bp BamHI/BstBI fragment of Syn hLAL were inserted into the 7882 HpaI/BstBI fragment of pALVIN-OV-1.1-I, thereby replacing the stuffer region with the hLAL CDS and creating pALVIN-OV-1.1-1-hLAL.

It was discovered that there was a cryptic splice site in the antisense strand of the hLAL CDS which prevented packaging of intact retroviral RNA. The cryptic splice site was removed by alteration of the DNA sequence without changing the amino acid sequence of hLAL. This change was performed by polymerase chain amplification of region 232 to 534 of pALVIN-OV-1.1-I-hLAL with primer 5'-AGAAACTGAGAGTGTCTTAT-3' (SEQ ID NO: 12) and primer 5'-TGACAGCTGTGGATCCAGAAACAAACATG-3' (SEQ ID NO: 13), creating a 329 bp amplicon. This amplicon was digested with BamHI and SexAI and ligated with the 8940 bp BamHI/SexAI fragment of pALVIN-OV-1.1-I-hLAL to create pALVIN-OV-1.1-I-hLAL-dSA.

Figure 10:
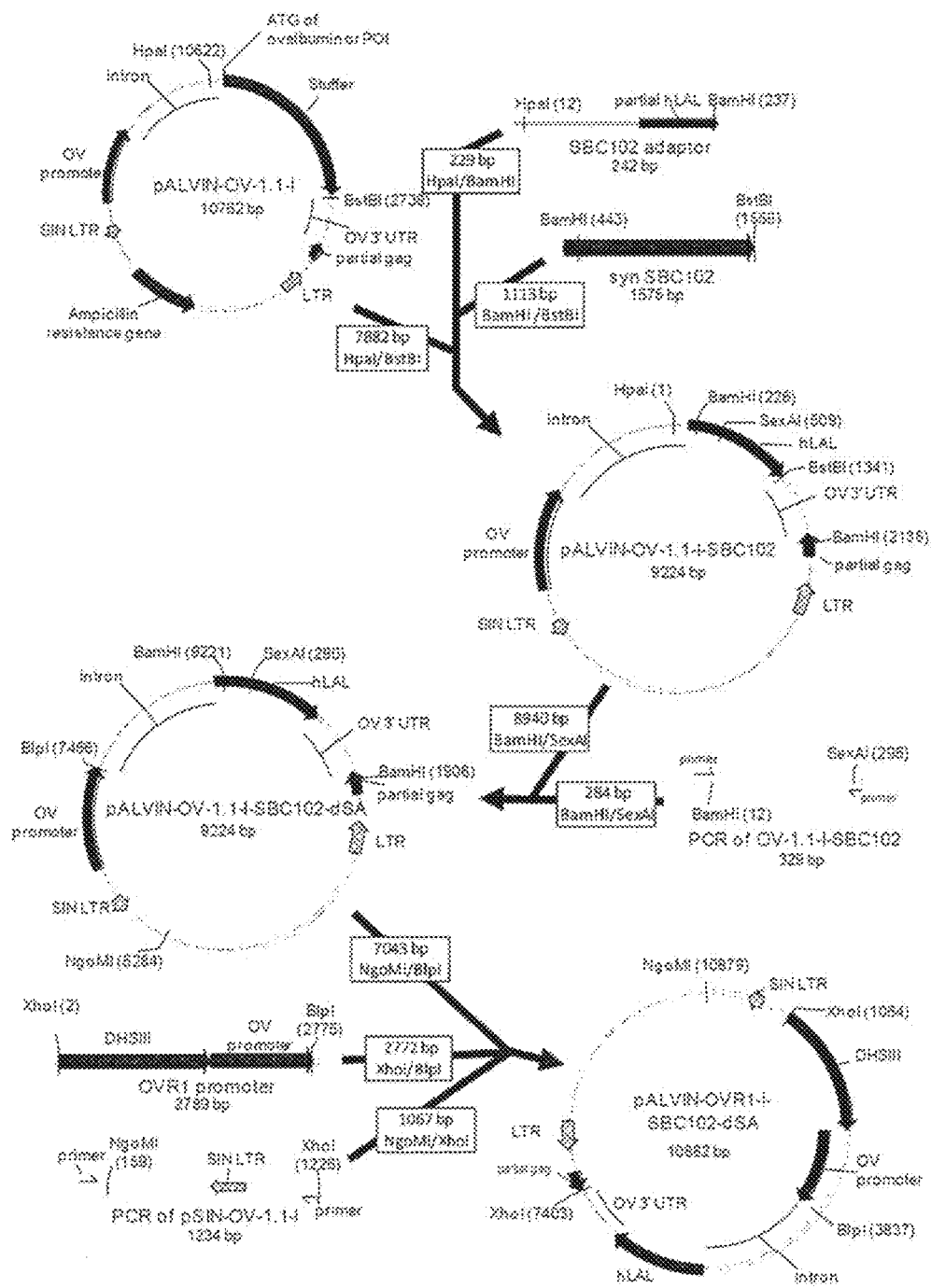
FIG. 10 depicts schematics of the steps used to construct the pALVIN-OVR1-I-hLAL-dSA vector.

A putative promoter enhancer which contains DNase hypersensitive site III (DHSIII) of the chicken ovalbumin gene (−3819 to −2169 relative to the OV promoter start site) (Kaye, Bellard et al. 1984) was inserted into pALVIN-OV-1.1-I-hLAL-dSA to create pALVIN-OVR1-I-hLAL-dSA. This was performed as follows: a DNA fragment which included the DHSIII enhancer and 1.1 kb proximal OV promoter termed OVR1 promoter (see FIG. 9; and SEQ ID NO: 11 for sequence) was isolated by digestion with XhoI and BlpI. To facilitate subcloning, an adaptor fragment, PCR of pSIN-OV-1.1-1 was generated by PCR amplification of region 6752 to 7974 of pALVIN-OV-1.1-I with primers 5'-GCCGCTCGAGCGAGGAATATAAAAAAATT-3' (SEQ ID NO: 14) and 5'-TCCGCGCACATTTCCCCGAA-3'(SEQ ID NO: 15) followed by digestion with NgoMI and XhoI. The 2772 bp XhoI/B1pI fragment of OVR1 promoter and 1067 bp NgoMI/XhoI fragment of PCR of pSIN-OV-1.1-I were inserted into the 7043 bp NgoMI/B1pI fragment of pALVIN-OV-1.1-I-hLAL-dSA, thereby creating pALVIN- OVR1-I-hLAL-dSA (see FIG. 10 for the construction schematics of pALVIN-OVR1-I-hLAL-dSA). The construction of the retroviral vector segment of the vector, denoted as pALVIN (aka pAVIJCR-A395.22.3.1-KM or pALV-SIN), is described in United States Patent Application 2008/0064862.

In addition, included is the production of LAL in accordance with the invention using a promoter and/or vector disclosed in US patent publication No. 2008/0064862, published Mar. 13, 2008, the disclosure of which is incorporated in its entirety herein by reference.

Example 2

Viral Particle Production

The G0 founder transgenic male, XLL109, carrying the hLAL transgene in its genome, was created by using a retroviral transgenesis method as follows. Replication-defective viral particles carrying the pALVIN-OVR1-I-hLAL-dSA vector were produced by transient transfection of an immortalized chicken fibroblast cell line. These chicken fibroblast cells were simultaneously transfected with three plasmids, pALVIN-OVR1-I-hLAL-dSA, pCMV-gag-pol and pCMV-VSV-G. pCMV-gag-pol expresses the gag and pol genes of RAV1 strain of the avian leukosis virus. pCMV-VSV-G expresses the envelope protein of the vesicular stomatitis virus. Four hours after transfection, the media was replaced with DMEM supplemented with 10% fetal bovine serum, 100 units/mL penicillin and 100 µg/mL streptomycin. Media was harvested at 48 hours post-transfection, filtered through a 0.45 micron filter (Millipore) and concentrated by ultracentrifugation. Concentrated retrovirus carrying the ALVIN-OVR1-I-hLAL-dSA transgene was collected and used in the transduction of early stage embryos. Note that because "p" is the notation for the plasmid form of vector, the "p" is absent from the transgene designations once the transgene is in the form of packaged vector or integrated transgene.

Example 3

Embryo Transgenesis

Integration of the ALVIN-OVR1-I-hLAL-dSA expression cassette into the genome of an embryo was achieved by transduction of early stage embryos (Speksnijder and Ivarie, 2000). Freshly laid fertilized White Leghorn eggs were obtained from a breeding colony. An aperture was made in the shell to provide access to the embryo. Seven microliters of concentrated replication deficient retrovirus particles carrying the ALVIN-OVR1-I-hLAL-dSA expression cassette described above were injected into the subgerminal cavity of the embryo. Eggs were sealed with hot glue, and then incubated and hatched under standard conditions. Progeny produced from these injections were given individual identification markers at hatch for identification and traceability. Blood samples from the progeny were transgene positive when analyzed by real-time PCR for the hLAL transgene using PCR primers specific for the hLAL coding sequence (as described below). This gave an indication that the transgenesis procedure was successful. The real-time PCR assay for the hLAL transgene utilizes Taqman® chemistry (Applied Biosystems). The forward and reverse primers were 5'-ACGACTGGCTTGCAGATGTCT-3' (SEQ ID NO: 16) and 5'-CCCCAAATGAAGTCAAGATGCT-3' (SEQ ID NO: 17), respectively. The Taqman® probe sequence was 5'-CCGGAATGCTCTCATGGAACACCAA-3'(SEQ ID NO: 18) and was labeled with FAM (as the emitter) at the 5' end and Iowa Black (as the quencher) at the 3' end. Primers, probe and 1 µl of extracted DNA was added to 30 µl Taqman® Universal Master Mix (Applied Biosystems). Control reactions included various dilutions of a plasmid bearing the hLAL sequence and DNA from wild-type chickens (data not shown). Standard cycling parameters were used on an Applied Biosystems 7500 Fast Real-Time PCR System.

Example 4

Identification of G0 Founder

Semen was collected from sexually mature males and DNA was extracted and assayed using the hLAL real-time PCR assay. The number of transgene copies in each sample was estimated using known standards (a plasmid bearing the hLAL gene) mixed with negative control semen DNA. The transgene cassette DNA content in male XLL109 was at a level that would allow transmission of the transgene to his progeny, as estimated by real-time PCR. This XLL109 male was the G0 transgenic founder and was bred with non-transgenic chickens to generate the G1 hemizygotic transgenic chickens.

Example 5

Propagation and Characterization of Hemizygotic G1 Avians

Figure 11:
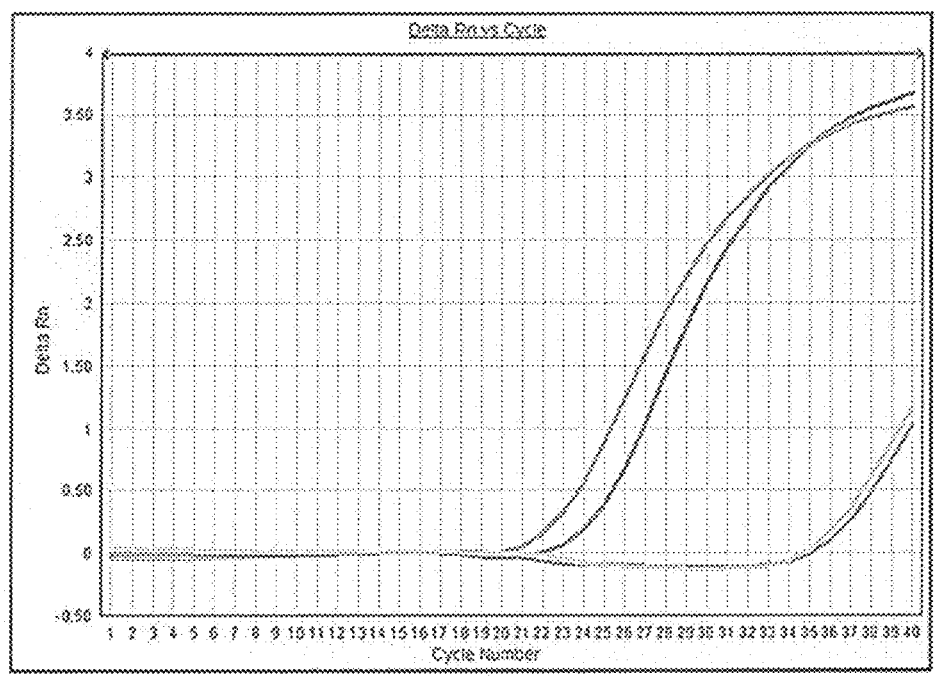
FIG. 11 depicts a real-time PCR analysis of blood DNA samples from a hemizygous transgenic G1 offspring of XLL109. The signals from duplicate DNA samples of hemizygous G1 progeny, 1LL7466, are indicated by the curves that initiate an increase in Delta Rn before cycle 22. The curves for two non-transgenic progeny are shown; these curves stay at or near baseline through at least 34 cycles.

Progeny sired by the transgenic founder XLL109 were tested for the presence of the transgene in blood cell DNA using the hLAL real-time PCR assay. Blood was collected from 1-2 week old progeny and DNA was extracted using a high-throughput technique (Harvey et al., 2002). The DNA solutions were not quantified prior to the Taqman assay to facilitate the high-throughput screen. Typically 1 µl of DNA solution contains 50 to 400 ng of DNA which is sufficient to generate a positive amplification signal. A total of 1,322 chicks sired by XLL109 were tested, and positive progeny were re-bled and tested for confirmation. According to the PCR results, 22 progeny were positive for the ALVIN-OVR1-I-hLAL-dSA transgene. An example of the Taqman results is shown in FIG. 11.

Example 6

Identification and Characterization of High-expression Line

One of the G1 chickens, 1LL7466, laid eggs with significantly higher levels of rhLAL protein in the egg white, as compared to the other G1 chickens. Southern blot analysis was performed on 1LL7466 and sibling G1 males to identify which sibling males had the same integration site as the high expressing chicken. Digests were performed with a restriction enzyme that cut only once within the transgene (BlpI), and the Southern blots were probed with a segment of the ovalbumin promoter or the hLAL coding sequence (FIGS. 12A-D). The position of the $2^{nd}$ restriction site, which resides in the flanking genomic region, varies depending on the site of integration. Thus the size of the BlpI band detected by the OV probe or hLAL probe is unique to each line generated.

Figure 12A:
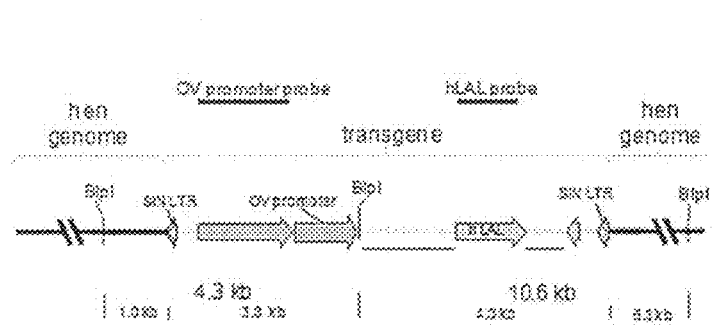
FIGS. 12A-D depict Southern analysis of G1 chickens carrying the ALVIN-OVR1-I-hLAL-dSA transgene.
Figure 12B:
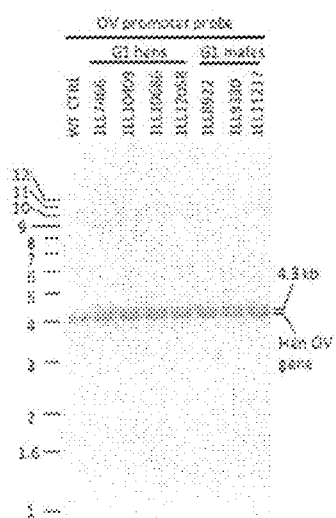
Figure 12C:
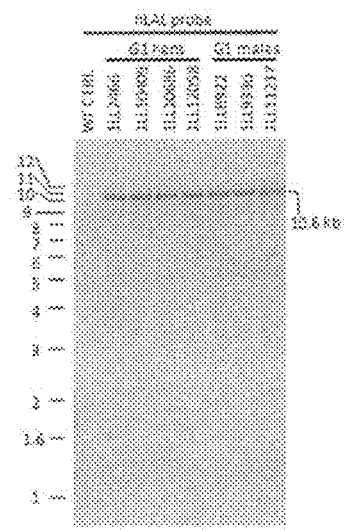
Figure 12D:

The OV probe detected a single band of 4.1 kb in BlpI-digested DNA from wild-type chickens, which corresponded to the expected size of a BlpI segment within the endogenous ovalbumin gene of the chicken genome (FIGS. 12B and 12D). A second band of 4.3 kb was detected with chicken 1LL7466, which corresponded to the transgene band. Three additional female siblings, 1LL10409, 1LL10686 and 1LL12058 and three additional male siblings, 1LL8922, 1LL9330 and 1LL11217 displayed the 4.3 kb band, indicating that these siblings might be of the same line (FIGS. 12B and 12D).

As expected the hLAL probe did not detect a band in DNA from wild-type chickens as the DNA sequence of the chicken lysosomal acid lipase gene and the coding sequence for the recombinant human lysosomal acid lipase are sufficiently differentiated to not permit hybridization under the conditions used in these Southern assays (FIG. 12C). The hLAL probe detected a single band of ~10.6 kb in BlpI-digested genomic DNA from the same chickens that were positive for the 4.3 kb band detected by the OV probe, indicating that these 7 G1 chickens have the same integration site and thus are of the same line.

No other bands were detected, indicating that 1LL7466, 1LL10409, 1LL10686, 1LL12058, 1LL8922, 1LL9330 and 1LL11217 all had a single integration site.

The Southern analysis also indicated that the transgene was integrated as the bands detected by the OV and hLAL probes were of different sizes and greater in size than from the transgene alone. A map showing the predicted structure of the integrated transgene and position of BlpI sites in the flanking genomic regions is shown in FIG. 12A.

Figure 13A:
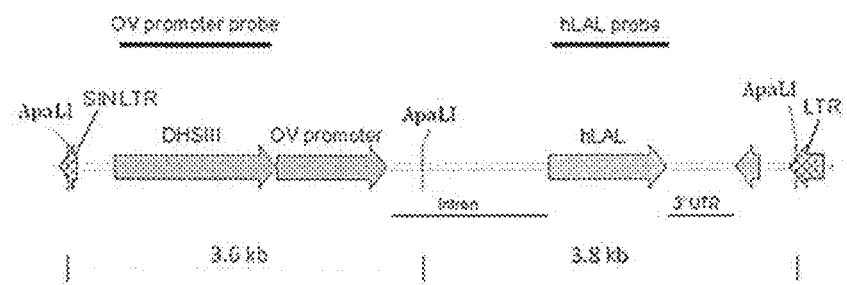
FIG. 13A depicts schematic of the ALVIN-OVR1-I-hLAL-dSA transgene. The size of ApaLI bands predicted to be detected by the OV probe and hLAL probe are also shown.
Figure 13B:
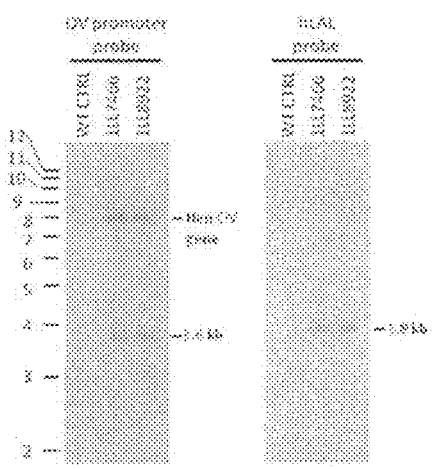
FIG. 13B depicts schematic of a Southern blot analysis of the ALVIN-OVR1-I-hLAL-dSA transgene for confirmation of transgene size. Southern blot of genomic DNA digested with ApaLI and probed with either the OV probe (left panel) or hLAL probe (right panel). WT CTRL is genomic DNA isolated from a non-transgenic chicken. The ID number of the G1s is indicated above each lane. The position and size (kb) of the molecular weight markers are shown to the left of the blots. The position and size of the detected transgene fragments (OV promoter probe, 3.6 kb; hLAL probe, 3.8 kb) and endogenous ovalbumin gene (7.7 kb) are shown to the right of the blots.

To confirm that the transgene is intact, two steps were taken. First, the hLAL coding sequence was isolated by PCR from 1LL7466. The PCR products were sequenced on both strands from the hLAL start codon to the stop codon. The DNA sequence was exactly as expected, indicating no changes in the DNA sequence of coding regions in the transgene. Second, Southern blot analysis was conducted using restriction enzyme ApaLI, which digests intact transgene into 2 segments, 3.6 and 3.8 kb (FIG. 13A). Both the 3.6 and 3.8 kb bands were detected in ApaLI-digested genomic DNA from G1s, indicating that the transgene was integrated in a fully intact form (FIG. 13B).

Example 7

Propagation and Characterization of G2s

Figure 14:
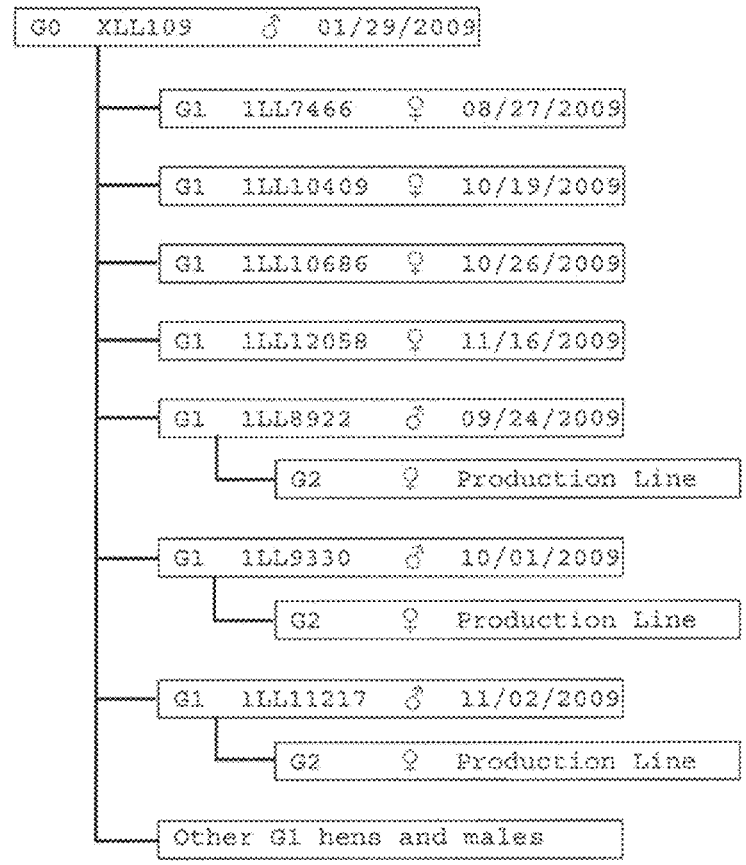
FIG. 14 depicts a lineage of transgenic chickens. Shown for each chicken are the generation number (G0, G1 or G2), identification number, gender and hatch date. Other G1 chickens are those of other lineages.

FIG. 14 shows the lineage of the hLAL G2s descended from a single G0 founder, XLL109. At the G1 stage, the transgene was characterized with regard to copy number, integrity, hLAL sequence and integration site—and seven G1 transgenics were identified and characterized (four chickens and three roosters). Propagation of the G2s was accomplished by artificial insemination of non-transgenic chickens with semen collected from the G1 sires 1LL8922, 1LL9330 and 1LL11217 (FIG. 14). Each inseminated chicken, her eggs and subsequent progeny were housed separately from the other progeny. Hatched progeny were tested for presence of the hLAL transgene using the hLAL real-time PCR assay. Because G1 founders were hemizygous with respect to the transgene, half of the progeny were expected to be transgenic G2s. Of 610 G2 progeny analyzed to date, 330 or 54% were transgenic.

Example 8

Genetic Analysis of the hLAL Avians

After identification of each G2 chicken by the hLAL real-time PCR assay of blood DNA, the production line is subjected to the following genetic assays: the hLAL gene was PCR-amplified from blood DNA and sequenced to confirm 100% homology with the human sequence; the transgene integration site was confirmed by integration site PCR, as described above. The PCR sequencing and integration site analysis was performed on: each chicken in a <10 chicken production line; 10% of chickens (minimum 10) for 11-100 chicken production line; 5% of chickens (minimum 10) for 101-1000 chicken production line; 1% of chickens (minimum 50) for 1001-10,000 chicken production line; 0.1% of chickens (minimum 100) for >10,001 chicken production line. Detailed records were maintained at every step of the growing and production phase.

Example 9

Purification of hLAL from Egg White

Egg white (EW) containing LAL was solubilized at pH 6 overnight and clarified through centrifugation (or depth filtration) with 0.2 um filtration. The EW was adjusted with 1 M NaOAc buffer (pH 4) to pH 6.

The clarified EW was loaded onto a Phenyl-HIC column (EW:column size=2:1) equilibrated with 20 mM phosphate/ 137 mM NaCl buffer (pH 6). After the completion of loading, the column was washed with equilibration buffer and 5 mM phosphate buffer (pH 6). The LAL was eluted with 30% propylene glycol with 5 mM Tris buffer (pH 7.2).

The eluted LAL fraction was adjusted to pH 5 with 1 M acid acid and then loaded onto a GigaCap S column (EW: column size=10:1). The column was equilibrated with 50 mM NaOAc buffer (pH 5). After completion of loading, the column was washed with the equilibration buffer. The LAL was eluted with 50 mM NaOAc/60 mM NaCl (pH 5).

Figure 15:
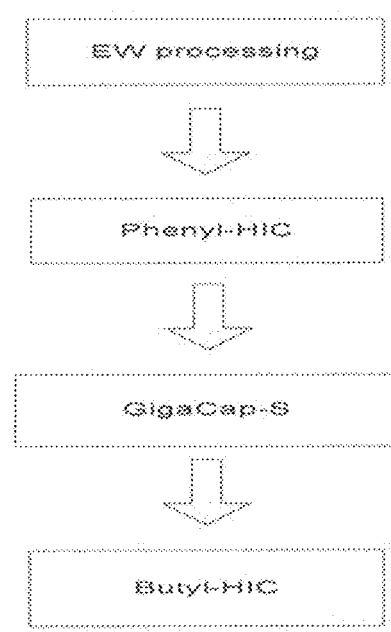
FIG. 15 depicts the purification steps of hLAL from egg white.

The LAL fraction off the GigaCap S column was adjusted to pH6 with 1 M Tris buffer and then loaded onto a Butyl-HIC column (EW:column size=10:1). The column was equilibrated with 20 mM phosphate/137 mM NaCl buffer (pH 6). After the completion of loading, the column was washed with equilibration buffer and 5 mM phosphate buffer (pH 6). The pure LAL was eluted with 50% propylene glycol with 5 mM Tris buffer (pH 7.2). FIG. 15 depicts the purification steps of hLAL from egg white.

Example 10

Carbohydrate analysis of Transgenic Avian Derived hLAL

The oligosaccharide structures were determined for avian derived human LAL by employing the following analysis techniques as are well known to practitioners of ordinary skill in the art.

Two hundred micrograms were digested with trypsin and chymotrypsin for 18 h at 37° C. in 0.1 M Tris-HCl, pH 8.2, containing 1 mM $CaCl_2$. The digestion products were enriched and freed of contaminants by Sep-Pak C18 cartridge column. After enrichment, the glycopeptides were digested with 2 µl of PNGaseF (7.5 unit/ml) in 50 µl of 20 mM sodium phosphate buffer, pH 7.5, for 18 h at 37 ° C. Released oligosaccharides were separated from peptide and enzyme by passage through a Sep-Pak C18 cartridge column.

The glycan fraction was dissolved in dimethylsulfoxide and then permethylated based on the method of Anumula and Taylor (Anumula and Taylor, 1992). The reaction was quenched by addition of water and per-O-methylated carbohydrates were extracted with dichloromethane. Per-O-methylated glycans were dried under a stream of nitrogen.

MALDI/TOF-MS (Matrix assisted laser desorption ionization time-of-flight mass spectrometry) was performed in the reflector positive ion mode using α-dihydroxybenzoic acid (DHBA, 20 mg/mL solution in 50% methanol:water) as a matrix. All spectra were obtained by using a Microflex LRF (Bruker).

MALDI-TOF-MS analysis and ESI MS/MS (electrospray ionization tandem mass spectrometry) were performed on the oligosaccharides after release from the peptide backbone and purification as is understood in the art. Samples of the individual polysaccharide species were also digested with certain enzymes and the digest products were analyzed by HPLC as is understood in the art.

It is believed that there are about six N-linked glycosylation sites present on human LAL. See, Zschenker, et al (2005) *J. Biochem.*, Vol 137, p 387-394, the disclosure of which is incorporated in its entirety by reference This reference also indicates that there may be an O-linked glycosyation site on Human LAL. The N-linked oligosaccharide structures identified are shown in FIG. 16.

The data revealed that many or all of these structures were found as an N-linked Glycosylation structure in LAL produced in accordance with the invention (FIG. 16). For example, A-n is found attached to LAL produced in accordance with the invention. For example, O-n is found attached to LAL produced in accordance with the invention. For example, at least one of B-n, C-n and D-n is found attached to LAL produced in accordance with the invention. For example, at least one of E-n and F-n is found attached to LAL produced in accordance with the invention. For example, at least one of I-n and J-n is found attached to LAL produced in accordance with the invention. For example, at least one of K-n and L-n is found attached to LAL produced in accordance with the invention. For example, at least one of M-n and N-n is found attached to LAL produced in accordance with the invention. For example, G-n is found attached to LAL produced in accordance with the invention. For example, H-n is found attached to LAL produced in accordance with the invention.

Example 11

N-glycan Species of Transgenic Avian Derived LAL

Purified samples of transgenic avian derived hLAL (600 μg/sample) were dialyzed using a Tube-O-Dialyzer (4.0 kDa cut-off membrane; G BioSciences) against nanopure water at 4° C. for about 24 hours to remove salts and other contaminants. Nanopure water was replaced four times during the entire dialysis period.

After dialysis, each of the samples was divided into three aliquots: ~¼ of sample weight for neutral and amino sugars analysis, ~¼ of sample weight for mannose-6-phosphate analysis, and ~½ of sample weight for oligosaccharide profiling. The aliquot intended for neutral and amino sugars analysis was hydrolyzed with 2 N trifluoroacetic acid (TFA) at 100° C. for 4 hours and the aliquot for mannose-6-phosphate analysis was hydrolyzed with 6.75 N TFA at 100° C. for 1.5 hours. The hydrolysates were then dried under $N_2$, redissolved with 50 μL $H_2O$, sonicated for 7 min ice and transferred to an injection vial. However, the neutral and amino sugar samples were diluted 2 times because the peaks produced from the originally dissolved hydrolysates were too large.

A mix of standards for neutral and amino sugars, and for mannose-6-phosphate with a known number of moles was hydrolyzed in the same manner and at the same time as the sample. Four concentration of the neutral and amino sugar standard mix (Fuc & GalNAc, 0.2, 0.4, 0.8, and 1.6 nmoles per 10 μL; GlcNAc, 0.5, 1.0, 2.0, and 4.0 nmoles per 10 μL; Gal & Man, 0.3, 0.6, 1.2, and 2.4 nmoles per 10 μL; and Glc, 0.1, 0.2, 0.4, and 0.8 nmoles per 10 μL) and mannose-6-phosphate (640, 1280, 2560, 5120 picomoles per10 μL) were prepared to establish a calibration equation. The number of moles of each sugar in the sample was quantified by linear interpolation from the calibration equation.

The neutral and amino sugars and mannose-6-phosphate were analyzed by HPAEC using a Dionex ICS3000 system equipped with a gradient pump, an electrochemical detector, and an autosampler. The individual neutral and amino sugars, and mannose-6-phosphate were separated by a Dionex CarboPac PA20 (3×150 mm) analytical column with an amino trap. The gradient programs used eluents A, degassed nanopure water and B, 200 mM NaOH for neutral and amino sugars, and C, 100 mM NaOH and D, 1 M sodium acetate in 100 mM NaOH for mannose-6-phosphate. Injection (10 μL/injection) was made every 40 minutes for neutral and amino sugar determination and every 35 minutes for mannose-6-phosphate determination. All methods were based on protocols described by Hardy and Townsend (Hardy, M. R., and Townsend, R. R., "High-pH anion-exchange chromatography of glycoprotein-derived carbohydrates", 1994, *Methods Enzymol.* 230: 208-225). Instrument control and data acquisition were accomplished using Dionex chromeleon software. Results are shown in Table 1 below. The control sample is ovomucoid purified from EW.

TABLE 1

Monosaccharide composition of control and LAL by HPAEC.

| Sample ID | Analyte | nano-moles | nano-moles/μg | mole % |
|---|---|---|---|---|
| Control | Fucose | nd | — | — |
| | N-acetyl galactosamine | 5.066 | 0.020 | 9.6 |
| | N-acetyl glucosamine | 26.947 | 0.108 | 51.4 |
| | Galactose | 3.876 | 0.016 | 7.4 |
| | Glucose | nd | — | — |
| | Mannose | 16.565 | 0.066 | 31.6 |
| | Mannose-6-phosphate | nd | — | — |
| | N-acetyl neuraminic acid | ndm | — | — |
| | N-glycolyl neuraminic acid | ndm | — | — |
| Transgenic Avian derived hLAL | Fucose | nd | — | — |
| | N-acetyl galactosamine | nd | — | — |
| | N-acetyl glucosamine | 17.932 | 0.120 | 37.6 |
| | Galactose | 0.879 | 0.006 | 1.8 |
| | Glucose | nd | — | — |
| | Mannose | 23.290 | 0.155 | 48.8 |
| | Mannose-6-phosphate | 5.642 | 0.038 | 11.8 |
| | N-acetyl neuraminic acid | ndm | — | — |
| | N-glycolyl neuraminic acid | ndm | — | — | nd = not detected; ndm = not determined.

Structural Features of LAL

LAL has 6 potential sites in its amino acid sequence for N-linked glycosylation, $Asn^{36}$, $Asn^{72}$, $Asn^{101}$, $Asn^{161}$, $Asn^{273}$, and $Asn^{321}$. Five of these, $Asn^{36}$, $Asn^{101}$ $Asn^{161}$, $Asn^{273}$ and $Asn^{321}$ were found to be glycosylated while $Asn^{72}$ was unglycosylated or substantially unglycosylated (substantially unglycosylated means in a mixture of LAL molecules, fewer $Asn^{72}$ are glycosylated than any of $Asn^{36}$, $Asn^{101}$ $Asn^{161}$, $Asn^{273}$ and $Asn^{321}$). Accordingly, one aspect of the invention is LAL (e.g., human LAL) which is unglycosylated and/or substantially unglycosylated at $Asn^{72}$, and production and use of such LAL. However, LAL having a glycosylated $Asn^{72}$ is within the scope of the invention. The N-glycan structures primarily consist of a mixture of bi-, tri- and tetraantennary structures with N-acetylglucosamine, mannose and mannose-6-phosphate (M6P) as the major sugars. Each site appears to have a favored set of structures (Table 2 and FIG. 17) which is one aspect of the invention. For example, M6P-modified N-glycans reside at least at $Asn^{101}$ $Asn^{161}$ and $Asn^{273}$. The non-phosphorylated structures are typical of N-glycans found on endogenous egg white proteins. No O-linked glycans were detected as determined by lack of N-acetylgalactosamine (GalNac). No sialic acid was detected which is consistent with previously determined N-glycan structures of other endogenous and exogenous proteins produced in accordance with the invention. The invention includes LAL glycosylated with one or more of the oligosaccharide structures disclosed herein.

TABLE 2

Site residence of LAL glycan structures as determined by LC/MS of glycopeptides.

| Site | Glycan structure |
|---|---|
| Asn$^{36}$ | GlcNAc4Man3GlcNAc2 |
|  | Hex1GlcNAc4Man3GlcNAc2 |
| Asn$^{72}$ | None detected |
| Asn$^{101}$ | Phos2Man7GlcNAc2 |
| Asn$^{161}$ | Phos1Man6GlcNAc2 |
|  | GlcNAc1Phos1Man6GlcNAc2 |
|  | Man3GlcNAc2 |
|  | GlcNAc2Man3GlcNAc2 |
|  | GlcNAc3Man3GlcNAc2 |
|  | GlcNAc4Man3GlcNAc2 |
|  | Hex1GlcNAc4Man3GlcNAc2 |
| Asn$^{273}$ | Man7GlcNAc2 |
|  | Man8GlcNAc2 |
|  | Man9GlcNAc2 |
|  | Phos1Man8GlcNAc2 |
|  | Phos1Man9GlcNAc2 |
| Asn$^{321}$ | GlcNAc2Man3GlcNAc2 |
|  | GlcNAc3Man3GlcNAc2 |
|  | GlcNAc4Man3GlcNAc2 |
|  | Hex1GlcNAc4Man3GlcNAc2 |
|  | GlcNAc5Man3GlcNAc2 |
|  | Hex1GlcNAc5Man3GlcNAc2 |
|  | GlcNAc6Man3GlcNAc2 |
|  | Hex1GlcNAc6Man3GlcNAc2 |

Hex, galactose; Phos, phosphate; Man, mannose; GlcNAc2, N-acetylglucosamine

Methods

Monosaccharide composition, including the neutrals, amino and M6P, was determined qualitatively and quantitatively by high pH anion exchange chromatography-pulsed amperometric detection (HPAEC-PAD).

The structures of the predominant glycans were determined with data from several mass spectrometry methods (MALDI-TOF, NSI-MS/MS and glycopeptide LC-MS).

Figure 18:
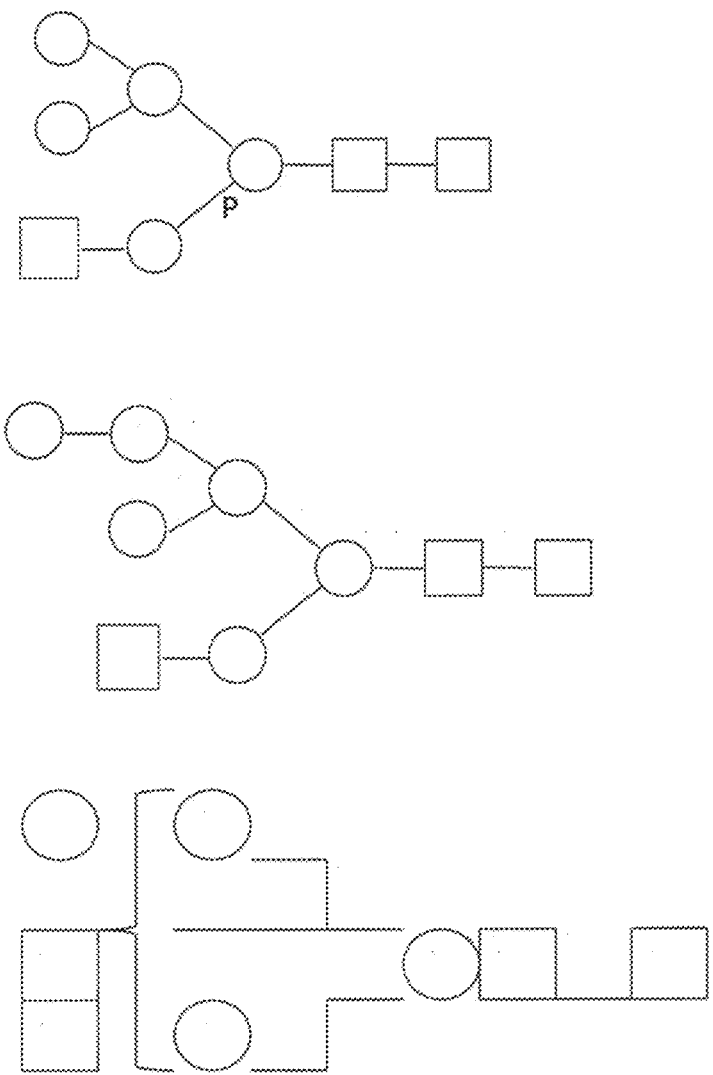
FIG. 18 depicts phosphorylated N-glycans released by PNGase and analyzed by MALDI-TOF. Structures are shown.
Figure 19:
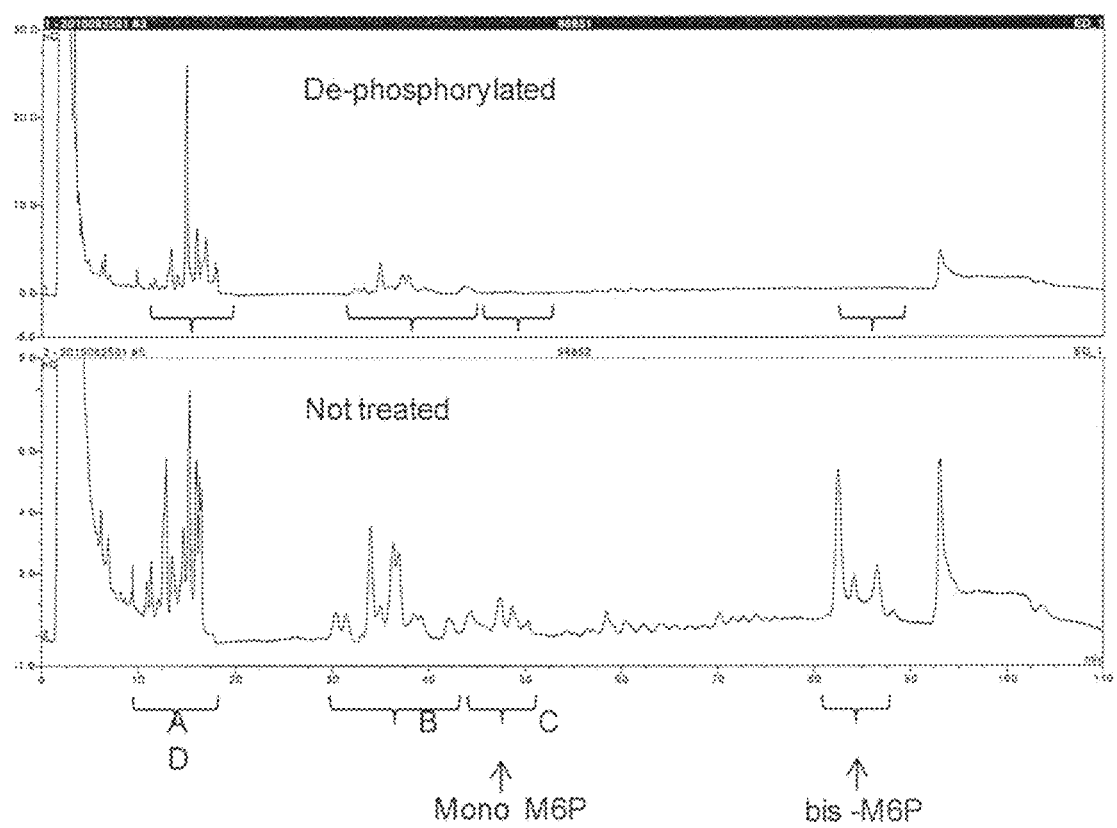
FIG. 19 depicts the effect of dephosphorylation of LAL on HPAEC-PAD retention time of N-glycans. LAL produced in accordance with the invention was dephosphorylated with bacterial alkaline phosphatase (upper panel) or left untreated (lower panel). Released N-glycans were analyzed by HPAEC-PAD.

MALDI-TOF was useful for determination of neutral N-glycans and was able to detect phosphorylated N-glycans (FIG. 18). NSI-MS/MS was employed to determine the nature of minor peaks in the MALDI-TOF spectra, some of which were attributed to phosphorylated N-glycans (FIG. 19). Efforts to improve the ability of MALDI-TOF to detect phosphorylated N-glycans were not fruitful.

LC/MS of glycopeptides was able to detect neutral and phosphorylated structures and was able to determine the position of specific structures in the amino acid sequence of LAL (data summarized in FIG. 17 and Table 2).

To determine which peaks in the HPAEC-PAD chromatogram are due to phosphorylated N-glycans, LAL was treated with phosphatase and analyzed (FIG. 3). Peaks in groups C and D decreased in area under the curve (AUC) while a peak in group A became more prominent. Peaks in group B did not change in proportion to the other peaks. Based on the knowledge that retention time is proportional to the degree of charge (either due to phosphorylation or sialylation), it is contemplated that group C is composed of N-glycans with one phosphate (mono M6P) and group D composed of N-glycans with two phosphates (bis-M6P).

The retention time was also affected by composition and relative structural position of the neutral and amino monosaccharides. Such examples include the presence of galactose, the presence of a bisecting GlcNac and the degree of GlcNac substitution. Such factors contribute to the multiplicity of peaks in the HPAEC-PAD chromatogram.

Example 12

In Vitro Enzyme Activity Analysis of Transgenic Avian Derived hLAL in Egg White

Activity of Lysosomal Acid Lipase in egg white was determined using the fluorogenic substrate 4-methylumbelliferyl-oleate assay essentially as described in Yan et al. (2006), *American Journal of Pathology*, Vol. 169, No. 3, p 916-926, the disclosure of which is incorporated in its entirety herein by reference.

A stock solution of 4-methylumbelliferyl oleate (4-MUO) was prepared consisting of 2.5 mM 4-MUO in 4% Triton X-100. The assay was performed in a microtiter plate each well containing 62.5 µl of 0.2 M Sodium Citrate (pH 5.5) in 0.01% Tween80, 12.5 µl of egg white sample and 25 µl of the 2.5 mM 4-MUO. Change in fluorescence was monitored for 30 minutes at 37° C. using a Bio-Tek Synergy HT fluorometric microplate reader (excitation 360 nm and emission 460 nm). Prior to assay, egg white containing the hLAL was diluted to an enzyme concentration that resulted in the reaction continuing linearly for at least 30 minutes. The reaction was stopped with 50 µl of 0.75 M Tris-HCl, pH 8.0 and the endpoint fluorescence signal was measured in the same plate reader used above (excitation 360 nm and emission 460 nm).

Units of activity were determined using 4-methylumbelliferyl as a standard. One unit (U) is defined as the amount of enzyme which results in the formation of 1 umole of 4-methylumbelliferyl/min under the assay conditions described above. Non-hLAL containing egg white was used as a negative control.

Egg white samples which were positive for hLAL contained between 1 U and 100 U of activity per ml egg white. Egg white from 21 G1 chickens was analyzed. Egg white from 10 of the chickens tested positive for hLAL activity.

Example 13

In Vitro Analysis of Transgenic Avian Derived LAL

The ability of LAL produced in the oviduct cells of transgenic avians (referred to herein as "SBC-102," "avian derived LAL," "LAL," or "hLAL") to bind to cells and be internalized to the lysosomal compartment, was examined in vitro using macrophage and fibroblast cells. When incubated with macrophage cells, fluorescently-labeled SBC-102 was found to localize to the lysosome. This effect could be attenuated by using a mannose polysaccharide competitor, implicating the N-acetylglucosamine/mannose (GlcNAc/mannose) receptor as a mechanism of recognition and uptake by these cells. SBC-102 increased the cell-associated LAL activity in both LAL-deficient human fibroblasts and normal murine fibroblasts after incubation in vitro, indicating that exposure to SBC-102 can result in substantial replacement of deficient enzymatic activity.

Mannose-6-phosphate (M6P) is present in the oligosaccharide structures of SBC-102 which have been shown to be involved in the delivery of lysosomal enzymes to a wide variety of cells types via the ubiquitous M6P receptor.

LAL was purified from the egg white of transgenic hens. Oregon Green NHS was obtained from Invitrogen™ (#0-

10241). The rat alveolar macrophage line, NR8383, and the mouse fibroblast line, NIH-3T3, were obtained from ATCC. LAL-deficient Wolman's fibroblasts were obtained from Coriell Institute for Medical Research and LysoTracker® Red was obtained from Invitrogen™.

Enzyme labeling: 4 mg of transgenic avian derived LAL in PBS was labeled with Oregon Green, according to the manufacturer's recommendations and reaction was subsequently dialyzed against PBS then concentrated.

Macrophage uptake: Fluorescently-labeled transgenic avian derived LAL (5 μg/mL) and LysoTracker® Red were incubated with NR8383 cells for 2 hours. Cells were examined by co-focal fluorescence microscopy using a sequential scanning mode at 488 nm and then 514 nm.

Competitive inhibition with mannan: Fluorescently-labeled SBC-102 (5 ug/mL) and mannan were incubated with NR8383 cells for 2 hours. Cells were trypsinized and LAL uptake measured by florescence-activated cell sorting using median fluorescence intensity as the endpoint.

Figure 20:
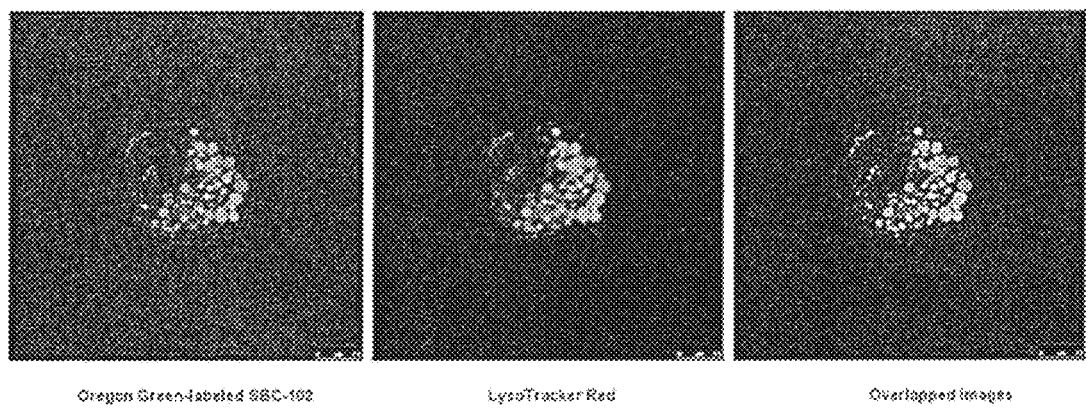
FIG. 20 depicts the co-localization of recombinant human LAL (SBC-102) and lysosomal marker in the lysosomes of these cells examined by confocal fluorescence microscopy using a sequential scanning mode.

The ability of transgenic avian derived LAL to be taken up and subsequently incorporated into the lysosomes of target cells was examined using the macrophage cell line, NR8383. Fluorescently-labeled transgenic avian derived LAL and the lysosomal marker, "LysoTracker® Red" (Invitrogen™), were incubated with cells for 2 hours. The co-localization of transgenic avian derived LAL and lysosomal marker in the lysosomes of these cells was subsequently examined by confocal fluorescence microscopy using a sequential scanning mode (FIG. 20). The LAL demonstrated localization to lysosomes, which is consistent with similar in vitro studies using rhLAL from a variety of sources.

Figure 21:
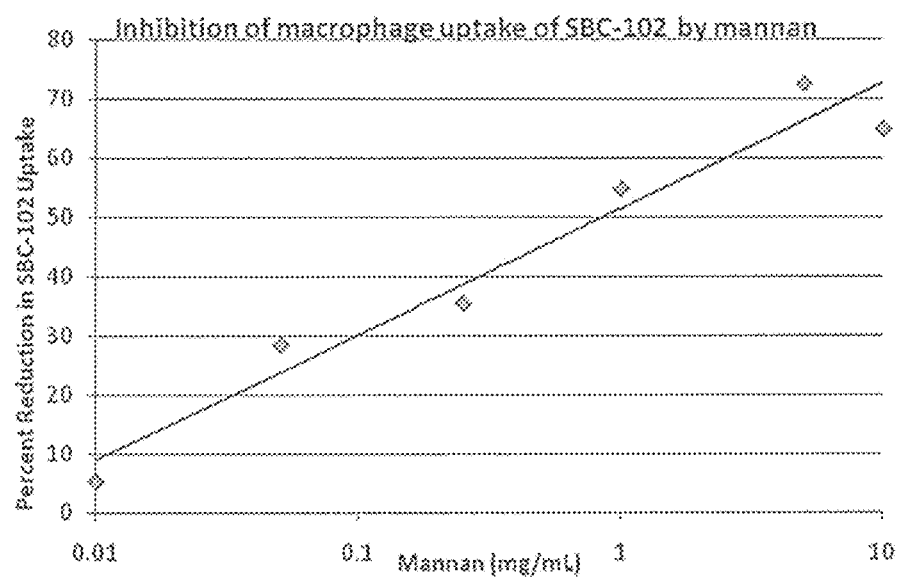
FIG. 21 depicts the binding specificity of recombinant human LAL (SBC-102) to the GlcNAc/mannose receptor assessed by competitive binding assays using the macrophage cell line, NR8383.

The binding specificity of transgenic avian derived LAL to the GlcNAc/mannose receptor has been assessed by competitive binding assays using the macrophage cell line, NR8383 (FIG. 21). Fluorescently-labeled (Oregon Green) transgenic avian derived LAL at 5 μg/mL and various concentrations of the mannose-containing oligosaccharide, mannan, were co-incubated with cells for 2 hours. The relative inhibition of transgenic avian derived LAL uptake by mannan, as compared with no mannan control, was quantified by fluorescence-activated cell sorting analysis using median fluorescence intensity as the endpoint. A mannose dose dependent inhibition in transgenic avian derived LAL binding/uptake was observed, which is consistent with transgenic avian derived LAL: GlcNAcR interaction.

In addition, mannose-6-phosphate mediated uptake in fibroblast cells was demonstrated by competition experiments with mannose-6-phosphate (results not shown).

Figure 22:
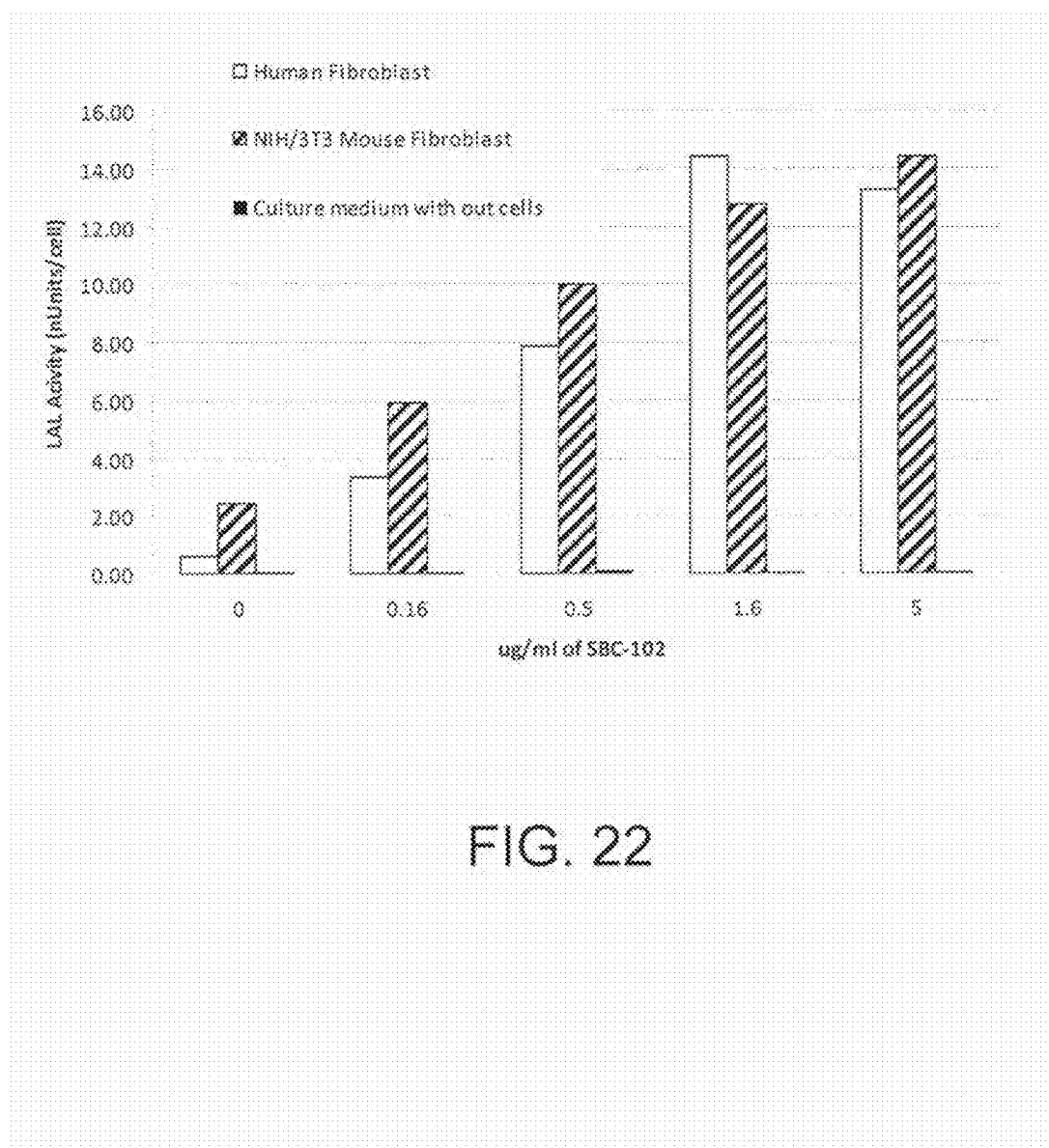
FIG. 22 depicts the activity of recombinant human LAL in cells in normal and LAL-deficient cells in vitro.

The ability of transgenic avian derived LAL exposure to increase LAL activity in cells has been examined using both normal and LAL-deficient cells in vitro. Fibroblasts isolated from a Wolman's patient and normal murine fibroblasts (NIH-3T3) were incubated in the presence of transgenic avian derived LAL at concentrations of either 0, 0.16 or 0.5 μg/mL for 5 hours. Cells were then washed to remove non-specific signal and cell lysates were assayed for LAL activity using 4-MUO substrate. Endogenous cell-associated LAL activity was lower in Wolman's fibroblasts compared to NIH-3T3 and dose-dependent increases in activity were observed in both cell types after incubation with transgenic avian derived LAL (FIG. 22).

Example 14

In Vivo Analysis of Transgenic Avian Derived LAL

LAL-deficient Yoshida Rats (i.e., Homozygous) (see Kuriyama et al. (1990), Journal of Lipid Research, vol. 31, p 1605-1611; Nakagawa et al., (1995) Journal of Lipid Research, vol. 36, p 2212-2218; and Yoshida and Kuriyama (1990) Laboratory Animal Science, vol. 40, p 486-489) were treated with either SBC-102 (5 mg/kg, IV) or placebo, once/week for four weeks beginning at four weeks of age. For each administration the SBC-102 was injected into the rat tail vein in two equal doses (2.5 mg/kg) 30 minutes apart. Rats and aged-matched wild-type controls were examined one week after the final dose. Analyses were done in triplicate.

Gross pathologic examination of the SBC-102 treated animals demonstrated normalization in liver color in addition to reduction in organ size. The SBC-102 treated rats showed essentially normal liver histology in marked contrast to the substantial accumulation of foamy macrophages in the vehicle-treated animals (data not presented). Serum alanine and aspartate transferase levels, which are elevated in $LAL^{-/-}$ rats, were also reduced in SBC-102 treated rats (not shown).

Figure 23:
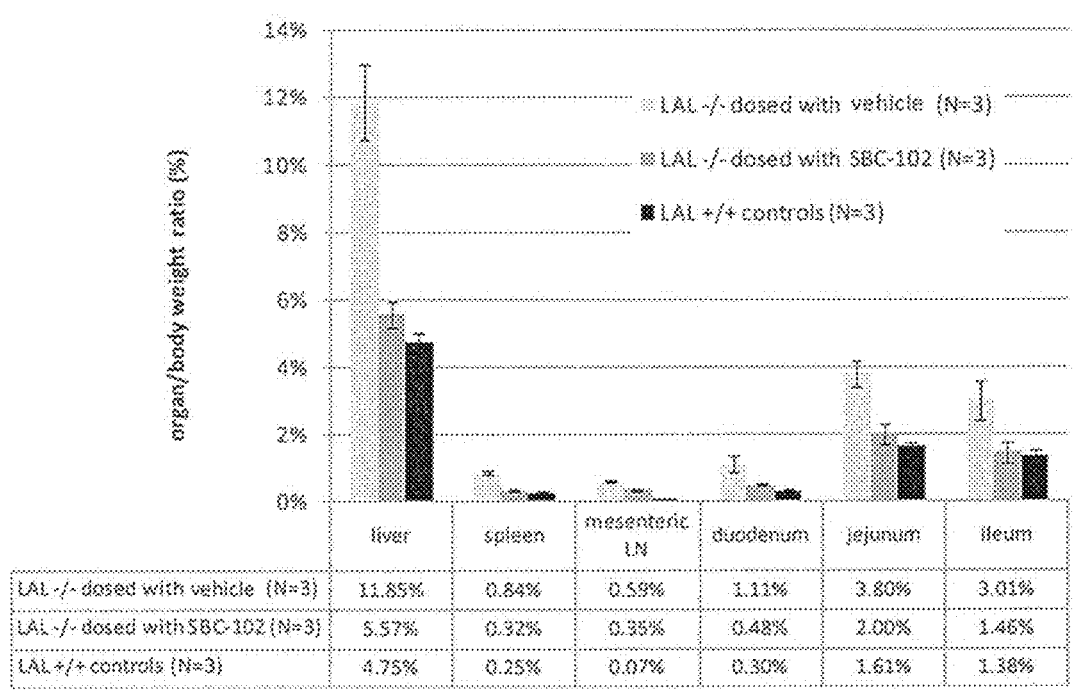
FIG. 23 depicts the effect of recombinant human LAL (SBC-102) treatment on internal organs mass of LAL deficient rats. Organ size is represented as percent of body weight determined at 8 weeks of age, in LAL$^{-/-}$ rats and LAL$^{+/+}$ rats after weekly administration of vehicle or SBC-102 at 5 mg/kg for 4 weeks.

Mass of internal organs and tissue was determined for each rat and the data is shown in FIG. 23. Organ size is represented as percent of body weight determined at 8 weeks of age, in $LAL^{-/-}$ rats and $LAL^{+/+}$ rats after weekly administration of vehicle or SBC-102 at 5 mg/kg for 4 weeks.

Figure 24:
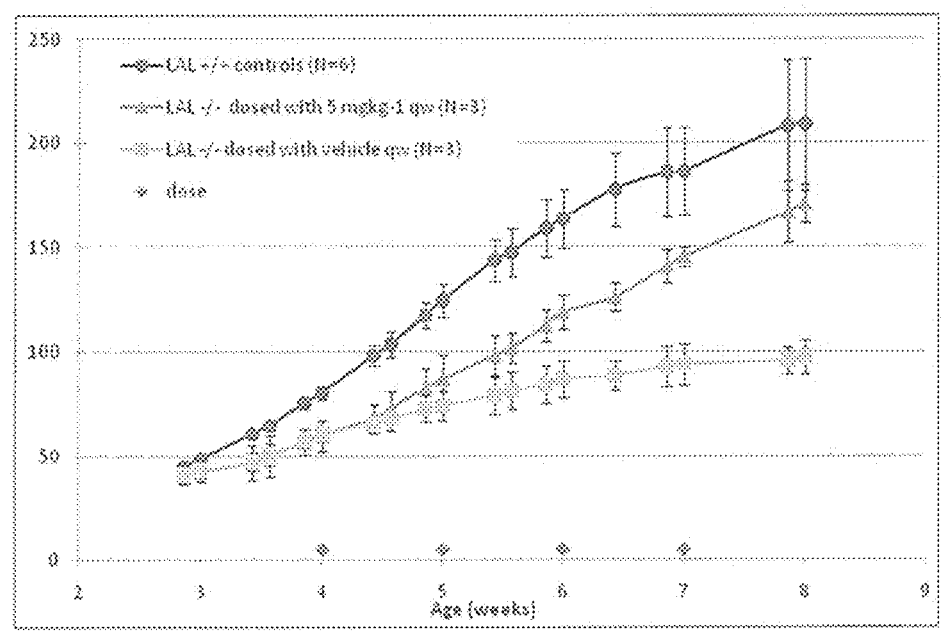
FIG. 24 depicts body weight in wild type and LAL-deficient rats after weekly administration of vehicle or SBC-102 at 5 mg·kg$^{-1}$ for 4 weeks. Dose administration is highlighted on X-axis by diamonds starting at 4 week.

Body weight of SBC-102- or vehicle-treated Yoshida rats were compared with wild type rats, as is shown in FIG. 24. SBC-102 (5 mg/kg) or vehicle was administered by IV injection either as a single dose or as split doses (given within 4 hour period) to $LAL^{-/-}$ rats. $LAL^{+/+}$ rats are age-matched littermate controls.

Example 15

Triglyceride Analysis

Triglyceride analysis was performed on liver and spleen tissue from wild type, homozygous placebo and homozygous SBC-102 treated animals. The triglyceride analyses were performed using standard methodologies (i.e., MBL International's Triglyceride Quantification Kit Catalog # JM-K622-100) and were done in triplicate.

TABLE 3

Liver and Spleen Triglyceeride levels in wild-type and LAL deficient rats
Triglyceride (ug/mg wet tissue)

|  | Wild Type (n = 3) | Placebo (n = 3) | SBC-102 (n = 3) |
| --- | --- | --- | --- |
| Liver | 48 | 84 | 57 |
| Spleen | 3 | 22 | 4 |

Liver Substrate Levels

Figure 25:
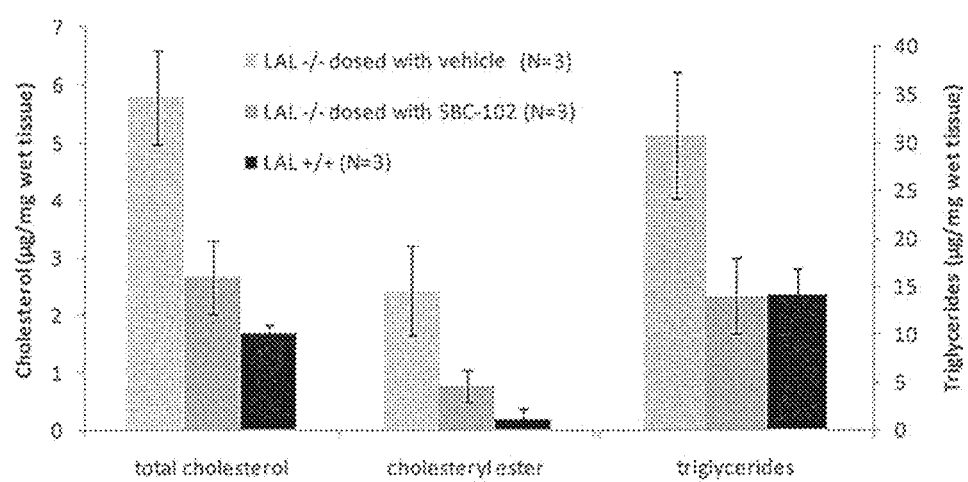
FIG. 25 shows liver cholesterol, cholesteryl ester and triglyceride levels determined at 8 weeks of age in WT and LAL deficient rats after weekly administration of vehicle or recombinant human LAL (SBC-102) at 5 mg·kg$^{-1}$ for 4 weeks.

FIG. 25 shows liver cholesterol, cholesteryl ester and triglyceride levels determined at 8 weeks of age, in WT and LAL deficient rats after weekly administration of vehicle or SBC-102 at 5 mg·kg$^{-1}$ for 4 weeks.

Example 16

Dose Response Study

Figure 26:
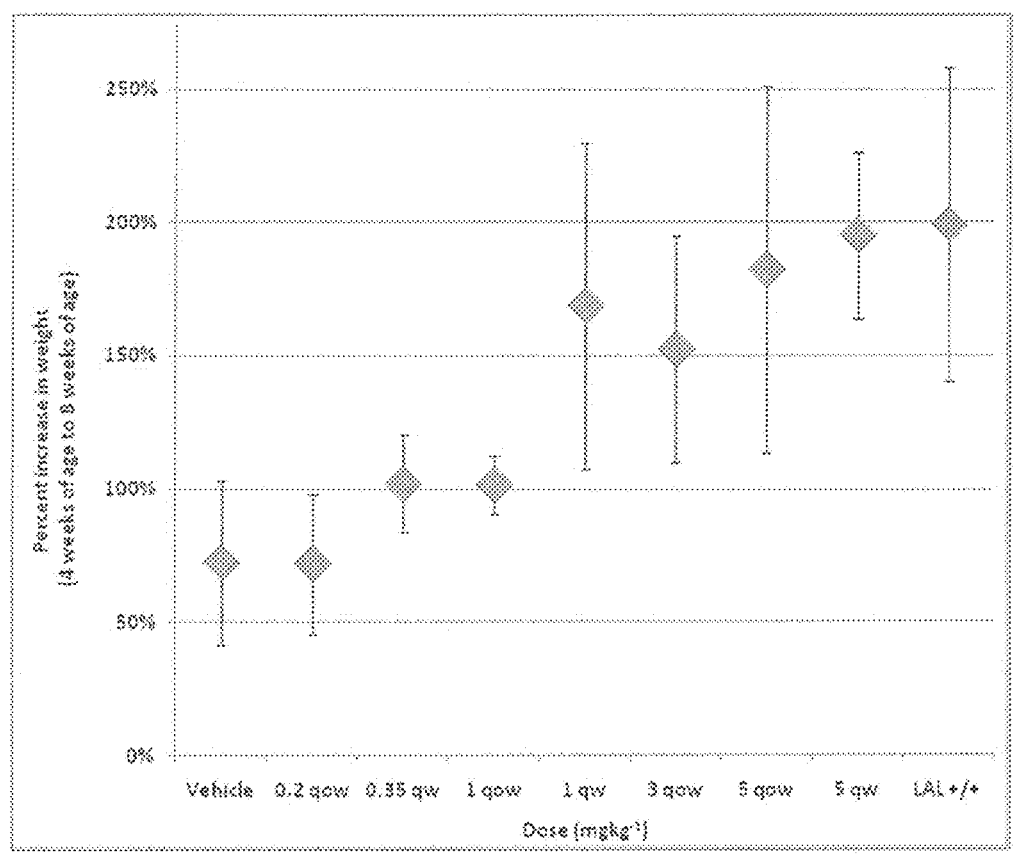
FIG. 26 depicts percent increase in body weight in LAL-deficient rats after 4 weeks administration recombinant human LAL (SBC-102) at the indicated levels and schedules, determined at 8 weeks of age.
Figure 27:
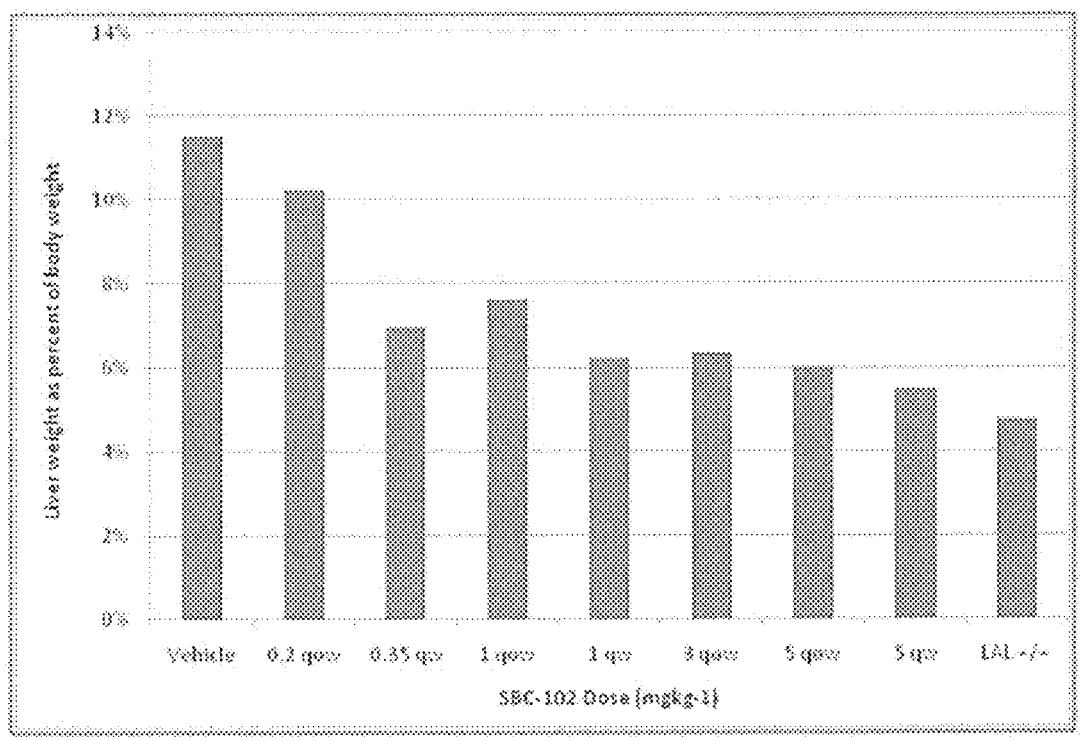
FIG. 27 shows liver weight, as a percent of body weight, in LAL-deficient rats after 4 weeks administration SBC-102 at the indicated levels and schedules, determined at 8 weeks of age.
Figure 28:
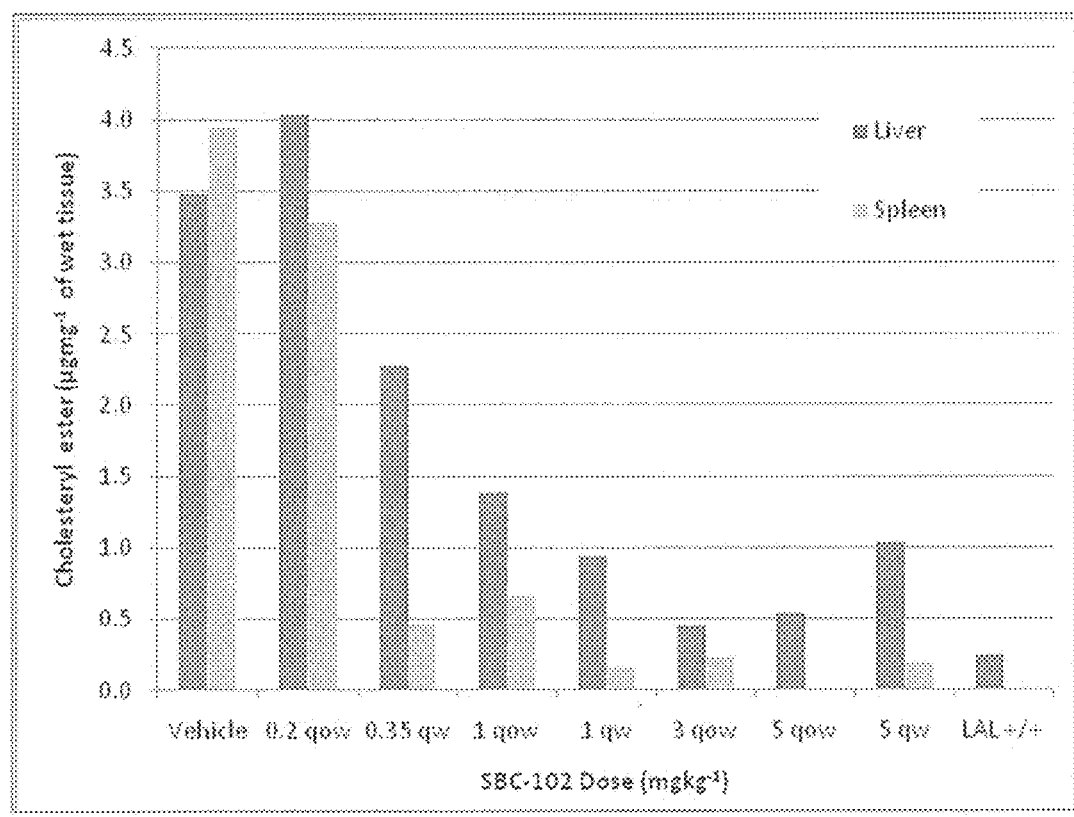
FIG. 28 shows tissue cholesteryl ester levels in LAL-deficient rats after 4 weeks administration SBC-102 at the indicated levels and schedules, determined at 8 weeks of age.

Based on the studies performed above, the pharmacodynamic (PD) effects of a range of doses and dose schedules (qw and qow) of LAL ("SBC-102") were examined in $LAL^{-/-}$ rats. In these studies, SBC-102 was administered by IV injections at dosages of 0.2, 1, 3 and 5 mg/kg, qow, or 0.35, 1 and 5 mg/kg, qw, for 1 month, beginning at 4 weeks of age. Results demonstrate improvements in body weight (BW) gain (FIG. 26), organomegaly (FIG. 27), and tissue substrate levels (FIG. 28). Serum transaminase levels were also reduced as the SBC-102 dose increased, with levels reaching essentially wild-type levels at the higher doses.

Example 17

Administration of Recombinant LAL in a Rat Model

The effects of repeat-dosing with recombinant human lysosomal acid lipase (LAL) on weight, tissue triglycerides and cholesterol, hepatomegaly, splenomegaly, lymphadenopathy, intestinal weight, and other parameters were evaluated in LAL Deficient Donryu rats described in Yoshida and Kuriyama (1990) Laboratory Animal Science, vol. 40, p 486-489 (see also Kuriyama et al. (1990) Journal of Lipid Research, vol. 31, p 1605-1611; Nakagawa et al., (1995) Journal of Lipid Research, vol. 36, p 2212-2218), the disclosure of which is incorporated in its entirety herein by reference.

At 4 weeks of age, Donryu rats homozygous for the LAL deletion (LAL $^{-/-}$) were assigned into groups to either be dosed with recombinant human LAL produced in a transgenic chicken oviduct system or a saline placebo. Wild-type, age-matched, littermate rats were used as controls. The LAL$^{-/-}$ rats were dosed once a week for four weeks (four doses total) or once every two weeks for four weeks (two doses total) by tail-vein injection as a single dose or in two equal doses given 30 minutes apart. Doses of LAL were 1 mg/kg or 5 mg/kg. Dosing schedule is shown in Table 4. The rats were pretreated with diphenhydramine (5 mg/kg) to counteract potential anaphylactic reactions, a procedure which is based on previous experiences in animal models of enzyme replacement therapy for the treatment of lysosomal storage disease (Shull et al. (1994) Proceedings of the National Academy of Science, vol. 91, p. 12937; Bielicki et al. (1999) The Journal of Biological Chemistry, 274, p. 36335; Vogler et al. (1999) Pediatric Research, 45, p. 838.), the disclosure of which is incorporated in its entirty herein by referernce.

Figure 29:
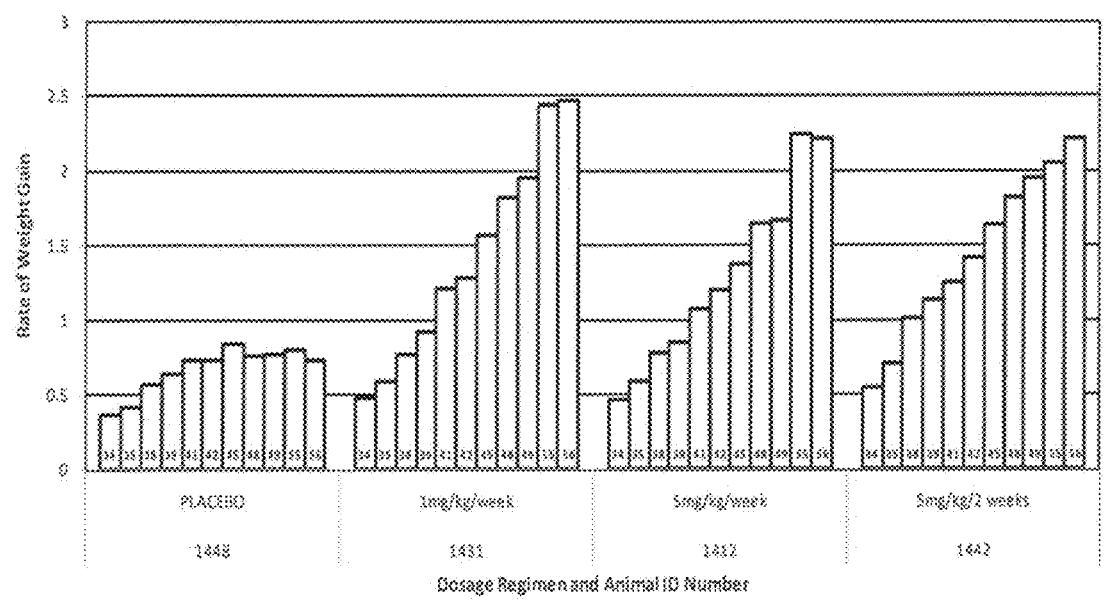
FIG. 29 shows the daily progress in weight gain of rats which were administered either 1 mg/kg of LAL per week or 5 mg/kg of LAL per week or 5 mg/kg of LAL per two weeks.

FIG. 29 shows the daily progress in weight gain of rats which were administered either 1 mg/kg of LAL per week or 5 mg/kg of LAL per week or 5 mg/kg of LAL per two weeks. It can be seen in the figure that there is little or no difference in therapeutic effect between the two dose sizes and frequencies.

TABLE 4

Weighing and Dosing Schedule

| Day from Birth | Assessments/Injections Performed |
|---|---|
| Day 13 | WEIGHED |
| Day 14 | |
| Day 20 | |
| Day 21 | Pups Weaned |
| Day 24 | |
| Day 25 | |
| Day 27 | |
| Day 28 | First Injection for administration once every week and once every two weeks |
| Day 31 | |
| Day 32 | |
| Day 34 | |
| Day 35 | Second Injection for administration once every week |
| Day 38 | |
| Day 39 | |
| Day 41 | |
| Day 42 | Third Injection for administration once every week; Second administration for once every two weeks |
| Day 45 | |
| Day 48 | |
| Day 49 | Fourth injection for administration once every week |
| Day 55 | |
| Day 56 | Necropsy |

Pathologic Examination of LAL $^{-/-}$ Rats Treated with Recombinant LAL

At the termination of the study described in Example 1, study animals were humanely euthanized and necropsied to examine gross pathology, histopathology, and clinical chemistry. The gross necropsy included examination of the external surface of the body, all orifices, and the cranial, thoracic, and abdominal cavities and their contents. Mass of internal organs and tissues were determined for the rats and the organs and tissues were harvested and fixed in 10% neutral-buffered formalin. Following fixation, the tissues were processed and histological slides of hematoxylin and eosin-stained sections were prepared and evaluated.

Figure 30:
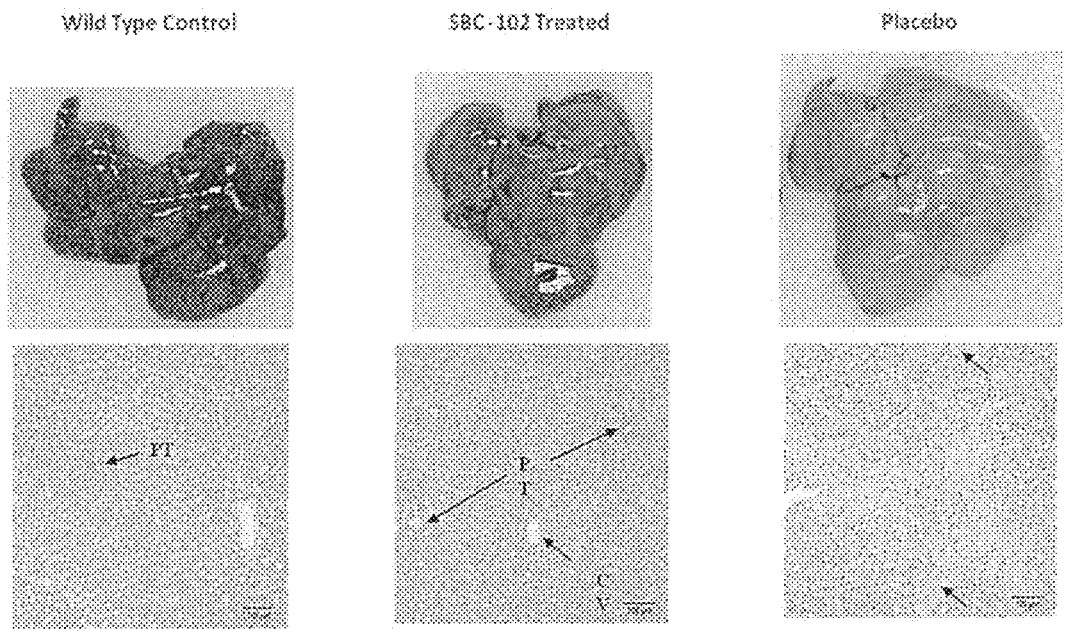
FIG. 30 depicts the gross pathological examination of treated animals showing a substantial normalization in liver size and color as can be seen in the dissection at the top panels and histopathology of liver tissue from LAL of treated rats showing normal liver histology in marked contrast to the substantial accumulation of foamy macrophages in the placebo-treated animals at the bottom panels.

The gross pathological examination of treated animals analyzed showed a substantial normalization in liver size and color as can be seen in the dissection shown in FIG. 30. Organ-to-body weight ratios were determined and demonstrated a reduction in the relative organ size for liver, spleen, mesenteric tissue, duodenum, jejunum and ileum in successfully treated animals which were dissected, as compared to the placebo treated rats (FIG. 23). Histopathology of liver tissue from LAL of treated rats analyzed shows essentially normal liver histology in marked contrast to the substantial accumulation of foamy macrophages in the placebo-treated animals (FIG. 30).

Example 18

Treatment of Wolman Disease (WD) by Administration of Recombinant LAL

At 7 weeks of age a female patient is admitted to the hospital because of difficulty in weight gain and poor progress since birth. At the initial physical examination the patient weighs 3.6 kg (birth weight 3.7 kg) and is thin, with loose skin folds. The abdomen is distended, with firm hepatomegaly of 6 cm and firm splenomegaly of about 4 cm. Enlarged lymph nodes are noted in the groin and muscular activity is weak.

The initial hemoglobin level is 9.2 gm, platelets 506,000, and white blood cells 11,550. Urinalysis is normal, and bone marrow smears reveal vacuolated lymphocytes and numerous foam cells. Serum chemical measurements: total lipids 834 mg/100 ml, phospholipids 176 mg/100 ml, triglycerides 141 mg/100 ml, cholesterol 129 mg/100 ml, bilirubin 0.3 mg/100 ml, alkaline phosphatase 9.0 BU %, SGOT 90 units, SGPT 50 units, cholinesterase 20 units, urea nitrogen 8.3 mg, fasting sugar 45 mg/100 ml. CT scan of the abdomen shows hepatosplenomegaly and bilateral symmetrically enlarged adrenal glands with calcification.

The patient is surgically implanted with a venous vascular access port for dosing. After connecting the port to an ambulatory infusion machine, the patient is pretreated with 1 mg/kg of diphenhydramine 20 minutes prior to LAL infusion in order to counteract potential anaphylactic infusion reactions. The patient is then administered LAL at 1 mg/kg over the course of 5 hours by intravenous infusion. This therapy is repeated one time every 7 days indefinitely.

Within two weeks of administering the first dose of LAL, the patient experiences a significant improvement in weight gain and normalization in size of key abdominal organs as determined by ultrasound. Laboratory results demonstrate that infusion of the LAL restores lysosomal acid lipase activity in the patient and leads to correction of related abnormalities.

Example 19

Treatment of Cholesteryl Ester Storage Disease (CESD) by Administration of Recombinant LAL A 3-year-old boy with a pruritic abdominal rash is examined by his pediatrician. Upon abdominal examination, hepatomegaly is noted by the physician and confirmed by ultrasound. At this point no diagnosis is made and the patient is monitored periodically.

At age 8, he is admitted to the hospital with gastroenteritis. Light microscopy of a liver biopsy shows increased intracytoplasmic glycogen and small lipid droplets in hepatocytes. Electron microscopy shows membrane-bound lipid droplets with small electron dense granules. A working diagnosis of glycogen storage disease type III (DeBrancher disease) is made, but skin fibroblast Debrancher activity is normal.

At age 10, hepatomegaly persists and a second liver biopsy is taken. Light microscopy shows altered lobular architecture of the hepatic parenchyma with distended hepatocytes containing cytoplasmic granules and vacuoles with mild periportal fibrosis. Fibroblast acid lipase activity is found to be 7% of normal, confirming the diagnosis of CESD. Plasma concentrations of total cholesterol (TC), triglycerides (TG), low-density lipoprotein cholesterol (LDL-C) are each above the 95th percentile for age and sex at 7.51, 3.24 and 5.58 mmol/L, respectively, while plasma high-density lipoprotein cholesterol (HDL-C) is below the 5th percentile at 0.47 mmol/L; he has combined hyperlipidemia (hypercholesterolemia, hypertriglyceridemia, hypoalphalipoproteinemia and hyperbetalipoproteinemia).

The patient is surgically implanted with a venous vascular access port for dosing. After connecting the port to an ambulatory infusion machine, the patient is pretreated with 5 mg/kg of diphenhydramine 20 minutes prior to LAL infusion in order to counteract potential anaphylactic infusion reactions. The patient is then administered LAL at 5 mg/kg over the course of 5 hours by intravenous infusion. This therapy is repeated one time every 14 days indefinitely.

Within two weeks of administering the first dose of LAL, the patient experiences a significant improvement in weight gain and normalization in size of key organs as determined by ultrasound. Laboratory results demonstrate that infusion of the LAL restores lysosomal acid lipase activity in the patient and leads to correction of related abnormalities.

Example 20

Description and Composition of the Medicinal Product

The drug substance of LAL described herein ("SBC-102") is a recombinant human lysosomal acid lipase (rhLAL) purified from the egg white produced from transgenic *Gallus*. The excipients used in SBC-102 are similar to those used for other products for lysosomal storage disorders (LSD) currently on the market, and have been selected to maintain stability of the drug product.

SBC-102 is a clear, colorless, sterile liquid provided in a clear, Type I borosilicate glass vial with a non-natural latex (butyl), FluroTec®-coated stopper and aluminum crimp seal. SBC-102 is provided as an aqueous solution comprised of SBC-102 (2 mg/mL), Trisodium Citrate Dihydrate (13.7 mg/mL, USP), Citric Acid Monohydrate (1.57 mg/mL, USP), Human Serum Albumin (10 mg/mL, USP), and Water for Injection (to final volume, USP). The pH of SBC-102 is 5.9±0.2. SBC-102 contains no preservatives and vials are intended for single use only.

TABLE 5

Excipients in SBC-102 (LAL)

| Excipient | CAS number | Grade | Function |
| --- | --- | --- | --- |
| Trisodium Citrate Dihydrate | 6132-04-03 | USP | Buffer |
| Citric Acid Monohydrate | 5949-29-1 | USP | Buffer |
| Human Serum Albumin | 70024-90-7 | USP | Stabilizer |

Components of the Drug Product

TABLE 6

Formulation of SBC-102

| Component | Concentration |
| --- | --- |
| SBC-102 (rhLAL) | 2 mg/mL* |
| Trisodium Citrate Dihydrate | 13.7 mg/mL |
| Citric Acid Monohydrate | 1.57 mg/mL |
| Human Serum Albumin | 10 mg/mL |
| Water for Injection, QS to | 1.0 mL |

Each example in the above specification is provided by way of explanation of the invention, not limitation of the invention. In fact, it will be apparent to those skilled in the art that various modifications, combinations, additions, deletions and variations can be made in the present invention without departing from the scope or spirit of the invention. For instance, features illustrated or described as part of one embodiment can be used in another embodiment to yield a still further embodiment. It is intended that the present invention cover such modifications, combinations, additions, deletions, and variations.

All documents (e.g., U.S. patents, U.S. patent applications, publications) cited in the above specification are incorporated herein by reference. Various modifications and variations of the present invention will be apparent to those skilled in the art without departing from the scope and spirit of the invention.

While this invention has been particularly shown and described with references to example embodiments thereof, it will be understood by those skilled in the art that various changes in form and details may be made therein without departing from the scope of the invention encompassed by the appended claims.

What is claimed is:

1. An isolated recombinant human lysosomal acid lipase glycoprotein (rhLAL), wherein the rhLAL consists essentially of an amino acid sequence selected from the group consisting of SEQ ID NO:2, SEQ ID NO:3, SEQ ID NO:4 and SEQ ID NO:19, with N-glycans bonded to the asparagine residues (Asn) that correspond to $Asn^{36}$, $Asn^{101}$, $Asn^{161}$, $Asn^{273}$ and $Asn^{321}$ of SEQ ID NO:1, with the proviso that the N-glycans do not comprise fucose, and the proviso that the rhLAL does not contain O-glycans.

2. The rhLAL of claim 1, wherein the amino acid sequence of said rhLAL is SEQ ID NO:2.

3. The rhLAL of claim 1, wherein the amino acid sequence of said rhLAL is SEQ ID NO:3.

4. The rhLAL of claim 1, wherein the amino acid sequence of said rhLAL is SEQ ID NO:4.

5. The rhLAL of claim 1, wherein the amino acid sequence of said rhLAL is SEQ ID NO:19.

6. The rhLAL of claim 1, with the further proviso that the N-glycans do not comprise xylose.

7. The rhLAL of claim 1, with the further proviso that the N-glycans do not comprise sialic acid.

8. The rhLAL of claim 1, wherein the rhLAL is produced by a process that comprises expressing a nucleic acid that encodes said amino acid sequence in an avian cell.

9. The rhLAL of claim 8, wherein the avian cell is an oviduct cell of a chicken.

10. An isolated recombinant human lysosomal acid lipase glycoprotein (rhLAL), wherein the rhLAL consists essentially of an amino acid sequence selected from the group consisting of SEQ ID NO:2, SEQ ID NO:3, SEQ ID NO:4 and SEQ ID NO:19, with N-glycans bonded to the asparagine residues (Asn) that correspond to $Asn^{36}$, $Asn^{101}$, $Asn^{161}$, $Asn^{273}$ and $Asn^{321}$ of SEQ ID NO:1, with the proviso that the N-glycans do not comprise fucose, and the proviso that the rhLAL does not contain O-glycans, and wherein the N-glycans bonded to the Asn residues that correspond to $Asn^{36}$, $Asn^{101}$, $Asn^{161}$, $Asn^{273}$ and $Asn^{321}$ of SEQ ID NO:1 are:
  a) at $Asn^{36}$, GlcNAc4Man3GlcNAc2, or Gal1GlcNAc4Man3GlcNAc2;
  b) at $Asn^{101}$, Phos2Man7GlcNAc2;
  c) at $Asn^{161}$, Phos1Man6GlcNAc2, GlcNAc1Phos1Man6GlcNAc2; Man3GlcNAc2; GlcNAc2Man3GlcNAc2; GlcNAc3Man3GlcNAc2; GlcNAc4Man3GlcNAc2, or Gal1GlcNAc4Man3GlcNAc2;
  d) at $Asn^{273}$, Man7GlcNAc2, Man8GlcNAc2, Man9GlcNAc2, Phos1Man8GlcNAc2, or Phos1Man9GlcNAc2; and
  e) at $Asn^{321}$, GlcNAc2Man3GlcNAc2, GlcNAc3Man3GlcNAc2, GlcNAc4Man3GlcNAc2, Gal1GlcNAc4Man3GlcNAc2, GlcNAc5Man3GlcNAc2, Gal1GlcNAc5Man3GlcNAc2, GlcNAc6Man3GlcNAc2, or Gal1GlcNAc6Man3GlcNAc2; wherein Man=mannose,
GlcNAc=N-Acetyl Glucosamine,
Phos=phosphate, and
Gal=galactose.

11. The rhLAL of claim 10, wherein the amino acid sequence of said rhLAL is SEQ ID NO:2.

12. The rhLAL of claim 10, wherein the amino acid sequence of said rhLAL is SEQ ID NO:3.

13. The rhLAL of claim 10, wherein the amino acid sequence of said rhLAL is SEQ ID NO:4.

14. The rhLAL of claim 10, wherein the amino acid sequence of said rhLAL is SEQ ID NO:19.

15. The rhLAL of claim 10, with the further proviso that the N-glycans do not comprise xylose.

16. The rhLAL of claim 10, with the further proviso that the N-glycans do not comprise sialic acid.

17. The rhLAL of claim 10, wherein the rhLAL is produced by a process that comprises expressing a nucleic acid that encodes said amino acid sequence in an avian cell.

18. The rhLAL of claim 17, wherein the avian cell is an oviduct cell of a chicken.

19. A pharmaceutical composition consisting essentially of an aqueous solution of
  a) 2 mg/mL of hLAL of claim 1;
  b) 13.7 mg/mL of trisodium citrate dehydrate;
  c) 1.57 mg/mL of citric acid monohydrate; and
  d) 10 mg/mL of human serum albumin; wherein the pH of the pharmaceutical composition is 5.9±0.2.

20. A pharmaceutical composition consisting essentially of an aqueous solution of
  a) 2 mg/mL of hLAL of claim 10;
  b) 13.7 mg/mL of trisodium citrate dehydrate;
  c) 1.57 mg/mL of citric acid monohydrate; and
  d) 10 mg/mL of human serum albumin; wherein the pH of the pharmaceutical composition is 5.9±0.2.

* * * * *

SEQUENCE LISTING

<160> NUMBER OF SEQ ID NOS: 20

<210> SEQ ID NO 1
<211> LENGTH: 399
<212> TYPE: PRT
<213> ORGANISM: HOMO SAPIENS

<400> SEQUENCE: 1

```
Met Lys Met Arg Phe Leu Gly Leu Val Val Cys Leu Val Leu Trp Thr
1               5                   10                  15

Leu His Ser Glu Gly Ser Gly Gly Lys Leu Thr Ala Val Asp Pro Glu
            20                  25                  30

Thr Asn Met Asn Val Ser Glu Ile Ile Ser Tyr Trp Gly Phe Pro Ser
        35                  40                  45

Glu Glu Tyr Leu Val Glu Thr Glu Asp Gly Tyr Ile Leu Cys Leu Asn
    50                  55                  60

Arg Ile Pro His Gly Arg Lys Asn His Ser Asp Lys Gly Pro Lys Pro
65                  70                  75                  80

Val Val Phe Leu Gln His Gly Leu Leu Ala Asp Ser Ser Asn Trp Val
                85                  90                  95

Thr Asn Leu Ala Asn Ser Ser Leu Gly Phe Ile Leu Ala Asp Ala Gly
            100                 105                 110

Phe Asp Val Trp Met Gly Asn Ser Arg Gly Asn Thr Trp Ser Arg Lys
        115                 120                 125

His Lys Thr Leu Ser Val Ser Gln Asp Glu Phe Trp Ala Phe Ser Tyr
    130                 135                 140

Asp Glu Met Ala Lys Tyr Asp Leu Pro Ala Ser Ile Asn Phe Ile Leu
145                 150                 155                 160

Asn Lys Thr Gly Gln Glu Gln Val Tyr Tyr Val Gly His Ser Gln Gly
                165                 170                 175

Thr Thr Ile Gly Phe Ile Ala Phe Ser Gln Ile Pro Glu Leu Ala Lys
            180                 185                 190

Arg Ile Lys Met Phe Phe Ala Leu Gly Pro Val Ala Ser Val Ala Phe
        195                 200                 205

Cys Thr Ser Pro Met Ala Lys Leu Gly Arg Leu Pro Asp His Leu Ile
    210                 215                 220

Lys Asp Leu Phe Gly Asp Lys Glu Phe Leu Pro Gln Ser Ala Phe Leu
225                 230                 235                 240

Lys Trp Leu Gly Thr His Val Cys Thr His Val Ile Leu Lys Glu Leu
                245                 250                 255

Cys Gly Asn Leu Cys Phe Leu Leu Cys Gly Phe Asn Glu Arg Asn Leu
            260                 265                 270

Asn Met Ser Arg Val Asp Val Tyr Thr Thr His Ser Pro Ala Gly Thr
        275                 280                 285

Ser Val Gln Asn Met Leu His Trp Ser Gln Ala Val Lys Phe Gln Lys
    290                 295                 300

Phe Gln Ala Phe Asp Trp Gly Ser Ser Ala Lys Asn Tyr Phe His Tyr
305                 310                 315                 320

Asn Gln Ser Tyr Pro Pro Thr Tyr Asn Val Lys Asp Met Leu Val Pro
                325                 330                 335

Thr Ala Val Trp Ser Gly Gly His Asp Trp Leu Ala Asp Val Tyr Asp
            340                 345                 350

Val Asn Ile Leu Leu Thr Gln Ile Thr Asn Leu Val Phe His Glu Ser
        355                 360                 365
```

```
Ile Pro Glu Trp Glu His Leu Asp Phe Ile Trp Gly Leu Asp Ala Pro
370                 375                 380

Trp Arg Leu Tyr Asn Lys Ile Ile Asn Leu Met Arg Lys Tyr Gln
385                 390                 395

<210> SEQ ID NO 2
<211> LENGTH: 378
<212> TYPE: PRT
<213> ORGANISM: HOMO SAPIENS

<400> SEQUENCE: 2

Ser Gly Gly Lys Leu Thr Ala Val Asp Pro Glu Thr Asn Met Asn Val
1               5                   10                  15

Ser Glu Ile Ile Ser Tyr Trp Gly Phe Pro Ser Glu Glu Tyr Leu Val
                20                  25                  30

Glu Thr Glu Asp Gly Tyr Ile Leu Cys Leu Asn Arg Ile Pro His Gly
            35                  40                  45

Arg Lys Asn His Ser Asp Lys Gly Pro Lys Pro Val Val Phe Leu Gln
        50                  55                  60

His Gly Leu Leu Ala Asp Ser Ser Asn Trp Val Thr Asn Leu Ala Asn
65                  70                  75                  80

Ser Ser Leu Gly Phe Ile Leu Ala Asp Ala Gly Phe Asp Val Trp Met
                85                  90                  95

Gly Asn Ser Arg Gly Asn Thr Trp Ser Arg Lys His Lys Thr Leu Ser
            100                 105                 110

Val Ser Gln Asp Glu Phe Trp Ala Phe Ser Tyr Asp Glu Met Ala Lys
        115                 120                 125

Tyr Asp Leu Pro Ala Ser Ile Asn Phe Ile Leu Asn Lys Thr Gly Gln
    130                 135                 140

Glu Gln Val Tyr Tyr Val Gly His Ser Gln Gly Thr Thr Ile Gly Phe
145                 150                 155                 160

Ile Ala Phe Ser Gln Ile Pro Glu Leu Ala Lys Arg Ile Lys Met Phe
                165                 170                 175

Phe Ala Leu Gly Pro Val Ala Ser Val Ala Phe Cys Thr Ser Pro Met
            180                 185                 190

Ala Lys Leu Gly Arg Leu Pro Asp His Leu Ile Lys Asp Leu Phe Gly
        195                 200                 205

Asp Lys Glu Phe Leu Pro Gln Ser Ala Phe Leu Lys Trp Leu Gly Thr
    210                 215                 220

His Val Cys Thr His Val Ile Leu Lys Glu Leu Cys Gly Asn Leu Cys
225                 230                 235                 240

Phe Leu Leu Cys Gly Phe Asn Glu Arg Asn Leu Asn Met Ser Arg Val
                245                 250                 255

Asp Val Tyr Thr Thr His Ser Pro Ala Gly Thr Ser Val Gln Asn Met
            260                 265                 270

Leu His Trp Ser Gln Ala Val Lys Phe Gln Lys Phe Gln Ala Phe Asp
        275                 280                 285

Trp Gly Ser Ser Ala Lys Asn Tyr Phe His Tyr Asn Gln Ser Tyr Pro
    290                 295                 300

Pro Thr Tyr Asn Val Lys Asp Met Leu Val Pro Thr Ala Val Trp Ser
305                 310                 315                 320

Gly Gly His Asp Trp Leu Ala Asp Val Tyr Asp Val Asn Ile Leu Leu
                325                 330                 335

Thr Gln Ile Thr Asn Leu Val Phe His Glu Ser Ile Pro Glu Trp Glu
            340                 345                 350
```

His Leu Asp Phe Ile Trp Gly Leu Asp Ala Pro Trp Arg Leu Tyr Asn
        355                 360                 365

Lys Ile Ile Asn Leu Met Arg Lys Tyr Gln
        370                 375

<210> SEQ ID NO 3
<211> LENGTH: 376
<212> TYPE: PRT
<213> ORGANISM: HOMO SAPIENS

<400> SEQUENCE: 3

Gly Lys Leu Thr Ala Val Asp Pro Glu Thr Asn Met Asn Val Ser Glu
1               5                   10                  15

Ile Ile Ser Tyr Trp Gly Phe Pro Ser Glu Glu Tyr Leu Val Glu Thr
            20                  25                  30

Glu Asp Gly Tyr Ile Leu Cys Leu Asn Arg Ile Pro His Gly Arg Lys
        35                  40                  45

Asn His Ser Asp Lys Gly Pro Lys Pro Val Val Phe Leu Gln His Gly
    50                  55                  60

Leu Leu Ala Asp Ser Ser Asn Trp Val Thr Asn Leu Ala Asn Ser Ser
65                  70                  75                  80

Leu Gly Phe Ile Leu Ala Asp Ala Gly Phe Asp Val Trp Met Gly Asn
                85                  90                  95

Ser Arg Gly Asn Thr Trp Ser Arg Lys His Lys Thr Leu Ser Val Ser
            100                 105                 110

Gln Asp Glu Phe Trp Ala Phe Ser Tyr Asp Glu Met Ala Lys Tyr Asp
        115                 120                 125

Leu Pro Ala Ser Ile Asn Phe Ile Leu Asn Lys Thr Gly Gln Glu Gln
    130                 135                 140

Val Tyr Tyr Val Gly His Ser Gln Gly Thr Thr Ile Gly Phe Ile Ala
145                 150                 155                 160

Phe Ser Gln Ile Pro Glu Leu Ala Lys Arg Ile Lys Met Phe Phe Ala
                165                 170                 175

Leu Gly Pro Val Ala Ser Val Ala Phe Cys Thr Ser Pro Met Ala Lys
            180                 185                 190

Leu Gly Arg Leu Pro Asp His Leu Ile Lys Asp Leu Phe Gly Asp Lys
        195                 200                 205

Glu Phe Leu Pro Gln Ser Ala Phe Leu Lys Trp Leu Gly Thr His Val
    210                 215                 220

Cys Thr His Val Ile Leu Lys Glu Leu Cys Gly Asn Leu Cys Phe Leu
225                 230                 235                 240

Leu Cys Gly Phe Asn Glu Arg Asn Leu Asn Met Ser Arg Val Asp Val
                245                 250                 255

Tyr Thr Thr His Ser Pro Ala Gly Thr Ser Val Gln Asn Met Leu His
            260                 265                 270

Trp Ser Gln Ala Val Lys Phe Gln Lys Phe Gln Ala Phe Asp Trp Gly
        275                 280                 285

Ser Ser Ala Lys Asn Tyr Phe His Tyr Asn Gln Ser Tyr Pro Pro Thr
    290                 295                 300

Tyr Asn Val Lys Asp Met Leu Val Pro Thr Ala Val Trp Ser Gly Gly
305                 310                 315                 320

His Asp Trp Leu Ala Asp Val Tyr Asp Val Asn Ile Leu Leu Thr Gln
                325                 330                 335

Ile Thr Asn Leu Val Phe His Glu Ser Ile Pro Glu Trp Glu His Leu

```
            340                 345                 350
Asp Phe Ile Trp Gly Leu Asp Ala Pro Trp Arg Leu Tyr Asn Lys Ile
            355                 360                 365

Ile Asn Leu Met Arg Lys Tyr Gln
    370                 375

<210> SEQ ID NO 4
<211> LENGTH: 373
<212> TYPE: PRT
<213> ORGANISM: HOMO SAPIENS

<400> SEQUENCE: 4

Thr Ala Val Asp Pro Glu Thr Asn Met Asn Val Ser Glu Ile Ile Ser
1               5                   10                  15

Tyr Trp Gly Phe Pro Ser Glu Glu Tyr Leu Val Glu Thr Glu Asp Gly
                20                  25                  30

Tyr Ile Leu Cys Leu Asn Arg Ile Pro His Gly Arg Lys Asn His Ser
            35                  40                  45

Asp Lys Gly Pro Lys Pro Val Val Phe Leu Gln His Gly Leu Leu Ala
        50                  55                  60

Asp Ser Ser Asn Trp Val Thr Asn Leu Ala Asn Ser Ser Leu Gly Phe
65                  70                  75                  80

Ile Leu Ala Asp Ala Gly Phe Asp Val Trp Met Gly Asn Ser Arg Gly
                85                  90                  95

Asn Thr Trp Ser Arg Lys His Lys Thr Leu Ser Val Ser Gln Asp Glu
            100                 105                 110

Phe Trp Ala Phe Ser Tyr Asp Glu Met Ala Lys Tyr Asp Leu Pro Ala
        115                 120                 125

Ser Ile Asn Phe Ile Leu Asn Lys Thr Gly Gln Glu Gln Val Tyr Tyr
    130                 135                 140

Val Gly His Ser Gln Gly Thr Thr Ile Gly Phe Ile Ala Phe Ser Gln
145                 150                 155                 160

Ile Pro Glu Leu Ala Lys Arg Ile Lys Met Phe Phe Ala Leu Gly Pro
                165                 170                 175

Val Ala Ser Val Ala Phe Cys Thr Ser Pro Met Ala Lys Leu Gly Arg
            180                 185                 190

Leu Pro Asp His Leu Ile Lys Asp Leu Phe Gly Asp Lys Glu Phe Leu
        195                 200                 205

Pro Gln Ser Ala Phe Leu Lys Trp Leu Gly Thr His Val Cys Thr His
    210                 215                 220

Val Ile Leu Lys Glu Leu Cys Gly Asn Leu Cys Phe Leu Leu Cys Gly
225                 230                 235                 240

Phe Asn Glu Arg Asn Leu Asn Met Ser Arg Val Asp Val Tyr Thr Thr
                245                 250                 255

His Ser Pro Ala Gly Thr Ser Val Gln Asn Met Leu His Trp Ser Gln
            260                 265                 270

Ala Val Lys Phe Gln Lys Phe Gln Ala Phe Asp Trp Gly Ser Ser Ala
        275                 280                 285

Lys Asn Tyr Phe His Tyr Asn Gln Ser Tyr Pro Pro Thr Tyr Asn Val
    290                 295                 300

Lys Asp Met Leu Val Pro Thr Ala Val Trp Ser Gly Gly His Asp Trp
305                 310                 315                 320

Leu Ala Asp Val Tyr Asp Val Asn Ile Leu Leu Thr Gln Ile Thr Asn
                325                 330                 335
```

```
Leu Val Phe His Glu Ser Ile Pro Glu Trp Glu His Leu Asp Phe Ile
            340                 345                 350

Trp Gly Leu Asp Ala Pro Trp Arg Leu Tyr Asn Lys Ile Ile Asn Leu
            355                 360                 365

Met Arg Lys Tyr Gln
            370

<210> SEQ ID NO 5
<211> LENGTH: 1150
<212> TYPE: DNA
<213> ORGANISM: HOMO SAPIENS

<400> SEQUENCE: 5
atgaaaatgc ggttcttggg gttggtggtc tgtttggttc tctggaccct gcattccgag      60
gggtccggag ggaaactgac agctgtggat cctgaaacaa acatgaatgt cagtgaaatt     120
atctcttact ggggattccc tagtgaggaa tacctagttg agacagaaga tggatatatt     180
ctgtgcctta accgaattcc tcatgggagg aagaaccatt ctgacaaagg tcccaaacca     240
gttgtcttcc tgcaacatgg cttgctggca gattctagta actgggtcac aaaccttgcc     300
aacagcagcc tgggcttcat tcttgctgat gctggttttg acgtgtggat gggcaacagc     360
agaggaaata cctggtctcg gaaacataag acactctcag tttctcagga tgaattctgg     420
gctttcagtt atgatgagat ggcaaaatat gacctaccag cttccattaa cttcattctg     480
aataagactg gccaagaaca agtgtattat gtgggtcatt ctcaaggcac cactataggt     540
tttatagcat tttcacagat ccctgagctg gctaaaagga ttaaaatgtt ttttgccctg     600
ggtcctgtgg cttccgtcgc cttctgtact agccctatgg ccaaactggg acgactgcca     660
gatcatctca ttaaggacct ctttggagac aaagaatttc ttccccagag tgcgtttttg     720
aagtggctgg gtacccacgt ttgcactcat gtcatactga aggagctctg tggaaatctc     780
tgttttcttc tgtgtggatt taatgagaga atttaaata tgtctagagt ggatgtgtat     840
acaacacatt ctcctgctgg aacttctgtg caaaacatgt tacactggag ccaggctgtt     900
aaattccaaa gtttcaagc ctttgactgg ggaagcagtg ccaagaatta tttttcatt ac     960 aaccagagtt atcctcccac atacaatgtg aaggacatgc tgtgccgac tgcagtctgg    1020 agcgggggtc acgactggct tgcagatgtc tacgacgtca atatcttact gactcagatc    1080
accaacttgg tgttccatga gagcatccg gaatgggagc атcтгactт catttgggc    1140 ctggatgccc                                                           1150

<210> SEQ ID NO 6
<211> LENGTH: 10882
<212> TYPE: DNA
<213> ORGANISM: Artificial Sequence
<220> FEATURE:
<223> OTHER INFORMATION: pALVIN-OVR1-I-SBC102-dSA

<400> SEQUENCE: 6
ctttccccgt caagctctaa atcgggggct ccctttaggg ttccgattta gtgctttacg      60
gcacctcgac cccaaaaaac ttgattaggg tgatggttca cgtagtgggc atcgccctg     120

atagacggtt tttcgccctt tgacgttgga gtccacgttc tttaatagtg gactcttgtt     180
ccaaactgga acaacactca accctatctc ggtctatcct ттттgатттат aagggatttt    240 gccgatttcg gccтаттgгт taaaaatga gctgatttaa caaaaattta cgcgaatttt      300

таасааата ttaacgctta caatttccat tcgccattca ggctgcgcaa ctgttgggaa    360
```

```
gggcgatcgg tgcgggcctc ttcgctatta cgccagctgg cgaaaggggg atgtgctgca      420
aggcgattaa gttgggtaac gccagggttt tcccagtcac gacgttgtaa aacgacggcc      480
agtgagcgcg tattccctaa cgatcacgtc ggggtcacca aatgaagcct tctgcttcat      540
gcatgtgctc gtagtcgtca gggaatcaac ggtccggcca tcaacccagg tgcacaccaa      600
tgtggtgaat ggtcaaatgg cgtttattgt atcgagctag gcacttaaat acaatatctc      660
tgcaatgcgg aattcagtgg ttcgtccaat ccgtccccct ccctatgcaa aagcgaaact      720
actatatcct gaggggactc ctaaccgcgt acaaccgaag ccccgctttt cgcctaaaca      780
tgctattgtc ccctcagtca agccttgccc gttacaaccc gattcgcaag ccttgccctc      840
cccacattat ccgtagcatt atttcctagc agtcatcaga gctacagaag atactctatg      900
ctgtagccaa gtctacaagt ttactattca gcgacctcct atattccgcg tgccagccga      960
tcaattacca atccaaccag ctatcacacg gaatacaaga actcgcctac gctcttcttt     1020
cgggctgctt ataagcctcc tgtaattttt ttatattcct cgctcgagtc tcttcagaat     1080
ggcacagcac cgctgcagaa aaatgccagg tggactatga actcacatcc aaaggagctt     1140
gacctgatac ctgattttct tcaaacaggg gaaacaacac aatcccacaa aacagctcag     1200
agagaaacca tcactgatgg ctacagcacc aaggtatgca atggcaatcc attcgacatt     1260
catctgtgac ctgagcaaaa tgatttatct ctccatgaat ggttgcttct ttccctcatg     1320
aaaaggcaat ttccacactc acaatatgca acaaagacaa acagagaaca attaatgtgc     1380
tccttcctaa tgttaaaatt gtagtggcaa agaggagaac aaaatctcaa gttctgagta     1440
ggttttagtg attggataag aggctttgac ctgtgagctc acctggactt catatccttt     1500
tggataaaaa gtgcttttat aactttcagg tctccgagtc tttattcatg agactgttgg     1560
tttagggaca gacccacaat gaaatgcctg gcataggaaa gggcagcaga gccttagctg     1620
accttttctt gggacaagca ttgtcaaaca atgtgtgaca aaactatttg tactgctttg     1680
cacagctgtg ctgggcaggg caatccattg ccacctatcc caggtaacct tccaactgca     1740
agaagattgt tgcttactct ctctagaccc ccaagtcaaa ccaactatgc aggtatgctg     1800
acaacactat gatgacagcc tgttctgatc aagatctcat tgttcatgg acaatttttg      1860 ttgcttgcag ctggtcttcc attgggaaag agtgtagtat atccttctca tctgacagaa     1920
aagcagaaat tctcatgctc cacacttaat ctacattgtt ttaaaccacc ggctacttct     1980
tggagaggaa aaatggcttt tataagactc acaaaacaaa gctctgcaag tcaaatgcat     2040
acaaaactgt tctgtaggtc tggaatcagg acactatgtg gaagtcaaat agagcagctt     2100
taaaaagcct ttgggatcat tctcatctta tatttgcagc acgatactat gacagtgata     2160
actgacataa ctgcatcaat ttccttgata tttatttgt cttaaagtac aagacataga      2220
gatggacgta aagatggaca tatgactcag gtctggacag gtccgtggtc catgtatgat     2280
aaaagagatg aagggaagga gaattgagac tgtctaagaa gggcttcagg gacgttctga     2340
aggcagattt gactgaatca gatgtactgt ccaagtctca tatgtagcaa tggaaggctg     2400
atattggaga aatataaaga aatggctgtg aactcaaagt gaccctgaac agaaaaggga     2460
tatggagtta aaataatgtc acagaactga ggtttatatg atataccatg ggctgcagag     2520
ggtcagagtg ctccaccatg ggcctctctt gggctgcagg gaacttctgt tctacacctg     2580
gaacacctcc tgccctcctc cgcactgacc tcagtgtcat cagggctgtt tctctcacat     2640
tttctcactc acctctccca actaccattg tacagcagtt gttcttacat attgctcctc     2700
ctgaggtaca tctagcatcg ttaagtcctc agacttggca aggagaatgt agatttccac     2760
```

```
agtatatatg ttttcacaaa aggaaggaga gaaacaaaag aaaatggcac tgactaaact   2820
tcagctagtg gtataggaaa gtaattctgc ttaacagaga ttgcagtgat ctctatgtat   2880
gtcctgaaga attatgttgt actttttcc  cccatttta  aatcaaacag tgctttacag   2940
aggtcagaat ggtttcttta ctgtttgtca attctattat ttcaatacag aacaatagct   3000
tctataactg aaatatattt gctattgtat attatgattg tccctcgaac catgaacact   3060
cctccagctg aatttcacaa ttcctctgtc atctgccagg ccattaagtt attcatggaa   3120
gatctttgag gaacactgca agttcatatc ataaacacat ttgaaattga gtattgtttt   3180
gcattgtatg gagctatgtt ttgctgtatc ctcagaataa aagtttgtta taaagcattc   3240
acacccataa aaagatagat ttaaatattc caactatagg aaagaaagtg tgtctgctct   3300
tcactctagt ctcagttggc tccttcacat gcacgcttct ttatttctcc tattttgtca   3360
agaaaataat aggtcaagtc ttgttctcat ttatgtcctg tctagcgtgg ctcagatgca   3420
cattgtacat acaagaagga tcaaatgaaa cagacttctg gtctgttact acaaccatag   3480
taataagcac actaactaat aattgctaat tatgttttcc atctccaagg ttcccacatt   3540
tttctgtttt cttaaagatc ccattatctg gttgtaactg aagctcaatg gaacatgagc   3600
aatatttccc agtcttctct cccatccaac agtcctgatg gattagcaga acaggcagaa   3660
aacacattgt tacccagaat taaaaactaa tatttgctct ccattcaatc caaaatggac   3720
ctattgaaac taaaatctaa cccaatccca ttaaatgatt tctatggtgt caaaggtcaa   3780
acttctgaag ggaacctgtg ggtgggtcac aattcagact atatattccc cagggctcag   3840
ccagtgtctg tacatacagc tagaaagctg tattgccttt agcagtcaag ctcgaaaggt   3900
aagcaactct ctggaattac cttctctcta tattagctct tacttgcacc taaacttttaa  3960 aaaattaaca attattgtgc tatgtgttgt atctttaagg gtgaagtacc tgcgtgatac   4020 ccctataaa  aacttctcac ctgtgtatgc attctgcact atttttattat gtgtaaaagc   4080 tttgtgtttg ttttcaggag gcttattctt tgtgcttaaa atatgttttt aatttcagaa   4140
catcttatcc tgtcgttcac tatctgatat gctttgcagt ttgcttgatt aacttctagc   4200
cctacagagt gcacagagag caaaatcatg gtgttcagtg aattctgggg agttatttta   4260
atgtgaaaat tctctagaag tttaattcct gcaaagtgca gctgctgatc actacacaag   4320
ataaaaatgt ggggggtgca taaacgtata ttcttacaat aatagataca tgtgaactta   4380
tatacagaaa agaaaatgag aaaaatgtgt gtgtgtatac tcacacacgt ggtcagtaaa   4440
aacttttgag gggtttaata cagaaaatcc aatcctgagg ccccagcact cagtacgcat   4500 ataagggct  gggctctgaa ggacttctga cttttcacaga ttatataaat ctcaggaaag   4560
caactagatt catgctggct ccaaaagctg tgctttatat aagcacactg gctatacaat   4620
agttgtacag ttcagctctt tataatagaa acagacagaa caagtataaa tcttctattg   4680
gtctatgtca tgaacaagaa ttcattcagt ggctctgttt tatagtaaac attgctattt   4740
tatcatgtct gcatttctct tctgtctgaa tgtcaccact aaaatttaac tccacagaaa   4800
gtttatacta cagtacacat gcatatcttt gagcaaagca aaccataacct gaaagtgcaa   4860 tagagcagaa tatgaattac atgcgtgtct ttctcctaga ctacatgacc ccatataaat   4920
tacattcctt atctattctg ccatcaccaa aacaaaggta aaaatacttt tgaagatcta   4980
ctcatagcaa gtagtgtgca acaaacagat atttctctac atttattttt agggaataaa   5040
aataagaaat aaaatagtca gcaagcctct gctttctcat atatctgtcc aaacctaaag   5100
```

```
tttactgaaa tttgctcttt gaatttccag ttttgcaagc ctatcagatt gtgttttaat    5160
cagaggtact gaaaagtatc aatgaattct agctttcact gaacaaaaat atgtagaggc    5220
aactggcttc tgggacagtt tgctacccaa aagacaactg aatgcaaata cataaataga    5280
tttatgaata tggttttgaa catgcacatg agaggtggat atagcaacag acacattacc    5340
acagaattac tttaaaacta cttgttaaca tttaattgcc taaaaactgc tcgtaattta    5400
ctgttgtagc ctaccataga gtaccctgca tggtactatg tacagcattc catccttaca    5460 tttttcactgt tctgctgttt gctctagaca actcagagtt caccatgaaa atgcggttct    5520 tgggggttggt ggtctgtttg gttctctgga ccctgcattc cgaggggtcc ggagggaaac    5580
tgacagctgt ggatccagaa acaaacatga atgtcagtga aattatctct tactggggat    5640
tccctagtga ggaataccta gttgagacag aagatggata tattctgtgc cttaaccgaa    5700
ttcctcatgg gaggaagaac cattctgaca aaggtcccaa accagttgtc ttcctgcaac    5760
atggcttgct ggcagattct agtaactggg tcacaaacct tgccaacagc agcctgggct    5820
tcattcttgc tgatgctggt tttgacgtgt ggatgggcaa cagcagagga aatacctggt    5880
ctcggaaaca taagacactc tcagtttctc aggatgaatt ctgggctttc agttatgatg    5940
agatggcaaa atatgaccta ccagcttcca ttaacttcat tctgaataag actggccaag    6000
aacaagtgta ttatgtgggt cattctcaag gcaccactat aggtttttata gcattttcac    6060 agatccctga gctggctaaa aggattaaaa tgttttttgc cctgggtcct gtggcttccg    6120
tcgccttctg tactagcccct atggccaaac tgggacgact gccagatcat ctcattaagg    6180
acctctttgg agacaaagaa tttcttcccc agagtgcgtt tttgaagtgg ctgggtaccc    6240
acgtttgcac tcatgtcata ctgaaggagc tctgtggaaa tctctgtttt cttctgtgtg    6300
gatttaatga gagaaattta aatatgtcta gagtggatgt gtatacaaca cattctcctg    6360
ctggaacttc tgtgcaaaac atgttacact ggagccaggc tgttaaattc caaaagtttc    6420
aagcctttga ctggggaagc agtgccaaga attattttca ttacaaccag agttatcctc    6480
ccacatacaa tgtgaaggac atgcttgtgc cgactgcagt ctggagcggg ggtcacgact    6540
ggcttgcaga tgtctacgac gtcaatatct tactgactca gatcaccaac ttggtgttcc    6600
atgagagcat tccggaatgg gagcatcttg acttcatttg gggcctggat gccccttgga    6660
ggctttataa taagattatt aatctaatga ggaaatatca gtgattcgaa gcggccgcaa    6720
gaagaaagct gaaaaactct gtcccttcca acaagaccca gagcactgta gtatcagggg    6780
taaaatgaaa agtatgttat ctgctgcatc cagacttcat aaaagctgga gcttaatcta    6840
gaaaaaaaat cagaaagaaa ttacactgtg agaacaggtg caattcactt ttcctttaca    6900
cagagtaata ctggtaactc atggatgaag gcttaaggga atgaaattgg actcacagta    6960
ctgagtcatc acactgaaaa atgcaacctg atacatcagc agaaggttta tggggaaaa    7020 atgcagcctt ccaattaagc cagatatctg tatgaccaag ctgctccaga attagtcact    7080
caaaatctct cagattaaat tatcaactgt caccaaccat tcctatgctg acaaggcaat    7140
tgcttgttct ctgtgttcct gatactacaa ggctcttcct gacttcctaa agatgcatta    7200
taaaaatctt ataattcaca tttctcccta aactttgact caatcatggt atgttggcaa    7260
atatggtata ttactattca aattgttttc cttgtaccca tatgtaatgg gtcttgtgaa    7320
tgtgctcttt tgttcctta atcataataa aaacatgttt aagcaaacac ttttcacttg    7380
tagtatttga aggtaccgga tctcgagccg ccttcaatgc cccaaaaacc aatccccagg    7440 ttttttaactc tcccgatttt ccaagtacca tagcccgctg agagagcgcc gcggtaatgg    7500
```

```
gatcccagga ccccggggaa tataagtctg aggggggacgt aagcaaccct tccttttgta   7560
acagggacaa catagcccct atttccttct tagaaggaga ggttttcccg caataggtct   7620
tacacgcgga cgaaatcacc tttatgacgg cttccatgct tgatccaccg ggcgaccgga   7680
atcacgcaga gcaaccggaa tcacgcctgg ggtggaccgc tcagtcgtcg ggcttccttc   7740
ccgtcttcca acgactctct gagttctcgg tagggtatgt tggccccctg cagtagggct   7800
ccctccgacg ccactcagct tctgccctcc taagccgcag ccccctctac tagggtcatc   7860
gtccgctccc cgaataagcg agacggatga ggacaggatc gccacgccgc ctgtggccga   7920
ccactattcc ctaacgatca cgtcggggtc accaaatgaa gccttctgct tcatgcatgt   7980
gctcgtagtc gtcagggaat caacggtccg gccatcaacc caggtgcaca ccaatgtggt   8040
gaatggtcaa atggcgttta ttgtatcgag ctaggcactt aaatacaata tctctgcaat   8100
gcggaattca gtggttcgtc caatccgtgt tagacccgtc tgttgccttc ctaacaaggc   8160
acgatcatac cacgatcata ccaccttact cccaccaatc ggcatgcacg gtgcttttc   8220 tctccttata aggcatgttg ctaactcatc gttacataag catgttgcaa gactacaaga   8280
gtattgcata agactacatt tccccctccc tatgcaaaag cgaaactact atatcctgag   8340
gggactccta accgcgtaca accgaagccc cgcttttcgc ctaaacatgc tattgtcccc   8400
tcagtcaagc cttgcccgtt acaacccgat tcgcaagcct tgccctcccc acattatccg   8460
tagcattatt tcctagcagt catcagagct acagaagata ctctatgctg tagccaagtc   8520
tacaagttta ctattcagcg acctcctata ttccgcgtgc cagccgatca attaccaatg   8580
cgcgcttggc gtaatcatgg tcatagctgt ttcctgtgtg aaattgttat ccgctcacaa   8640
ttccacacaa catacgagcc ggaagcataa agtgtaaagc ctggggtgcc taatgagtga   8700
gctaactcac attaattgcg ttgcgctcac tgcccgcttt ccagtcggga aacctgtcgt   8760
gccagctgca ttaatgaatc ggccaacgcg cggggagagg cggtttgcgt attgggcgct   8820
cttccgcttc ctcgctcact gactcgctgc gctcggtcgt tcggctgcgg cgagcggtat   8880
cagctcactc aaaggcggta atacggttat ccacagaatc aggggataac gcaggaaaga   8940
acatgtgagc aaaaggccag caaaaggcca ggaaccgtaa aaaggccgcg ttgctggcgt   9000
ttttccatag gctccgcccc cctgacgagc atcacaaaaa tcgacgctca agtcagaggt   9060
ggcgaaaccc gacaggacta taaagatacc aggcgtttcc ccctggaagc tccctcgtgc   9120
gctctcctgt tccgaccctg ccgcttaccg gatacctgtc cgcctttctc ccttcgggaa   9180
gcgtggcgct ttctcatagc tcacgctgta ggtatctcag ttcggtgtag gtcgttcgct   9240
ccaagctggg ctgtgtgcac gaaccccccg ttcagcccga ccgctgcgcc ttatccggta   9300
actatcgtct tgagtccaac ccggtaagac acgacttatc gccactggca gcagccactg   9360
gtaacaggat tagcagagcg aggtatgtag gcggtgctac agagttcttg aagtggtggc   9420
ctaactacgg ctacactaga aggacagtat ttggtatctg cgctctgctg aagccagtta   9480
ccttcggaaa aagagttggt agctcttgat ccggcaaaca aaccaccgct ggtagcggtg   9540
gtttttttgt ttgcaagcag cagattacgc gcagaaaaaa aggatctcaa gaagatcctt   9600
tgatcttttc tacggggtct gacgctcagt ggaacgaaaa ctcacgttaa gggattttgg   9660
tcatgagatt atcaaaaagg atcttcacct agatcctttt aaattaaaaa tgaagtttta   9720
aatcaatcta aagtatatat gagtaaactt ggtctgacag ttaccaatgc ttaatcagtg   9780
aggcacctat ctcagcgatc tgtctatttc gttcatccat agttgcctga ctccccgtcg   9840
```

```
tgtagataac tacgatacgg gagggcttac catctggccc cagtgctgca atgataccgc   9900
gagacccacg ctcaccggct ccagatttat cagcaataaa ccagccagcc ggaagggccg   9960
agcgcagaag tggtcctgca actttatccg cctccatcca gtctattaat tgttgccggg  10020
aagctagagt aagtagttcg ccagttaata gtttgcgcaa cgttgttgcc attgctacag  10080
gcatcgtggt gtcacgctcg tcgtttggta tggcttcatt cagctccggt tcccaacgat  10140
caaggcgagt tacatgatcc cccatgttgt gcaaaaaagc ggttagctcc ttcggtcctc  10200
cgatcgttgt cagaagtaag ttggccgcag tgttatcact catggttatg gcagcactgc  10260
ataattctct tactgtcatg ccatccgtaa gatgcttttc tgtgactggt gagtactcaa  10320
ccaagtcatt ctgagaatag tgtatgcggc gaccgagttg ctcttgcccg gcgtcaatac  10380
gggataatac cgcgccacat agcagaactt taaaagtgct catcattgga aaacgttctt  10440
cggggcgaaa actctcaagg atcttaccgc tgttgagatc cagttcgatg taacccactc  10500
gtgcacccaa ctgatcttca gcatctttta ctttcaccag cgtttctggg tgagcaaaaa  10560
caggaaggca aaatgccgca aaaaagggaa taagggcgac acggaaatgt tgaatactca  10620
tactcttcct ttttcaatat tattgaagca tttatcaggg ttattgtctc atgagcggat  10680
acatatttga atgtatttag aaaaataaac aaataggggg tccgcgcaca tttccccgaa  10740
aagtgccacc tgacgcgccc tgtagcggcg cattaagcgc ggcgggtgtg gtggttacgc  10800
gcagcgtgac cgctacactt gccagcgccc tagcgcccgc tcctttcgct ttcttccctt  10860
cctttctcgc cacgttcgcc gg                                           10882
```

<210> SEQ ID NO 7
<211> LENGTH: 7780
<212> TYPE: DNA
<213> ORGANISM: Artificial Sequence
<220> FEATURE:
<223> OTHER INFORMATION: Proviral sequence of pALVIN-OVR1-I-SBC102-dSA

<400> SEQUENCE: 7

```
aatgaagcct tctgcttcat gcatgtgctc gtagtcgtca gggaatcaac ggtccggcca     60
tcaacccagg tgcacaccaa tgtggtgaat ggtcaaatgg cgtttattgt atcgagctag    120
gcacttaaat acaatatctc tgcaatgcgg aattcagtgg ttcgtccaat ccgtcccct     180 ccctatgcaa aagcgaaact actatatcct gagggggactc ctaaccgcgt acaaccgaag    240
ccccgctttt cgcctaaaca tgctattgtc ccctcagtca agccttgccc gttacaaccc    300
gattcgcaag ccttgccctc cccacattat ccgtagcatt atttcctagc agtcatcaga    360
gctacagaag atactctatg ctgtagccaa gtctacaagt ttactattca gcgacctcct    420
atattccgcg tgccagccga tcaattacca atccaaccag ctatcacacg gaatacaaga    480
actcgcctac gctcttcttt cgggctgctt ataagcctcc tgtaattttt ttatattcct    540
cgctcgagtc tcttcagaat ggcacagcac cgctgcagaa aaatgccagg tggactatga    600
actcacatcc aaaggagctt gacctgatac ctgattttct tcaaacaggg gaaacaacac    660
aatcccacaa acagctcag agagaaacca tcactgatgg ctacagcacc aaggtatgca    720
atggcaatcc attcgacatt catctgtgac ctgagcaaaa tgatttatct ctccatgaat    780
ggttgcttct ttccctcatg aaaaggcaat ttccacactc acaatatgca acaaagacaa    840
acagagaaca attaatgtgc tccttcctaa tgttaaaatt gtagtggcaa agaggagaac    900
aaaatctcaa gttctgagta ggtttttagtg attggataag aggctttgac ctgtgagctc    960
acctggactt catatccttt tggataaaaa gtgcttttat aactttcagg tctccgagtc   1020
```

```
tttattcatg agactgttgg tttagggaca gacccacaat gaaatgcctg cataggaaa       1080 gggcagcaga gccttagctg accttttctt gggacaagca ttgtcaaaca atgtgtgaca      1140
aaactatttg tactgctttg cacagctgtg ctgggcaggg caatccattg ccacctatcc      1200
caggtaacct tccaactgca agaagattgt tgcttactct ctctagaccc caagtcaaa       1260 ccaactatgc aggtatgctg acaacactat gatgacagcc tgttctgatc aagatctcat      1320
ttgttcatgg acaattttg ttgcttgcag ctggtcttcc attgggaaag agtgtagtat       1380
atccttctca tctgacagaa aagcagaaat tctcatgctc cacacttaat ctacattgtt      1440
ttaaaccacc ggctacttct tggagaggaa aaatggcttt tataagactc acaaaacaaa      1500
gctctgcaag tcaaatgcat acaaaactgt tctgtaggtc tggaatcagg acactatgtg     1560
gaagtcaaat agagcagctt taaaaagcct ttgggatcat tctcatctta tatttgcagc      1620
acgatactat gacagtgata actgacataa ctgcatcaat ttccttgata ttttatttgt      1680
cttaaagtac aagacataga gatggacgta aagatggaca tatgactcag gtctggacag      1740
gtccgtggtc catgtatgat aaaagagatg aagggaagga gaattgagac tgtctaagaa      1800
gggcttcagg gacgttctga aggcagattt gactgaatca gatgtactgt ccaagtctca      1860
tatgtagcaa tggaaggctg atattggaga aatataaaga aatggctgtg aactcaaagt      1920
gaccctgaac agaaaaggga tatggagtta aaataatgtc acagaactga gtttatatg       1980 ataccatg gctgcagag gtcagagtg ctccaccatg ggcctctctt gggctgcagg          2040
gaacttctgt tctacacctg gaacacctcc tgccctcctc cgcactgacc tcagtgtcat      2100
cagggctgtt tctctcacat tttctcactc acctctccca actaccattg tacagcagtt      2160
gttcttacat attgctcctc ctgaggtaca tctagcatcg ttaagtcctc agacttggca      2220
aggagaatgt agatttccac agtatatatg ttttcacaaa aggaaggaga gaaacaaaag     2280
aaaatggcac tgactaaact tcagctagtg gtataggaaa gtaattctgc ttaacagaga     2340
ttgcagtgat ctctatgtat gtcctgaaga attatgttgt actttttcc cccattttta      2400 aatcaaacag tgcttacag aggtcagaat ggtttcttta ctgtttgtca attctattat       2460
ttcaatacag aacaatagct tctataactg aaatatattt gctattgtat attatgattg      2520
tccctcgaac catgaacact cctccagctg aatttcacaa ttcctctgtc atctgccagg      2580
ccattaagtt attcatggaa gatctttgag gaacactgca agttcatatc ataaacacat      2640
ttgaaattga gtattgtttt gcattgtatg gagctatgtt ttgctgtatc ctcagaataa      2700
aagtttgtta taaagcattc acacccataa aaagatagat ttaaatattc caactatagg     2760
aaagaaagtg tgtctgctct tcactctagt ctcagttggc tccttcacat gcacgcttct      2820
ttatttctcc tattttgtca agaaaataat aggtcaagtc ttgttctcat ttatgtcctg      2880
tctagcgtgg ctcagatgca cattgtacat acaagaagga tcaaatgaaa cagacttctg     2940
gtctgttact acaaccatag taataagcac actaactaat aattgctaat tatgtttcc      3000 atctccaagg ttcccacatt tttctgtttt cttaaagatc ccattatctg gttgtaactg      3060
aagctcaatg gaacatgagc aatatttccc agtcttctct cccatccaac agtcctgatg      3120
gattagcaga acaggcagaa aacacattgt tacccagaat taaaaactaa tatttgctct     3180
ccattcaatc caaatggac ctattgaaac taaaatctaa cccaatccca ttaaatgatt       3240
tctatggtgt caaaggtcaa acttctgaag ggaacctgtg ggtgggtcac aattcagact     3300
atatattccc cagggctcag ccagtgtctg tacatacagc tagaaagctg tattgccttt     3360
```

```
agcagtcaag ctcgaaaggt aagcaactct ctggaattac cttctctcta tattagctct    3420
tacttgcacc taaactttaa aaaattaaca attattgtgc tatgtgttgt atctttaagg    3480
gtgaagtacc tgcgtgatac cccctataaa aacttctcac ctgtgtatgc attctgcact    3540
attttattat gtgtaaaagc tttgtgtttg ttttcaggag gcttattctt tgtgcttaaa    3600
atatgttttt aatttcagaa catcttatcc tgtcgttcac tatctgatat gctttgcagt    3660
ttgcttgatt aacttctagc cctacagagt gcacagagag caaaatcatg gtgttcagtg    3720
aattctgggg agttatttta atgtgaaaat tctctagaag tttaattcct gcaaagtgca    3780
gctgctgatc actacacaag ataaaaatgt ggggggtgca taaacgtata ttcttacaat    3840
aatagataca tgtgaactta tatacagaaa agaaaatgag aaaaatgtgt gtgtgtatac    3900
tcacacacgt ggtcagtaaa aacttttgag gggtttaata cagaaaatcc aatcctgagg    3960
ccccagcact cagtacgcat ataaagggct gggctctgaa ggacttctga ctttcacaga    4020
ttatataaat ctcaggaaag caactagatt catgctggct ccaaaagctg tgctttatat    4080
aagcacactg gctatacaat agttgtacag ttcagctctt tataatagaa acagacagaa    4140
caagtataaa tcttctattg gtctatgtca tgaacaagaa ttcattcagt ggctctgttt    4200
tatagtaaac attgctattt tatcatgtct gcatttctct tctgtctgaa tgtcaccact    4260
aaaatttaac tccacagaaa gtttatacta cagtacacat gcatatcttt gagcaaagca    4320
aaccatacct gaaagtgcaa tagagcagaa tatgaattac atgcgtgtct ttctcctaga    4380
ctacatgacc ccatataaat tacattcctt atctattctg ccatcaccaa aacaaaggta    4440
aaaatacttt tgaagatcta ctcatagcaa gtagtgtgca acaaacagat atttctctac    4500
atttattttt agggaataaa aataagaaat aaaatagtca gcaagcctct gctttctcat    4560
atatctgtcc aaacctaaag tttactgaaa tttgctcttt gaatttccag ttttgcaagc    4620
ctatcagatt gtgttttaat cagaggtact gaaaagtatc aatgaattct agctttcact    4680
gaacaaaaat atgtagaggc aactggcttc tgggacagtt tgctacccaa aagcaactg     4740 aatgcaaata cataaataga tttatgaata tggttttgaa catgcacatg agaggtggat    4800
atagcaacag acacattacc acagaattac tttaaaacta cttgttaaca tttaattgcc    4860
taaaaactgc tcgtaattta ctgttgtagc ctaccataga gtaccctgca tggtactatg    4920
tacagcattc catccttaca ttttcactgt tctgctgttt gctctagaca actcagagtt    4980
caccatgaaa atgcggttct tggggttggt ggtctgtttg gttctctgga ccctgcattc    5040
cgaggggtcc ggagggaaac tgacagctgt ggatccagaa acaaacatga atgtcagtga    5100
aattatctct tactggggat tccctagtga ggaataccta gttgagacag aagatggata    5160
tattctgtgc cttaaccgaa ttcctcatgg gaggaagaac cattctgaca aggtcccaa     5220 accagttgtc ttcctgcaac atggcttgct ggcagattct agtaactggg tcacaaacct    5280
tgccaacagc agcctgggct tcattcttgc tgatgctggt tttgacgtgt ggatgggcaa    5340
cagcagagga aatacctggt ctcggaaaca taagacactc tcagtttctc aggatgaatt    5400
ctgggctttc agttatgatg agatggcaaa atatgaccta ccagcttcca ttaacttcat    5460
tctgaataag actggccaag aacaagtgta ttatgtgggt cattctcaag caccactat     5520 aggttttata gcattttcac agatccctga gctggctaaa aggattaaaa tgttttttgc    5580
cctgggtcct gtggcttccg tcgccttctg tactagccct atggccaaac tgggacgact    5640
gccagatcat ctcattaagg acctctttgg agacaaagaa tttcttcccc agagtgcgtt    5700
tttgaagtgg ctgggtaccc acgtttgcac tcatgtcata ctgaaggagc tctgtggaaa    5760
```

```
tctctgtttt cttctgtgtg gatttaatga gagaaattta aatatgtcta gagtggatgt    5820
gtatacaaca cattctcctg ctggaacttc tgtgcaaaac atgttacact ggagccaggc    5880
tgttaaattc caaaagtttc aagcctttga ctggggaagc agtgccaaga attattttca    5940
ttacaaccag agttatcctc ccacatacaa tgtgaaggca atgcttgtgc cgactgcagt    6000
ctggagcggg ggtcacgact ggcttgcaga tgtctacgac gtcaatatct tactgactca    6060
gatcaccaac ttggtgttcc atgagagcat tccggaatgg gagcatcttg acttcatttg    6120
gggcctggat gccccttgga ggctttataa taagattatt aatctaatga ggaaatatca    6180
gtgattcgaa gcggccgcaa gaagaaagct gaaaaactct gtcccttcca acaagaccca    6240
gagcactgta gtatcagggg taaaatgaaa agtatgttat ctgctgcatc cagacttcat    6300
aaaagctgga gcttaatcta gaaaaaaaat cagaaagaaa ttacactgtg agaacaggtg    6360
caattcactt ttcctttaca cagagtaata ctggtaactc atggatgaag gcttaaggga    6420
atgaaattgg actcacagta ctgagtcatc acactgaaaa atgcaacctg atacatcagc    6480
agaaggttta tgggggaaaa atgcagcctt ccaattaagc cagatatctg tatgaccaag    6540
ctgctccaga attagtcact caaaatctct cagattaaat tatcaactgt caccaaccat    6600
tcctatgctg acaaggcaat tgcttgttct ctgtgttcct gatactacaa ggctcttcct    6660
gacttcctaa agatgcatta taaaaatctt ataattcaca tttctcccta aactttgact    6720
caatcatggt atgttggcaa atatggtata ttactattca aattgttttc cttgtaccca    6780
tatgtaatgg gtcttgtgaa tgtgctcttt tgttccttta atcataataa aaacatgttt    6840
aagcaaacac ttttcacttg tagtatttga aggtaccgga tctcgagccg ccttcaatgc    6900
ccccaaaacc aatccccagg tttttaactc tcccgatttt ccaagtacca tagcccgctg    6960
agagagcgcc gcggtaatgg gatcccagga cccccgggaa tataagtctg aggggacgt     7020 aagcaaccct tccttttgta acagggacaa catagcccct atttccttct tagaaggaga    7080
ggttttcccg caataggtct tacacgcgga cgaaatcacc tttatgacgg cttccatgct    7140
tgatccaccg ggcgaccgga atcacgcaga gcaaccggaa tcacgcctgg ggtggaccgc    7200
tcagtcgtcg ggcttccttc ccgtcttcca acgactctct gagttctcgg tagggtatgt    7260 tggcccctg cagtagggct ccctccgacg ccactcagct tctgccctcc taagccgcag     7320 cccctctac tagggtcatc gtccgctccc cgaataagcg agacggatga ggacaggatc     7380
gccacgccgc ctgtggccga ccactattcc ctaacgatca cgtcggggtc accaaatgaa    7440
gccttctgct tcatgcatgt gctcgtagtc gtcagggaat caacggtccg gccatcaacc    7500
caggtgcaca ccaatgtggt gaatggtcaa atggcgttta ttgtatcgag ctaggcactt    7560
aaatacaata tctctgcaat gcggaattca gtggttcgtc caatccgtgt tagacccgtc    7620
tgttgccttc ctaacaaggc acgatcatac cacgatcata ccaccttact cccaccaatc    7680
ggcatgcacg gtgctttttc tctccttata aggcatgttg ctaactcatc gttacataag    7740
catgttgcaa gactacaaga gtattgcata agactacatt                          7780
```

<210> SEQ ID NO 8
<211> LENGTH: 10762
<212> TYPE: DNA
<213> ORGANISM: Artificial Sequence
<220> FEATURE:
<223> OTHER INFORMATION: pALVIN-OV-1.1-I
<220> FEATURE:
<221> NAME/KEY: misc_feature
<222> LOCATION: (1)..(2735)

<223> OTHER INFORMATION: n is a, c, g, or t

<400> SEQUENCE: 8

| | | |
|---|---|---|
| nnnnnnnnnn nnnnnnnnnn nnnnnnnnnn nnnnnnnnnn nnnnnnnnnn nnnnnnnnnn | 60 | |
| nnnnnnnnnn nnnnnnnnnn nnnnnnnnnn nnnnnnnnnn nnnnnnnnnn nnnnnnnnnn | 120 | |
| nnnnnnnnnn nnnnnnnnnn nnnnnnnnnn nnnnnnnnnn nnnnnnnnnn nnnnnnnnnn | 180 | |
| nnnnnnnnnn nnnnnnnnnn nnnnnnnnnn nnnnnnnnnn nnnnnnnnnn nnnnnnnnnn | 240 | |
| nnnnnnnnnn nnnnnnnnnn nnnnnnnnnn nnnnnnnnnn nnnnnnnnnn nnnnnnnnnn | 300 | |
| nnnnnnnnnn nnnnnnnnnn nnnnnnnnnn nnnnnnnnnn nnnnnnnnnn nnnnnnnnnn | 360 | |
| nnnnnnnnnn nnnnnnnnnn nnnnnnnnnn nnnnnnnnnn nnnnnnnnnn nnnnnnnnnn | 420 | |
| nnnnnnnnnn nnnnnnnnnn nnnnnnnnnn nnnnnnnnnn nnnnnnnnnn nnnnnnnnnn | 480 | |
| nnnnnnnnnn nnnnnnnnnn nnnnnnnnnn nnnnnnnnnn nnnnnnnnnn nnnnnnnnnn | 540 | |
| nnnnnnnnnn nnnnnnnnnn nnnnnnnnnn nnnnnnnnnn nnnnnnnnnn nnnnnnnnnn | 600 | |
| nnnnnnnnnn nnnnnnnnnn nnnnnnnnnn nnnnnnnnnn nnnnnnnnnn nnnnnnnnnn | 660 | |
| nnnnnnnnnn nnnnnnnnnn nnnnnnnnnn nnnnnnnnnn nnnnnnnnnn nnnnnnnnnn | 720 | |
| nnnnnnnnnn nnnnnnnnnn nnnnnnnnnn nnnnnnnnnn nnnnnnnnnn nnnnnnnnnn | 780 | |
| nnnnnnnnnn nnnnnnnnnn nnnnnnnnnn nnnnnnnnnn nnnnnnnnnn nnnnnnnnnn | 840 | |
| nnnnnnnnnn nnnnnnnnnn nnnnnnnnnn nnnnnnnnnn nnnnnnnnnn nnnnnnnnnn | 900 | |
| nnnnnnnnnn nnnnnnnnnn nnnnnnnnnn nnnnnnnnnn nnnnnnnnnn nnnnnnnnnn | 960 | |
| nnnnnnnnnn nnnnnnnnnn nnnnnnnnnn nnnnnnnnnn nnnnnnnnnn nnnnnnnnnn | 1020 | |
| nnnnnnnnnn nnnnnnnnnn nnnnnnnnnn nnnnnnnnnn nnnnnnnnnn nnnnnnnnnn | 1080 | |
| nnnnnnnnnn nnnnnnnnnn nnnnnnnnnn nnnnnnnnnn nnnnnnnnnn nnnnnnnnnn | 1140 | |
| nnnnnnnnnn nnnnnnnnnn nnnnnnnnnn nnnnnnnnnn nnnnnnnnnn nnnnnnnnnn | 1200 | |
| nnnnnnnnnn nnnnnnnnnn nnnnnnnnnn nnnnnnnnnn nnnnnnnnnn nnnnnnnnnn | 1260 | |
| nnnnnnnnnn nnnnnnnnnn nnnnnnnnnn nnnnnnnnnn nnnnnnnnnn nnnnnnnnnn | 1320 | |
| nnnnnnnnnn nnnnnnnnnn nnnnnnnnnn nnnnnnnnnn nnnnnnnnnn nnnnnnnnnn | 1380 | |
| nnnnnnnnnn nnnnnnnnnn nnnnnnnnnn nnnnnnnnnn nnnnnnnnnn nnnnnnnnnn | 1440 | |
| nnnnnnnnnn nnnnnnnnnn nnnnnnnnnn nnnnnnnnnn nnnnnnnnnn nnnnnnnnnn | 1500 | |
| nnnnnnnnnn nnnnnnnnnn nnnnnnnnnn nnnnnnnnnn nnnnnnnnnn nnnnnnnnnn | 1560 | |
| nnnnnnnnnn nnnnnnnnnn nnnnnnnnnn nnnnnnnnnn nnnnnnnnnn nnnnnnnnnn | 1620 | |
| nnnnnnnnnn nnnnnnnnnn nnnnnnnnnn nnnnnnnnnn nnnnnnnnnn nnnnnnnnnn | 1680 | |
| nnnnnnnnnn nnnnnnnnnn nnnnnnnnnn nnnnnnnnnn nnnnnnnnnn nnnnnnnnnn | 1740 | |
| nnnnnnnnnn nnnnnnnnnn nnnnnnnnnn nnnnnnnnnn nnnnnnnnnn nnnnnnnnnn | 1800 | |
| nnnnnnnnnn nnnnnnnnnn nnnnnnnnnn nnnnnnnnnn nnnnnnnnnn nnnnnnnnnn | 1860 | |
| nnnnnnnnnn nnnnnnnnnn nnnnnnnnnn nnnnnnnnnn nnnnnnnnnn nnnnnnnnnn | 1920 | |
| nnnnnnnnnn nnnnnnnnnn nnnnnnnnnn nnnnnnnnnn nnnnnnnnnn nnnnnnnnnn | 1980 | |
| nnnnnnnnnn nnnnnnnnnn nnnnnnnnnn nnnnnnnnnn nnnnnnnnnn nnnnnnnnnn | 2040 | |
| nnnnnnnnnn nnnnnnnnnn nnnnnnnnnn nnnnnnnnnn nnnnnnnnnn nnnnnnnnnn | 2100 | |
| nnnnnnnnnn nnnnnnnnnn nnnnnnnnnn nnnnnnnnnn nnnnnnnnnn nnnnnnnnnn | 2160 | |
| nnnnnnnnnn nnnnnnnnnn nnnnnnnnnn nnnnnnnnnn nnnnnnnnnn nnnnnnnnnn | 2220 | |
| nnnnnnnnnn nnnnnnnnnn nnnnnnnnnn nnnnnnnnnn nnnnnnnnnn nnnnnnnnnn | 2280 | |

```
nnnnnnnnnn nnnnnnnnnn nnnnnnnnnn nnnnnnnnnn nnnnnnnnnn nnnnnnnnnn    2340
nnnnnnnnnn nnnnnnnnnn nnnnnnnnnn nnnnnnnnnn nnnnnnnnnn nnnnnnnnnn    2400
nnnnnnnnnn nnnnnnnnnn nnnnnnnnnn nnnnnnnnnn nnnnnnnnnn nnnnnnnnnn    2460
nnnnnnnnnn nnnnnnnnnn nnnnnnnnnn nnnnnnnnnn nnnnnnnnnn nnnnnnnnnn    2520
nnnnnnnnnn nnnnnnnnnn nnnnnnnnnn nnnnnnnnnn nnnnnnnnnn nnnnnnnnnn    2580
nnnnnnnnnn nnnnnnnnnn nnnnnnnnnn nnnnnnnnnn nnnnnnnnnn nnnnnnnnnn    2640
nnnnnnnnnn nnnnnnnnnn nnnnnnnnnn nnnnnnnnnn nnnnnnnnnn nnnnnnnnnn    2700
nnnnnnnnnn nnnnnnnnnn nnnnnnnnnn nnnnnttcga agcggccgca agaagaaagc    2760
tgaaaaactc tgtcccttcc aacaagaccc agagcactgt agtatcaggg gtaaaatgaa    2820
aagtatgtta tctgctgcat ccagacttca taaaagctgg agcttaatct agaaaaaaaa    2880
tcagaaagaa attacactgt gagaacaggt gcaattcact tttcctttac acagagtaat    2940
actggtaact catggatgaa ggcttaaggg aatgaaattg gactcacagt actgagtcat    3000
cacactgaaa aatgcaacct gatacatcag cagaaggttt atgggggaaa aatgcagcct    3060
tccaattaag ccagatatct gtatgaccaa gctgctccag aattagtcac tcaaaatctc    3120
tcagattaaa ttatcaactg tcaccaacca ttcctatgct gacaaggcaa ttgcttgttc    3180
tctgtgttcc tgatactaca aggctcttcc tgacttccta aagatgcatt ataaaaatct    3240
tataattcac atttctccct aaactttgac tcaatcatgg tatgttggca aatatggtat    3300
attactattc aaattgtttt ccttgtaccc atatgtaatg ggtcttgtga atgtgctctt    3360
ttgttccttt aatcataata aaaacatgtt taagcaaaca cttttcactt gtagtatttg    3420
aaggtaccgg atctcgagcc gccttcaatg cccccaaaac caatcccag  gtttttaact    3480 ctcccgattt tccaagtacc atagcccgct gagagagcgc cgcggtaatg ggatcccagg    3540
accccgggga ataagtct gaggggggacg taagcaaccc ttccttttgt aacagggaca    3600
acatagcccc tatttccttc ttagaaggag aggttttccc gcaataggtc ttacacgcgg    3660
acgaaatcac ctttatgacg gcttccatgc ttgatccacc gggcgaccgg aatcacgcag    3720
agcaaccgga atcacgcctg gggtggaccg ctcagtcgtc gggcttcctt cccgtcttcc    3780
aacgactctc tgagttctcg gtagggtatg ttggccccct gcagtagggc tccctccgac    3840
gccactcagc ttctgccctc ctaagccgca gcccctcta ctagggtcat cgtccgctcc    3900
ccgaataagc gagacggatg aggacaggat cgccacgccg cctgtggccg accactattc    3960
cctaacgatc acgtcggggt caccaaatga agccttctgc ttcatgcatg tgctcgtagt    4020
cgtcagggaa tcaacggtcc ggccatcaac ccaggtgcac accaatgtgg tgaatggtca    4080
aatgcgtttt attgtatcga gctaggcact taaatacaat atctctgcaa tgcggaattc    4140
agtggttcgt ccaatccgtg ttagacccgt ctgttgcctt cctaacaagg cacgatcata    4200
ccacgatcat accaccttac tcccaccaat cggcatgcac ggtgcttttt ctctccttat    4260
aaggcatgtt gctaactcat cgttacataa gcatgttgca agactacaag agtattgcat    4320
aagactacat ttcccccctcc ctatgcaaaa gcgaaactac tatatcctga ggggactcct    4380
aaccgcgtac aaccgaagcc ccgcttttcg cctaaacatg ctattgtccc ctcagtcaag    4440
ccttgcccgt tacaacccga ttcgcaagcc ttgccctccc cacattatcc gtagcattat    4500
ttcctagcag tcatcagagc tacagaagat actctatgct gtagccaagt ctacaagttt    4560
actattcagc gacctcctat attccgcgtg ccagccgatc aattaccaat gcgcgcttgg    4620
```

```
cgtaatcatg gtcatagctg tttcctgtgt gaaattgtta tccgctcaca attccacaca    4680
acatacgagc cggaagcata aagtgtaaag cctggggtgc ctaatgagtg agctaactca    4740
cattaattgc gttgcgctca ctgcccgctt tccagtcggg aaacctgtcg tgccagctgc    4800
attaatgaat cggccaacgc gcggggagag gcggtttgcg tattgggcgc tcttccgctt    4860
cctcgctcac tgactcgctg cgctcggtcg ttcggctgcg gcgagcggta tcagctcact    4920
caaaggcggt aatacggtta tccacagaat caggggataa cgcaggaaag aacatgtgag    4980
caaaaggcca gcaaaaggcc aggaaccgta aaaaggccgc gttgctggcg ttttttccata    5040 ggctccgccc cctgacgag catcacaaaa atcgacgctc aagtcagagg tggcgaaacc    5100
cgacaggact ataaagatac caggcgtttc ccctggaag ctccctcgtg cgctctcctg    5160
ttccgaccct gccgcttacc ggatacctgt ccgcctttct cccttcggga agcgtggcgc    5220
tttctcatag ctcacgctgt aggtatctca gttcggtgta ggtcgttcgc tccaagctgg    5280
gctgtgtgca cgaaccccc gttcagcccg accgctgcgc cttatccggt aactatcgtc    5340
ttgagtccaa cccggtaaga cacgacttat cgccactggc agcagccact ggtaacagga    5400
ttagcagagc gaggtatgta ggcggtgcta cagagttctt gaagtggtgg cctaactacg    5460
gctacactag aaggacagta tttggtatct gcgctctgct gaagccagtt accttcggaa    5520
aaagagttgg tagctcttga tccggcaaac aaaccaccgc tggtagcggt ggtttttttg    5580
tttgcaagca gcagattacg cgcagaaaaa aaggatctca agaagatcct ttgatctttt    5640
ctacggggtc tgacgctcag tggaacgaaa actcacgtta agggattttg gtcatgagat    5700
tatcaaaaag gatcttcacc tagatccttt taaattaaaa atgaagtttt aaatcaatct    5760
aaagtatata tgagtaaact tggtctgaca gttaccaatg cttaatcagt gaggcaccta    5820
tctcagcgat ctgtctattt cgttcatcca tagttgcctg actccccgtc gtgtagataa    5880
ctacgatacg ggagggctta ccatctggcc ccagtgctgc aatgataccg cgagacccac    5940
gctcaccggc tccagattta tcagcaataa accagccagc cggaagggcc gagcgcagaa    6000
gtggtcctgc aactttatcc gcctccatcc agtctattaa ttgttgccgg gaagctagag    6060
taagtagttc gccagttaat agtttgcgca acgttgttgc cattgctaca ggcatcgtgg    6120
tgtcacgctc gtcgtttggt atggcttcat tcagctccgg ttcccaacga tcaaggcgag    6180
ttacatgatc ccccatgttg tgcaaaaaag cggttagctc cttcggtcct ccgatcgttg    6240
tcagaagtaa gttggccgca gtgttatcac tcatggttat ggcagcactg cataattctc    6300
ttactgtcat gccatccgta agatgctttt ctgtgactgg tgagtactca accaagtcat    6360
tctgagaata gtgtatgcgg cgaccgagtt gctcttgccc ggcgtcaata cgggataata    6420
ccgcgccaca tagcagaact ttaaaagtgc tcatcattgg aaaacgttct cggggcgaa    6480 aactctcaag gatcttaccg ctgttgagat ccagttcgat gtaacccact cgtgcaccca    6540
actgatcttc agcatctttt actttcacca gcgtttctgg gtgagcaaaa acaggaaggc    6600
aaaatgccgc aaaaaaggga ataagggcga cacggaaatg ttgaatactc atactcttcc    6660
tttttcaata ttattgaagc atttatcagg gttattgtct catgagcgga tacatatttg    6720
aatgtattta gaaaaataaa caaataggg ttccgcgcac atttccccga aaagtgccac    6780
ctgacgcgcc ctgtagcggc gcattaagcg cggcgggtgt ggtggttacg cgcagcgtga    6840
ccgctacact tgccagcgcc ctagcgcccg ctcctttcgc tttcttccct tcctttctcg    6900
ccacgttcgc cggctttccc cgtcaagctc taaatcgggg gctccctttt agggttccgat    6960 ttagtgcttt acggcacctc gacccccaaa aacttgatta gggtgatggt tcacgtagtg    7020
```

```
ggccatcgcc ctgatagacg gttttcgcc ctttgacgtt ggagtccacg ttctttaata    7080
gtggactctt gttccaaact ggaacaacac tcaaccctat ctcggtctat tcttttgatt    7140
tataagggat tttgccgatt tcggcctatt ggttaaaaaa tgagctgatt taacaaaaat    7200
ttaacgcgaa ttttaacaaa atattaacgc ttacaatttc cattcgccat tcaggctgcg    7260
caactgttgg gaagggcgat cggtgcgggc ctcttcgcta ttacgccagc tggcgaaagg    7320
gggatgtgct gcaaggcgat taagttgggt aacgccaggg ttttcccagt cacgacgttg    7380
taaaacgacg gccagtgagc gcgtattccc taacgatcac gtcggggtca ccaaatgaag    7440
ccttctgctt catgcatgtg ctcgtagtcg tcagggaatc aacggtccgg ccatcaaccc    7500
aggtgcacac caatgtggtg aatggtcaaa tggcgtttat tgtatcgagc taggcactta    7560
aatacaatat ctctgcaatg cggaattcag tggttcgtcc aatccgtccc cctccctatg    7620
caaaagcgaa actactatat cctgagggga ctcctaaccg cgtacaaccg aagcccccgct   7680 tttcgcctaa acatgctatt gtcccctcag tcaagccttg cccgttacaa cccgattcgc    7740
aagccttgcc ctccccacat tatccgtagc attatttcct agcagtcatc agagctacag    7800
aagatactct atgctgtagc caagtctaca agtttactat tcagcgacct cctatattcc    7860
gcgtgccagc cgatcaatta ccaatccaac cagctatcac acggaataca agaactcgcc    7920
tacgctcttc tttcgggctg cttataagcc tcctgtaatt tttttatatt cctcgttaag    7980
tcctcagact tggcaaggag aatgtagatt tccacagtat atatgttttc acaaaaggaa    8040
ggagagaaac aaaagaaaat ggcactgact aaacttcagc tagtggtata ggaaagtaat    8100
tctgcttaac agagattgca gtgatctcta tgtatgtcct gaagaattat gttgtacttt    8160
tttcccccat ttttaaatca acagtgctt tacagaggtc agaatggttt ctttactgtt    8220
tgtcaattct attatttcaa tacagaacaa tagcttctat aactgaaata tatttgctat    8280
tgtatattat gattgtccct cgaaccatga acactcctcc agctgaattt cacaattcct    8340
ctgtcatctg ccaggccatt aagttattca tggaagatct ttgaggaaca ctgcaagttc    8400
atatcataaa cacatttgaa attgagtatt gttttgcatt gtatggagct atgttttgct    8460
gtatcctcag aataaaagtt tgttataaag cattcacacc cataaaaaga tagatttaaa    8520
tattccaact ataggaaaga aagtgtgtct gctcttcact ctagtctcag ttggctcctt    8580
cacatgcacg cttctttatt tctcctattt tgtcaagaaa ataataggtc aagtcttgtt    8640
ctcatttatg tcctgtctag cgtggctcag atgcacattg tacatacaag aaggatcaaa    8700
tgaaacagac ttctggtctg ttactacaac catagtaata agcacactaa ctaataattg    8760
ctaattatgt tttccatctc caaggttccc acatttttct gttttcttaa agatcccatt    8820
atctggttgt aactgaagct caatggaaca tgagcaatat ttcccagtct tctctcccat    8880
ccaacagtcc tgatggatta gcagaacagg cagaaaacac attgttaccc agaattaaaa    8940
actaatattt gctctccatt caatccaaaa tggacctatt gaaactaaaa tctaacccaa    9000
tcccattaaa tgatttctat ggtgtcaaag gtcaaacttc tgaagggaac ctgtgggtgg    9060
gtcacaattc agactatata ttccccaggg ctcagccagt gtctgtacat acagctagaa    9120
agctgtattg cctttagcag tcaagctcga aaggtaagca actctctgga attaccttct    9180
ctctatatta gctcttactt gcacctaaac tttaaaaaat taacaattat tgtgctatgt    9240
gttgtatctt taagggtgaa gtacctgcgt gatacccct ataaaaactt ctcacctgtg    9300
tatgcattct gcactatttt attatgtgta aaagctttgt gtttgtttc aggaggctta    9360
```

```
ttctttgtgc ttaaaatatg tttttaattt cagaacatct tatcctgtcg ttcactatct      9420
gatatgcttt gcagtttgct tgattaactt ctagccctac agagtgcaca gagagcaaaa      9480
tcatggtgtt cagtgaattc tggggagtta ttttaatgtg aaaattctct agaagtttaa      9540
ttcctgcaaa gtgcagctgc tgatcactac acaagataaa aatgtggggg gtgcataaac      9600
gtatattctt acaataatag atacatgtga acttatatac agaaagaaa atgagaaaaa       9660
tgtgtgtgtg tatactcaca cacgtggtca gtaaaaactt ttgaggggtt taatacagaa      9720
aatccaatcc tgaggcccca gcactcagta cgcatataaa gggctgggct ctgaaggact      9780
tctgactttc acagattata taaatctcag gaaagcaact agattcatgc tggctccaaa      9840
agctgtgctt tatataagca cactggctat acaatagttg tacagttcag ctctttataa      9900
tagaaacaga cagaacaagt ataaatcttc tattggtcta tgtcatgaac aagaattcat      9960
tcagtggctc tgttttatag taaacattgc tattttatca tgtctgcatt tctcttctgt     10020
ctgaatgtca ccactaaaat ttaactccac agaaagttta tactacagta cacatgcata     10080
tctttgagca aagcaaacca tacctgaaag tgcaatagag cagaatatga attacatgcg     10140
tgtctttctc ctagactaca tgaccccata taaattacat tccttatcta ttctgccatc     10200
accaaaacaa aggtaaaaat acttttgaag atctactcat agcaagtagt gtgcaacaaa     10260
cagatatttc tctacattta tttttaggga ataaaaataa gaaataaaat agtcagcaag     10320
cctctgcttt ctcatatatc tgtccaaacc taaagtttac tgaaatttgc tctttgaatt     10380
tccagttttg caagcctatc agattgtgtt ttaatcagag gtactgaaaa gtatcaatga     10440
attctagctt tcactgaaca aaaatatgta gaggcaactg gcttctggga cagtttgcta     10500
cccaaaagac aactgaatgc aaatacataa atagatttat gaatatggtt ttgaacatgc     10560
acatgagagg tggatatagc aacagacaca ttaccacaga attactttaa aactacttgt     10620
taacatttaa ttgcctaaaa actgctcgta atttactgtt gtagcctacc atagagtacc     10680
ctgcatggta ctatgtacag cattccatcc ttacattttc actgttctgc tgtttgctct     10740
agacaactca gagttcacca tg                                              10762

<210> SEQ ID NO 9
<211> LENGTH: 242
<212> TYPE: DNA
<213> ORGANISM: Artificial Sequence
<220> FEATURE:
<223> OTHER INFORMATION: Adaptor sequence

<400> SEQUENCE: 9 cccggggttgt taacatttaa ttgcctaaaa actgctcgta atttactgtt gtagcctacc      60
atagagtacc ctgcatggta ctatgtacag cattccatcc ttacattttc actgttctgc     120
tgtttgctct agacaactca gagttcacca tgaaaatgcg gttcttgggg ttggtggtct     180
gtttggttct ctggaccctg cattccgagg ggtccggagg gaaactgaca gctgtggatc     240
ct                                                                    242

<210> SEQ ID NO 10
<211> LENGTH: 1575
<212> TYPE: DNA
<213> ORGANISM: Artificial Sequence
<220> FEATURE:
<223> OTHER INFORMATION: Syn SBC102

<400> SEQUENCE: 10
ccattatctg gttgtaactg aagctcaatg gaacatgagc aatatttccc agtcttctct       60
```

```
cccatccaac agtcctgatg gattagcaga acaggcagaa aacacattgt tacccagaat    120
taaaaactaa tatttgctct ccattcaatc caaaatggac ctattgaaac taaaatctaa    180
cccaatccca ttaaatgatt tctatggtgt caaaggtcaa acttctgaag ggaacctgtg    240
ggtgggtcac aattcagact atatattccc cagggctcag ccagtgtctg tacatacagc    300
tagaaagctg tattgccttt agcagtcaag ctcgaaagac aactcagagt tcaccatgaa    360
aatgcggttc ttggggttgg tggtctgttt ggttctctgg accctgcatt ccaggggtc     420 cggagggaaa ctgacagctg tggatcctga acaaacatg aatgtcagtg aaattatctc     480
ttactgggga ttccctagtg aggaatacct agttgagaca gaagatggat atattctgtg    540
ccttaaccga attcctcatg ggaggaagaa ccattctgac aaaggtccca accagttgt     600 cttcctgcaa catggcttgc tggcagattc tagtaactgg gtcacaaacc ttgccaacag    660
cagcctgggc ttcattcttg ctgatgctgg ttttgacgtg tggatgggca acagcagagg    720
aaatacctgg tctcggaaac ataagacact ctcagtttct caggatgaat tctgggcttt    780
cagttatgat gagatggcaa aatatgacct accagcttcc attaacttca ttctgaataa    840
gactggccaa gaacaagtgt attatgtggg tcattctcaa ggcaccacta taggttttat    900
agcattttca cagatccctg agctggctaa aaggattaaa atgttttttg ccctgggtcc    960
tgtggcttcc gtcgccttct gtactagccc tatggccaaa ctgggacgac tgccagatca   1020
tctcattaag gacctctttg gagacaaaga atttcttccc cagagtgcgt ttttgaagtg   1080
gctgggtacc cacgtttgca ctcatgtcat actgaaggag ctctgtggaa atctctgttt   1140
tcttctgtgt ggatttaatg agagaaattt aaatatgtct agagtggatg tgtatacaac   1200
acattctcct gctggaactt ctgtgcaaaa catgttacac tggagccagg ctgttaaatt   1260
ccaaaagttt caagcctttg actggggaag cagtgccaag aattattttc attacaacca   1320
gagttatcct cccacataca atgtgaagga catgcttgtg ccgactgcag tctggagcgg   1380
gggtcacgac tggcttgcag atgtctacga cgtcaatatc ttactgactc agatcaccaa   1440
cttggtgttc catgagagca ttccggaatg ggagcatctt gacttcattt ggggcctgga   1500
tgccccttgg aggctttata ataagattat taatctaatg aggaaatatc agtgattcga   1560
agcggccgcc ccggg                                                    1575
```

<210> SEQ ID NO 11
<211> LENGTH: 2789
<212> TYPE: DNA
<213> ORGANISM: Artificial Sequence
<220> FEATURE:
<223> OTHER INFORMATION: OVR1 promoter

<400> SEQUENCE: 11

```
ctcgagtctc ttcagaatgg cacagcaccg ctgcagaaaa atgccaggtg gactatgaac     60
tcacatccaa aggagcttga cctgatacct gattttcttc aaacagggga acaacacaa    120 tcccacaaaa cagctcagag agaaaccatc actgatggct acagcaccaa ggtatgcaat    180
ggcaatccat tcgacattca tctgtgacct gagcaaaatg atttatctct ccatgaatgg    240
ttgcttcttt ccctcatgaa aaggcaattt ccacactcac aatatgcaac aaagacaaac    300
agagaacaat taatgtgctc cttcctaatg ttaaaattgt agtggcaaag aggagaacaa    360
aatctcaagt tctgagtagg ttttagtgat tggataagag ctttgacct gtgagctcac     420 ctggacttca tatcctttg gataaaaagt gcttttataa ctttcaggtc tccgagtctt    480
```

```
tattcatgag actgttggtt tagggacaga cccacaatga aatgcctggc ataggaaagg      540
gcagcagagc cttagctgac cttttcttgg gacaagcatt gtcaaacaat gtgtgacaaa      600
actatttgta ctgctttgca cagctgtgct gggcagggca atccattgcc acctatccca      660
ggtaaccttc caactgcaag aagattgttg cttactctct ctagaccccc aagtcaaacc      720
aactatgcag gtatgctgac aacactatga tgacagcctg ttctgatcaa gatctcattt      780
gttcatggac aatttttgtt gcttgcagct ggtcttccat tgggaaagag tgtagtatat      840
ccttctcatc tgacagaaaa gcagaaattc tcatgctcca cacttaatct acattgtttt      900
aaaccaccgg ctacttcttg gagaggaaaa atggctttta taagactcac aaaacaaagc      960
tctgcaagtc aaatgcatac aaaactgttc tgtaggtctg gaatcaggac actatgtgga     1020
agtcaaatag agcagcttta aaaagccttt gggatcattc tcatcttata tttgcagcac     1080
gatactatga cagtgataac tgacataact gcatcaattt ccttgatatt ttatttgtct     1140
taaagtacaa gacatagaga tggacgtaaa gatggacata tgactcaggt ctggacaggt     1200
ccgtggtcca tgtatgataa aagagatgaa gggaaggaga attgagactg tctaagaagg     1260
gcttcaggga cgttctgaag gcagatttga ctgaatcaga tgtactgtcc aagtctcata     1320
tgtagcaatg gaaggctgat attggagaaa tataaagaaa tggctgtgaa ctcaaagtga     1380
ccctgaacag aaaagggata tggagttaaa ataatgtcac agaactgagg tttatatgat     1440
ataccatggg ctgcagaggg tcagagtgct ccaccatggg cctctcttgg gctgcaggga     1500
acttctgttc tacacctgga acacctcctg ccctcctccg cactgacctc agtgtcatca     1560
gggctgtttc tctcacattt tctcactcac ctctcccaac taccattgta cagcagttgt     1620
tcttacatat tgctcctcct gaggtacatc tagcatcgtt aagtcctcag acttggcaag     1680
gagaatgtag atttccacag tatatatgtt ttcacaaaag gaaggagaga aacaaaagaa     1740
aatggcactg actaaacttc agctagtggt ataggaaagt aattctgctt aacagagatt     1800
gcagtgatct ctatgtatgt cctgaagaat tatgttgtac ttttttcccc cattttaaa      1860 tcaaacagtg ctttacagag gtcagaatgg tttctttact gtttgtcaat tctattattt     1920
caatacagaa caatagcttc tataactgaa atatatttgc tattgtatat tatgattgtc     1980
cctcgaacca tgaacactcc tccagctgaa tttcacaatt cctctgtcat ctgccaggcc     2040
attaagttat tcatggaaga tctttgagga acactgcaag ttcatatcat aaacacattt     2100
gaaattgagt attgttttgc attgtatgga gctatgtttt gctgtatcct cagaataaaa     2160
gtttgttata aagcattcac acccataaaa agatagattt aaatattcca actataggaa     2220
agaaagtgtg tctgctcttc actctagtct cagttggctc cttcacatgc acgcttcttt     2280
atttctccta ttttgtcaag aaaataatag gtcaagtctt gttctcattt atgtcctgtc     2340
tagcgtggct cagatgcaca ttgtacatac aagaaggatc aaatgaaaca gacttctggt     2400
ctgttactac aaccatagta ataagcacac taactaataa ttgctaatta tgttttccat     2460
ctccaaggtt cccacatttt tctgtttct taaagatccc attatctggt tgtaactgaa       2520
gctcaatgga acatgagcaa tatttcccag tcttctctcc catccaacag tcctgatgga     2580
ttagcagaac aggcagaaaa cacattgtta cccagaatta aaaactaata tttgctctcc     2640
attcaatcca aaatggacct attgaaacta aaatctaacc caatcccatt aaatgatttc     2700
tatggtgtca aaggtcaaac ttctgaaggg aacctgtggg tgggtcacaa ttcagactat     2760
atattcccca gggctcagcc agtgtctgt                                      2789
```

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 12
agaaactgag agtgtcttat                                               20

<210> SEQ ID NO 13
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 13
tgacagctgt ggatccagaa acaaacatg                                     29

<210> SEQ ID NO 14
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 14
gccgctcgag cgaggaatat aaaaaaatt                                     29

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 15
tccgcgcaca tttccccgaa                                               20

<210> SEQ ID NO 16
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 16
acgactggct tgcagatgtc t                                             21

<210> SEQ ID NO 17
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 17
ccccaaatga agtcaagatg ct                                            22

<210> SEQ ID NO 18
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 18
ccggaatgct ctcatggaac accaa                                                    25

<210> SEQ ID NO 19
<211> LENGTH: 372
<212> TYPE: PRT
<213> ORGANISM: HOMO SAPIENS

<400> SEQUENCE: 19

Ala Val Asp Pro Glu Thr Asn Met Asn Val Ser Glu Ile Ile Ser Tyr
1               5                   10                  15

Trp Gly Phe Pro Ser Glu Glu Tyr Leu Val Glu Thr Glu Asp Gly Tyr
            20                  25                  30

Ile Leu Cys Leu Asn Arg Ile Pro His Gly Arg Lys Asn His Ser Asp
        35                  40                  45

Lys Gly Pro Lys Pro Val Val Phe Leu Gln His Gly Leu Leu Ala Asp
    50                  55                  60

Ser Ser Asn Trp Val Thr Asn Leu Ala Asn Ser Ser Leu Gly Phe Ile
65                  70                  75                  80

Leu Ala Asp Ala Gly Phe Asp Val Trp Met Gly Asn Ser Arg Gly Asn
                85                  90                  95

Thr Trp Ser Arg Lys His Lys Thr Leu Ser Val Ser Gln Asp Glu Phe
            100                 105                 110

Trp Ala Phe Ser Tyr Asp Glu Met Ala Lys Tyr Asp Leu Pro Ala Ser
        115                 120                 125

Ile Asn Phe Ile Leu Asn Lys Thr Gly Gln Glu Gln Val Tyr Tyr Val
    130                 135                 140

Gly His Ser Gln Gly Thr Thr Ile Gly Phe Ile Ala Phe Ser Gln Ile
145                 150                 155                 160

Pro Glu Leu Ala Lys Arg Ile Lys Met Phe Phe Ala Leu Gly Pro Val
                165                 170                 175

Ala Ser Val Ala Phe Cys Thr Ser Pro Met Ala Lys Leu Gly Arg Leu
            180                 185                 190

Pro Asp His Leu Ile Lys Asp Leu Phe Gly Asp Lys Glu Phe Leu Pro
        195                 200                 205

Gln Ser Ala Phe Leu Lys Trp Leu Gly Thr His Val Cys Thr His Val
    210                 215                 220

Ile Leu Lys Glu Leu Cys Gly Asn Leu Cys Phe Leu Leu Cys Gly Phe
225                 230                 235                 240

Asn Glu Arg Asn Leu Asn Met Ser Arg Val Asp Val Tyr Thr Thr His
                245                 250                 255

Ser Pro Ala Gly Thr Ser Val Gln Asn Met Leu His Trp Ser Gln Ala
            260                 265                 270

Val Lys Phe Gln Lys Phe Gln Ala Phe Asp Trp Gly Ser Ser Ala Lys
        275                 280                 285

Asn Tyr Phe His Tyr Asn Gln Ser Tyr Pro Pro Thr Tyr Asn Val Lys
    290                 295                 300

Asp Met Leu Val Pro Thr Ala Val Trp Ser Gly Gly His Asp Trp Leu
305                 310                 315                 320

Ala Asp Val Tyr Asp Val Asn Ile Leu Leu Thr Gln Ile Thr Asn Leu
                325                 330                 335

Val Phe His Glu Ser Ile Pro Glu Trp Glu His Leu Asp Phe Ile Trp
            340                 345                 350

Gly Leu Asp Ala Pro Trp Arg Leu Tyr Asn Lys Ile Ile Asn Leu Met

```
                    355                 360                 365
Arg Lys Tyr Gln
    370

<210> SEQ ID NO 20
<211> LENGTH: 399
<212> TYPE: PRT
<213> ORGANISM: HOMO SAPIENS

<400> SEQUENCE: 20

Met Lys Met Arg Phe Leu Gly Leu Val Val Cys Leu Val Leu Trp Thr
1               5                   10                  15

Leu His Ser Glu Gly Ser Gly Gly Lys Leu Thr Ala Val Asp Pro Glu
            20                  25                  30

Thr Asn Met Asn Val Ser Glu Ile Ile Ser Tyr Trp Gly Phe Pro Ser
        35                  40                  45

Glu Glu Tyr Leu Val Glu Thr Glu Asp Gly Tyr Ile Leu Cys Leu Asn
    50                  55                  60

Arg Ile Pro His Gly Arg Lys Asn His Ser Asp Lys Gly Pro Lys Pro
65                  70                  75                  80

Val Val Phe Leu Gln His Gly Leu Leu Ala Asp Ser Ser Asn Trp Val
                85                  90                  95

Thr Asn Leu Ala Asn Ser Ser Leu Gly Phe Ile Leu Ala Asp Ala Gly
            100                 105                 110

Phe Asp Val Trp Met Gly Asn Ser Arg Gly Asn Thr Trp Ser Arg Lys
        115                 120                 125

His Lys Thr Leu Ser Val Ser Gln Asp Glu Phe Trp Ala Phe Ser Tyr
    130                 135                 140

Asp Glu Met Ala Lys Tyr Asp Leu Pro Ala Ser Ile Asn Phe Ile Leu
145                 150                 155                 160

Asn Lys Thr Gly Gln Glu Gln Val Tyr Tyr Val Gly His Ser Gln Gly
                165                 170                 175

Thr Thr Ile Gly Phe Ile Ala Phe Ser Gln Ile Pro Glu Leu Ala Lys
            180                 185                 190

Arg Ile Lys Met Phe Phe Ala Leu Gly Pro Val Ala Ser Val Ala Phe
        195                 200                 205

Cys Thr Ser Pro Met Ala Lys Leu Gly Arg Leu Pro Asp His Leu Ile
    210                 215                 220

Lys Asp Leu Phe Gly Asp Lys Glu Phe Leu Pro Gln Ser Ala Phe Leu
225                 230                 235                 240

Lys Trp Leu Gly Thr His Val Cys Thr His Val Ile Leu Lys Glu Leu
                245                 250                 255

Cys Gly Asn Leu Cys Phe Leu Cys Gly Phe Asn Glu Arg Asn Leu
            260                 265                 270

Asn Met Ser Arg Val Asp Val Tyr Thr Thr His Ser Pro Ala Gly Thr
        275                 280                 285

Ser Val Gln Asn Met Leu His Trp Ser Gln Ala Val Lys Phe Gln Lys
    290                 295                 300

Phe Gln Ala Phe Asp Trp Gly Ser Ser Ala Lys Asn Tyr Phe His Tyr
305                 310                 315                 320

Asn Gln Ser Tyr Pro Pro Thr Tyr Asn Val Lys Asp Met Leu Val Pro
                325                 330                 335

Thr Ala Val Trp Ser Gly Gly His Asp Trp Leu Ala Asp Val Tyr Asp
            340                 345                 350
```

```
Val Asn Ile Leu Leu Thr Gln Ile Thr Asn Leu Val Phe His Glu Ser
    355                 360             365

Ile Pro Glu Trp Glu His Leu Asp Phe Ile Trp Gly Leu Asp Ala Pro
    370             375                 380

Trp Arg Leu Tyr Asn Lys Ile Ile Asn Leu Met Arg Lys Tyr Gln
385             390             395
```